United States Patent
Saitou et al.

(10) Patent No.: US 7,932,281 B2
(45) Date of Patent: Apr. 26, 2011

(54) AMINE-BASED COMPOUND AND USE THEREOF

(75) Inventors: Atsushi Saitou, Tokyo (JP); Shigeyuki Kikumoto, Tokyo (JP); Masahiro Ono, Tokyo (JP); Ryo Matsui, Tokyo (JP); Masashi Yamamoto, Tokyo (JP); Tomohiro Sawa, Tokyo (JP); Shigeru Suzuki, Tokyo (JP); Mikiro Yanaka, Tokyo (JP)

(73) Assignee: Kureha Corporation, Tokyo (JP)

( * ) Notice: Subject to any disclaimer, the term of this patent is extended or adjusted under 35 U.S.C. 154(b) by 1002 days.

(21) Appl. No.: 10/591,722

(22) PCT Filed: Mar. 10, 2005

(86) PCT No.: PCT/JP2005/004189
§ 371 (c)(1),
(2), (4) Date: Oct. 30, 2006

(87) PCT Pub. No.: WO2005/085209
PCT Pub. Date: Sep. 15, 2005

(65) Prior Publication Data
US 2007/0208007 A1    Sep. 6, 2007

(30) Foreign Application Priority Data

Mar. 10, 2004  (JP) ................. 2004-068229
Dec. 3, 2004   (JP) ................. 2004-350599

(51) Int. Cl.
*A61K 31/4178*  (2006.01)
*C07D 233/54*   (2006.01)

(52) U.S. Cl. ............... 514/396; 514/397; 548/335.1

(58) Field of Classification Search ............... 514/396, 514/397; 548/335.1
See application file for complete search history.

(56) References Cited

U.S. PATENT DOCUMENTS

| | | |
|---|---|---|
| 3,634,316 A | 1/1972 | Ito et al. |
| 5,086,069 A | 2/1992 | Klein et al. |
| 5,633,231 A | 5/1997 | Habich et al. |
| 5,886,044 A | 3/1999 | Widdowson et al. |
| 6,077,954 A | 6/2000 | Cook et al. |
| 6,096,773 A | 8/2000 | Scott et al. |
| 6,197,965 B1 | 3/2001 | Cook et al. |
| 6,204,294 B1 | 3/2001 | Bryan et al. |
| 6,329,523 B1 | 12/2001 | Cook et al. |
| 6,750,348 B1 | 6/2004 | Bridger et al. |
| 7,091,217 B2 | 8/2006 | Bridger et al. |
| 7,098,215 B2 | 8/2006 | Yamazaki et al. |
| 7,176,227 B2 | 2/2007 | Yamazaki et al. |
| 2004/0157818 A1 | 8/2004 | Yanaka et al. |
| 2004/0171638 A1 | 9/2004 | Bridger et al. |
| 2004/0254221 A1 | 12/2004 | Yamazaki et al. |
| 2005/0165063 A1 | 7/2005 | Yamazaki et al. |
| 2006/0128750 A1 | 6/2006 | Bridger et al. |
| 2006/0264434 A1 | 11/2006 | Bridger et al. |
| 2007/0208033 A1 | 9/2007 | Yamazaki et al. |

FOREIGN PATENT DOCUMENTS

| | | |
|---|---|---|
| EP | 0 183 271 A2 | 6/1986 |
| EP | 0 628 551 | 12/1994 |
| EP | 0 646 598 | 4/1995 |
| GB | 1268419 | 3/1972 |
| JP | 7-89988 | 4/1995 |
| WO | 98/05961 | 2/1998 |
| WO | WO 98/06397 A1 | 2/1998 |
| WO | WO 99/33787 A1 | 7/1999 |
| WO | WO 00/06086 A2 | 2/2000 |
| WO | 00/56729 | 9/2000 |
| WO | WO 00/56729 A1 | 9/2000 |
| WO | WO 01/10842 A2 | 2/2001 |
| WO | WO 01/79168 A1 | 10/2001 |
| WO | 02/22600 | 3/2002 |
| WO | WO 02/22600 A1 | 3/2002 |
| WO | WO 02/94261 A1 | 5/2002 |
| WO | 02/49993 | 6/2002 |
| WO | 02/062766 | 8/2002 |
| WO | WO 03/029218 A1 | 4/2003 |
| WO | WO 2004/024697 A1 | 3/2004 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Golub et al. Science (1999), vol. 286 531-537.*
Lala et al. Cancer and Metastasis Reviews (1998), 17(1), 91-106.*
Molino, M. et al., "CXCR4 on human endothelial cells can serve as both a mediator of biological responses and as a receptor for HIV-2," Biochimica et Biophysica Acta (BBA), Molecular Basis of Disease, vol. 1500, pp. 227-240 (2000).
Saishin Idaku, vol. 53, No. 9, pp. 2031-2038 (1998) with English translation of abstract.
Nikkei Science, Oct., p. 26-37 (1998) with English version Bartlett, John G. et al, "Improving HIV Therapy," Scientific American, pp. 84-89 (Jul. 1998).

(Continued)

*Primary Examiner* — Rebecca L Anderson
*Assistant Examiner* — Samantha L Shterengarts
(74) *Attorney, Agent, or Firm* — Greenblum & Bernstein, P.L.C.

(57) ABSTRACT

Amine compounds represented by Formula (1) are efficacious against diseases such as a viral infectious disease with HIV, rheumatism, and cancer metastasis:

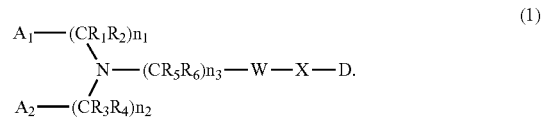

(1)

11 Claims, No Drawings

OTHER PUBLICATIONS

Molecular Medicine, vol. 36, No. 9, pp. 1012-1017 (1999) with English translation of abstract.

Nikkei Science, Oct., pp. 42-49 (1998) with English version Baltimore, David et al, "HIV Vaccines: Prospects and Challenges," Scientific American, pp. 78-83 (Jul. 1998).

Feng, Yu et al, "HIV-1 Entry Cofactor: Functional cDNA Cloning of a Seven-Transmembrane, G Protein-Coupled Receptor," Science, 272, 872-877 (1996).

Bleul, Conrad C. et al, "The lymphocyte chemoattractant SDF-1 is a ligand for LESTR/fusin and blocks HIV-1 entry," Nature, 382, 829-831 (1996).

Schols, Dominique et al, "Inhibition of T-tropic HIV Strains by Selective Antagonization of the Chemokine Receptor CXCR4," J. Exp. Med., 186, 1383-1387 (1997).

Murakami, Tsutomu et al, "A Small Molecule CXCR4 Inhibitor that Blocks T Cell Line-tropic HIV-1 Infection," J. Exp. Med., 186, 1389-1393 (1997).

Doranz, Benjamin J. et al, "A Small-molecule Inhibitor Directed against the Chemokine Receptor CXCR4 Prevents its Use as an HIV-1 Coreceptor," J. Exp. Med., 186, 1395-1400 (1997).

Muller, Anja et al, "Involvement of chemokine receptors in breast cancer metastasis," Nature, 410, 50-56 (2001).

Supplementary European Search Report dated Nov. 27, 2009 that issued with respect to European Patent Application No. 03795301.5.

Database Caplus Chemical Abstract Service, XP00255118, Abstract of JP 11-269146, Oct. 5, 1999.

Database Caplus Chemical Abstract Service, XP00255119, Abstract of JP 52-059794, May 17, 1977.

\* cited by examiner

AMINE-BASED COMPOUND AND USE THEREOF

This application is a 371 U.S. national stage application of International Application PCT/JP2005/004189 filed Mar. 10, 2005, which claims priority of Japanese patent applications 068229/2004 filed Mar. 10, 2004, and 350599/2004 filed Dec. 3, 2004.

TECHNICAL FIELD

The present invention relates to an amine compound or a pharmacologically acceptable salt thereof, or a prodrug thereof, in particular, an amine compound having anti-virus activity based on antagonism against a chemokine receptor CXCR4. Furthermore, the present invention relates to a therapeutical drug including the above-mentioned compounds as active ingredients for associated diseases such as rheumatic diseases and cancer metastatic diseases, particularly based on antagonism against the chemokine receptor CXCR4.

BACKGROUND ART

Examples of therapeutic drugs against the acquired immunodeficiency syndrome (AIDS) caused by an infection with the human immunodeficiency virus (HIV) include a reverse transcriptase inhibitor and a protease inhibitor. However, therapeutic effectiveness of those drugs has been lost due to the emergence of drug resistant HIV mutants (see, for example, Non-patent Document 1). Also, the polypharmacy using the combination of such drugs has such disadvantages that it requires many conditions to be observed in administration, that it is complex, that it needs many kinds of drugs to be administered, and that it causes various side effects (see, for example, Non-patent Document 2). Moreover, particularly in case of using the protease inhibitor, it is known that the probability of causing emergence and screening of the resistant strain will increase unless the administration of approximately 100% of the drugs is kept, in spite of the complex administration method and many side effects thereof (see, for example, Non-patent Document 3).

Alternatively, development of vaccine has been attempted because many viral diseases were destroyed or remarkably weakened by vaccines in the past. However, this is considered to be extremely difficult since mutations are occurred frequently in HIV (see, for example, Non-patent Document 4).

Although several kinds of compounds having an anti-HIV effect have been reported as described above, it is now strongly desired to develop a novel antiviral drug which has excellent anti-retrovirus effect, is capable of opposing to the expression of the resistance, and which has little toxicity and causes little side effect, thereby allowing a long term administration.

Chemokine is one kind of cytokine which renders chemotaxis to leukocytes, and is a secretory protein. Chemokine is classified into CXC-chemokine, CC-chemokine, C-chemokine, CX3C-chemokine according to the cysteine (Cys) sequence at N-terminal, and the total number thereof is said to be about 30. The chemokine receptor includes several subtypes. Among them, it is known that the CXCR4 to which a ligand CXC-chemokine SDF-1α binds is utilized as a coreceptor on infection to a host cell of a T cell-directive HIV (see, for example, Non-patent Document 5 and Non-patent Document 6). The HIV invades through binding of its envelope protein gp120 to the CXCR4 on the surface of a host cell. That is, the drug having antagonism against the CXCR4 is expected as an anti-HIV drug based on a novel mechanism of invasion inhibition, and there have been reported three low-molecular compounds as such drugs: AMD3100 (see, for example, Non-patent Document 7), T22 (see, for example, Non-patent Document 8), and ALX40-4C (see, for example, Non-patent Document 9).

On the other hand, it has been elucidated that the CXCR4 associates with various diseases besides HIV infection. For example, there has been reported its association with a rheumatic disease (see, for example, Patent Document 1), a cancer metastatic disease (see, for example, Non-patent Document 10), or the like.

As a therapeutic drug for such diseases, it is strongly desired to develop a novel low-molecular drug which has CXCR4 antagonism, and which has little toxicity and causes little side effect, thereby allowing a long-term administration.

[Patent Document 1] WO 00/06086
[Non-patent Document 1] Saishin Igaku, Vol. 53, No. 9, p. 2031 (1998)
[Non-patent Document 2] Nikkei Science, October, p. 29 (1998)
[Non-patent Document 3] Molecular Medicine, Vol. 36, No. 9, p. 1012 (1999)
[Non-patent Document 4] Nikkei Science, October, p. 42 (1998)
[Non-patent Document 5] Science, 272, 872 (1996)
[Non-patent Document 6] Nature, 382, 829 (1996)
[Non-patent Document 7] J. Exp. Med, 186, 1383 (1997)
[Non-patent Document 8] J. Exp. Med, 186, 1389 (1997)
[Non-patent Document 9] J. Exp. Med, 186, 1395 (1997)
[Non-patent Document 10] Nature, 410, 50 (2001)

DISCLOSURE OF THE INVENTION

Problems to be Solved by the Invention

An object of the present invention is to provide a drug and a prodrug thereof having an excellent anti-retrovirus effect, and also a novel chemical structure having an excellent CXCR4 antagonism against SDF-1α, and high safety.

As a result of studies to develop a compound having an excellent anti-retrovirus effect, and also having a novel chemical structure useful as an excellent CXCR4 antagonist against SDF-1α, the inventors of the present invention have found a group of amine compounds which exhibit protection characteristics in a cell vaccinated with HIV-1 and therefore are regarded as having a potentiality for treatments of AIDS, AIDS-associated complication, and the like, and which also exhibit a powerful CXCR4 antagonism and therefore are regarded as having a potentiality for treatments of rheumatic disease, cancer metastatic diseases, and the like. The group of amine compounds has been applied for a patent (PCT/JP 03/11381), after that, the inventors of the present invention have found a more useful compound thereafter. Thus, another object of the present invention is to provide a compound represented by the general formula (1) defined below, which has an anti-virus activity for mainly HIV and a CXCR4 antagonism, and the present invention is to provide a drug composed of the compound represented by the general formula (1), for treating virus-infected patients and patients suffering from rheumatism, cancer, or the like.

Means for Solving the Problems

The present invention relates to a compound represented by the following general formula (1), a pharmacologically acceptable salt thereof, or a prodrug thereof:

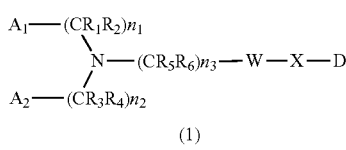

(1)

where
$n_1$, $n_2$, and $n_3$ each represent an integer of 0 to 3;
$R_1$, $R_2$, $R_3$, $R_4$, $R_5$, and $R_6$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms, in this instance $R_5$ and $R_6$ each may form a carbonyl group with a carbon atom bound thereto; and
$A_1$ and $A_2$ each independently represent a hydrogen atom, a substitutable monocyclic or polycyclic heteroaromatic ring, a partly saturated substitutable polycyclic heteroaromatic ring, a substitutable monocyclic or polycyclic aromatic ring, a partly saturated substitutable polycyclic aromatic ring, a substitutable heterocycle, or a group represented by the following formula (2):

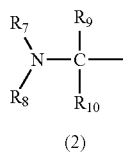

(2)

where
$R_7$, $R_8$, $R_9$, and $R_{10}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms;
W represents any one of a substitutable benzene ring and groups represented by the following formulae (10) and (11);

[Formula 3]

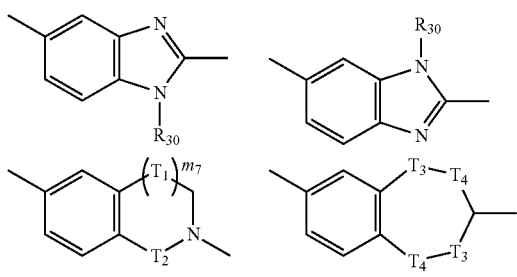

(10)

[Formula 4]

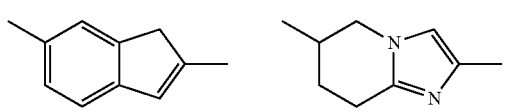

(11)

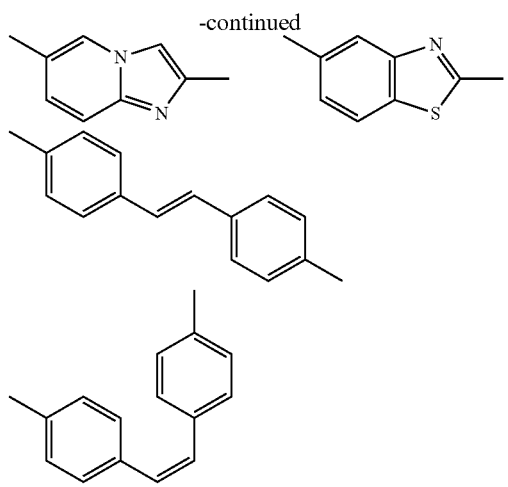

where
$R_{30}$ represents a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms, a methanesulfonyl group, a p-toluenesulfonyl group, a phenyl group, an acyl group, a carboxyl group, or a cyano group;
$m_7$ represents an integer of 0 to 2;
$T_1$ and $T_2$ represent $CH_2$ or CO;
$T_3$ and $T_4$ have a relationship of $T_3$=NH and $T_4$=CO, or $T_3$=CO and $T_4$=NH;
X represents a substitutable monocyclic or polycyclic heteroaromatic ring, a substitutable monocyclic or polycyclic aromatic ring, O, $CH_2$, $NR_{11}$, $CHR_{35}$, or a group represented by the following formula (3) or (12);
$R_{11}$ represents a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms;
$R_{35}$ represents a carboxyl group or an alkoxycarbonyl group;

[Formula 5]

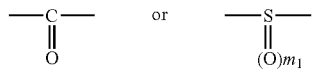

(3)

wherein
$m_1$ represents an integer of 1 or 2:

[Formula 6]

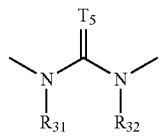

(12)

where
$T_5$ represents an oxygen atom or a sulfur atom;
$R_{31}$ and $R_{32}$ represent a hydrogen atom or an alkyl group having 1 to 3 carbon atoms, and $R_{31}$ and $R_{32}$ may be coupled to each other to form a ring;

[Formula 7]

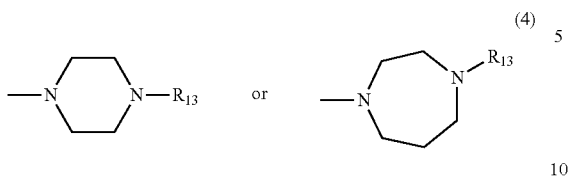
(4)

D represents a group represented by the above formula (4) or the following formula (6),.

in the formula (4), $R_{13}$ represents a hydrogen atom, a substitutable alkyl group having 1 to 15 carbon atoms, a substitutable alkenyl group having 2 to 15 carbon atoms, a substitutable alkynyl group having 2 to 15 carbon atoms, a substitutable cyclic alkyl group having 3 to 15 carbon atoms, or a group represented by the following formula (5):

[Formula 8]

(5)

where $m_2$ represents an integer of 2 to 4;

$R_{14}$, $R_{15}$, $R_{16}$, and $R_{17}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms;

[Formula 9]

—Q—Y—B       (6)

where

Q represents a single bond when X is O, a single bond or a group represented by the formula (3) when X is $NR_{11}$, or a single bond, S, O, $NR_{12}$, or a group represented by the formula (13) when X is a substitutable monocyclic or polycyclic heteroaromatic ring, a substitutable monocyclic or polycyclic aromatic ring, $CH_2$ or is represented by the formula (3) or (12);

[Formula 10]

(13)

$R_{12}$ represents a hydrogen atom, a substitutable alkyl group having 1 to 15 carbon atoms, a substitutable alkenyl group having 2 to 15 carbon atoms, a substitutable alkynyl group having 2 to 15 carbon atoms, a substitutable cyclic alkyl group having 3 to 15 carbon atoms, a methanesulfonyl group, a p-toluenesulfonyl group, a phenyl group, an acyl group, a carboxyl group, a cyano group, or a group represented by the formula (15);

[Formula 11]

(15)

$R_{34}$ represents a substitutable alkyl group having 1 to 15 carbon atoms, a substitutable cyclic alkyl group having 3 to 15 carbon atoms, or a phenyl group;

for example in embodiments of the invention $R_{12}$ may represent the substituted alkyl group $—(CH_2)_m COOR_{36}$, wherein m represents an integer of 1 or 2 and $R_{36}$ represents a hydrogen atom or an alkyl group having 1 to 5 carbon atoms;

Y represents a group represented by the following formula (7):

[Formula 12]

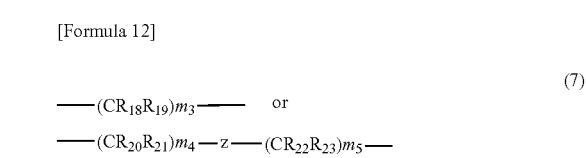
(7)

where $m_3$ represents an integer of 0 to 6;

$R_{18}$ and $R_{19}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, a substitutable cyclic alkyl group having 3 to 15 carbon atoms, or a substitutable aromatic ring, and $R_{12}$ and $R_{18}$ may form a ring;

$m_4$ and $m_5$ represent an integer of 0 to 2;

$R_{20}$, $R_{21}$, $R_{22}$, and $R_{23}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms;

z represents a substitutable cyclic alkylene group having 3 to 15 carbon atoms, a substitutable monocyclic or polycyclic heteroaromatic ring, a partly saturated substitutable polycyclic heteroaromatic ring, a substitutable monocyclic or polycyclic aromatic ring, a partly saturated substitutable polycyclic aromatic ring, a substitutable heterocycle, S, O, $NR_{12}$, S=O, O=S=O, or the formula (16);

[Formula 13]

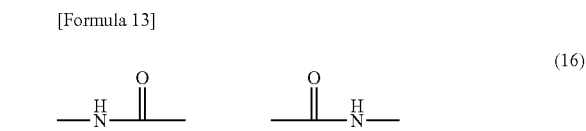
(16)

B represents any one of the groups represented by the following formulae (8) and (14):

[Formula 14]

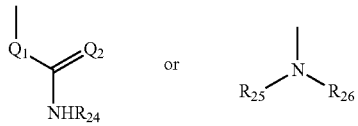

(8)

where $Q_1$ represents S, O, or NH and $Q_2$ represents S, O, or $NR_{27}$;

$R_{24}$ and $R_{27}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, a substitutable cyclic alkyl group having 3 to 15 carbon atoms, or a substitutable aromatic ring, and $R_{24}$ and $R_{27}$ may form a ring;

$R_{25}$ and $R_{26}$, when above X is $CH_2$, each independently represent a hydrogen atom, a substitutable alkyl group having 1 to 15 carbon atoms, a substitutable cyclic alkyl group having 3 to 15 carbon atoms, a substitutable alkenyl group having 2 to 15 carbon atoms and having 1 to 3 double bonds, or a substitutable alkynyl group having 2 to 15 carbon atoms and having 1 to 3 triple bonds, and $R_{25}$ and $R_{26}$ may form a ring and, depending on circumstances, the ring may be formed by binding through a heteroatom, a cyclic alkyl group, an aromatic ring, a heteroaromatic ring, or a heterocycle;

$R_{25}$ and $R_{26}$, when above X is not $CH_2$, each independently represent a hydrogen atom, a substituent represented by the following formula (9), a substitutable alkyl group having 1 to 15 carbon atoms, a substitutable cyclic alkyl group having 3 to 15 carbon atoms, a substitutable alkenyl group having 2 to 15 carbon atoms and having 1 to 3 double bonds, or a substitutable alkynyl group having 2 to 15 carbon atoms and having 1 to 3 triple bonds, and $R_{25}$ and $R_{26}$ may form a ring and, depending on circumstances, the ring may be formed by binding through a heteroatom, a cyclic alkyl group, an aromatic ring, a heteroaromatic ring, or a heterocycle:

[Formula 15]

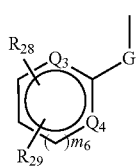

(9)

where $m_6$ is 0 or 1, where when $m_6$=0, $Q_3$ represents CH or N and $Q_4$ represents N, S, or O, and when $m_6$=1, $Q_3$ and $Q_4$ each independently represent CH or N;

G represents a substitutable alkylene group having 1 to 15 carbon atoms or a substitutable alkenylene group having 2 to 15 carbon atoms;

$R_{28}$ represents an alkyl group having 1 to 15 carbon atoms, a substitutable alkenyl group having 2 to 15 carbon atoms, a substitutable alkynyl group having 2 to 15 carbon atoms, an alkoxy group, a haloalkyl group, a haloalkoxy group, a hydroxyalkoxy group, a halogen atom, an amino group, an alkylamino group, a carboxyl group, an alkoxycarbonyl group, a carbamoyl group, an alkylcarbamoyl group, a saturated heterocycle, or a heteroaromatic ring, which is substituted at any position except a nitrogen atom which may be present on the ring or may represent a hydrogen atom when $m_6$=1 and $Q_3$ and $Q_2$ simultaneously represent CH;

$R_{29}$ represents a hydrogen atom or the same group as $R_{24}$, and may be coupled with G to form a ring.

[Formula 16]

(14)

where $R_{33}$ represent the same group as that of $R_{12}$.

Further, one or two or more asymmetric carbon atoms may exist in the compound represented by the general formula (1), where when one asymmetric carbon atom exists, the compound may be in the form of any one of a pure optically-active substance represented by the absolute configuration R or S, a mixture thereof in a predetermined ratio, and a racemic mixture thereof or when two or more asymmetric carbon atoms exist, the compound may be in the form of any one of an optically pure diastereomer, a racemic mixture thereof, and a combination thereof in an predetermined ratio.

The terms as used in this specification are defined as described below, and they may be used singly or in combination.

An alkyl group represents a saturated hydrocarbon group with any structure of a linear chain, a branched chain, or a ring. Examples of the alkyl group include a methyl group, an ethyl group, an n-propyl group, an isopropyl group, an n-butyl group, an isobutyl group, a pentyl group, and a neopentyl group.

An alkenyl group represents a hydrocarbon group with any structure of a linear chain, a branched chain, or a ring having a double bond. Examples of the alkenyl group include an allyl group, a 1-butenyl group, a 2-butenyl group, an isobutenyl group, and a cyclohexenyl group.

An alkynyl group represents a hydrocarbon group with any structure of a linear chain, a branched chain, or a ring having a triple bond. Examples of the alkynyl group include a propynyl group and a 1-butynyl group.

A cyclic alkyl group represents a cyclic hydrocarbon group. Examples of the cyclic alkyl group include a cyclopropyl group, a cyclobutyl group, a cyclopentyl group, a cyclohexyl group, and a cycloheptyl group.

An aromatic ring represents an aromatic ring formed of a hydrocarbon. Examples of a monocyclic aromatic ring include a benzene ring; and examples of a polycyclic aromatic ring include a naphthalene ring and an anthracene ring. Examples of a partly saturated polycyclic aromatic ring include a dihydronaphthalene ring, a tetralin ring, an indan ring and the like. A heteroaromatic ring represents an aromatic ring having one or two or more nitrogen atoms, oxygen atoms, or sulfur atoms in the ring. Examples of a monocyclic heteroaromatic ring include a pyrrole ring, a furan ring, a thiophene ring, a pyridine ring, a pyrimidine ring, a pyridazine ring, a pyrazine ring, an imidazole ring, a pyrazole ring, an oxazole ring, a thiazole ring, a thiadiazole ring, an oxadiazole ring, and a triazole ring. Examples of a polycyclic heteroaromatic ring include a quinoline ring, an isoquinoline ring, a benzimidazole ring, an indazole ring, a benzothiazole ring, a benzoxazole ring, an indole ring, a benzofuran ring, and a benzothiophene ring.

Examples of a partly saturated polycyclic aromatic ring include a tetrahydroisoquinoline ring and a tetrahydroquinoline ring. A heterocycle represents a saturated ring that may have one or two or more nitrogen atoms, oxygen atoms, or sulfur atoms in the ring. Examples of the heterocycle include pyrrolidine, piperidine, piperazine, morpholine, and thiomorpholine.

An alkylene group represents a hydrocarbon group that can be bonded to two groups at the terminals. Examples of the alkylene group include an ethylene group, a propylene group, an isopropylene group, a butylene group, an isobutylene group, and a 2,2-dimethylethylene group.

An alkenylene group represents an alkylene group having a double bond. Examples of the alkenylene group include a propenylene group, a 2-butenylene group, and a 1,3-butadienylene group.

An alkynylene group represents an alkylene group having a triple bond. Examples of the alkynylene group include a propynylene group and a butynylene group.

An acyl group is group to which a hydrogen atom, an alkyl group, a monocyclic or polycyclic heteroaromatic ring or monocycle or a polycyclic aromatic-ring bonds through a carbonyl group. These groups each may substitute at any position. Examples of the acyl group include a formyl group, an acetyl group, a benzoyl group, and a trifluoroacetyl group.

B represents $R_{25}(R_{26})N-$, where $R_{25}$ and $R_{26}$ may form a ring. Examples of a ring formed by binding $R_{25}$ and $R_{26}$ directly together with a nitrogen atom to which they are bound include a pyrrolidine ring, a piperidine ring, a hexamethyleneimine ring, and a heptamethyleneimine ring. Examples of a ring formed by binding $R_{25}$ and $R_{26}$ through a heteroatom together with a nitrogen atom to which they are bound include a morpholine ring and a piperazine ring. Examples of a ring formed by binding $R_{25}$ and $R_{26}$ through an aromatic ring together with a nitrogen atom to which they are bound include a tetrahydroisoquinoline ring and a dihydroindole ring.

When $R_{25}$ and/or $R_{26}$ is a group represented by the formula (8) and $R_{29}$ and G in the formula form a ring, examples of $R_{25}$ and $R_{26}$ include a tetralinyl group, an indanyl group, a tetrahydroquinolyl group, and a tetrahydroisoquinolyl group.

The term "substitutable" group in the expressions for each substituent includes a hydroxyl group, a thiol group, a formyl group, a carboxyl group, a sulfonyl group, an amino group, an amide group, a carbamoyl group, a cyano group, an alkoxy group, an alkoxycarbonyl group, an alkylamino group, an acylamino group, an alkoxycarbonylamino group, alkylthio group, an aminosulfonyl group, a dialkylaminosulfonyl group, a methanesulfonyl group, a p-toluenesulfonyl group, a phenyl group, and is substitutable with a halogen atom, a morphorino group, a tetrahydrofuranyl group, a 5-methyl-2-oxo-1,3-dioxol-4-yl group, a 3-oxo-1,3-dihydro-isobenzofuranyl group, an acyloxy group, an alkoxycarbonyloxy group, a tetrazol-5-yl group, or the like. Here, the alkoxy group represents a group in which a substitutable alkyl group, a cyclohexyl group, or a cynnamyl group binds through an oxygen atom. The acylamino group represents a group in which an alkyl group or a phenyl group binds to an amino group through a carbonyl group. The acyloxy group represents a group in which an alkyl group binds to an oxygen atom through a carbonyl group. The alkoxycarbonyloxy group represents a group in which an alkoxy group binds to an oxygen atom through a carbonyl group. Further, examples of the "substitutable" groups in $A_1$ and $A_2$ include an alkyl group, a hydroxyalkyl group, an alkoxyalkyl group, an aminoalkyl group, an aryl group, and heteroaryl group other than the group described above.

The prodrug is a precursor substance that becomes an effective drug through chemical or biochemical metabolism after administration to the living body. Specifically, the prodrug is a compound which is obtained by binding one or more appropriate groups, that is eliminated by metabolism in the living body, such as alkoxycarbonyl group or dialkylaminosulfone group with N in the ring or chain of a heterocycle or the like contained in the compound represented by the general formula (1). Alternatively, the prodrug is a compound coupled with one or more ester groups, amide groups, or the like that utilize alcohol or carboxylic acid, which may be contained in the compound represented by the general formula (1).

In addition, examples of a pharmacologically acceptable salt include trifluoroacetates, hydrochlorides, acetates, sulfates, nitrates, lactates, maleates, methanesulfonates, toluenesulfonates, tartrates, citrates, oxalates, malonates, succinates, fumarates, propionates, butyrates, glucuronates, terephthalates, and phosphates. Preferable examples thereof include hydrochlorides, maleates, tartrates, and citrates. Tartrates are more preferable.

The following compounds can be exemplified as the amine compound of the present invention:

2-[(4-dipropylamino-butyl)-(4-{[(1H-imidazol-2-ylmethyl)-(1-methyl-1H-imidazol-2-ylmethyl)-amino]-methyl}-benzyl)-amino]-ethanol [Compound No. 1]

[4-(6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 2]

[4-(6-{[bis-(1H-imidazol-2-ylmethyl)-amino]-methyl}-1-propyl-1H-benzimidazol-2-yl)-butyl]-dipropyl-amine [Compound No. 3]

[4-(6-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 4]

[4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 5]

4-{[N-(1H-imidazol-2-ylmethyl)-amino]-methyl-N-(4-dipropylamino-butyl)-benzamide [Compound No. 6]

2-(4-dipropylamino-butyl)-5-{[(1H-imidazol-2-ylmethyl)-(1-methyl-1H-imidazol-2-ylmethyl)-amino]-methyl}-2,3-dihydro-isoindol-1-one [Compound No. 7]

2-(4-dipropylamino-butyl)-6-{[(1H-imidazol-2-ylmethyl)-(1-methyl-1H-imidazol-2-ylmethyl)-amino]-methyl}-2,3-dihydro-isoindol-1-one [Compound No. 8]

N-(4-{[(1H-imidazol-2-ylmethyl)-amino]-methyl}-benzyl)-N-methyl-N',N'-dipropyl-butane-1,4-diamine [Compound No. 9]

N-methyl-N-[4-({[1-(1-methyl-1H-imidazol-2-ylmethyl)-1H-imidazol-2-ylmethyl]-amino}-methyl)-benzyl-N',N'-dipropylbutane-1,4-diamine [Compound No. 10]

[4-(6-{[(1H-imidazol-2-ylmethyl)-(1-methyl-1H-imidazol-2-ylmethyl)-amino]-methyl}-1H-inden-2-yl)-butyl]-dipropyl-amine [Compound No. 11]

1-(4-dipropylaminobutyl)-3-(4-{[(1H-imidazol-2-ylmethyl)-(1-methyl-1H-imidazol-2-ylmethyl)-amino]-methyl}-phenyl)-urea [Compound No. 12]

[4-(6-{[(1H-imidazol-2-ylmethyl)-(1-methyl-1H-imidazol-2-ylmethyl)-amino]-methyl}-1-methyl-1H-benzimidazol-2-yl)-butyl]-dipropyl-amine [Compound No. 13]

3-(3-dipropylaminopropyl)-8-{[(1H-imidazol-2-ylmethyl)-(1-methyl-1H-imidazol-2-ylmethyl)-amino]-methyl}-3,4-dihydro-1H-benzo[e][1,4]diazepin-2,5-dione [Compound No. 14]

4-{[(3,5-dimethyl-pyridin-2-ylmethyl)-(1-methyl-1H-imidazol-2-ylmethyl)-amino]-methyl}-N-(4-dipropylaminomethyl-phenyl)-benzamide [Compound No. 15]

4-{[(5-ethyl-pyridin-2-ylmethyl)-(1-methyl-1H-imidazol-2-ylmethyl)-amino]-methyl}-N-(4-dipropylaminomethyl-phenyl)-benzamide [Compound No. 16]

[4-(6-{[(1H-imidazol-2-ylmethyl)-(1-methyl-1H-imidazol-2-ylmethyl)-amino]-methyl}-3,4-dihydro-1H-isoquinolin-2-yl)-butyl]-dipropyl-amine [Compound No. 17]

[3-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropyl-amine [Compound No. 18]

6-{[(1H-imidazol-2-ylmethyl)-(1-methyl-1H-imidazol-2-ylmethyl)-amino]-methyl}-5,6,7,8-tetrahydro-imidazo[1,2-a]pyridin-2-carboxylic acid-(4-dipropylamino-butyl)-amide [Compound No. 19]

N-(4-dipropylamino-butyl)-4-{[(1-methyl-1H-imidazol-2-ylmethyl)-(5-methyl-pyridin-2-ylmethyl)-amino]-methyl}-benzamide [Compound No. 20]

N-(4-dipropylamino-butyl)-N-(4-{[(1H-imidazol-2-ylmethyl)-(1-methyl-1H-imidazol-2-ylmethyl)-amino]-methyl}-benzyl)-methanesulfonamide [Compound No. 21]

N-(4-dipropylamino-butyl)-N-(4-{[(1H-imidazol-2-ylmethyl)-(1-methyl-1H-imidazol-2-ylmethyl)-amino]-methyl}-benzyl)-4-methyl-benzenesulfonamide [Compound No. 22]

N-ethyl-N-(4-{[(1H-imidazol-2-ylmethyl)-(1-methyl-1H-imidazol-2-ylmethyl)-amino]-methyl}-benzyl)-N',N'-dipropyl-butane-1,4-diamine [Compound No. 23]

N-(4-{[(1H-imidazol-2-ylmethyl)-(1-methyl-1H-imidazol-2-ylmethyl)-amino]-methyl}-benzyl)-N-phenyl-N',N'-dipropyl-butane-1,4-diamine [Compound No. 24]

N-(4-dipropylamino-butyl)-N-(4-{[(1H-imidazol-2-ylmethyl)-(1-methyl-1H-imidazol-2-ylmethyl)-amino]-methyl}-benzyl)-acetamide [Compound No. 25]

1-(4-dipropylamino-butyl)-3-(4-{[(1H-imidazol-2-ylmethyl)-(1-methyl-1H-imidazol-2-ylmethyl)-amino]-methyl}-phenyl)-1-methyl-urea [Compound No. 26]

1-(4-dipropylamino-butyl)-3-(4-{[(1H-imidazol-2-ylmethyl)-(1-methyl-1H-imidazol-2-ylmethyl)-amino]-methyl}-phenyl)-1,3-dimethyl-urea [Compound No. 27]

N-methyl-N-[4-({(1-methyl-1H-imidazol-2-ylmethyl)-[1-(toluene-4-sulfonyl)-1H-imidazol-2-ylmethyl]-amino}-methyl)-benzyl]-N'',N''-dipropyl-butane-1,4-diamine [Compound No. 28]

[4-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropyl-amine [Compound No. 29]

6-{[(1H-imidazol-2-ylmethyl)-(1-methyl-1H-imidazol-2-ylmethyl)-amino]-methyl}-imidazo[1,2-a]pyridine-2-carboxylic acid-(4-dipropyl)-amino-butyl)-amide [Compound No. 30]

N-(4-{[(1H-imidazol-2-ylmethyl)-(1-methyl-1H-imidazol-2-ylmethyl)-amino]-methyl}-benzyl)-N',N'-dipropyl-N-(2,2,2-trifluoro-ethyl)-butane-1,4-diamine [Compound No. 31]

N-(4-{[(1-methanesulfonyl-1H-imidazol-2-ylmethyl)-(1-methyl-1H-imidazol-2-ylmethyl)-amino]-methyl}-benzyl)-N-methyl-N'',N''-dipropyl-butane-1,4-diamine [Compound No. 32]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionitrile [Compound No. 33]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid methyl ester [Compound No. 34]

1-(4-dipropylamino-butyl)-3-(4-{[(1H-imidazol-2-ylmethyl)-(1-methyl-1H-imidazol-2-ylmethyl)-amino]-methyl}-phenyl)-thiourea [Compound No. 35]

{3-[6-(4-{[(1H-imidazol-2-ylmethyl)-(1-methyl-1H-imidazol-2-ylmethyl)-amino]-methyl}-phenyl)-pyridin-2-yl]-propyl}-dipropyl-amine [Compound No. 36]

N-(4-dipropylamino-butyl)-2,2,2-trifluoro-N-(4-{[(1H-imidazol-2-ylmethyl)-(1-methyl-1H-imidazol-2-ylmethyl)-amino]-methyl}-benzyl)-acetamide [Compound No. 37]

[4-(5-{[(1H-imidazol-2-ylmethyl)-(1-methyl-1H-imidazol-2-ylmethyl)-amino]-methyl}-1,3-dihydro-isoindol-2-yl)-butyl]-dipropyl-amine [Compound No. 38]

{4-(1E)-[2-(4-{[(1H-imidazol-2-ylmethyl)-(1-methyl-1H-imidazol-2-ylmethyl)-amino]-methyl}-phenyl)-vinyl]-benzyl}-dipropyl-amine [Compound No. 39]

{[4-((1Z)-2-{4-[(dipropylamino)-methyl]-phenyl}-vinyl)-phenyl]-methyl}-(imidazol-2-ylmethyl)-[(1-methylimidazol-2-yl)-methyl]-amine [Compound No. 40]

{[4-((1E)-2-{4-[2-(dipropylamino)-ethyl]-phenyl}-vinyl)-phenyl]-methyl}-(imidazol-2-ylmethyl)-[(1-methylimidazol-2-yl)-methyl]-amine [Compound No. 41]

{[4-((1E)-2-{4-[(dipropylamino)-methyl]-phenyl}-vinyl)-phenyl]-methyl}-bis-(imidazol-2-ylmethyl)-amine [Compound No. 42]

[4-(6-{[(1H-imidazol-2-yl-methyl)-(1-methyl-imidazol-2-yl-methyl)-amino]-methyl}-benzothiazol-2-yl)-benzyl]-dipropyl-amine [Compound No. 43]

(4-{[(1H-imidazol-2-ylmethyl)-(1-methyl-1H-imidazol-2-ylmethyl)-amino]-methyl}-benzyl)-methyl-(4-piperidin-1-ylbutyl)amine [Compound No. 44]

2-(2-(4-dipropylamino-butyl)-6-{[(1H-imidazol-2-ylmethyl)-(1-methyl-1H-imidazol-2-ylmethyl)-amino]-methyl}-benzimidazol-1-yl)-ethanol [Compound No. 45]

[3-(6-{[(1H-imidazol-2-ylmethyl)-(1-methyl-1H-imidazol-2-ylmethyl)-amino]-methyl}-1-propyl-1H-benzimidazol-2-yl)-propyl]-dipropyl-amine [Compound No. 46]

[4-(6-{[(1H-imidazol-2-ylmethyl)-(1-methyl-1H-imidazol-2-ylmethyl)-amino]-methyl}-1-isopropyl-1H-benzimidazol-2-yl)-butyl]-dipropyl-amine [Compound No. 47]

[5-(6-{[(1H-imidazol-2-ylmethyl)-(1-methyl-1H-imidazol-2-ylmethyl)-amino]-methyl}-1-propyl-1H-benzimidazol-2-yl)-pentyl]-dipropyl-amine [Compound No. 48]

N-(4-{[(1H-imidazol-2-ylmethyl)-(5,6,7,8-tetrahydrohydroquinolin-8-yl)-amino]-methyl}-benzyl)-N-methyl-N',N'-dipropyl-butane-1,4-diamine [Compound No. 49]

N-(4-dipropylamino-butyl)-N-(4-{[(1H-imidazol-2-ylmethyl)-(5,6,7,8-tetrahydro-quinolin-8-yl)-amino]-methyl}-benzyl)-methanesulfonamide [Compound No. 50]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid [Compound No. 51]

(4-dipropylamino-butyl)-(4-{[(1H-imidazol-2-ylmethyl)-(1-methyl-1H-imidazol-2-ylmethyl)-amino]-methyl}-benzyl)-cyanamide [Compound No. 52]

(4-dipropylamino-butyl)-(4-{[(1H-imidazol-2-ylmethyl)-(1-methyl-1H-imidazol-2-ylmethyl)-amino]-methyl}-benzyl)-formamide [Compound No. 53]

[(4-{[(1-carboxymethyl-1H-imidazol-2-ylmethyl)-(1-methyl-1H-imidazol-2-ylmethyl)-amino]-methyl}-benzyl)-(4-dipropylamino-butyl)amino]-acetic acid [Compound No. 54]

[4-(1-benzyl-6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 55]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid ethyl ester [Compound No. 56]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid isopropyl ester [Compound No. 57]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid benzyl ester [Compound No. 58]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid butyl ester [Compound No. 59]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-5-methyl-2-oxo-[1,3]-dioxol-4-ylmethyl ester [Compound No. 60]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-1-ethyl-propoxycarbonyloxy methyl ester [Compound No. 61]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-1-(cyclohexyloxycarbonyloxy)-ethyl ester [Compound No. 62]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-methoxycarbonyloxy methyl ester [Compound No. 63]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-ethoxycarbonyloxy methyl ester [Compound No. 64]

2,2-dimethyl-propionic acid-3-[(4-dipropylamino-butyl)-(4-{[(1H-imidazol-2-ylmethyl)-(1-methyl-1H-imidazol-2-ylmethyl)-amino]-methyl}-benzyl)-amino]-propionyloxy methyl ester [Compound No. 65]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-3-oxo-1,3-dihydro-isobenzofuran-1-yl ester [Compound No. 66]

Hexanoic acid-3-[(4-dipropylamino-butyl)-(4-{[(1H-imidazol-2-ylmethyl)-(1-methyl-1H-imidazol-2-ylmethyl)-amino]-methyl}-benzyl)-amino]-propionyloxymethyl ester [Compound No. 67]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-3-cyclopentyl-propionyloxymethyl ester [Compound No. 68]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid diethylcarbamoyloxymethyl ester [Compound No. 69]

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid t-butoxycarbonylmethyl ester [Compound No. 70]

3-[(4-dipropylamino-butyl)-(4-{[(1H-imidazol-2-ylmethyl)-(1-methyl-1H-imidazol-2-ylmethyl)-amino]-methyl}-benzyl)-amino]-N-ethyl-propionamide [Compound No. 71]

3-[(4-{[bis-(1H-imidazol-2-ylmethyl)-amino]-methyl}-benzyl)-(4-dipropylamino-butyl)-amino]-propionic acid [Compound No. 72]

3-[(4-{[bis-(1H-imidazol-2-ylmethyl)-amino]-methyl}-benzyl)-(4-dipropylamino-butyl)-amino]-propionate [Compound No. 73]

3-[(4-{[bis-(1H-imidazol-2-ylmethyl)-amino]-methyl}-benzyl)-(4-dipropylamino-butyl)-amino]-propionic acid-5-methyl-2-oxo-[1,3]dioxol-4-ylmethyl ester [Compound No. 74]

3-[(4-{[bis-(1H-imidazol-2-ylmethyl)-amino]-methyl}-benzyl)-(4-dipropylamino-butyl)-amino]-propionic acid-1-(cyclohexyloxycarbonyloxy)-ethyl ester [Compound No. 75]

2,2-dimethyl-propionic acid-3-[(4-{[bis-(1H-imidazol-2-ylmethyl)-amino]-methyl}-benzyl)-(4-dipropylamino-butyl)-amino]-propionyloxymethyl ester [Compound No. 76]

3-[(4-{[bis-(1H-imidazol-2-ylmethyl)-amino]-methyl}-benzyl)-(4-dipropylamino-butyl)-amino]-propionic acid-3-oxo-1,3-dihydro-isobenzofuran-1-yl ester [Compound No. 77]

3-[(4-{[bis-(1H-imidazol-2-ylmethyl)-amino]-methyl}-benzyl)-(4-dipropylamino-butyl)-amino]-propionic acid diethylcarbamoyloxymethyl ester [Compound No. 78]

3-[(4-{[bis-(1H-imidazol-2-ylmethyl)-amino]-methyl}-benzyl)-(4-dipropylamino-butyl)-amino]-N-ethyl-propionamide [Compound No. 79]

(1H-imidazol-2-ylmethyl)-(1-methyl-1H-imidazol-2-ylmethyl)-[2-(4-piperidin-1-yl-butyl)-3-propyl-3H-benzimidazol-5-ylmethyl]-amine [Compound No. 80]

3-[(4-[[(1H-imidazol-2-ylmethyl)-(1-methyl-1H-imidazol-2-ylmethyl)-amino]-methyl]-benzyl)-(4-piperidin-1-yl-butyl)-amino]-propionic acid [Compound No. 81]

[(4-dipropylamino-butyl)-(4-[[(1H-imidazol-2-ylmethyl)-(1-methyl-1H-imidazol-2-ylmethyl)-amino]-methyl]-benzyl)-amino]-acetonitrile [Compound No. 82]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid methyl ester [Compound No. 83]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid [Compound No. 84]

3-[(4-dipropylamino-butyl)-(4-[[(1H-imidazol-2-ylmethyl)-(1-methyl-1H-imidazol-2-ylmethyl)-amino]-methyl]-benzyl)-amino]-propionic acid-1-isopropoxycarbonyloxy-ethyl ester [Compound No. 85]

3-[(4-[[bis-(1H-imidazol-2-ylmethyl)-amino]-methyl]-benzyl)-(4-dipropylamino-butyl)-amino]-propionic acid methyl ester [Compound No. 86]

[(4-[[bis-(1H-imidazol-2-ylmethyl)-amino]-methyl]-benzyl)-(4-dipropylamino-butyl)-amino]-acetic acid methyl ester [Compound No. 87]

[(4-[[bis-(1H-imidazol-2-ylmethyl)-amino]-methyl]-benzyl)-(4-dipropylamino-butyl)-amino]-acetic acid [Compound No. 88]

[(4-dipropylamino-butyl)-([[(1H-imidazol-2-ylmethyl)-(1-methyl-1H-imidazol-2-ylmethyl)-amino]-methyl]-benzyl)-amino]-acetic acid benzyl ester [Compound No. 89]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-morpholin-4-yl-ethyl ester [Compound No. 90]

[[4-(dipropyl-amino)-butyl]-(4-[[1H-imidazol-2-ylmethyl)-(1-methyl-1H-imidazol-2-ylmethyl)-amino]-methyl]-benzyl)-amino]-acetic acid ethyl ester [Compound No. 91]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-methoxy-ethyl ester [Compound No. 92]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid cinnamyl ester [Compound No. 93]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-(2-hydroxy-ethoxy)-ethyl ester [Compound No. 94]

(4-dipropylamino-butyl)-(4-[[(1H-imidazol-2-ylmethyl)-(1-methyl-1H-imidazol-2-ylmethyl)-amino]-methyl]-benzyl)-carbamic acid t-butyl ester [Compound No. 95]

N-(2-chloro-4-[[(1H-imidazol-2-ylmethyl)-(1-methyl-1H-imidazol-2-ylmethyl)-amino]-methyl]-benzyl)-N-methyl-N',N'-dipropyl-butane-1,4-diamine [Compound No. 96]

[(4-[[bis-(1H-imidazol-2-ylmethyl)-amino]-methyl]-benzyl)-(4-dipropylamino-butyl)-amino]-acetic acid ethyl ester [Compound No. 97]

[(4-dipropylamino-butyl)-(4-[[(1H-imidazol-2-ylmethyl)-(1-methyl-1H-imidazol-2-ylmethyl)-amino]-methyl]-benzyl)-amino]-acetic acid-3,7,11-trimethyl-dodeca-2,6,10-trienyl ester [Compound No. 98]

2-[(4-dipropylamino-butyl)-(4-[[(1H-imidazol-2-ylmethyl)-(1-methy-1H-imidazol-2-ylmethyl)-amino]-methyl]-benzyl)-amino]-N,N-dimethyl-acetamide [Compound No. 99]

[(4-[[bis-(1-methyl-1H-imidazol-2-ylmethyl)-amino]-methyl]-benzyl)-(4-dipropylamino-butyl)-amino]-acetic acid [Compound No. 100]

[(4-[[bis-(1-methyl-1H-imidazol-2-ylmethyl)-amino]-methyl]-benzyl)-(4-dipropylamino-butyl)-amino]-acetic acid ethyl ester [Compound No. 101]

[(4-dipropylamino-butyl)-([[(1H-imidazol-2-ylmethyl)-(1-methyl-1H-imidazol-2-ylmethyl)-amino]-methyl]-benzyl)-amino]-acetic acid-(R)-(−)-tetrahydrofuran-2-ylmethyl ester [Compound No. 102]

([4-[(4-[[(1H-imidazol-2-ylmethyl)-(1-methyl-1H-imidazol-2-ylmethyl)-amino]-methyl]-benzyl)-methyl-amino]-butyl]-propyl-amino)-acetic acid [Compound No. 103]

([4-[carboxymethyl-(4-[[(1H-imidazol-2-ylmethyl)-(1-methyl-1H-imidazol-2-ylmethyl)-amino]-methyl]-benzyl)-amino]-butyl]-propyl-amino)-acetic acid [Compound No. 104]

(2-[[(1-carboxymethyl-1H-imidazol-2-ylmethyl)-(4-[[(4-dipropylamino-butyl)-methyl-amino]-methyl]-benzyl)-amino]-methyl]-imidazol-1-yl)-acetic acid [Compound No. 105]

(2-[[(4-[[(4-dipropylamino-butyl)-methyl-amino]-methyl]-benzyl)-(1-methyl-1H-imidazol-2-ylmethyl)-amino]-methyl]-imidazol-1-yl)-acetic acid [Compound No. 106]

4-[[(4-dipropylamino-butyl)-methyl-amino]-methyl]-N-(1H-imidazol-2-ylmethyl)-N-(1-methyl-1H-imidazol-2-ylmethyl)-benzamide [Compound No. 107]

2-[(4-dipropylamino-butyl)-(4-[[(1H-imidazol-2-ylmethyl)-(1-methyl-1H-imidazol-2-ylmethyl)-amino]-methyl]-benzyl)-amino]-malonic acid diethyl ester [Compound No. 108]

(2-{2-[(4-{[(1H-imidazol-2-ylmethyl)-(1-methyl-1H-imidazol-2-ylmethyl)-amino]-methyl}-benzyl)-methyl-amino]-ethoxy}-ethyl)-dipropyl-amine [Compound No. 109]

N-(4-{[(1H-imidazol-2-ylmethyl)-(1-methyl-1H-imidazol-2-ylmethyl)-amino]-methyl}-benzyl)-N',N'-dipropyl-N-(1H-tetrazol-5-ylmethyl)-butane-1,4-diamine [Compound No. 110]

5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 111]

5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid [Compound No. 112]

(2S)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 113]

(2S)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid [Compound No. 114]

5-dipropylamino-(2R)-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 115]

5-dipropylamino-(2R)-[(4-{[(1H-imidazol-2-ylmethyl)-(1-methyl-1H-imidazol-2-ylmethyl)-amino]-methyl}-benzyl)-methyl-amino]-pentanoic acid [Compound No. 116]

(2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 117]

(2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid [Compound No. 118]

[(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid ethyl ester [Compound No. 119]

[(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid [Compound No. 120]

2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid ethyl ester [Compound No. 121]

2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid [Compound No. 122]

The present invention relates to a CXCR4 antagonist including the above-mentioned compounds or a pharmaceutically acceptable salt thereof as an active ingredient.

The CXCR4 antagonist or salt thereof according to the present invention may be used in treatment or prevention of a viral disease such as AIDS, cancer treatment, or treatment or prevention of rheumatism, etc.

The pharmacologically acceptable salt is a salt which may be formed by the amine compound represented by the above described formula (1), and may be any salt that is pharmacologically acceptable. For example, trifluoroacetates, hydrochlorides, acetates, sulfates, nitrates, lactates, maleates, methanesulfonates, toluenesulfonates, tartrates, citrates, oxalates, malonates, succinates, fumarates, propionates, butyrates, glucuronates, terephthalates, phosphates and the like can be given. Hydrochlorides, maleates, tartrates, and citrates are preferable, and tartrates are more preferable.

Those compounds may form a hydrate or a solvate.

One or two or more asymmetric carbon atoms may exist in the compound represented by the general formula (1). When one asymmetric carbon atoms exists, the compound may be in any form of a pure optically-active substance represented as absolute configuration of R or S, a mixture thereof in an arbitrary ratio, and a racemic mixture thereof, and when two or more asymmetric carbon atoms exist in the compound, the compound may be in any form of an optically pure diastereomer, a racemic mixture thereof, and a combination thereof in an arbitrary ratio.

The medical preparation including the compound of the present invention represented by the general formula (1) or pharmacologically acceptable salt thereof as an active ingredient may be administered orally or parenterally in a form of tablet, powder, granule, capsule, pill, suppository, injection, eye-drops, solution, troche, aerosol, suspension, emulsion, syrup, or the like, mixed with a well-known pharmacologically acceptable carrier, excipient, diluent, extender, decaying agent, stabilizer, preservative, buffer, emulsifier, perfuming agent, colorant, sweetener, thickening agent, flavor, solubilizing agent, and other additives. Specific examples of the additives include: water; vegetable oil; alcohol such as ethanol or benzyl alcohol; carbohydrate such as glycol, glycerol triacetate, gelatin, lactose, or starch; magnesium stearate; potassium stearate; tarc; lanoline; vaseline; macrogol; crystalline cellulose; hydroxypropyl cellulose, and the like. While the dose may vary depending on the kind and degree of disease, the kind of the compound to be administered, the administration path, and the age, sex, and weight of the patient, in general, 0.1 to 5,000 mg, particularly 1 to 3,000 mg per one adult is preferably administered. In the case of a prodrug, it is preferable to administer 1 to 5,000 mg per adult.

Effect of the Invention

The novel amine compound according to the present invention, a pharmacologically acceptable salt thereof, or a prodrug thereof can provide a novel CXCR4 antagonist. The novel CXCR4 antagonist of the present invention has a CXCR4 antagonism, and shows, based on the CXCR4 antagonism, excellent effects as a therapeutic or preventive drug for a disease such as: a viral infectious disease such as HIV; rheumatism; or cancer metastasis.

BEST MODE FOR CARRYING OUT THE INVENTION

First, a method of producing a CXCR4 antagonist of the present invention will now be described in more detail with reference to production examples of the compound of the present invention. Hereinafter, unless particularly stated, reagents used are commercially available products (manufactured by e.g. Tokyo Kasei Kogyo Co. Ltd. (Tokyo), Kanto Chemical Co., Inc. (Tokyo), etc.) readily available to a person skilled in the art.

EXAMPLE 1

Production Example 1

Synthesis of 2-[(4-dipropylamino-butyl)-(4-{[(1H-imidazol-2-ylmethyl)-(1-methyl-1H-imidazol-2-ylmethyl)-amino]-methyl}-benzyl)-amino]-ethanol [Compound No. 1]

EXAMPLE 1-1

Synthesis of 4-(1,3-dioxo-1,3-dihydro-isoindol-2-ylmethyl)-benzaldehyde

Methyl 4-(aminomethyl)-benzoate hydrochloride (manufactured by Aldrich Corporation) (773 mg) was dissolved in THF (50 ml) and then gradually added with lithium aluminum hydride (300 mg) under ice-cooling. The solution was stirred at room temperature for 3 hours and then cooled with ice, followed by gradual addition of a concentrated sodium hydroxide aqueous solution until foam was not observed. Filtration through Celite was carried out using chloroform as a solvent and then the filtrate was concentrated and dried. The dried product was dissolved in purified water (10 ml) and THF (10 ml). After having been cooled with ice, the solution was added with N-carbethoxyphthalimide (1.26 g) and sodium carbonate (900 mg). After the mixture was stirred at room temperature for 4 hours, THF was distilled off and chloroform was then added to the residue to carry out extraction. The organic layer was dried with anhydrous sodium sulfate and the solvent was then distilled off. Subsequently, the residue was further dried under vacuum. Next, this compound was dissolved in chloroform (20 ml) and then added with manganese dioxide (chemically processed product) (5.0 g), followed by stirring at room temperature for 3 hours. After filtration through Celite, the filtrate was concentrated and then purified through silica gel column chromatography (chloroform/methanol), thereby obtaining the subject compound (259 mg) as a white solid.

MS(FAB,Pos.):m/z=266[M+H]$^+$ $^1$H-NMR(500 MHz,CDCl$_3$):δ=4.92(2H,s),7.58(2H,d, J=8.3 Hz),7.72-7.76(2H,m),7.83-7.89(4H,m),9.98(1H,s).

EXAMPLE 1-2

Synthesis of N,N-dipropylbutane-1,4-diamine

N-(4-aminobutyl)-carbamic acid t-butyl ester (manufactured by Tokyo Kasei Kogyo Co., Ltd.) (500 mg) was dissolved in methanol (10 ml) and then added with propionaldehyde (manufactured by Tokyo Kasei Kogyo Co., Ltd.) (0.418 ml), sodium cyanoborohydride (404 mg), and trimethyl orthoacetate (1.60 g), and the whole was stirred at room temperature for 12 hours. After completion of the reaction, the solvent was distilled off. Then, the resultant was added with chloroform, washed with distilled water and a saturated saline solution, and then dried with anhydrous sodium sulfate. After concentration and evaporation to dryness of the solution, methanol (4.0 ml) and a 4 mol/l hydrogen chloride/dioxane solution (4.0 ml) were added to the dried product and the whole was stirred at room temperature for 2 hours. After completion of the reaction, the solvent was distilled off and then dioxane was added to wash the residue, thereby obtaining a hydrochloride (654 mg) of the subject compound.
MS(FAB,Pos.):m/z=173[M+H]$^+$

EXAMPLE 1-3

Synthesis of 2-{4-[(4-dipropylamino-butyl-amino)-methyl]-benzyl}-isoindol-1,3-dione The compound (103 mg) obtained in Example 1-1 was dissolved in anhydrous methanol (10 ml) and then added with the hydrochloride (114 mg) of the compound obtained in Example 1-2. Then, the solution was added with triethylamine (0.108 ml) and anhydrous magnesium sulfate (3 g), followed by stirring at room temperature for 1 hour. Anhydrous magnesium sulfate was removed from the solution by filtration through Celite. Then, methanol was distilled off and the resultant was dried using a vacuum pump. The resultant was dissolved in anhydrous methanol (10 ml) and gradually added with sodium borohydride (22.0 mg) under ice-cooling. The solution was warmed back to room temperature and then stirred for 1 hour. After completion of the reaction, methanol was distilled off and the residue was then added with water and chloroform to extract the organic layer. After the organic layer was dried with anhydrous sodium sulfate, the solvent was distilled off and the residue was then purified through silica gel column chromatography (chloroform/methanol/water), thereby obtaining the subject compound (60.3 mg) as a pale-yellow viscous liquid.
MS(FAB,Pos.):m/z=420[M+H]$^+$

EXAMPLE 1-4

Synthesis of [4-(1,3-dioxo-1,3-dihydro-isoindol-2-ylmethyl)-benzyl]-(4-dipropylamino-butyl)-carbamic acid t-butyl ester The compound (60.3 mg) obtained in Example 1-3 was dissolved in chloroform and then added with di-t-butyldicarbonate (47.0 mg). After having been stirred at room temperature for 30 minutes, the solution was subjected to concentration and then purification through silica gel column chromatography (chloroform/methanol) thereby obtaining the subject compound (70.0 mg) as a colorless viscous liquid.
MS(FAB,Pos.):m/z=522[M+H]$^+$

EXAMPLE 1-5

Synthesis of (4-aminomethyl-benzyl)-(4-dipropylamino-butyl)-carbamic acid t-butyl ester The compound (70.0 mg) obtained in Example 1-4 was added with a 40% methylamine/methanol solution (3.0 ml) and then stirred at room temperature for 14 hours. After completion of the reaction, the solvent was distilled off. Then, the residue was added with a 1 mol/l sodium hydroxide aqueous solution and chloroform to extract the aqueous layer therefrom with chloroform. The extract was dried with anhydrous sodium sulfate and the solvent was distilled off, thereby obtaining the subject compound (65.5 mg) as a colorless viscous liquid.

EXAMPLE 1-6

Synthesis of (4-dipropylamino-butyl)-(4-{[(1H-imidazol-2-ylmethyl)-amino]-methyl}-benzyl)-carbamic acid t-butyl ester The compound (0.78 g) obtained in Example 1-5 was dissolved in methanol (20 ml) and added with 2-imidazole carboxaldehyde (214 mg) and the whole was stirred at room temperature for 17 hours. After the solvent was distilled off, the resultant was dried under vacuum, dissolved in methanol (15 ml), and then added with sodium borohydride (217.8 mg). The whole was stirred at room temperature for 45 minutes. The reaction solution was added with a saturated aqueous ammonium chloride solution (10 ml) and stirred at room temperature for 15 minutes.

Then, the reaction solution was added with a saturated saline solution and subjected to extraction with chloroform, followed by drying with anhydrous sodium sulfate. After the solvent was distilled off, the resultant residue was purified through silica gel column chromatography (chloroform/ethyl acetate), thereby obtaining the subject compound (1.01 g) as a yellow solid.
MS(FAB,Pos.):m/z=472[M+H]$^+$
$^1$H-NMR(500 MHz,CDCl$_3$):δ=0.86(6H,t,J=7.3 Hz),1.26-1.49(17H,m),2.32-2.35(6H,m),3.12(1H,brs),3.21(1H,brs), 3.79(2H,brs),3.92(2H,brs),4.12(1H,brs),4.13(1H,brs),6.99 (2H,s),7.20(2H,brs),7.25(2H,d,J=7.5 Hz).

EXAMPLE 1-7

Synthesis of (4-dipropylamino-butyl)-(4-{[(1H-imidazol-2-ylmethyl)-(1-methyl-1H-imidazol-2-ylmethyl)-amino]-methyl}-benzyl)-carbamic acid t-butyl ester The compound (231 mg) obtained in Example 1-6 was dissolved in anhydrous methanol (5.0 ml) The solution was added with sodium cyanoborohydride (61.6 mg), acetic acid (2.00 ml), and 1-methyl-2-imidazole carboxaldehyde (80.9 mg) and the whole was stirred at room temperature for 6 days under a nitrogen atmosphere. After completion of the reaction, the solvent was distilled off. The resultant was then dissolved in chloroform and added with a saturated aqueous sodium hydrogen carbonate solution and the whole was stirred for a while. The solution was subjected to extraction with chloroform and the extract was then washed with a saturated aqueous sodium hydrogen carbonate solution and a saturated saline solution. The organic layer was dried with anhydrous sodium sulfate. Subsequently, the solvent was distilled off and the residue was then purified through silica gel column chromatography (chloroform/methanol/water), thereby obtaining the subject compound (197 mg) as a colorless oily substance.
MS(FAB,Pos.):m/z=566[M+H]$^+$

EXAMPLE 1-8

Synthesis of N-(4-{[(1H-imidazol-2-ylmethyl)-(1-methyl-1H-imidazol-2-ylmethyl)-amino]-methyl}-benzyl)-N',N'-dipropylbutane-1,4-diamine The compound (197 mg) obtained in Example 1-7 was dissolved in methanol (1.0 ml) and added with a 10% hydrogen chloride/methanol solution (3.0 ml) and the whole was stirred overnight at room temperature. After completion of the reaction, the solvent was distilled off and a hydrochloride (159 mg) of the subject compound was obtained as a white solid.
MS(FAB,Pos.):m/z=466[M+H]$^+$
$^1$H-NMR(500 MHz,DMSO-d$_6$+D$_2$O):δ=0.87(6H,t,J=7.3 Hz),1.59-1.67(8H, m),2.87(2H,brs),2.94-2.97(4H,m),3.01 (2H,brs),3.66(3H,s),3.69(2H,s),4.03(4H,s),4.13(2H,s),7.34

(2H,d,J=8.2 Hz),7.39(2H,d,J=8.2 Hz),7.40(1H,d,J=2.0 Hz), 7.41(1H,d,J=2.0 Hz),7.53(2H,s).

EXAMPLE 1-9

Synthesis of 2-[(4-dipropylamino-butyl)-(4-{[(1H-imidazol-2-ylmethyl)-(1-methyl-1H-imidazol-2-ylmethyl)-amino]-methyl}-benzyl)-amino]-ethanol [Compound No. 1]

The compound (209 mg) obtained in Example 1-8 was dissolved in anhydrous methanol (8.4 ml) and added with [1,4]-dioxan-2,5-diol (54.0 mg) and sodium cyanoborohydride (56.6 mg). Then, the solution was adjusted to pH 5 with acetic acid and stirred at room temperature for 19.5 hours. After completion of the reaction, the solvent was distilled off. The resultant was added with a 1 mol/l sodium hydroxide aqueous solution (1.0 ml) and subjected to extraction with chloroform, followed by drying with magnesium sulfate. The solvent was distilled off and the residue was then purified through silica gel column chromatography (chloroform/methanol) and treated with hydrochloric acid, thereby obtaining a hydrochloride (175.8 mg) of the subject compound as a white solid.

MS(FAB,Pos.):m/z=510[M+H]$^+$ $^1$H-NMR(500 MHz,DMSO-d$_6$+D$_2$O):δ=0.92(6H,t,J=7.1 Hz),1.64-1.68(6H,m),1.78-1.82(2H,m),3.00-3.08(10H,m), 3.71(3H,s),3.74(4H,s),4.09(2H,s),4.17(2H,s),4.30(2H,q, J=13.9 Hz),7.41(2H,d,J=7.8 Hz),7.48(4H,d,J=5.6 Hz),7.61 (2H,s).

EXAMPLE 2

Production Example 2

Synthesis of [4-(6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 2]

EXAMPLE 2-1

Synthesis of methyl 4-amino-3-{(5-t-butoxycarbonylamino)-pentanoyl}-aminobenzoate In DMF (20 ml), 5-t-butoxycarbonylamino valeric acid (1.45 g), WSCI hydrochloride (1.74 g), and HOBt (1.25 g) were dissolved and the whole was stirred for 15 minutes. Then, the solution was added with methyl 3,4-diaminobenzoate (manufactured by Lancaster) (1.00 g) and the whole was stirred at room temperature for 4 hours. After completion of the reaction, the solvent was distilled off under reduced pressure. The residue was dissolved in chloroform and then washed with a saturated aqueous ammonium chloride solution and a 1 mol/l sodium hydroxide aqueous solution. Subsequently, the resultant was subjected to extraction with chloroform and the extract was then washed with a saturated saline solution, followed by drying with anhydrous sodium sulfate. After filtration, the solvent was distilled off under reduced pressure. The residue was purified through silica gel column chromatography (chloroform/ethyl acetate), thereby obtaining the subject compound (1.46 g).

MS(FAB,Pos.):m/z=365[M+H]$^+$

EXAMPLE 2-2

Synthesis of 2-(4-dipropylamino-butyl)-3H-benzimidazol-5-carboxylic acid methyl ester The compound (1.46 g) obtained in Example 2-1 was dissolved in methanol (7.3 ml) and then added with a 4 mol/l hydrogen chloride/dioxane solution (7.3 ml), followed by stirring overnight at 40° C. After completion of the reaction, the solvent was distilled off under reduced pressure and the residue was dried under vacuum. The dried product was dissolved in methanol (15 ml) and added with triethylamine (0.597 ml), trimethyl orthoformate (1.0 ml), and propionaldehyde (0.309 ml) and the whole was stirred at room temperature for 30 minutes. The solution was added with sodium cyanoborohydride (272 mg) and stirred at room temperature for 30 minutes. Furthermore, the solution was added with propionaldehyde (0.310 ml) and sodium cyanoborohydride (270 mg), followed by stirring at room temperature for 4 hours. After completion of the reaction, the solvent was distilled off under reduced pressure. The residue was dissolved in chloroform and then washed with a 1 mol/l sodium hydroxide aqueous solution, followed by extraction with chloroform. The organic layer was washed with a saturated saline solution and then dried with anhydrous sodium sulfate. After filtration, the solvent was distilled off under reduced pressure and the residue was then purified through silica gel column chromatography (chloroform/ethyl acetate), thereby obtaining the subject compound (315 mg) as a brown oily substance.

MS(FAB,Pos.):m/z=332[M+H]$^+$

EXAMPLE 2-3

Synthesis of {4-[6-chloromethyl-1-(toluene-4-sulfonyl)-1H-benzimidazol-2-yl]-butyl}-dipropyl-amine Lithium aluminum hydride (108 mg) was suspended in THF (60 ml) and a THF solution (60 ml) containing the compound (315 mg) obtained in Example 2-2 was dropped therein, and the whole was stirred at room temperature for 1 hour. After completion of the reaction, sodium sulfate decahydrate was added to the solution until bubbling was stopped, and a 1 mol/l sodium hydroxide aqueous solution was then gradually added to the mixture until a white precipitate was generated. After filtration, the solvent was distilled off under reduced pressure. The residue was dried under vacuum, and the dried product was dissolved in dichloromethane (10 ml) and then added with triethylamine (263 μl) and p-toluenesulfonyl chloride (364 mg), followed by stirring at room temperature for 2.5 hours. After completion of the reaction, the solution was washed with water and subjected to extraction with chloroform. The organic layer was washed with a saturated saline solution and then dried with anhydrous sodium sulfate. After filtration, the solvent was distilled off under reduced pressure and the residue was then purified through silica gel column chromatography (chloroform/methanol), thereby obtaining the subject compound (113 mg) as a brown solid.

MS(FAB,Pos.):m/z=476[M+H]$^+$

EXAMPLE 2-4

Synthesis of [4-(6-aminomethyl-1H-benzimidazol-2-yl)-butyl]-dipropyl-amine

The compound (113 mg) obtained in Example 2-3 was dissolved in DMF (2.0 ml) and added with potassium phthalimide (69.0 mg) and the whole was stirred at room temperature for 2 days. After completion of the reaction, the solvent was distilled off under reduced pressure and the residue was then dissolved in chloroform, followed by washing with water. After extraction with chloroform, the organic layer was washed with a saturated saline solution and dried with anhydrous sodium sulfate. After filtration, the solvent was distilled off under reduced pressure. The residue was dried under vacuum, and the dried product was dissolved in a 40% methylamine/methanol solution (1.5 ml), followed by stirring overnight at room temperature. After completion of the reaction, the solvent was distilled off under reduced pressure and the residue was then dissolved in chloroform, followed by washing with water and a 1 mol/l sodium hydroxide aqueous solution. After extraction with chloroform, the extract was washed with a saturated saline solution and dried with anhydrous sodium sulfate. After filtration, the solvent was distilled off under reduced pressure and the residue was then purified through silica gel column chromatography (chloroform/methanol), thereby obtaining the subject compound (39.8 mg) as a brown solid.

MS(FAB,POS.):M/Z=303[M+H]$^+$

EXAMPLE 2-5

Synthesis of [4-(6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 2]

The compound (39.8 mg) obtained in Example 2-4 was dissolved in methanol (1.0 ml) and then added with 2-imidazole carboxaldehyde (13.3 mg) and trimethyl orthoformate (0.030 ml) and the whole was stirred at room temperature for 30 minutes. The solution was gradually added with sodium borohydride (10.5 mg), followed by stirring at room temperature for 1 hour. After completion of the reaction, the solvent was distilled off under reduced pressure and the residue was then dissolved in chloroform. After having been washed with water, the solution was subjected to extraction with chloroform. The organic layer was washed with a saturated saline solution and then dried with anhydrous sodium sulfate. After filtration, the solvent was distilled off under reduced pressure.

The resultant was dissolved in methanol (1.0 ml) and added with 1-methyl-2-imidazole carboxaldehyde (63.2 mg), acetic acid (0.023 ml), trimethyl orthoformate (0.030 ml), and sodium cyanoborohydride (23.2 mg) and the whole was stirred at room temperature for 30 minutes. The solution was added with acetic acid (0.045 ml) and stirred at room temperature for 4 hours. After completion of the reaction, the solvent was distilled off under reduced pressure and the residue was then dissolved in chloroform. After having been washed with a 1 mol/l sodium hydroxide aqueous solution, the solution was subjected to extraction with chloroform. The organic layer was washed with a saturated saline solution and then dried with anhydrous sodium sulfate. After filtration, the solvent was distilled off under reduced pressure. The residue was purified through silica gel column chromatography (chloroform/methanol) and treated with hydrochloric acid, thereby obtaining a hydrochloride (27.6 mg) of the subject compound as a white solid.

MS(FAB,Pos.):m/z=477[M+H]$^+$
$^1$H-NMR(500 MHz,DMSO-d$_6$):δ=0.89(3H,t,J=7.3 Hz), 1.63-1.69(4H,m),1.70-1.81(2H,m),1.94-2.01(2H,m),2.84-3.00(4H,m),3.03-3.09(2H,m),3.19-3.23(2H,m),3.72(3H,s), 3.90(2H,s),4.13(2H,s),4.21(2H,s),4.41(2H,t,J=7.3 Hz),7.49 (1H,s),7.53(1H,s),7.59(1H,d,J=8.4Hz),7.64-7.66(3H,m), 7.81(1H,s),10.50(1H,s).

EXAMPLE 3

Production Example 3

Synthesis of [4-(6-{[bis-(1H-imidazol-2-ylmethyl)-amino]-methyl}-1-propyl-1H-benzimidazol-2-yl)-butyl]-dipropyl-amine [Compound No. 3]

EXAMPLE 3-1

Synthesis of methyl 4-amino-3-propylamino-benzoate

In DMF (40 ml), methyl 3,4-diaminobenzoate (2.01 g) was dissolved and then the solution was added with potassium carbonate (2.00 g) and methyl iodide (1.4 ml) and the whole was stirred at room temperature for 22 hours. After completion of the reaction, the solvent was distilled off under reduced pressure. The residue was dissolved in ethyl acetate and washed with water, followed by extraction with ethyl acetate. The organic layer was washed with a saturated saline solution and dried with anhydrous sodium sulfate. After filtration, the solvent was distilled off under reduced pressure and the residue was then purified through silica gel column chromatography (hexane/ethyl acetate), thereby obtaining the subject compound (1.06 g).

MS(FAB,Pos.):m/z=209[M+H]$^+$
$^1$H-NMR(500 MHz,CDCl$_3$):δ=1.05(3H,t,J=7.3 Hz),1.71 (2H,sext.,J=7.3 Hz),3.12(2H,t,J=7.1 Hz),3.86(3H,s),6.69 (1H,d,J=8.1 Hz),7.35(1H,s),7.45(1H,d,J=8.1 Hz).

EXAMPLE 3-2

Synthesis of methyl 4-(5-t-butoxycarbonylamino-pentanoylamino)-3-propylamino-benzoate In chloroform (10 ml), 5-t-butoxycarbonylamino valeric acid (574 mg), WSCI hydrochloride (690 mg), and HOBt (487 mg) were dissolved. Then, the solution was stirred at room temperature for 30 minutes. The solution was added with the compound (503 mg) obtained in Example 3-1 and stirred overnight at room temperature. After completion of the reaction, the solvent was distilled off under reduced pressure and the residue was then dissolved in chloroform. After having been washed with a saturated aqueous sodium hydrogen carbonate solution, a saturated aqueous ammonium chloride solution, and a saturated saline solution, the resultant was dried with anhydrous sodium sulfate. After filtration, the solvent was distilled off under reduced pressure and the residue was then purified through silica gel column chromatography (chloroform/ethyl acetate), thereby obtaining the subject compound (540 mg) as a colorless viscous substance.

MS(FAB,Pos.):m/z=408[M+H]$^+$
$^1$H-NMR(500 MHz,CDCl$_3$):δ=0.97(3H,t,J=7.3 Hz),1.37 (9H,s),1.37-1.46(2H,m),1.51-1.66(4H,m),2.37(2H,t,J=7.3 Hz),2.93(2H,q,J=6.6 Hz),3.04(2H,q,J=7.1 Hz),3.81(3H,s), 5.14(1H,br),6.83(1H,br),7.16(1H,s),7.20(1H,d,J=8.1 Hz), 7.45(1H,d,J=88.1 Hz),9.24(1H,s).

EXAMPLE 3-3

Synthesis of 2-(4-dipropylamino-butyl)-3-propyl-3H-benzimidazol-5-carboxylic acid methyl ester The compound (540 mg) obtained in Example 3-2 was dissolved in methanol (10 ml) and added with a 4 mol/l hydrogen chloride/dioxane solution (5.0 ml) and the whole was stirred at room temperature for 1.5 hours. After completion of the reaction, the solvent was distilled off under reduced pressure and the residue was then dissolved in methanol, followed by neutralization with the addition of an anion-exchange resin (Amberlite IRA-410). The solvent was distilled off.

The resultant was then dissolved in methanol (12 ml). Subsequently, the solution was added with acetic acid (0.425 ml) and sodium cyanoborohydride (135 mg), followed by cooling to 0° C. The solution was added with propionaldehyde (0.114 ml) and stirred at room temperature for 1 hour, followed by cooling to 0° C. again. The solution was added with sodium cyanoborohydride (132 mg) and propionaldehyde (0.115 ml) and then stirred overnight at room temperature. After completion of the reaction, the solvent was distilled off under reduced pressure and then the residue was dissolved in chloroform. The solution was washed with a 1 mol/l sodium hydroxide aqueous solution and then subjected to extraction with chloroform.

The organic layer was washed with a saturated saline solution and dried with anhydrous sodium sulfate. After filtration, the solvent was distilled off under reduced pressure and the residue was then purified through silica gel column chromatography (chloroform/methanol), thereby obtaining the subject compound (361 mg) as a colorless oily substance.

MS(FAB,Pos.):m/z=374[M+H]$^+$ $^1$H-NMR(500 MHz,CDCl$_3$):δ=0.88(6H,t,J=7.3 Hz),1.00 (3H,t,J=7.3 Hz),1.49(4H,q,J=7.5 Hz),1.74-1.82(4H,m),1.87 (2H,sext.,J=7.6 Hz),1.91-2.09(4H,m) 2.93-3.01(4H,m),3.00 (2H,t,J=7.1 Hz),3.09(2H,t,J=7.6 Hz),3.96(3H,s),4.15(2H,t, J=7.6 Hz),7.66(1H,d,J=8.5 Hz),7.96(1H,d,J=8.5 Hz),8.08 (1H,s).

EXAMPLE 3-4

Synthesis of [2-(4-dipropylamino-butyl)-3-propyl-3H-benzimidazol-5-yl]-methanol

Lithium aluminum hydride (138 mg) was suspended in THF (7.0 ml) and then the whole was cooled to 0° C. After that, a THF solution (7.0 ml) containing the compound (361 mg) obtained in Example 3-3 was dropped in the suspension, followed by stirring at 0° C. for 1 hour. After completion of the reaction, sodium sulfate decahydrate was added to the solution until bubbling was stopped, and a 1 mol/l sodium hydroxide aqueous solution was then added to the mixture until a white precipitate was generated. The solid component was separated through filtration and the solvent was then distilled off from the filtrate under reduced pressure. The residue was dried under vacuum, thereby obtaining the subject compound (302 mg) as a pale-yellow oily substance.

MS(FAB,Pos.):m/z=346[M+H]$^+$ $^1$H-NMR(500 MHz,DMSO-d$_6$):δ=0.82(6H,t,J=7.3 Hz), 0.89(3H,t,J=7.3 Hz),1.37(4H,sext.,J=7.3 Hz),1.50(2H, quint.,J=7.3 Hz),1.70-1.81(4H,m),2.29(4H,t,J=7.3 Hz),2.39 (2H,t,J=7.1 Hz),2.84(2H,t,J=7.6 Hz),4.11(2H,t,J=7.3 Hz), 4.59(2H,d,J=5.2 Hz),5.16(1H,t,J=5.5 Hz),7.09(1H,d,J=8.2 Hz),7.42(1H,s),7.45(1H,d,J=8.2 Hz).

EXAMPLE 3-5

Synthesis of 2-[2-(4-dipropylamino-butyl)-3-propyl-3H-benzimidazol-5-ylmethyl]-isoindol-1,3-dione The compound (302 mg) obtained in Example 3-4 was dissolved in toluene (6.0 ml) and added with triphenylphosphine (275 mg) and phthalimide (193 mg) and the whole was cooled to 0° C. In this solution, a 40% diethyl azodicarboxylate/toluene solution (452 mg) was dropped and the whole was stirred overnight at room temperature. After completion of the reaction, the solvent was distilled off under reduced pressure. The residue was dissolved in chloroform and washed with water. Then, the resultant was subjected to extraction with chloroform and washed with a saturated saline solution. The organic layer was dried with anhydrous sodium sulfate. After filtration, the solvent was distilled off under reduced pressure and the residue was then purified through silica gel column chromatography (chloroform/methanol), thereby obtaining the subject compound (174 mg) as a pale-yellow solid.

MS(FAB,Pos.):m/z=475[M+H]$^+$ $^1$H-NMR(500 MHz,DMSO-d$_6$):δ=0.79-0.83(6H,m),0.86 (3H,t,J=7.3 Hz),1.31-1.40(4H,m),1.46-1.51(2H,m),1.63-1.80(4H,m),2.29(4H,br),2.39(2H,br),2.83(2H,t,J=7.6 Hz), 4.12(2H,t,J=7.3 Hz),4.87(2H,s),7.08(1H,d,J=8.3 Hz),7.46-7.48(2H,m),7.83-7.89(2H,m),7.90-7.93(2H,m).

EXAMPLE 3-6

Synthesis of [4-(6-aminomethyl-1-propyl-1H-benzimidazol-2-yl)-butyl]-dipropyl-amine The compound (173 mg) obtained in Example 3-5 was dissolved in a 40% methylamine/methanol solution (1.8 ml) and the whole was stirred at room temperature for 17 hours. After completion of the reaction, the solvent was distilled off under reduced pressure and the residue was then purified through silica gel column chromatography (chloroform/ethyl acetate), thereby obtaining the subject compound (130 mg) as a pale-yellow oily substance.

MS(FAB,Pos.):m/z=345[M+H]$^+$

EXAMPLE 3-7

Synthesis of [4-(6-{[bis-(1H-imidazol-2-ylmethyl)-amino]-methyl}-1-propyl-1H-benzimidazol-2-yl)-butyl]-dipropyl-amine [Compound No. 3]

The compound (130 mg) obtained in Example 3-6 was dissolved in methanol (3.0 ml) and added with trimethyl orthoformate (0.130 ml) and 2-imidazole carboxaldehyde (37.3 mg) and the whole was stirred for 1 hour. After having been cooled to 0° C., the solution was added with sodium borohydride (21.5 mg) and stirred at room temperature for 3 hours. After completion of the reaction, the solvent was distilled off under reduced pressure and the residue was then dissolved in chloroform. The solution was washed with a 1 mol/l sodium hydroxide aqueous solution and then subjected to extraction with chloroform. The organic layer was washed with a saturated saline solution and then dried with anhydrous sodium sulfate. After filtration, the solvent was distilled off under reduced pressure. Then, the residue was purified through silica gel column chromatography (chloroform/methanol) and treated with hydrochloric acid, thereby obtaining a hydrochloride (16.4 mg) of the subject compound as a white solid.

MS(FAB,Pos.):m/z=505[M+H]$^+$ $^1$H-NMR(500 MHz,DMSO-d$_6$):δ=0.91(6H,t,J=7.3 Hz), 0.99(3H,t,J=7.3 Hz),1.66-1.71(4H,m),1.78-1.82(4H,m), 1.83-1.96(2H,m),2.97-3.00(4H,m),3.08-3.16(2H,m),3.25 (2H,t,J=7.2 Hz),3.87(2H,s),4.16(4H,s),4.54(2H,t,J=7.7 Hz), 7.52-7.55(1H,m),7.61(3H,s),7.64-7.70(1H,m),8.43(1H,s), 10.31(1H,br).

EXAMPLE 4

Production Example 4

Synthesis of [4-(6-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 4]

EXAMPLE 4-1

Synthesis of [4-(6-{[(1H-imidazol-2-ylmethyl)-amino]-methyl}-1-propyl-1H-benzimidazol-2-yl)-butyl]-dipropyl-amine The compound (130 mg) obtained in Example 3-6 was dissolved in methanol (3.0 ml) and added with trimethyl orthoformate (0.130 ml) and 2-imidazole carboxaldehyde (37.3 mg) and the whole was stirred for 1 hour. After having been cooled to 0° C., the solution was added with sodium borohydride (21.5 mg) and stirred at room temperature for 3 hours. After completion of the reaction, the solvent was distilled off under reduced pressure and the residue was then dissolved in chloroform. The solution was washed with a 1 mol/l sodium hydroxide aqueous solution and then subjected to extraction with chloroform. The organic layer was washed with a saturated saline solution and then dried with anhydrous sodium sulfate. After filtration, the solvent was distilled off under reduced pressure. Then, the residue was purified through silica gel column chromatography (chloroform/methanol), thereby obtaining the subject compound (64.0 mg) as a pale-yellow oily substance.

EXAMPLE 4-2

Synthesis of [4-(6-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 4]

The compound (64.0 mg) obtained in Example 4-1 was dissolved in methanol (1.3 ml) and added with acetic acid (0.065 ml) and 1-methyl-2-imidazole carboxaldehyde (16.6 mg) and the whole was cooled to 0° C. Then, the solution was added with sodium cyanoborohydride (14.2 mg) and stirred at room temperature for 2 days. After completion of the reaction, the solvent was distilled off under reduced pressure and the residue was then dissolved in chloroform. After washing with a 1 mol/l sodium hydroxide aqueous solution, the solution was subjected to extraction with chloroform. The organic layer was washed with a saturated saline solution and dried with anhydrous sodium sulfate.

After filtration, the solvent was distilled off under reduced pressure. Subsequently, the residue was purified through silica gel column chromatography (chloroform/methanol) and treated with hydrochloric acid, thereby obtaining a hydrochloride (30.0 mg) of the subject compound as a white solid.

MS(FAB,Pos.):m/z=519[M+H]$^+$
$^1$H-NMR(500 MHz,DMSO-d$_6$):δ=0.91(6H,t,J=7.3 Hz), 0.99(3H,t,J=7.3 Hz),1.66-1.74(4H,m),1.78-1.84(4H,m),1.93 (2H,t,J=7.3 Hz),2.94-3.00(4H,m),3.13(2H,br),3.26(2H,t, J=7.3 Hz),3.73(3H,s),3.90(2H,s),4.13(2H,s),4.21(2H,s),4.53 (2H,t,J=7.6 Hz),7.53-7.55(3H,m),7.63(2H,s),7.70(1H,d, J=8.2 Hz),8.41(1H,s),10.48(1H,br).

EXAMPLE 5

Production Example 5

Synthesis of [4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 5]

EXAMPLE 5-1

Synthesis of 3-nitro-4-propylamino-benzonitrile

In DMF (20 ml), 3-nitro-4-aminobenzonitrile (1.12 g) was dissolved, and the solution was added with 60% sodium hydride (411 mg), followed by stirring at room temperature for 30 minutes. The solution was added with 1-iodopropane (805 μl) and stirred at room temperature for 1 hour. After completion of the reaction, the solvent was distilled off under reduced pressure and the residue was then dissolved in ethyl acetate. The resultant was washed with water and then subjected to extraction with ethyl acetate. The organic layer was washed with a saturated saline solution and dried with anhydrous sodium sulfate.

After filtration, the solvent was distilled off under reduced pressure, thereby obtaining a crude product (1.58 g) of the subject compound as a yellow solid.

MS(FAB,Pos.):m/z=206[M+H]$^+$

EXAMPLE 5-2

Synthesis of 3-amino-4-propylamino-benzonitrile

In ethanol (170 ml), the compound (1.58 g) obtained in Example 5-1 and stannous chloride dihydrate (7.81 g) were dissolved. Then, the solution was heated to 60° C. and sodium borohydride (144 mg) was gradually added therein, followed by stirring at 60° C. for 2 hours. After completion of the reaction, water was added to the solution, and the whole was neutralized with a 1 mol/l sodium hydroxide aqueous solution. Then, ethanol was distilled off under reduced pressure. The resultant was subjected to extraction with ethyl acetate. The extract was washed with a saturated saline solution and dried with anhydrous sodium sulfate. After filtration, the solvent was distilled off under reduced pressure. The residue was purified through silica gel column chromatography (hexane/ethyl acetate), thereby obtaining the subject compound (1.18 mg) as a pale-yellow solid.

MS(FAB,Pos.):m/z=176[M+H]$^+$
$^1$H-NMR(500 MHz,CDCl$_3$):δ=1.04(3H,t,J=7.6 Hz),1.70 (2H,sext.,J=7.3 Hz),3.13(2H,q,J=7.1 Hz),6.58(1H,d,J=8.1 Hz),6.94(1H,s),7.17(1H,d,J=8.1 Hz).

EXAMPLE 5-3

Synthesis of t-butyl [4-(5-cyano-2-propylamino-phenylcarbamoyl)-butyl]-carbamate In chloroform (31 ml), 5-t-butoxycarbonylamino valeric acid (1.57 g), WSCI hydrochloride (1.98 g), and HOBt (1.39 g) were dissolved. Then, the solution was stirred at room temperature for 30 minutes. The solution was dropped in a chloroform solution (10 ml) containing the compound (1.18 g) obtained in Example 5-2. Then, the whole was stirred at room temperature for 12 hours. After completion of the reaction, the solvent was distilled off under reduced pressure. The residue was dissolved in chloroform and then washed with a saturated aqueous sodium hydrogen carbonate solution, a saturated aqueous ammonium chloride solution, and a saturated saline solution, followed by drying with anhydrous sodium sulfate. After filtration, the solvent was distilled off under reduced pressure and the residue was then purified through silica gel column chromatography (chloroform/ethyl acetate) to remove only highly-polar components, thereby obtaining a mixture (2.52 g) containing the subject compound as a yellow oily substance.

MS(FAB,Pos.):m/z=375[M+H]$^+$

EXAMPLE 5-4

Synthesis of 2-(4-dipropylamino-butyl)-1-propyl-1H-benzimidazol-5-carbonitrile

The compound (2.52 g) obtained in Example 5-3 was dissolved in methanol (20 ml) and added with a 4 mol/l hydrogen chloride/dioxane solution (12 ml) and the whole was stirred at room temperature for 2 hours. After completion of the reaction, the solvent was distilled off under reduced pressure. The residue was dissolved in chloroform and washed with a 1 mol/l sodium hydroxide aqueous solution, followed by extraction with chloroform. The organic layer was washed with a saturated saline solution and then dried with anhydrous sodium sulfate. After filtration, the solvent was distilled off under reduced pressure.

The resultant was dissolved in methanol (40 ml). Then, the solution was added with acetic acid (0.250 ml) and propionaldehyde (1.21 ml), followed by cooling to 0° C. The solution was added with sodium cyanoborohydride (1.39 g) and stirred at room temperature for 13 hours. After completion of the reaction, the solvent was distilled off under reduced pressure. The residue was dissolved in chloroform and washed with a 1 mol/l sodium hydroxide aqueous solution, followed by extraction with chloroform. The organic layer was washed with a saturated saline solution and then dried with anhydrous sodium sulfate. After filtration, the solvent was distilled off under reduced pressure and the residue was then purified through silica gel column chromatography (hexane/ethyl acetate), thereby obtaining the subject compound (1.41 g) as a yellow oily substance.

MS(FAB,Pos.):m/z=341[M+H]$^+$

EXAMPLE 5-5

Synthesis of [4-(5-{[(1H-imidazol-2-ylmethyl)-(1-methyl-1H-imidazol-2-ylmethyl)-amino]-methyl}-1-propyl-1H-benzimidazol-2-yl)-butyl]-dipropyl-amine [Compound No. 5]

Lithium aluminum hydride (588 mg) was suspended in THF (30 ml) and then the whole was cooled to 0° C. After that, a THF solution (30 ml) containing the compound (1.40 g) obtained in Example 5-4 was dropped in the suspension and the whole was stirred at 0° C. for 1 hour. After completion of the reaction, sodium sulfate decahydrate was added to the solution until bubbling was stopped, and a 1 mol/l sodium hydroxide aqueous solution was then added to the mixture until a white precipitate was generated. A solid component was separated through filtration and the solvent was then distilled off from the filtrate under reduced pressure. The residue was purified through silica gel column chromatography (chloroform/methanol).

The purified product was dissolved in methanol (12 ml) and added with trimethyl orthoformate (0.78 ml) and 2-imidazole carboxaldehyde (228 mg), followed by stirring for 1 hour. Then, the solution was cooled to 0° C. The solution was added with sodium borohydride (188 mg) and stirred at room temperature for 1 hour. After completion of the reaction, the solvent was distilled off under reduced pressure and the residue was then dissolved in a 1 mol/l hydrochloric acid. The aqueous layer was washed with chloroform. The resultant was added with a 1 mol/l sodium hydroxide aqueous solution and the whole was subjected to extraction with chloroform. The organic layer was washed with a saturated saline solution and then dried with anhydrous sodium sulfate. After filtration, the solvent was distilled off under reduced pressure. Then, the residue was purified through silica gel column chromatography (chloroform/ethyl acetate).

The purified product was dissolved in methanol (6.0 ml) and then added with acetic acid (0.20 ml) and sodium cyanoborohydride (50.0 mg). The solution was gradually added with 1-methyl-2-imidazole carboxaldehyde (59.8 mg), followed by stirring at room temperature for 6 hours. After completion of the reaction, the solvent was distilled off under reduced pressure and the residue was then dissolved in chloroform. After having been washed with a 1 mol/l sodium hydroxide aqueous solution, the solution was subjected to extraction with chloroform. The organic layer was washed with a saturated saline solution and then dried with anhydrous sodium sulfate. After filtration, the solvent was distilled off under reduced pressure. The residue was purified through silica gel column chromatography (chloroform/ethyl acetate) and treated with hydrochloric acid, thereby obtaining a hydrochloride (242 mg) of the subject compound as a white solid.

MS(FAB,Pos.):m/z=519[M+H]$^+$ $^1$H-NMR(500 MHz,DMSO-d$_6$):δ=0.89-0.95(9H,m),1.67-1.94(10H,m),2.96-3.00(4H,m),3.12-3.13(2H,m),3.26(2H,t,J=7.3 Hz),3.72(3H,s),3.91(2H,s),4.13(2H,s),4.21(2H,s),4.41 (2H,t,J=7.3 Hz),7.49(1H,s),7.52(1H,s),7.64(2H,s),7.72(1H,d,J=8.5 Hz),7.82(1H,s),7.90(1H,d,J=8.5 Hz),10.61(1H,s).

EXAMPLE 6

Production Example 6

Synthesis of 4-([N-(1H-imidazol-2-ylmethyl)-amino]-methyl-N-(4-dipropylamino-butyl)-benzamide [Compound No. 6]

EXAMPLE 6-1

Synthesis of 4-{[t-butoxycarbonyl-(1H-imidazol-2-ylmethyl)-amino]-methyl}-benzoic acid Commercially available methyl bromomethylbenzoate (manufactured by Aldrich Corporation) (10.0 g) was dissolved in DMF (100 ml), and the solution was added with potassium phthalimide (manufactured by Tokyo Kasei Kogyo Co., Ltd.) (9.70 g) and the whole was stirred at room temperature for 1.5 hours. After completion of the reaction, the solution was concentrated and added with water, followed by extraction with chloroform. The resultant was washed with a saturated saline solution and dried with anhydrous sodium sulfate, and the solvent was distilled off, thereby obtaining a white solid (12.9 g). Subsequently, 7.56 g of the solid was dissolved in methanol (100 ml), and the solution was added with hydrazine monohydrate (manufactured by Nacalai Tesque, Inc.) (6.25 ml) and the whole was stirred at 60° C. for 1.5 hours. After completion of the reaction, the precipitated solid was filtrated out and the solvent was distilled off. The resultant was added with water and subjected to extraction with chloroform. The resultant was washed with a 0.3 mol/l sodium hydroxide aqueous solution and a saturated saline solution and dried with anhydrous sodium sulfate, and the solvent was distilled off. Methanol (120 ml) and 2-imidazole carboxaldehyde (manufactured by Aldrich Corporation) (2.35 g) were added to the resultant and the whole was stirred at room temperature for 2 days. After completion of the reaction, the precipitated solid was filtrated out. The liquid layer was concentrated and evaporated to dryness, and washing was performed by adding anhydrous methanol (30 ml). Then, the solid was filtrated out. The resultant solid and the solid that had been previously filtrated out were suspended in methanol (86 ml), and sodium borohydride (1.42 g) was added under ice-cooling. The solution was stirred at room temperature for 1 hour, and the solvent was distilled off. After addition of water, extraction was performed with chloroform, and the organic layer was washed with a saturated saline solution and dried with anhydrous sodium sulfate, followed by concentration under reduced pressure and drying, thereby obtaining a colorless oily substance (4.32 g). 4.28 g of the oily substance was dissolved in DMF (65 ml), and the solution was added with di-t-butyldicarbonate (8.90 ml) and stirred at room temperature for 1 hour.

After completion of the reaction, the solvent was distilled off, and the residue was dissolved in chloroform, followed by washing with a saturated saline solution. After drying with anhydrous sodium sulfate, the solvent was distilled off, and THF (43 ml), methanol (43 ml), and a 1 mol/l sodium hydroxide aqueous solution (43 ml) were added to the resultant, followed by stirring at room temperature for 14 hours. After completion of the reaction, the solvent was distilled off, and water (5.0 ml) was added to the resultant. Further, 1 mol/l hydrochloric acid was carefully added to the solution, and the acid-precipitate was filtrated out and dried, thereby obtaining the subject compound (4.87 g) as a white solid.

MS(FAB,Pos.):m/z=332[M+H]$^+$

EXAMPLE 6-2

Synthesis of [4-(4-dipropylamino-butylcarbamoyl)-benzyl]-(1H-imidazol-2-ylmethyl)-carbamic acid t-butyl ester The compound (203 mg) obtained in Example 1-2 was dissolved in DMF (5.0 ml) and chloroform (5.0 ml), and then added with triethylamine (0.374 ml), WSCI hydrochloride (382 mg), HOBt (200 mg), and the compound (463 mg) obtained in Example 6-1. The whole was stirred at room temperature for 23 hours. After completion of the reaction, the solvent was distilled off. Then, the resultant was added with chloroform and washed with water and a saturated saline solution, followed by drying with anhydrous sodium sulfate. The solvent was distilled off and the residue was purified through silica gel column chromatography (chloroform/methanol/water), thereby obtaining the subject compound (168 mg) as colorless foam.

MS(FAB,Pos.):m/z=486[M+H]$^+$

EXAMPLE 6-3

Synthesis of 4-{[N-(1H-imidazol-2-ylmethyl)-amino]-methyl-N-(4-dipropylamino-butyl)-benzamide [Compound No. 6]

The compound (117 mg) obtained in Example 6-2 was dissolved in methanol (1.2 ml) and then added with a 4 mol/l hydrogen chloride/dioxane solution (1.2 ml) and the whole was stirred at room temperature for 5 hours. After completion of the reaction, the solvent was distilled off. Then, the residue was dissolved in water and then purified through solid-phase extraction column (Sep-Pak, tC18, manufactured by Waters Corporation), thereby obtaining a hydrochloride (118 mg) of the subject compound as a white solid.

MS(FAB,Pos.):m/z=386[M+H]$^+$ $^1$H-NMR(500 MHz,DMSO-d$_6$):δ=0.89(6H,t,J=7.3 Hz), 1.54-1.62(2H,m),1.61-1.83(6H,m),2.93-3.01(4H,m),3.00-3.01(2H,m),3.30(2H,dd,J=6.1,12.3 Hz),4.37(2H,s),4.52(2H,s),7.62-7.64(4H,m),7.92(2H,d,J=8.1 Hz),8.71(1H,d,J=4.4 Hz).

EXAMPLE 7

Production Example 7

Synthesis of 2-(4-dipropylamino-butyl)-5-{[(1H-imidazol-2-ylmethyl)-(1-methyl-1H-imidazol-2-ylmethyl)-amino]-methyl}-2,3-dihydro-isoindol-1-one [Compound No. 7]

EXAMPLE 7-1

Synthesis of 4-methyl phthalic acid dimethyl ester

In methanol (60 ml), 4-methylphthalic acid (3.00 g) was dissolved. Then, WSCI hydrochloride (9.62 g) and 4-dimethylaminopyridine (3.07 g) were added to the solution, and the whole was stirred at room temperature for 3.5 hours. The reaction solution was added with water to stop the reaction and then the whole was subjected to extraction with chloroform. The organic layer was washed with water, 1 mol/l hydrochloric acid, and a saturated saline solution, and then dried with anhydrous sodium sulfate. The solvent was distilled off and the residue was purified through silica gel column chromatography (hexane/ethyl acetate), thereby obtaining the subject compound (2.54 g) as a colorless oily substance.

MS(FAB,Pos.):m/z=209[M+H]$^+$ $^1$H-NMR(500 MHz,CDCl$_3$):δ=2.42(3H,s),3.89(3H,s), 3.91(3H,s),7.33(1H,dd,J=1.7,8.6 Hz),7.47(1H,d,J=1.2 Hz), 7.68(1H,d,J=7.8 Hz).

EXAMPLE 7-2

Synthesis of 4-(1,3-dioxo-1,3-dihydro-isoindol-2-ylmethyl)-phthalic acid dimethyl ester The compound (202 mg) obtained in Example 7-1 was dissolved in carbon tetrachloride (7.1 ml) and added with N-bromosuccinimide (205 mg) and 2,2'-azobisisobutyronitrile (15.8 mg) and the whole was refluxed under heating for 20 hours. The solution was further added with carbon tetrachloride (7.0 ml) and N-bromosuccinimide (51.3 mg) and the whole was refluxed under heating for additional 4 hours. After having been left for cooling, the solution was added with water to stop the reaction and then subjected to extraction with chloroform. The organic layer was washed with water and a saturated saline solution and then dried with anhydrous sodium sulfate. The solvent was distilled off and the residue was then dissolved in DMF (5.8 ml) The solution was added with potassium phthalimide (359 mg) and stirred at room temperature for 16 hours. The residue obtained by distilling the solvent off was purified through silica gel column chromatography (hexane/ethyl acetate), thereby obtaining the subject compound (226 mg) as a white solid.

MS(FAB,Pos.):m/z=354[M+H]$^+$
$^1$H-NMR(500 MHz,CDCl$_3$):δ=3.88(3H,s),3.90(3H,s), 4.89(2H,s),7.60(1H,dd,J=1.8,8.1 Hz),7.71(1H,d,J=7.9 Hz), 7.74(2H,dd,J=2.9,5.5 Hz),7.75(1H,m),7.87(2H,dd,J=2.9,5.5 Hz).

EXAMPLE 7-3

Synthesis of
4-(t-butoxycarbonylamino-methyl)-phthalic acid dimethyl ester

The compound (909 mg) obtained in Example 7-2 was suspended in methanol (22 ml). Hydrazine monohydrate (0.13 ml) was dropped in this suspension and the whole was refluxed under heating for 4 hours. After completion of the reaction, the solvent was distilled off under reduced pressure and then the residue was subjected to extraction with chloroform. The organic layer was washed with water and then with a saturated saline solution, followed by drying with anhydrous sodium sulfate. The residue obtained by distilling the solvent off was dissolved in DMF (15 ml) and added with triethylamine (0.54 ml) and di-t-butyldicarbonate (851 mg), followed by stirring at room temperature for 15 hours. After the solvent was distilled off, the residue was subjected to extraction with chloroform. The organic layer was washed with water and a saturated saline solution and then dried with anhydrous sodium sulfate. The residue obtained by distilling the solvent off was purified through silica gel column chromatography (hexane/ethyl acetate), thereby obtaining the subject compound (779 mg) as a yellow oily substance.
MS(FAB,Pos.):m/z=324[M+H]$^+$
$^1$H-NMR(500 MHz,CDCl$_3$):δ=1.47(9H,s),3.90(3H,s), 3.91(3H,s),4.38(2H,d,J=6.1 Hz),4.94(1H,br),7.46(1H,d, J=8.5 Hz),7.61(1H,d,J=1.5 Hz),7.72(1H,d,J=7.8 Hz).

EXAMPLE 7-4

Synthesis of
4-(t-butoxycarbonylamino-methyl)-phthalic acid

The compound (76.4 mg) obtained in Example 7-3 was dissolved in methanol (4.5 ml). A 1 mol/l sodium hydroxide aqueous solution (2.3 ml) was dropped in this solution and the whole was stirred at room temperature for 2 hours. The solution was neutralized by addition of 1 mol/l hydrochloric acid (2.3 ml). The residue obtained by distilling the solvent off was purified through silica gel column chromatography (chloroform/methanol), thereby obtaining the subject compound (65.3 mg) as a pale-yellow oily substance.
MS(FAB,Pos.):m/z=296[M+H]$^+$
$^1$H-NMR(500 MHz, CD$_3$OD):δ=1.45(9H,s),4.30(2H,s), 7.45(1H,d,J=7.6 Hz),7.80(1H,s),7.88(1H,d,J=8.1 Hz).

EXAMPLE 7-5

Synthesis of [2-(4-di-n-propylamino-butyl)-1,3-di-oxo-2,3-dihydro-1H-isoindol-5-ylmethyl]-carbamic acid t-butyl ester The compound (123 mg) obtained in Example 7-4 was dissolved in xylene (5.0 ml). A xylene solution (5.0 ml) containing the compound (83.4 mg) obtained in Example 1-2 was dropped to the solution and the whole was refluxed under heating for 63 hours. The solution was added with water to stop the reaction and then subjected to extraction with chloroform. The organic layer was washed with water and a saturated saline solution, followed by drying with anhydrous sodium sulfate. The residue obtained by distilling the solvent off was then purified through silica gel column chromatography (hexane/ethyl acetate), thereby obtaining the subject compound (88.4 mg) as a yellow solid.
MS(FAB,Pos.):m/z=432[M+H]$^+$
$^1$H-NMR(500 MHz,CDCl$_3$):δ=0.85(6H,t,J=7.4 Hz),1.40-1.50(6H,m),1.47(9H,m),1.64-1.70(2H,m),2.34(4H,t,J=7.4 Hz),2.42(2H,t,J=7.5 Hz),3.69(2H,t,J=7.3 Hz),4.45(2H,d, J=6.1 Hz),5.04(1H,br),7.62(1H, d,J=7.5 Hz),7.76(1H,d, J=0.8 Hz),7.79(1H,d,J=7.6 Hz).

EXAMPLE 7-6

Synthesis of N-[2-(4-dipropylamino-butyl)-1-oxo-2, 3-dihydro-1H-isoindol-5-ylmethyl]-acetamide and N-[2-(4-dipropylamino-butyl)-3-oxo-2,3-dihydro-1H-isoindol-5-ylmethyl]-acetamide The compound (86.5 mg) obtained in Example 7-5 was dissolved in acetic acid (2.0 ml) and the whole was heated to 60° C. The solution was added with a zinc powder (130 mg) in several additions, followed by refluxing under heating for 10 hours. After cooling the solution to room temperature, the solution was subjected to filtration through Celite and concentrated. The resultant was neutralized with a saturated aqueous sodium hydrogen carbonate solution and subjected to extraction with chloroform. The organic layer was washed with a saturated aqueous sodium hydrogen carbonate solution and a saturated saline solution, and then dried with anhydrous sodium sulfate. The solvent was distilled off, thereby obtaining a mixture (66.1 mg) of the subject compounds as a yellow oily substance.
1-oxo compound
MS(FAB,Pos.):m/z=360[M+H]$^+$
$^1$H-NMR(500 MHz,CDCl$_3$):δ=0.85(6H,t,J=7.3 Hz),1.39-1.48(6H,m),1.65-1.68(2H,m),2.07(3H,s),2.32(4H,m),2.43 (2H,t,J=7.3 Hz),3.61(2H,t,J=7.3 Hz),4.34(2H,s),4.52(2H,d, J=5.8 Hz),6.14(1H,br),7.33(1H,d,J=7.8 Hz),7.38(1H,s),7.74 (1H,d,J=7.8 Hz).
3-oxo compound
MS(FAB,Pos.):m/z=360[M+H]$^+$
$^1$H-NMR(500 MHz,CDCl$_3$):δ=0.85(6H,t,J=7.3 Hz),1.39-1.48(6H,m),1.65-1.68(2H,m),2.05(3H,s),2.32(4H,m),2.43 (2H,t,J=7.3 Hz),3.62(2H,t,J=7.3 Hz),4.35(2H,s),4.51(2H,d, J=5.8 Hz),6.14(1H,br),7.40(1H,s),7.47(1H,dd,J=1.6,7.7 Hz),7.70(1H,d,J=1.0 Hz).

EXAMPLE 7-7

Synthesis of 2-(4-dipropylamino-butyl)-5-{[(1H-imidazol-2-ylmethyl)-amino]-methyl}-2,3-dihydro-isoindol-1-one The compound (66.1 mg) obtained in Example 7-6 was added with 1 mol/l hydrochloric acid, followed by refluxing under heating for 18 hours. The residue obtained by concentration was dissolved in methanol and added with an anion-exchange resin (Amberlite IRA-410) to adjust the solution to pH 8. The resin was filtrated out and the solvent in the filtrate was distilled off. Subsequently, the residue was dissolved in methanol (2.0 ml) and added with trimethyl orthoformate (0.070 ml) and 2-imidazole carboxaldehyde (28.8 mg), followed by stirring at room temperature for 20 hours. After having been cooled to 0° C., the solution was added with sodium borohydride (22.7 mg) and stirred for 3 hours after having been warmed to room temperature. Then, the solution was added with water to stop the reaction and subjected to extraction with chloroform.

The organic layer was washed with water and a saturated saline solution and dried with anhydrous sodium sulfate. The residue obtained by distilling the solvent off was purified through silica gel column chromatography (chloroform/methanol), thereby obtaining the subject compound (13.4 mg) as a colorless oily substance.

MS(FAB,Pos.):m/z=398[M+H]$^+$
$^1$H-NMR(500 MHz,CDCl$_3$):δ=0.85(6H,t,J=7.3 Hz),1.39-1.52(6H,m),1.64-1.70(2H,m),2.34-2.36(4H,m),2.44(2H,t,J=7.3 Hz),3.62(2H,t,J=7.2 Hz),3.89(2H,s),3.94(2H,s),4.34 (2H,s),7.00(2H,s),7.39(1H,d,J=6.7 Hz),7.40(1H,s),7.76(1H,d,J=8.1 Hz).

EXAMPLE 7-8

Synthesis of 2-(4-dipropylamino-butyl)-5-{[(1H-imidazol-2-ylmethyl)-(1-methyl-1H-imidazol-2-ylmethyl)-amino]-methyl}-2,3-dihydro-isoindol-1-one [Compound No. 7]

The compound (20.3 mg) obtained in Example 7-7 was dissolved in methanol (2.0 ml). The solution was added with 1-methyl-2-imidazole carboxaldehyde (6.8 mg) and sodium cyanoborohydride (6.4 mg). The solution was adjusted to pH 4 by addition of acetic acid, followed by stirring at room temperature for 6 hours. Then, the solution was added with a saturated aqueous sodium hydrogen carbonate solution to stop the reaction and then subjected to extraction with chloroform. After that, the organic layer was washed with water and a saturated saline solution and then dried with anhydrous sodium sulfate. After the solvent was distilled off, the residue was purified through silica gel column chromatography (chloroform/methanol) and treated with hydrochloric acid, thereby obtaining a hydrochloride (24.0 mg) of the subject compound as a pale-yellow solid.

MS(FAB,Pos.):m/z=492[M+H]$^+$
$^1$H-NMR(500 MHz,CDCl$_3$):δ=0.85(6H,t,J=7.4 Hz),1.39-1.52(6H,m),1.65(2H,m),2.33-2.36(4H,m),2.44(2H,t,J=7.4 Hz),3.51(2H,s),3.59(3H,s),3.60(2H,s),3.63(2H,t,J=7.5 Hz),3.77(2H,s),4.37(2H,s),6.90(1H,d,J=1.5 Hz),7.01(1H,d,J=1.2 Hz),7.09(1H,br),7.12(1H,br),7.48(1H,s),7.57(1H,d,J=8.8 Hz),7.82(1H,d,J=7.8 Hz).

EXAMPLE 8

Production Example 8

Synthesis of 2-(4-dipropylamino-butyl)-6-{[(1H-imidazol-2-ylmethyl)-(1-methyl-1H-imidazol-2-ylmethyl)-amino]-methyl}-2,3-dihydro-isoindol-1-one [Compound No. 8]

EXAMPLE 8-1

Synthesis of 2-(4-dipropylamino-butyl)-6-{[(1H-imidazol-2-ylmethyl)-amino]-methyl}-2,3-dihydro-isoindol-1-one The compound (66.1 mg) obtained in Example 7-6 was added with 1 mol/l hydrochloric acid, followed by refluxing under heating for 18 hours. The residue obtained by concentration was dissolved in methanol and added with an anion-exchange resin (Amberlite IRA-410) to adjust the solution to pH 8. The resin was filtrated out and the solvent in the filtrate was distilled off. The residue was dissolved in methanol (2.0 ml) and added with trimethyl orthoformate (0.070 ml) and 2-imidazole carboxaldehyde (28.8 mg) followed by stirring at room temperature for 20 hours. After having been cooled to 0° C., the solution was added with sodium borohydride (22.7 mg) and stirred for 3 hours after having been warmed to room temperature. Then, the solution was added with water to stop the reaction and subjected to extraction with chloroform.

The organic layer was washed with water and a saturated saline solution and dried with anhydrous sodium sulfate. The residue obtained by distilling the solvent off was purified through silica gel column chromatography (chloroform/methanol), thereby obtaining the subject compound (22.9 mg) as a colorless oily substance.

MS(FAB,Pos.):m/z=398[M+H]$^+$
$^1$H-NMR(500 MHz,CDCl$_3$):δ=0.85(6H,t,J=7.3 Hz),1.39-1.52(6H,m),1.65-1.71(2H,m),2.33-2.36(4H,m),2.44(2H,t,J=7.3 Hz),3.64(2H,t,J=7.3 Hz),3.89(2H,s),3.93(2H,s),4.37 (2H,s),7.00(2H,s),7.39(1H,d,J=7.8 Hz),7.46(1H,d,J=7.8 Hz),7.86(1H,s).

EXAMPLE 8-2

Synthesis of 2-(4-dipropylamino-butyl)-6-{[(1H-imidazol-2-ylmethyl)-(1-methyl-1H-imidazol-2-ylmethyl)-amino]-methyl)-2,3-dihydro-isoindol-1-one [Compound No. 8]

The compound (15.1 mg) obtained in Example 8-1 was dissolved in methanol (1.5 ml). The solution was added with 1-methyl-2-imidazole carboxaldehyde (5.0 mg) and sodium cyanoborohydride (4.8 mg). The solution was adjusted to pH 4 by addition of acetic acid, followed by stirring at room temperature for 2.5 hours. Then, the solution was added with a saturated aqueous sodium hydrogen carbonate solution to stop the reaction and then subjected to extraction with chloroform. After that, the organic layer was washed with water and a saturated saline solution and then dried with anhydrous sodium sulfate. After the solvent was distilled off, the residue was purified through silica gel column chromatography (chloroform/methanol) and treated with hydrochloric acid, thereby obtaining a hydrochloride (16.5 mg) of the subject compound as a pale-yellow solid.

MS(FAB,Pos.):m/z=492[M+H]$^+$
$^1$H-NMR(500 MHz,CDCl$_3$):δ=0.85(6H,t,J=7.4 Hz),1.39-1.52(6H,m),1.65-1.71(2H,m),2.33-2.36(4H,m),2.44(2H,t,J=7.3 Hz),3.54(2H,s),3.57(2H,s),3.59-3.63(2H,m),3.61(3H,s),3.76(2H,s),4.37(2H,s),6.88(1H,s),6.89(1H,s),7.01(1H,s),7.02(1H,s),7.41(1H,dd,J=0.6,7.7 Hz),7.59(1H,dd,J=1.6,7.7 Hz),7.94(1H,d,J=0.8 Hz).

EXAMPLE 9

Production Example 9

Synthesis of N-(4-{[(1H-imidazol-2-ylmethyl)-amino]-methyl}-benzyl)-N-methyl-N',N'-dipropyl-butane-1,4-diamine [Compound No. 9]

EXAMPLE 9-1

Synthesis of 4-{[(4-dipropylamino-butyl)-methyl-amino]-methyl}-benzonitrile

The compound (185 mg) obtained in Example 1-2 was dissolved in anhydrous methanol (3.7 ml). The solution was added with 4-formyl benzonitrile (154 mg) and trimethyl orthoformate (0.351 ml) and the whole was stirred at room temperature. After completion of the reaction, the solvent was distilled off. Then, the resultant was added with water and subjected to extraction with chloroform. The extract was dried with magnesium sulfate and the solvent was distilled off under reduced pressure.

The resultant was dissolved in anhydrous methanol (9.2 ml) and added with a 36% formaldehyde aqueous solution (0.134 ml). The solution was added with sodium cyanoborohydride (201 mg) and adjusted to pH 5 by addition of acetic acid, followed by stirring at room temperature for 24 hours. The solution was added with a 1 mol/l sodium hydroxide aqueous solution and subjected to extraction with chloroform. The extract was dried with magnesium sulfate. After the solvent was distilled off under reduced pressure, the residue was purified through silica gel column chromatography (chloroform/ethyl acetate), thereby obtaining the subject compound (296 mg) as a colorless oily substance.

MS(FAB,Pos.):m/z=302[M+H]$^+$ $^1$H-NMR(500 MHz,CDCl$_3$):δ=0.87(6H,t,J=7.3 Hz),1.40-1.51(8H,m),2.17(3H,s),2.33-2.40(8H,m),3.51(2H,s),7.44 (2H,dd,J=0.5,6.6 Hz),7.60(2H,dd,J=2.0,6.6 Hz).

EXAMPLE 9-2

Synthesis of N-(4-{[(1H-imidazol-2-ylmethyl)-amino]-methyl}-benzyl)-N-methyl-N',N'-dipropyl-butane-1,4-diamine [Compound No. 9]

The compound (13.2 g) obtained in Example 9-1 was dissolved in ethanol (530 ml) and a 1 mol/l sodium hydroxide aqueous solution (133 ml) and Raney nickel (1.3 g) were added thereto. The whole was stirred at room temperature for 4 hours under a hydrogen atmosphere.

After completion of the reaction, the resultant was subjected to filtration through Celite and the solvent was distilled off. The resultant was subjected to extraction with chloroform and dried with magnesium sulfate and the solvent was distilled off.

The resultant was dissolved in anhydrous methanol (580 ml) and added with 2-imidazole carboxaldehyde (5.07 g) and trimethyl orthoformate (14.4 ml), followed by stirring at room temperature for 3 hours. The solution was added with sodium borohydride (3.32 g) under ice-cooling, followed by stirring at room temperature for 2 hours. The solution was added with water and the solvent was distilled off, followed by extraction with chloroform. The extract was dried with magnesium sulfate. After the solvent was distilled off under reduced pressure, the residue was purified through silica gel column chromatography (chloroform/methanol) and treated with hydrochloric acid, thereby obtaining a hydrochloride (13.0 g) of the subject compound as a white solid.

MS(FAB,Pos.):m/z=386[M+H]$^+$ $^1$H-NMR(500 MHz,DMSO-d$_6$):δ=0.90(6H,t,J=7.3 Hz), 1.63-1.81(8H,m),2.63(3H,d,J=4.6 Hz),2.94-3.06(8H,m), 4.36(2H,s),4.53(2H,s),7.67-7.71(6H,m),10.39(1H,brs), 11.13(1H,brs).

EXAMPLE 10

Production Example 10

Synthesis of N-methyl-N-[4-({[1-(1-methyl-1H-imidazol-2-ylmethyl)-1H-imidazol-2-ylmethyl]-amino}-methyl)-benzyl-N',N'-dipropylbutane-1,4-diamine [Compound No. 10]

EXAMPLE 10-1

Synthesis of 2-hydroxymethyl-1-methyl imidazole

1-Methyl imidazole (42.1 g) and paraformaldehyde (5.00 g) were stirred under heating at 120° C. for 3 hours.

Paraformaldehyde (13.0 g) was further added thereto and the whole was stirred at 120° C. for 8 hours. The resultant was stirred at 120° C. for additional 3 hours. The resultant was added with isobutyl acetate (40 ml) and the whole was refluxed at 135° C. for 3 hours. The resultant was added with isobutyl acetate (40 ml) and stirred and left for cooling. The resultant was cooled to room temperature and subjected to filtration and washing with ethyl acetate, followed by drying, thereby obtaining the subject compound (36.2 g) as a white solid.

EXAMPLE 10-2

Synthesis of 2-chloromethyl-1-methyl imidazole hydrochloride

The compound (56.1 g) obtained in Example 10-1 was gradually added to thionyl chloride (119 ml) under ice-cooling. After completion of dropping, the whole was refluxed at 65° C. for 15 minutes. Excess thionyl chloride was distilled off under reduced pressure and the solution was further subjected to azeotropic distillation with toluene, thereby obtaining a hydrochloride (82.4 g) of the subject compound as a yellow solid.

EXAMPLE 10-3

Synthesis of N-methyl-N-[4-({[1-(1-methyl-1H-imidazol-2-ylmethyl)-1H-imidazol-2-ylmethyl] amino}-methyl)-benzyl-N',N'-dipropylbutane-1,4-diamine [Compound No. 10]

The compound (39.1 mg) obtained in Example 9-2 was dissolved in DMF (0.80 ml) and added with 60% sodium hydride (12.2 mg) under a nitrogen atmosphere while the whole was stirred under ice-cooling. The solution was warmed back to room temperature. After having been stirred for 30 minutes, the resultant was added with the compound (16.9 mg) obtained in Example 10-2, followed by stirring at room temperature for 3 hours. The solution was added with water (18 μl) under ice-cooling to stop the reaction. After the solvent was distilled off under reduced pressure, the residue was dissolved in chloroform and added with water. The aqueous layer was extracted with chloroform. The organic layer was washed with a saturated saline solution and dried with anhydrous sodium sulfate. After filtration, the solvent was distilled off under reduced pressure. The reside was purified through silica gel column chromatography (chloroform/methanol) and treated with hydrochloric acid, thereby obtaining a hydrochloride (44.0 mg) of the subject compound as a white solid.

MS(FAB,Pos.):m/z=480[M+H]$^+$
$^1$H-NMR(500 MHz,CDCl$_3$):δ=0.86(6H,t,J=7.4 Hz),1.40-1.52(8H,m),2.15(3H,s),2.34(4H,t,J=2.2 Hz),2.37(2H,t,J=5.8 Hz),2.39(2H,t,J=16.5 Hz),3.45(2H,s),3.47(3H,s),3.81(2H,s),3.94(2H,s),6.75(1H,d, J=1.2 Hz),6.86(1H,d,J=1.2 Hz), 6.93(1H,d,J=1.2 Hz),7.01(1H,d,J=1.5 Hz),7.26(2H,s),7.27 (2H,s).

EXAMPLE 11

Production Example 11

Synthesis of [4-(6-{[(1H-imidazol-2-ylmethyl)-(1-methyl-1H-imidazol-2-ylmethyl)-amino]-methyl}-1H-inden-2-yl)-butyl]-dipropyl-amine [Compound No. 11]

EXAMPLE 11-1

Synthesis of 4-(t-butyldiphenylsilyloxy)-butane-1-ol

In DMF (120 ml), 1,4-butanediol (4.0 g) was dissolved. The solution was added with imidazole (3.02 g) and t-butyldiphenylchloro silane (12.2 g), and the whole was stirred at room temperature for 15 hours. The reaction solution was concentrated under reduced pressure and then added with a saturated aqueous ammonium chloride solution, followed by extraction with chloroform. The organic layer was washed with a saturated saline solution and dried with anhydrous sodium sulfate, followed by concentration under reduced pressure. The residue was purified through silica gel column chromatography (hexane/ethyl acetate) thereby obtaining the subject compound (6.56 g) as a colorless oily substance.
$^1$H-NMR(500 MHz,CDCl$_3$):δ=1.05(9H,s),1.63-1.71(4H,m),2.05(1H,t,J=5.1 Hz),3.66(2H,dt,J=5.1,5.9 Hz),3.70(2H,t,J=5.9 Hz),7.37-7.45(6H,m),7.67(4H,d,J=8.5 Hz).

EXAMPLE 11-2

Synthesis of 4-(t-butyldiphenylsilyloxy)butylaldehyde

The compound (6.56 g) obtained in Example 11-1 was dissolved in dichloromethane (262 ml) and then added with Molecular Sieves 4A (32.8 g), N-methylmorpholin-N-oxide (7.02 g), and tetrapropylammonium perruthenate (702 mg) and the whole was stirred at room temperature for 2 hours. The reaction solution was filtrated through Celite and the filtrate was then concentrated under reduced pressure. The residue was purified through silica gel column chromatography (hexane/ethyl acetate), thereby obtaining the subject compound (3.86 g) as a colorless oily substance.

EXAMPLE 11-3

Synthesis of 5-bromo-2-[4-(t-butyldiphenylsilyloxy) butyliden]indan-1-one

In THF (75 ml), 5-bromoindanone (2.50 g) was dissolved. The solution was added with a 1 mol/l lithium bistrimethylsilyl amide/hexane solution (11.8 ml) while being stirred at −78° C., followed by stirring for 30 minutes. Subsequently, a THF solution (15 ml) containing the compound (3.86 g) obtained in Example 11-2 was gradually added to the solution, and the whole was stirred for additional 3 hours. The reaction solution was added with a saturated aqueous ammonium chloride solution and then subjected to extraction with chloroform. The organic layer was dried with anhydrous sodium sulfate and concentrated under reduced pressure. The residue was again dissolved in DMF (75 ml) and then the whole was added with methanesulfonyl chloride (2.71 g) and triethylamine (2.63 g) while being stirred under ice-cooling, followed by heating to room temperature and stirring for 1 hour. Subsequently, the solution was added with 1,8-diazabicyclo[5,4,0]undec-7-ene (3.97 g) and stirred at 70° C. for 1 hour. The reaction solution was concentrated under reduced pressure and the residue was then added with a saturated aqueous ammonium chloride solution, followed by extraction with chloroform. The organic layer was dried with anhydrous sodium sulfate and concentrated under reduced pressure. The residue was purified through silica gel column chromatography (hexane/diethyl ether), thereby obtaining the subject compound (4.56 g) as a brown oily substance.
$^1$H-NMR(500 MHz,CDCl$_3$):δ=1.06(9H,s),1.77(2H,quint.,J=6.1 Hz),2.42(2H,dt,J=6.1,7.6 Hz),3.62(2H,s),3.71 (2H,t,J=7.1 Hz),6.88(1H,t,J=7.6 Hz),7.34-7.44(7H,m),7.54 (1H,d,J=8.3 Hz),7.64(4H,d,J=8.1 Hz),7.71(1H,d,J=8.3 Hz).

EXAMPLE 11-4

Synthesis of 5-bromo-2-[4-(t-butyldiphenylsilyloxy) butyl]indan-1-one

The compound (4.56 g) obtained in Example 11-3 was dissolved in THF (136 ml). Then, the solution was added with a 1 mol/l K-Selectride/THF solution (8.76 ml) while being stirred at −78° C., followed by stirring at the same temperature for 1 hour. The reaction solution was added with a saturated aqueous ammonium chloride solution and then subjected to extraction with chloroform. The organic layer was washed with a saturated saline solution and dried with anhydrous sodium sulfate, followed by concentration under reduced pressure. The residue was purified through silica gel column chromatography (hexane/diethyl ether), thereby obtaining the subject compound (2.03 g) as a yellow oily substance.

EXAMPLE 11-5

Synthesis of 5-bromo-2-[4-(t-butyldiphenylsilyloxy) butyl]indan-1-ol

The compound (2.03 g) obtained in Example 11-4 was dissolved in methanol (61 ml) and THF (31 ml) and added with sodium borohydride (0.442 g) under ice-cooling and the whole was stirred at room temperature for 2 hours. The reaction solution was added with a saturated aqueous ammonium chloride solution and then subjected to extraction with chloroform. The organic layer was dried with anhydrous sodium sulfate and concentrated under reduced pressure. The residue was purified through silica gel column chromatography (hexane/ethyl acetate), thereby obtaining the subject compound (1.54 g) as a yellow oily substance.

EXAMPLE 11-6

Synthesis of [4-(5-bromo-1-methoxymethoxy-1-indan-2-yl)-butoxy]-t-butyldiphenylsilane The compound (1.54 g) obtained in Example 11-5 was dissolved in DMF (46.2 ml) and added with 60% sodium hydride (235 mg) and chloromethylmethylether (592 mg) while the whole was stirred under ice-cooling, followed by stirring at room temperature for 24 hours.

The reaction solution was added with water and subjected to extraction with chloroform. After having been washed with a saturated saline solution, the organic layer was dried with anhydrous sodium sulfate, concentrated under reduced pressure, and dried under vacuum. The residue was purified through silica gel column chromatography (hexane/ethyl acetate), thereby obtaining the subject compound (1.64 g) as a yellow oily substance.

EXAMPLE 11-7

Synthesis of 3-(5-bromo-1-methoxymethoxy-indan-2-yl)butylaldehyde

The compound (1.64 g) obtained in Example 11-6 was dissolved in THF (49.2 ml) and added with a 1 mol/l tetrabutyl ammonium fluoride/THF solution (4.69 ml) and the whole was stirred at room temperature for 3 hours. The reaction solution was concentrated under reduced pressure and added with water, followed by extraction with chloroform. After having been washed with a saturated saline solution, the organic layer was dried with anhydrous sodium sulfate, concentrated under reduced pressure, and dried under vacuum. The residue was dissolved in dichloromethane (41 ml) again. Then, the solution was added with Molecular Sieves 4A (5.15 g), N-methylmorpholin-N-oxide (1.10 g), and tetrapropylammonium perruthenate (109 mg), followed by stirring at room temperature for 1 hour. The reaction solution was filtrated through Celite and the filtrate was then concentrated under reduced pressure. The residue was purified through silica gel column chromatography (hexane/ethyl acetate), thereby obtaining the subject compound (0.574 g) as a pale-yellow oily substance.

EXAMPLE 11-8

Synthesis of 5-bromo-2-(3-dipropylaminobutyl)-1-methoxymethoxy-indane

The compound (574.0 mg) obtained in Example 11-7 was dissolved in 1,2-dichloroethane (28.7 ml), added with di-n-propylamine (266.3 mg) and sodium triacetoxyborohydride (743.6 mg) while the whole was stirred at room temperature, followed by stirring for 20 hours. The reaction solution was added with a 1 mol/l sodium hydroxide aqueous solution and subjected to extraction with chloroform. The organic solvent was washed with a saturated saline solution and then dried with anhydrous sodium sulfate, followed by concentration under reduced pressure. The residue was purified through silica gel column chromatography (chloroform/methanol), thereby obtaining the subject compound (552.4 mg) as a yellow oily substance.

EXAMPLE 11-9

Synthesis of 5-cyano-2-(3-dipropylaminobutyl)-1-methoxymethoxy-indane

The compound (552 mg) obtained in Example 11-8 was dissolved in DMF (1.67 ml) and added with zinc cyanide (94.3 mg) and tetrakistriphenyl phosphine palladium (61.8 mg), followed by stirring at 80° C. for 48 hours. The reaction solution was added with chloroform and washed with a 7% aqueous ammonium solution and a saturated saline solution. The resultant was dried with anhydrous sodium sulfate and concentrated under reduced pressure. The residue was purified through silica gel column chromatography (chloroform/methanol), thereby obtaining the subject compound (436.8 mg) as a yellow oily substance.

EXAMPLE 11-10

Synthesis of 5-aminomethyl-2-(3-dipropylaminobutyl)-1-methoxymethoxy-indane

The compound (436 mg) obtained in Example 11-9 was dissolved in THF (21.8 ml) and added with lithium aluminum hydride (138.7 mg) and the whole was stirred at room temperature for 24 hours. The reaction solution was added with ethyl acetate, methanol, and a 10% aqueous potassium sodium tartrate solution, and the whole was stirred for 1 hour, followed by extraction with chloroform. The extract was washed with a saturated saline solution and then dried with anhydrous sodium sulfate, followed by concentration under reduced pressure. The residue was purified through silica gel column chromatography (chloroform/ethyl acetate), thereby obtaining the subject compound (189.7 mg) as a yellow oily substance.

EXAMPLE 11-11

Synthesis of 2-[2-(4-dipropylaminobutyl)-1-methoxymethoxy-indan-5-ylmethyl]-isoindol-1,3-dione The compound (189 mg) obtained in Example 11-10 was dissolved in DMF (5.6 ml) and added with potassium carbonate (108.5 mg) and carbethoxyphthalimide (172.0 mg) and the whole was stirred at room temperature for 3 hours. The reaction solution was added with water and subjected to extraction with chloroform. The extract was dried with anhydrous sodium sulfate and concentrated under reduced pressure. The residue was purified through silica gel column chromatography (chloroform/methanol), thereby obtaining the subject compound (253 mg) as a yellow oily substance.
MS(FAB,Pos.):m/z=493[M+H]$^+$

EXAMPLE 11-12

Synthesis of 2-[2-(4-dipropylamino-butyl)-3H-inden-5-ylmethyl]-isoindol]-1,3-dione The compound (113.0 mg) obtained in Example 11-11 was dissolved in dioxane (2.2 ml) and the whole was stirred at room temperature for 24 hours. The reaction solution was concentrated under reduced pressure. The residue was dissolved in chloroform and washed with a saturated aqueous sodium hydrogen carbonate solution and then with a saturated saline solution. The resultant was dried with anhydrous sodium sulfate and concentrated under reduced pressure. The residue was purified through silica gel column chromatography (chloroform/methanol), thereby obtaining the subject compound (98.8 mg) as a yellow oily substance.
MS(FAB,Pos.):m/z=449[M+H]$^+$

EXAMPLE 11-13

Synthesis of [4-(6-aminomethyl-1H-inden-2-yl)-butyl]-dipropyl-amine

The compound (82.0 mg) obtained in Example 11-12 was dissolved in methanol (4.1 ml) and added with hydrazine monohydrate (0.082 ml) and the whole was refluxed under heating for 3 hours. The reaction solution was concentrated under reduced pressure. Then, the residue was added with water and subjected to extraction with chloroform. The organic layer was washed with a saturated saline solution, dried with anhydrous sodium sulfate, and concentrated under reduced pressure. The residue was purified through silica gel column chromatography (chloroform/ethyl acetate), thereby obtaining the subject compound (40.1 mg) as a yellow oily substance.

MS(FAB,Pos.):m/z=301[M+H]$^+$

EXAMPLE 11-14

Synthesis of [4-(6-{[(1H-imidazol-2-ylmethyl)-amino]-methyl}-1H-inden-2-yl)-butyl]-dipropyl-amine The compound (40.1 mg) obtained in Example 11-13 was dissolved in methanol (2.0 ml) and added with 2-imidazole carboxaldehyde (19.2 mg) and trimethyl orthoformate (42.5 mg) and the whole was stirred at room temperature for 30 minutes. Subsequently, the solution was added with sodium borohydride (15.1 mg) under ice-cooling, followed by stirring at room temperature for additional 30 minutes. The reaction solution was concentrated under reduced pressure. The residue was added with water, and extracted with chloroform. The organic layer was washed with a saturated saline solution and dried with anhydrous sodium sulfate, followed by concentration under reduced pressure. The residue was purified through silica gel column chromatography (chloroform/methanol), thereby obtaining the subject compound (27.3 mg) as a yellow oily substance.

MS(FAB,Pos.):m/z=380[M+H]$^+$

EXAMPLE 11-15

Synthesis of [4-(6-{[(1H-imidazol-2-ylmethyl)-(1-methyl-1H-imidazol-2-ylmethyl)-amino]-methyl}-1H-inden-2-yl)-butyl]-dipropyl-amine [Compound No. 11]

The compound (27.3 mg) obtained in Example 11-14 was dissolved in methanol (1.37 ml) and added with sodium cyanoborohydride (9.0 mg) and 1-methyl-2-imidazole carboxaldehyde (11.8 mg). The solution was adjusted to pH 4 by addition of acetic acid, followed by stirring at room temperature for 3 hours. Then, the reaction solution was concentrated under reduced pressure. The residue was dissolved in chloroform, washed with a saturated aqueous sodium hydrogen carbonate solution, and dried with anhydrous sodium sulfate, followed by concentration under reduced pressure. The residue was purified through silica gel column chromatography (chloroform/ethyl acetate) and treated with hydrochloric acid, thereby obtaining a hydrochloride (31.5 mg) of the subject compound as a white solid.

MS(FAB,Pos.):m/z=475[M+H]$^+$ $^1$H-NMR(500 Mz, DMSO-d$_6$+D$_2$O):δ=0.90(6H,t,J=7.3 Hz),1.60-1.68(8H, m),2.96-3.31(8H,m),3.69(5H,m),4.01-4.15(6H,m),6.52(1H,s),7.05-7.62(7H,m).

EXAMPLE 12

Production Example 12

Synthesis of 1-(4-dipropylaminobutyl)-3-(4-{[(1H-imidazol-2-ylmethyl)-(1-methyl-1H-imidazol-2-ylmethyl)-amino]-methyl}-phenyl)-urea [Compound No. 12]

EXAMPLE 12-1

Synthesis of 1-(4-cyano-phenyl)-3-(4-dipropylaminobutyl)-urea

The compound (581.4 mg) obtained in Example 1-2 was dissolved in anhydrous toluene (17 ml) and then added with 4-vinylidene aminobenzonitrile (manufactured by Aldrich Corporation) (485.7 mg) and the whole was stirred at room temperature for 1.5 hours. After completion of the reaction, the solvent was distilled off. The residue was purified through silica gel column chromatography (chloroform/ethyl acetate), thereby obtaining the subject compound (478 mg) as a yellow oily substance.

MS(FAB,Pos.):m/z=317[M+H]$^+$ $^1$H-NMR(500 MHz,CDCl$_3$):δ=0.88(6H,t,J=7.3 Hz),1.43-1.59(8H,m),2.37-2.44(6H,m),3.25(2H,dd,J=6.1,11.2 Hz),6.06(1H,br),6.90(1H,br),7.48(2H,d,J=8.8 Hz),7.54(2H,d,J=8.8 Hz).

EXAMPLE 12-2

Synthesis of 1-(4-aminomethylmethylphenyl)-3-(4-dipropylaminobutyl)-urea

The compound (466.4 mg) obtained in Example 12-1 was dissolved in anhydrous THF (14 ml) and the whole was cooled with ice. Lithium aluminum hydride (223.1 mg) was added thereto and the whole was stirred at room temperature for 2.5 hours. After the reaction has been stopped by addition of ethyl acetate, an aqueous potassium sodium tartrate solution was added thereto and the whole was stirred, followed by extraction with chloroform. The extract was washed with a saturated saline solution and dried with magnesium sulfate. The solvent was distilled off and the residue was purified through silica gel column chromatography (chloroform/methanol), thereby obtaining the subject compound (195 mg) as a yellow oily substance.

MS(FAB,Pos.):m/z=321[M+H]$^+$

EXAMPLE 12-3

Synthesis of 1-(4-dipropylaminobutyl)-3-(4-{[(1H-imidazol-2-ylmethyl)-amino]-methyl}-phenyl)-urea The compound (195.6 mg) obtained in Example 12-2 was dissolved in anhydrous methanol (7.8 ml) and added with 2-imidazole carboxaldehyde (88.4 mg) and trimethyl orthoformate (0.200 ml) and the whole was stirred at room temperature for 14 hours. Then, the solution was added with sodium borohydride (69.2 mg) and stirred at room temperature for 1.5 hours. After completion of the reaction, the solvent was distilled off under reduced pressure. The resultant was added with water and subjected to extraction with chloroform. The extract was washed with a saturated saline solution and dried with magnesium sulfate. The solvent was distilled off and the residue was purified through silica gel column chromatography (chloroform/methanol), thereby obtaining the subject compound (101 mg) as a colorless oily substance.

MS(FAB,Pos.):m/z=401[M+H]$^+$

EXAMPLE 12-4

1-(4-dipropylaminobutyl)-3-(4-{[(1H-imidazol-2-ylmethyl)-(1-methyl-1H-imidazol-2-ylmethyl)-amino]-methyl}-phenyl)-urea [Compound No. 12]

The compound (101 mg) obtained in Example 12-3 was dissolved in anhydrous methanol (4.0 ml) and added with 1-methyl-2-imidazole carboxaldehyde (41.8 mg) and sodium cyanoborohydride (47.1 mg). The solution was adjusted to pH 5 by addition of acetic acid, followed by stirring at room temperature for 20 hours. After completion of the reaction, the solvent was distilled off. The resultant was added with a 1 mol/l sodium hydroxide aqueous solution and subjected to extraction with chloroform. The extract was dried with magnesium sulfate and the solvent was distilled off. The residue was purified through silica gel column chromatography (chloroform/ethyl acetate) and treated with hydrochloric acid, thereby obtaining a hydrochloride (80.3 mg) of the subject compound as a white solid.

MS(FAB,Pos.):m/z=495[M+H]$^+$
$^1$H-NMR(500 MHz,DMSO-d$_6$):δ=0.89(6H,t,J=7.3 Hz), 1.46(2H,quint.,J=6.9 Hz),1.63-1.69(6H,m),2.94-2.99(4H, m),3.01-3.06(2H,m),3.09(2H,m),3.57(2H,s),3.69(3H,s), 4.04(2H,s),4.11(2H,s),6.64(1H,br), 7.20(2H,d,J=8.7 Hz), 7.30(2H,d,J=8.7 Hz),7.55(2H,dd,J=2.0,6.4 Hz),7.64(2H,s), 9.01(1H,brs),10.09(1H,br),14.67-14.74(2H,br).

EXAMPLE 13

Production Example 13

Synthesis of [4-(6-{[(1H-imidazol-2-ylmethyl)-(1-methyl-1H-imidazol-2-ylmethyl)-amino]-methyl}-1-methyl-1H-benzimidazol-2-yl)-butyl]-dipropyl-amine [Compound No. 13]

EXAMPLE 13-1

Synthesis of 4-amino-3-(5-t-butoxycarbonylamino-pentanoylamino)-benzoic acid methyl ester In DMF (20 ml), 5-t-butoxycarbonylamino valeric acid (manufactured by Aldrich Corporation) (1.45 g), WSCI hydrochloride (1.74 g), and HOBt (1.25 g) were dissolved and the whole was stirred for 15 minutes. Then, the solution was added with methyl 3,4-diaminobenzoate (1.00 g) and stirred at room temperature for 4 hours. After completion of the reaction, the solvent was distilled off under reduced pressure. The residue was dissolved in chloroform and then washed with a saturated aqueous ammonium chloride solution and a 1 mol/l sodium hydroxide aqueous solution. Subsequently, the resultant was subjected to extraction with chloroform and the extract was then washed with a saturated saline solution, followed by drying with anhydrous sodium sulfate. After filtration, the solvent was distilled off under reduced pressure. The residue was purified through silica gel column chromatography (chloroform/ethyl acetate), thereby obtaining the subject compound (1.46 g).

MS(FAB,Pos.):m/z=365[M+H]$^+$

EXAMPLE 13-2

Synthesis of 2-(4-amino-butyl)-3-methyl-3H-benzimidazol-5-carboxylic acid methyl ester The compound (366 mg) obtained in Example 13-1 was dissolved in DMF (7.0 ml) and then added with 60% sodium hydride (44.3 mg) and the whole was stirred for 1 hour. Subsequently, methyl iodide (222 μl) was gradually added thereto and the whole was stirred at room temperature for 2 hours. After completion of the reaction, the solvent was distilled off under reduced pressure and the residue was dissolved in chloroform. The resultant was washed with saturated sodium hydrogen carbonate and subjected to extraction with chloroform. After having been washed with a saturated saline solution, the extract was dried with anhydrous sodium sulfate. After filtration, the solvent was distilled off under reduced pressure.

The resultant was dissolved in methanol (5.0 ml) and added with a 4 mol/l hydrogen chloride/dioxane solution (5.0 ml), followed by stirring at room temperature for 2 hours. After completion of the reaction, the solvent was distilled off under reduced pressure. Then, the residue was dissolved in chloroform and washed with a 1 mol/l sodium hydroxide aqueous solution, followed by extraction with chloroform. The extract was washed with a saturated saline solution and dried with anhydrous sodium sulfate. After filtration, the solvent was distilled off under reduced pressure, thereby obtaining the subject compound (218.9 mg) as a pale-brown oily substance.

MS(FAB,Pos.):m/z=262[M+H]$^+$

EXAMPLE 13-3

Synthesis of 2-(4-dipropylamino-butyl)-3-methyl-3H-benzimidazol-5-carboxylic acid methyl ester The compound (219 mg) obtained in Example 13-2 was dissolved in methanol (4.2 ml). The solution was added with acetic acid (200 μl), sodium cyanoborohydride (170.9 mg), and gradually added with propionaldehyde (180 μl) and the whole was stirred at room temperature for 2 hours. After completion of the reaction, the solvent was distilled off under reduced pressure. Then, the residue was dissolved in chloroform and washed with a 1 mol/l sodium hydroxide aqueous solution, followed by extraction with chloroform. The organic layer was washed with a saturated saline solution and then dried with anhydrous sodium sulfate. After filtration, the solvent was distilled off under reduced pressure, thereby obtaining the subject compound (305 mg) as a brown oily substance.

MS(FAB,Pos.):m/z=346[M+H]$^+$
$^1$H-NMR(500 MHz,DMSO-d$_6$):δ=0.82(6H,t,J=7.3 Hz), 1.37(4H,sext.,J=7.3 Hz),1.51(4H,quint.,J=7.3 Hz),1.78(4H, quint.,J=7.6 Hz),2.26-2.37(4H,br),2.40-2.49(2H,br),2.89-2.94(2H,m),3.81(3H,s),3.88(3H,s),7.62(1H,d,J=8.3 Hz), 7.80(1H,d,J=8.3 Hz),8.13(1H,s).

EXAMPLE 13-4

Synthesis of [2-(4-dipropylamino-butyl)-3-methyl-3H-benzimidazol-5-yl]-methanol

Lithium aluminum hydride (120 mg) was suspended in THF (3.0 ml) and then cooled to 0° C. After that, a solution of the compound (305 mg) obtained in Example 13-3 in THF (4.5 ml) was dropped in the suspension. The whole was warmed back to room temperature and stirred for 2 hours.

47

After completion of the reaction, sodium sulfate decahydrate was gradually added to the solution until bubbling was stopped, and a 1 mol/l sodium hydroxide aqueous solution was then added to the mixture until a white precipitate was generated. Solid matter was separated by filtration and the solvent was then distilled off from the filtrate under reduced pressure. The residue was purified through silica gel column chromatography (chloroform/ethyl acetate), thereby obtaining the subject compound (246 mg) as a brown oily substance.

MS(FAB,Pos.):m/z=318[M+H]$^+$

EXAMPLE 13-5

Synthesis of 2-[2-(4-dipropylamino-butyl)-3-methyl-3H-benzimidazol-5-ylmethyl]-isoindol-1,3-dione The compound (245 mg) obtained in Example 13-4 was dissolved in chloroform (5.0 ml). The solution was added with methanesulfonyl chloride (177 mg) and triethylamine (107 μl), followed by stirring at room temperature for 2 hours. Then, lithium chloride (65.2 mg) was added thereto and the whole was stirred overnight. After completion of the reaction, the solution was washed with a saturated aqueous sodium hydrogen carbonate solution and subjected to extraction with chloroform. The organic layer was washed with a saturated saline solution and then dried with anhydrous sodium sulfate. The solvent was distilled off.

The resultant was dissolved in DMF (3.0 ml) and added with potassium phthalimide (164 mg), followed by stirring at room temperature for 3 days.

After completion of the reaction, the solvent was distilled off under reduced pressure. The residue was dissolved in chloroform and washed with water, followed by extraction with chloroform. The organic layer was washed with a saturated saline solution and dried with anhydrous sodium sulfate.

After filtration, the solvent was distilled off under reduced pressure. The residue was purified through silica gel column chromatography (chloroform/methanol/water), thereby obtaining the subject compound (232 mg) as a pale-yellow solid.

MS(FAB,Pos.):m/z=447[M+H]$^+$

EXAMPLE 13-6

Synthesis of [4-(6-aminomethyl-1-methyl-1H-benzimidazol-2-yl)-butyl]-dipropyl-amine The compound (232 mg) obtained in Example 13-5 was dissolved in a 40% methylamine/methanol solution (3.0 ml) and the whole was stirred at room temperature for 20 hours. After completion of the reaction, the solvent was distilled off under reduced pressure. The residue was dissolved in chloroform and then washed with a 1 mol/l sodium hydroxide aqueous solution, followed by extraction with chloroform. The organic layer was washed with a saturated saline solution and then dried with anhydrous sodium sulfate. After filtration, the solvent was distilled off under reduced pressure. The residue was purified through silica gel column chromatography (chloroform/methanol/water), thereby obtaining the subject compound (17.0 mg) as a pale-yellow oily substance.

MS(FAB,Pos.):m/z=317[M+H]$^+$

48

EXAMPLE 13-7

Synthesis of [4-(6-{[(1H-imidazol-2-ylmethyl)-(1-methyl-1H-imidazol-2-ylmethyl)-amino]-methyl}-1-methyl-1H-benzimidazol-2-yl)-butyl]-dipropylamine [Compound No. 13]

The compound (17.0 mg) obtained in Example 13-6 was dissolved in methanol (0.5 ml) and added with trimethyl orthoformate (20 μl) and 2-imidazole carboxaldehyde (6.4 mg) and the whole was stirred at room temperature for 1 hour. After having been cooled to 0° C., the solution was added with sodium borohydride (6.0 mg) and warmed back to room temperature, followed by stirring for 30 minutes. After completion of the reaction, the solvent was distilled off under reduced pressure. The residue was then dissolved in chloroform and washed with a saturated aqueous sodium hydrogen carbonate solution, followed by extraction with chloroform. The organic layer was washed with a saturated saline solution and then dried with anhydrous sodium sulfate. After filtration, the solvent was distilled off under reduced pressure.

The resultant was dissolved in methanol (1.0 ml). The solution was added with 1-methyl-2-imidazole carboxaldehyde (18.0 mg), acetic acid (20 μl), and sodium cyanoborohydride (12.5 mg) and the whole was stirred at room temperature for 1 hour. After completion of the reaction, the solvent was distilled off under reduced pressure. Then, the residue was dissolved in chloroform and washed with a saturated aqueous sodium hydrogen carbonate solution, followed by extraction with chloroform. The organic layer was washed with a saturated saline solution and then dried with anhydrous sodium sulfate. After filtration, the solvent was distilled off under reduced pressure. Then, the residue was purified through silica gel column chromatography (chloroform/methanol) and treated with hydrochloric acid, thereby obtaining a hydrochloride (19.2 mg) of the subject compound as a pale-yellow solid.

MS(FAB,Pos.):m/z=491[M+H]$^+$ $^1$H-NMR(500 MHz,DMSO-d$_6$):δ=0.91(6H,t,J=7.3 Hz), 1.67-1.71(4H,m),1.76-1.86(2H,m),1.87-1.96(2H,m),2.96-3.04(2H,m),3.08-3.14(2H,m),3.25(2H,t,J=7.3 Hz),3.74(3H,s),3.89(2H,s),4.07(3H,s),4.13(2H,s),4.21(2H,s),7.51-7.54 (3H,m),7.63(2H,s),7.68(1H,d,J=8.4 Hz),8.29(1H,s).

EXAMPLE 14

Production Example 14

Synthesis of 3-(3-dipropylaminopropyl)-8-{[(1H-imidazol-2-ylmethyl)-(1-methyl-1H-imidazol-2-ylmethyl)-amino]-methyl}-3,4-dihydro-1H-benzo[e][1,4]diazepin-2,5-dione [Compound No. 14]

EXAMPLE 14-1

Synthesis of 2-[5-t-butoxycarbonylamino-2-(9H-fluoren-9-ylmethoxycarbonyl amino)-pentanoylamino]-terephthalic acid dimethyl ester In anhydrous pyridine (30 ml), 2-amino-terephthalic acid dimethyl ester (manufactured by Merck Ltd.) (1.46 g) and 5-t-butoxycarbonylamino-2-(9H-fluoren-9-ylmethoxycarbonylamino)-valeric acid (manufactured by Watanabe Chemical Industries, Ltd.) (3.18 g) were dissolved. The whole was cooled to −15° C. and added with phosphorus oxychloride (0.718 ml), followed by stirring at room temperature for 1 hour. After completion of the reaction, the whole was poured in ice-cold water and subjected to extraction with ethyl acetate. The extract was washed with a saturated aqueous sodium hydrogen carbonate solution and a saturated saline solution and dried with magnesium sulfate. After the solvent was distilled off, the resultant was subjected to azeotropic distillation with toluene. The residue was purified through silica gel column chromatography (chloroform/ethyl acetate), thereby obtaining the subject compound (3.33 g) as a white crystal.

MS(FAB,Pos.):m/z=646[M+H]$^+$
$^1$H-NMR(500 MHz,CDCl$_3$):δ=1.44(9H,s),1.62-1.64(2H,m),1.79-1.84(1H,m),2.06-2.18(1H,m),3.20-3.21(2H,br),3.83(3H,s),3.95(3H,s),4.28(1H,t,J=7.1 Hz),4.37(1H,t,J=7.3 Hz),4.43(1H,d,J=5.1 Hz),4.52(1H,dd,J=6.8,10.4 Hz),5.21 (1H,d,J=6.3 Hz),7.32(2H,t,J=6.1 Hz),7.40(2H,t,J=7.6 Hz),7.66(2H,d,J=7.3 Hz),7.70(2H,d,J=7.3 Hz),7.77(3H,d,J=7.8 Hz),8.10(1H,d,J=8.3 Hz),9.32(1H,s),11.56(1H,s).

EXAMPLE 14-2

Synthesis of 2-(2-amino-5-t-butoxycarbonylamino-pentanoylamino)-terephthalic acid dimethyl ester The compound (236.0 mg) obtained in Example 14-1 was dissolved in anhydrous DMF (4.7 ml) and added with diethylamine (4.7 ml) and the whole was stirred at room temperature for 1 hour. After completion of the reaction, the solvent was distilled off under reduced pressure. The residue was purified through silica gel column chromatography (chloroform/methanol), thereby obtaining the subject compound (194.7 mg) as a colorless viscous solid.

MS(FAB,Pos.):m/z=424[M+H]$^+$
$^1$H-NMR(500 MHz,CDCl$_3$):δ=1.43(9H,s),1.64-1.72(4H,m),3.17-3.19(2H,m),3.58-3.61(1H,m),3.94(3H,s),3.97(3H,s),7.76(1H,dd,J=1.7,8.3 Hz),8.02(1H,s),8.11(1H,d,J=8.1 Hz),9.41(1H,s),12.08(1H,s).

EXAMPLE 14-3

Synthesis of 3-(3-t-butoxycarbonylamino-propyl)-2,5-dioxo-2,3,4,5-tetrahydro-1H-benzo[e][1,4]diazepin-8-carboxylic acid ethyl ester The compound (303.8 mg) obtained in Example 14-2 and sodium t-butoxide (manufactured by Wako Pure Chemical Industries, Ltd.) (138.4 mg) were dissolved in anhydrous THF (6.0 ml) and the whole was stirred at 60° C. for 15 hours. After completion of the reaction, water was added thereto and the whole was subjected to extraction with chloroform.

The extract was dried with magnesium sulfate and the solvent was distilled off under reduced pressure. The residue was purified through silica gel column chromatography (chloroform/ethyl acetate), thereby obtaining the subject compound (36.6 mg) as a white solid.

MS(FAB,Pos.):m/z=392[M+H]$^+$
$^1$H-NMR(500 MHz,CDCl$_3$):δ=1.41(9H,s),1.43(1H,br),1.65-1.82(2H,m), 2.05-2.11(1H,m),3.18(2H,d,J=6.6 Hz),3.77(1H,d,J=6.1 Hz),3.96(3H,s),4.88(1H,brs),7.13(1H,brs),7.73(1H,s),7.90(1H,dd,J=1.5,8.0 Hz),8.04(1H,d,J=8.3 Hz),8.66(1H,brs).

EXAMPLE 14-4

Synthesis of [3-(8-hydroxymethyl-2,5-dioxo-2,3,4,5-tetrahydro-1H-benzo[e][1,4]diazepin-3-yl)-propyl]-carbamic acid t-butyl ester The compound (35.1 mg) obtained in Example 14-3 was dissolved in anhydrous THF (1.0 ml) and added with Lithium aluminum hydride (6.8 mg) and the whole was stirred at room temperature for 30 minutes. After completion of the reaction, an aqueous potassium sodium tartrate solution was added thereto and the whole was vigorously stirred at room temperature, followed by extraction with chloroform. The extract was dried with magnesium sulfate and the solvent was distilled off. The residue was purified through silica gel column chromatography (chloroform/methanol) thereby obtaining the subject compound (16.9 mg) as a white solid.

MS(FAB,Pos.):m/z=364[M+H]$^+$
$^1$H-NMR(500 MHz,CDCl$_3$):δ=0.90(1H,d,J=6.3 Hz),1.42 (9H,s),1.62(2H,br),2.03-2.05(1H,m),3.14-3.15(2H,m),3.68 (1H,dd,J=5.6,11.7 Hz),4.70(2H,t,J=3.9 Hz),6.87-6.96(1H, m),7.04(1H,d,J=6.6 Hz),7.11(1H,d,J=7.3 Hz),7.83(1H,d, J=8.1 Hz),8.94(1H,br).

EXAMPLE 14-5

Synthesis of 3-(3-dipropylaminopropyl)-8-hydroxymethyl-3,4-dihydro-1H-benzo[e][1,4]diazepin-2,5-dione The compound (224 mg) obtained in Example 14-4 was dissolved in methanol (2.2 ml) and added with a 4 mol/l hydrogen chloride/dioxane solution (2.2 ml), and the whole was stirred at room temperature for 1 hour. After completion of the reaction, the solvent was distilled off under reduced pressure. The resultant was treated with an anion-exchange resin (Amberlite IRA-410).

The resultant was dissolved in anhydrous methanol (5.1 ml) and added with propionaldehyde (0.104 ml), trimethyl orthoformate (0.158 ml), and sodium cyanoborohydride (121 mg) and the whole was stirred at room temperature for 21 hours.

After completion of the reaction, the solvent was distilled off under reduced pressure. The resultant was added with water and subjected to extraction with chloroform. The extract was dried with magnesium sulfate. The solvent was distilled off and the residue was purified through silica gel column chromatography (chloroform/ethyl acetate), thereby obtaining the subject compound (36.0 mg) as a yellow oily substance.

MS(FAB,Pos.):m/z=348[M+H]$^+$

EXAMPLE 14-6

Synthesis of 2-(1-methyl-1H-imidazol-2-ylmethyl)-isoindol-1,3-dione

The compound (83.50 g) obtained in Example 10-2 was suspended in DMF (250 ml) and added with sodium t-butoxide (49.00 g) at −30° C. The solution was further added with a potassium phthalimide salt (95.0 g) and then the whole was stirred at 70° C. for 2 hours. After completion of the reaction, the resultant was added into water (800 ml). The precipitated crystal was filtrated, washed with water, and dried, thereby obtaining the subject compound (101.5 g) as a white solid.

EXAMPLE 14-7

Synthesis of C-(1-methyl-1H-imidazol-2-yl)-methylamine

The compound (5.89 g) obtained in Example 14-6 was suspended in methanol (118 ml) and added with hydrazine monohydrate (1.89 ml), and the whole was refluxed under heating for 2.5 hours. After the solution was left for cooling, the precipitate was filtrated through Celite and the filtrate was distilled off under reduced pressure, thereby obtaining the subject compound (898.5 mg) as a yellow oily substance.

MS(EI):m/z=111[M]$^+$ $^1$H-NMR(500 MHz,CDCl$_3$):δ=1.99(2H,br),3.63(3H,s),3.90(2H,s),6.81 (1H,d,J=1.2 Hz),6.92(1H,d,J=1.2 Hz).

EXAMPLE 14-8

Synthesis of 3-(3-dipropylaminopropyl)-8-{[(1H-imidazol-2-ylmethyl)-(1-methyl-1H-imidazol-2-ylmethyl)-amino]-methyl}-3,4-dihydro-1H-benzo[e][1,4]diazepin-2,5-dione [Compound No. 14]

The compound (36.0 mg) obtained in Example 14-5 was dissolved in chloroform (0.6 ml) and added with manganese dioxide (chemically processed product) (180 mg), and the whole was stirred at room temperature for 3 hours. After completion of the reaction, the solution was filtrated through Celite and the solvent was distilled off. The resultant was dissolved in anhydrous methanol (1.4 ml) and added with the compound (16.7 mg) obtained in Example 14-7 and trimethyl orthoformate (0.033 ml), and the whole was stirred at room temperature for 16 hours. Sodium borohydride (11.3 mg) was added thereto and the whole was stirred at room temperature for 4 hours, followed by addition of water. The solvent was distilled off under reduced pressure, followed by extraction with chloroform. The extract was dried with magnesium sulfate and the solvent was distilled off under reduced pressure. The resultant was dissolved in anhydrous methanol (1.2 ml) and added with 2-imidazole carboxaldehyde (14.4 mg) and sodium cyanoborohydride (18.9 mg). The solution was adjusted to pH 5 with acetic acid and stirred at room temperature for 2 days. After completion of the reaction, the solvent was distilled off. The resultant was added with a 1 mol/l sodium hydroxide aqueous solution and subjected to extraction with chloroform, followed by drying with magnesium sulfate. The solvent was distilled off. The residue was purified through silica gel column chromatography (chloroform/methanol) and treated with hydrochloric acid, thereby obtaining a hydrochloride (19.4 mg) of the subject compound as a white solid.

MS(FAB,Pos.):m/z=521[M+H]$^+$ $^1$H-NMR(500 MHz,DMSO-d$_6$+D$_2$O):δ=0.87-0.90(6H,m),1.61-1.64(4H,m),1.79-1.83(4H,m),2.96-3.00(4H,m),3.07-3.08(2H,m),3.76(3H,s),4.03(1H,br),4.10(2H,br),4.24(4H,s),7.53-7.55(1H,m),7.61-7.63(4H,m),7.65(2H,s).

EXAMPLE 15

Production Example 15

Synthesis of 4-{[(3,5-dimethyl-pyridin-2-ylmethyl)-(1-methyl-1H-imidazol-2-ylmethyl)-amino]-methyl}-N-(4-dipropylaminomethyl-phenyl)-benzamide [Compound No. 15]

EXAMPLE 15-1

Synthesis of (4-nitro-benzyl)-dipropyl-amine

4-Nitrobenzylamine hydrochloride was subjected to desalting, thereby obtaining a free compound (3.94 g). The free compound was dissolved in anhydrous methanol (80 ml) and added with sodium cyanoborohydride (5.88 g), trimethyl orthoformate (7.18 ml), and propionaldehyde (4.67 ml), and the whole was stirred at room temperature for 2 hours under a nitrogen atmosphere. After completion of the reaction, the solvent was distilled off. The resultant was dissolved in chloroform and added with a saturated aqueous sodium hydrogen carbonate solution, and the whole was stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off, and the residue was purified through silica gel column chromatography (hexane/ethyl acetate), thereby obtaining the subject compound (2.61 g) as a yellow oily substance.

MS(FAB,Pos.):m/z=237[M+H]$^+$

EXAMPLE 15-2

Synthesis of 4-dipropylaminomethyl-aniline

The compound (2.61 g) obtained in Example 15-1 was dissolved in methanol (25 ml). The solution was added with THF (13 ml), activated carbon (261 mg), and iron trichloride hexahydrate (26.1 mg) and the whole was refluxed for 30 minutes. After having been cooled to room temperature, the solution was added with hydrazine monohydrate (1.88 ml) and then the whole was refluxed for 3 hours. After completion of the reaction, the resultant was subjected to filtration through Celite. The filtrate was subjected to extraction with chloroform and washed with distilled water and a saturated saline solution. The organic layer was dried with anhydrous sodium sulfate and the solvent was distilled off. The residue was purified through silica gel column chromatography (chloroform/ethyl acetate), thereby obtaining the subject compound (865 mg) as a yellow oily substance.

MS(FAB,Pos.):m/z=207[M+H]$^+$

EXAMPLE 15-3

Synthesis of [4-(4-dipropylaminomethyl-phenylcarbamoyl)-benzyl]-carbamic acid t-butyl ester Commercially available 4-(t-butoxycarbonylamino-methyl)-benzoic acid (manufactured by Watanabe Chemical Industries, Ltd.) (1.16 g) was dissolved in chloroform (20 ml) and then added with WSCI hydrochloride (1.21 g), HOBt (963 mg), and the compound (865 mg) obtained in Example 15-2, and the whole was stirred overnight at room temperature. After completion of the reaction, a 1 mol/l sodium hydroxide aqueous solution was added thereto and the whole was stirred for a while. The solution was subjected to extraction with chloroform and washed with a saturated aqueous ammonium chloride solution, a saturated aqueous sodium hydrogen carbonate solution, and a saturated saline solution. The organic layer was dried with anhydrous sodium sulfate and the solvent was distilled off. The residue was then purified through silica gel column chromatography (chloroform/methanol), thereby obtaining the subject compound (545 mg) as a yellow solid.

MS(FAB,Pos.):m/z=440[M+H]$^+$

EXAMPLE 15-4

Synthesis of 4-aminomethyl-N-(4-dipropylaminomethyl-phenyl)-benzamide

The compound (545 mg) obtained in Example 15-3 was dissolved in anhydrous methanol (10 ml) and added with a 4 mol/l hydrogen chloride/dioxane solution (10.0 ml), and the whole was stirred at room temperature for 1 hour. After completion of the reaction, the solvent was distilled off. The resultant was added with a 1 mol/l sodium hydroxide aqueous solution and subjected to extraction with chloroform, followed by washing with a saturated saline solution. The organic layer was dried with anhydrous sodium sulfate and the solvent was distilled off, thereby obtaining the subject compound (389 mg) as a colorless crystal.
MS(FAB,Pos.):m/z=340[M+H]$^+$

EXAMPLE 15-5

Synthesis of N-(4-dipropylaminomethyl-phenyl)-4-{[(1-methyl-1H-imidazol-2-ylmethyl)amino]methyl}-benzamide The compound (389 mg) obtained in Example 15-4 was dissolved in anhydrous methanol (10 ml) and then added with trimethyl orthoformate (188 μl) and 2-imidazole carboxaldehyde (139 mg). The whole was stirred overnight at room temperature under a nitrogen atmosphere. Then, sodium borohydride (43.4 mg) was added thereto in an ice bath and the whole was stirred at room temperature for 2.5 hours. After completion of the reaction, distilled water was added thereto and the whole was stirred for a while. The solution was subjected to extraction with chloroform and washed with a saturated saline solution. The organic layer was dried with anhydrous sodium sulfate and the solvent was then distilled off. The residue was purified through silica gel column chromatography (chloroform/ethyl acetate), thereby obtaining the subject compound (346 mg) as a yellow solid.
MS(FAB,Pos.):m/z=440[M+H]$^+$

EXAMPLE 15-6

Synthesis of 3,5-dimethyl-pyridine-2-carboxaldehyde

In dichloromethane (15.0 ml), 2,3,5-trimethyl-pyridine (manufactured by Tokyo Kasei Kogyo Co., Ltd.) (1.29 g) was dissolved. After having been cooled to 0° C., the reaction solution was added with m-chloroperbenzoic acid (2.53 g), followed by stirring at room temperature for 1.5 hours. The reaction solution was added with a 1 mol/l sodium hydroxide aqueous solution and then subjected to extraction with chloroform. Subsequently, the organic layer was washed with a saturated saline solution and dried with anhydrous sodium sulfate. The drying agent was filtrated out and the solvent was then distilled off, followed by dissolving the resultant residue in dichloromethane (25.0 ml). The reaction solution was added with trifluoroacetic anhydride (2.8 ml) and the whole was refluxed under heating for 3.5 hours. After the reaction solution was cooled to room temperature, the solvent was distilled off. The resultant residue was dissolved in methanol (60.0 ml). After having been cooled to 0° C., the reaction solution was added with a 12.5% sodium methoxide/methanol solution to adjust the solution to pH 10, and the whole was stirred at room temperature for 16.5 hours. After the solvent was distilled off, the residue was added with distilled water and subjected to extraction with chloroform. The organic layer was washed with a saturated saline solution and dried with anhydrous sodium sulfate. The drying agent was filtrated out and the solvent was then distilled off, followed by dissolving the residue in chloroform (30.0 ml). The reaction solution was added with manganese dioxide (chemically processed product) (6.10 g) and then stirred at room temperature for 18 hours. The reaction solution was filtrated through Celite. The solvent in the filtrate was distilled off and the resultant residue was then purified through silica gel column chromatography (chloroform/ethyl acetate), thereby obtaining the subject compound (1.14 g) as a yellow oily substance.
MS(FAB,Pos.):m/z=136[M+H]$^+$
$^1$H-NMR(500 MHz,CDCl$_3$):δ=2.40(3H,s),2.63(3H,s),7.43(1H,brs),8.4 8(1H,brs),10.16(1H,s).

EXAMPLE 15-7

Synthesis of 4-{[(3,5-dimethyl-pyridin-2-ylmethyl)-(1-methyl-1H-imidazol-2-ylmethyl)-amino]-methyl}-N-(4-dipropylaminomethyl-phenyl)-benzamide [Compound No. 15]

The compound (155 mg) obtained in Example 15-5 was dissolved in anhydrous methanol (3.0 ml) and added with sodium cyanoborohydride (33.7 mg), acetic acid (0.50 ml), and the compound (58.0 mg) obtained in Example 15-6, and the whole was stirred at room temperature for 2 days under a nitrogen atmosphere. After completion of the reaction, the solvent was distilled off. The resultant was dissolved in chloroform and added with a 1 mol/l sodium hydroxide aqueous solution, followed by stirring for a while. Then, the solution was subjected to extraction with chloroform and washed with a saturated aqueous sodium hydrogen carbonate solution and a saturated saline solution. The organic layer was dried with anhydrous sodium sulfate and the solvent was distilled off. The residue was purified through silica gel column chromatography (chloroform/ethyl acetate) and treated with hydrochloric acid, thereby obtaining a hydrochloride (174 mg) of the subject compound as a white solid.
MS(FAB,Pos.):m/z=553[M+H]$^+$
$^1$H-NMR(500 MHz,DMSO-d$_6$+D$_2$O):δ=0.88(6H,t,J=7.5 Hz),1.65-1.76(4H,m),2.37(3H,s),2.40(3H,s),2.92-2.98(4H, m),3.75(3H,s),3.84(2H, s),4.16(2H,s),4.18(2H,s),4.28(2H, s),7.51(2H,d,J=8.4 Hz),7.54(1H,d,J=2.0 Hz),7.54-7.55(1H, m),7.56(1H,s),7.57(1H,d,J=2.1 Hz),7.85(2H,d,J=8.5 Hz), 7.87(1H,s),7.88(1H,d,J=2.1 Hz),8.16(1H,d,J=2.0 Hz),8.53 (1H,s).

EXAMPLE 16

Production Example 16

Synthesis of 4-{[(5-ethyl-pyridin-2-ylmethyl)-(1-methyl-1H-imidazol-2-ylmethyl)-amino]-methyl}-N-(4-dipropylaminomethyl-phenyl)-benzamide [Compound No. 16]

EXAMPLE 16-1

Synthesis of 5-ethyl-pyridine-2-carboxaldehyde

In dichloromethane (25.0 ml), 5-ethyl-2-methyl-pyridine (manufactured by Tokyo Kasei Kogyo Co., Ltd.) (2.31 g) was dissolved. After having been cooled to 0° C., the reaction solution was added with m-chloroperbenzoic acid (4.43 g) and the whole was stirred at room temperature for 2.5 hours. The reaction solution was added with a 1 mol/l sodium hydroxide aqueous solution and then subjected to extraction with chloroform. Subsequently, the organic layer was washed with a saturated saline solution and dried with anhydrous sodium sulfate. The drying agent was filtrated out and the solvent was then distilled off. The resultant was dissolved in dichloromethane (40.0 ml). The reaction solution was added with trifluoroacetic anhydride (5.6 ml) and the whole was refluxed under heating for 3.5 hours. After the reaction solution was cooled to room temperature, the solvent was distilled off. The resultant was dissolved in methanol (80.0 ml). After having been cooled to 0° C., the reaction solution was added with a 12.5% sodium methoxide/methanol solution to adjust the reaction solution to pH 10, followed by stirring at room temperature for 16.5 hours. After the solvent was distilled off, the residue was added with distilled water and subjected to extraction with chloroform. The organic layer was washed with a saturated saline solution and dried with anhydrous sodium sulfate. The drying agent was filtrated out and the solvent was then distilled off. The resultant was dissolved in chloroform (50.0 ml). The reaction solution was added with manganese dioxide (chemically processed product) (7.44 g) and then stirred at room temperature for 18 hours. The reaction solution was filtrated through Celite. The solvent in the filtrate was distilled off and the resultant residue was then purified through silica gel column chromatography (chloroform/ethyl acetate), thereby obtaining the subject compound (515.6 mg) as a yellow oily substance.

MS(FAB,POS.):m/z=136[M+H]$^+$ $^1$H-NMR(500 MHz,CDCl$_3$):δ=1.31(3H,t,J=7.6 Hz),2.77 (2H,q,J=7.6 Hz), 7.70(1H,d,J=7.8 Hz),7.91(1H,d,J=7.8 Hz), 10.06(1H,s).

EXAMPLE 16-2

Synthesis of 4-{[(5-ethyl-pyridin-2-ylmethyl)-(1-methyl-1H-imidazol-2-ylmethyl)-amino]-methyl}-N-(4-dipropylaminomethyl-phenyl)-benzamide [Compound No. 16]

The compound (191 mg) obtained in Example 15-5 was dissolved in anhydrous methanol (4.0 ml) and added with sodium cyanoborohydride (41.5 mg), acetic acid (0.50 ml), and the compound (71.4 mg) obtained in Example 16-1 and the whole was stirred at room temperature for 2 days under a nitrogen atmosphere. After completion of the reaction, the solvent was distilled off. The resultant was dissolved in chloroform and added with a 1 mol/l sodium hydroxide aqueous solution, followed by stirring for a while. Then, the solution was subjected to extraction with chloroform and washed with a saturated aqueous sodium hydrogen carbonate solution and a saturated saline solution. The organic layer was dried with anhydrous sodium sulfate and the solvent was distilled off. The residue was purified through silica gel column chromatography (chloroform/ethyl acetate) and treated with hydrochloric acid, thereby obtaining a hydrochloride (222 mg) of the subject compound as a white solid.

MS(FAB,Pos.):m/z=553[M+H]$^+$ $^1$H-NMR(500 MHz,DMSO-d$_6$+D$_2$O):δ=0.88(6H,t,J=7.3 Hz),1.20(3H,t,J=7.6 Hz),1.66-1.77(4H,m),2.77(2H,q,J=7.6 Hz),2.91-2.98(4H,m),3.78(3H,s),3.86(2H,s),4.18(2H,s), 4.22(2H,s),4.28(2H,s),7.51(2H, s),7.52(2H,d,J=8.4 Hz),7.57 (2H,d,J=8.7 Hz),7.87(2H,d,J=8.2 Hz),7.88(2H,d,J=8.7 Hz), 7.98(1H,d,J=8.2 Hz),8.37(1H,dd,J=2.0,8.2 Hz),8.68(1H,d, J=1.8 Hz).

EXAMPLE 17

Production Example 17

Synthesis of [4-(6-{[(1H-imidazol-2-ylmethyl)-(1-methyl-1H-imidazol-2-ylmethyl)-amino]-methyl}-3, 4-dihydro-1H-isoquinolin-2-yl)-butyl]-dipropyl-amine [Compound No. 17]

EXAMPLE 17-1

Synthesis of 6-bromo-3,4-dihydro-2H-isoquinolin-1-one

In benzene (71 ml), 5-bromoindanone (5.47 g) was suspended. The solution was added with concentrated sulfuric acid (14 ml) and the whole was vigorously stirred. Then, the solution was gradually added with sodium azide (2.52 g), followed by stirring at room temperature for 30 minutes. The resultant was added with ethyl acetate, washed with water and a saturated saline solution, and dried with magnesium sulfate. The solvent was distilled off.

The residue was purified through silica gel column chromatography (chloroform/ethyl acetate), thereby obtaining the subject compound (2.25 g) as a white solid.

MS(FAB,Pos.):m/z=226,228[M+H]$^+$ $^1$H-NMR(500 MHz,CDCl$_3$):δ=2.99(2H,t,J=6.8 Hz),3.57 (2H,dt,J=2.9,6.7 Hz),6.23(1H,br),7.40-(1H,s),7.50(1H,dd, J=2.0,8.3 Hz),7.93(1H,d,J=8.3 Hz).

EXAMPLE 17-2

Synthesis of 1-(6-bromo-3,4-dihydro-1H-isoquinolin-2-yl)-2,2,2-trifluoro-ethanone The compound (2.253 g) obtained in Example 17-1 was dissolved in anhydrous THF (11 ml) and added with a 1 mol/l borane-THF complex/THF solution (manufactured by Kanto Chemical Co., Inc.) (55.4 ml). The whole was refluxed overnight under heating. After the whole was left for cooling, methanol was added thereto and the solvent was distilled off. The resultant was added with 1 mol/l hydrochloric acid and refluxed under heating for 3 hours. After completion of the reaction, the solution was cooled with ice and added with a 1 mol/l sodium hydroxide aqueous solution and 27% ammonium water, followed by extraction with chloroform. The extract was dried with magnesium sulfate and the solvent was distilled off.

The resultant was dissolved in anhydrous dichloromethane (40 ml), added with triethylamine (1.53 ml), and cooled with ice. Trifluoroacetic anhydride (1.55 ml) was added thereto and the whole was stirred at room temperature for 1 hour. After completion of the reaction, the resultant was added with a saturated aqueous sodium hydrogen carbonate solution, subjected to extraction with chloroform, and dried with magnesium sulfate. The solvent was distilled off under reduced pressure, thereby obtaining the subject compound (2.23 g) as a white solid.

MS(FAB,Pos.):m/z=308,310[M+H]$^+$

EXAMPLE 17-3

Synthesis of 1,2,3,4-tetrahydro-isoquinolin-6-carbonitrile

The compound (2.23 g) obtained in Example 17-2 was dissolved in NMP (27 ml) and added with cuprous cyanide (1.56 g) and the whole was refluxed under heating for 4 hours. After completion of the reaction, the whole was cooled with ice and added with water and ammonium water. The resultant was subjected to extraction with chloroform and dried with magnesium sulfate. The solvent was distilled off under reduced pressure. The resultant was dissolved in diethyl ether and added with a 4 mol/l hydrogen chloride/dioxane solution. The precipitate was filtrated and washed with diethylether. The resultant was dried under heating, thereby obtaining a hydrochloride (1.95 g) of the subject compound as a brown solid.

MS(FAB,Pos.):m/z=159[M+H]$^+$
$^1$H-NMR(500 MHz,DMSO-d$_6$):δ=3.06(2H,t,J=6.4 Hz), 3.34-3.36(2H,m),4.32(2H,t,J=4.6 Hz),7.45(1H,d,J=8.1 Hz), 7.71(1H,dd,J=1.7,7.8 Hz),7.76(1H,s).

EXAMPLE 17-4

Synthesis of (4,4-diethoxy-butyl)-dipropyl-amine

In anhydrous methanol (53 ml), 4,4-diethoxy-butylamine (manufactured by Aldrich Corporation) (1.33 g) was dissolved. The solution was added with propionaldehyde (1.23 ml), trimethyl orthoformate (2.45 ml), and sodium cyanoborohydride (1.40 g) and the whole was stirred at room temperature for 2 hours. After completion of the reaction, the solvent was distilled off. The resultant was added with water, subjected to extraction with chloroform, and dried with magnesium sulfate and the solvent was distilled off. The residue was purified through silica gel column chromatography (chloroform/methanol), thereby obtaining the subject compound (1.03 g) as a colorless oily substance.

MS(FAB,Pos.):m/z=246[M+H]$^+$
$^1$H-NMR(500 MHz,CDCl$_3$):δ=0.87(6H,t,J=7.3 Hz),1.21 (6Ht,J=7.0 Hz),1.42-1.48(4H,m),1.49-1.54(2H,m),1.59-1.64(2H,m),2.36-2.39(4H,m),2.44(2H,t,J=7.5 Hz),3.50(2H, quint.,J=7.1 Hz),3.65(2H,quint.,J=7.1 Hz),4.50(1H,t,J=5.6 Hz).

EXAMPLE 17-5

Synthesis of 4-dipropylamino-butylaldehyde

The compound (1.03 g) obtained in Example 17-4 was dissolved in THF (10 ml) and added with 1 mol/l hydrochloric acid (10 ml). The whole was stirred at room temperature for 17 hours and the solvent was distilled off. The solution was added with a 1 mol/l sodium hydroxide aqueous solution and subjected to extraction with chloroform. The extract was dried with magnesium sulfate and the solvent was distilled off, thereby obtaining the subject compound (697 mg) as a colorless oily substance.

MS(FAB,Pos.):m/z=172[M+H]$^+$
$^1$H-NMR(500 MHz,CDCl$_3$):δ=0.86(6H,t,J=7.6 Hz),1.39-1.46(4H,m),1.77(2H,quint.,J=7.1 Hz),2.32-2.36(4H,m), 2.40-2.46(2H,m),9.76(1H,s).

EXAMPLE 17-6

Synthesis of 2-(4-dipropylamino-butyl)-1,2,3,4-tetrahydro-isoquinolin-6-carbonitrile The compound (439 mg) obtained in Example 17-3 was dissolved in a 1 mol/l sodium hydroxide aqueous solution. The whole was subjected to extraction with chloroform and dried with magnesium sulfate and the solvent was distilled off.

The resultant was dissolved in anhydrous dichloromethane (6.7 ml) and added with the compound (331 mg) obtained in Example 17-5 and sodium triacetoxyborohydride (1.23 g), and the whole was reacted at room temperature for 2 days. The resultant was added with a saturated aqueous sodium hydrogen carbonate solution, subjected to extraction with chloroform, and dried with magnesium sulfate. The solvent was distilled off. The residue was purified through silica gel column chromatography (chloroform/ethyl acetate), thereby obtaining the subject compound (220 mg) as a colorless oily substance.

MS(FAB,Pos.):m/z=314[M+H]$^+$

EXAMPLE 17-7

Synthesis of [4-(6-{[(1H-imidazol-2-ylmethyl)-amino]-methyl}-3,4-dihydro-1H-isoquinolin-2-yl)-butyl]-dipropylamine The compound (220 mg) obtained in Example 17-6 was dissolved in anhydrous THF (8.8 ml) and added with Lithium aluminum hydride (106 mg). The whole was stirred at room temperature for 2 hours. After completion of the reaction, the solution was added with ethyl acetate and an aqueous sodium potassium tartrate solution, and the whole was stirred, followed by extraction with chloroform. The extract was dried with magnesium sulfate and the solvent was distilled off.

The resultant was dissolved in anhydrous methanol (8.3 ml) and added with 2-imidazole carboxaldehyde (100 mg) and trimethyl orthoformate (0.23 ml), and the whole was stirred at room temperature for 16 hours. The solution was added with sodium borohydride (79.4 mg) and the whole was stirred at room temperature for 6 hours. The resultant was added with water, subjected to extraction with chloroform, and dried with magnesium sulfate. The solvent was distilled off. The residue was purified through silica gel column chromatography (chloroform/methanol), thereby obtaining the subject compound (104 mg) as a colorless oily substance.

MS(FAB,Pos.):m/z=398[M+H]$^+$

EXAMPLE 17-8

Synthesis of [4-(6-{[(1H-imidazol-2-ylmethyl)-(1-methyl-1H-imidazol-2-ylmethyl)-amino]-methyl}-3,4-dihydro-1H-isoquinolin-2-yl)-butyl]-dipropyl-amine [Compound No. 17]

The compound (104 mg) obtained in Example 17-7 was dissolved in anhydrous methanol (4.0 ml) and added with 1-methyl-2-imidazole carboxaldehyde (42.9 mg) and sodium cyanoborohydride (49.0 mg). The solution was adjusted to pH 5 with acetic acid and stirred at room temperature for 16.5 hours. After completion of the reaction, the solvent was distilled off. The resultant was added with a 1 mol/l sodium hydroxide aqueous solution, subjected to extraction with chloroform, and dried with magnesium sulfate. The solvent was distilled off. The residue was purified through silica gel column chromatography (chloroform/ethyl acetate) and treated with hydrochloric acid, thereby obtaining a hydrochloride (115 mg) of the subject compound as a white solid.

MS(FAB,Pos.):m/z=492[M+H]$^+$
$^1$H-NMR(500 MHz,DMSO-d$_6$+D$_2$O):δ=0.92(6H,t,J=7.3 Hz),1.64-1.70(4H, m),1.72-1.76(2H,m),1.85-1.86(2H,m), 2.99-3.03(4H,m),3.08-3.12(2H,m),3.18-3.27(4H,m),3.68 (3H,s),3.70(4H,s),4.09(2H,s),4.19(2H,s),4.20(1H,d,J=18.9

Hz),4.45(1H,d,J=15.7 Hz),7.06(1H,d,J=8.1 Hz),7.17(1H,d, J=8.4 Hz),7.21(1H,s),7.48(2H,s),7.60(2H,s).

EXAMPLE 18

Production Example 18

Synthesis of [3-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropyl-amine [Compound No. 18]

EXAMPLE 18-1

Synthesis of 3-dipropylaminomethyl-benzoic acid methyl ester

In DMF (12.5 ml), 3-bromomethyl benzoic acid methyl ester (831 mg) was dissolved. The solution was added with dipropylamine (971 μl) and the whole was stirred at room temperature for 2 hours. After completion of the reaction, the solvent was distilled off under reduced pressure. The residue was dissolved in chloroform and washed with a saturated aqueous sodium hydrogen carbonate solution, followed by extraction with chloroform. The organic layer was washed with a saturated saline solution and dried with anhydrous sodium sulfate. After filtration, the solvent was distilled off under reduced pressure, thereby obtaining the subject compound (858 mg) as a brown solid.

EXAMPLE 18-2

Synthesis of 3-dipropylaminomethyl-benzoic acid

The compound (858 mg) obtained in Example 18-1 was dissolved in methanol (18 ml) and added with a 1 mol/l sodium hydroxide aqueous solution (9.0 ml) and the whole was stirred overnight at room temperature. After completion of the reaction, the solvent was distilled off under reduced pressure. The residue was dissolved in a 1 mol/l hydrochloric acid. After addition of chloroform, the resultant was added with sodium chloride to make the aqueous layer to be a saturated saline solution. The whole was subjected to extraction with chloroform and dried with anhydrous sodium sulfate. After filtration, the solvent was distilled off under reduced pressure. The residue was dried under vacuum, thereby obtaining the subject compound (781 mg) as a white solid.
MS(FAB,Pos.):m/z=236[M+H]$^+$
$^1$H-NMR(500 MHz,DMSO-d$_6$):δ=0.86(6H,t,J=7.3 Hz), 1.72(4H,sext.,J=7.3 Hz),2.51(4H,quint.,J=1.8 Hz),3.62(2H, s),4.40(3H,s),7.60(1H, d,J=7.8 Hz),7.95(1H,d,J=7.0 Hz), 8.00(1H,d,J=7.8 Hz),8.17(1H,s),10.70(1H,br).

EXAMPLE 18-3

Synthesis of 4-amino-3-(3-dipropylaminomethyl-benzoylamino)-benzoic acid methyl ester The compound (300 mg) obtained in Example 18-2, WSCI hydrochloride (365 mg), and HOBt (260 mg) were dissolved in chloroform (6.0 ml), and the whole was stirred for 1 hour. Then, 3,4-diaminobenzoic acid methyl ester (198 mg) was added thereto and the whole was stirred for 2 hours. A solid was precipitated, so DMF (2.0 ml) was added thereto and stirring was continued for additional 4 hours. After completion of the reaction, the solvent was distilled off under reduced pressure. Then, the residue was dissolved in chloroform and washed with a saturated ammonium chloride aqueous solution, a saturated aqueous sodium hydrogen carbonate solution, and a saturated saline solution. Then, the resultant was dried with anhydrous sodium sulfate. After filtration, the solvent was distilled off under reduced pressure. The residue was purified through silica gel column chromatography (chloroform/methanol), thereby obtaining the subject compound (381 mg) as a brown oily substance.
MS(FAB,Pos.):m/z=384[M+H]$^+$

EXAMPLE 18-4

Synthesis of 4-amino-3-[(3-dipropylaminomethyl-benzoyl)-methyl-amino]-benzoic acid methyl ester The compound (380 mg) obtained in Example 18-3 was dissolved in DMF (7.6 ml) and 60% sodium hydride (60.0 mg) was added thereto, and the whole was stirred for 1 hour. After that, methyl iodide (213 mg) was gradually added thereto and the whole was stirred at room temperature for 2 hours. After completion of the reaction, the solvent was distilled off under reduced pressure. The residue was dissolved in chloroform and washed with a saturated aqueous sodium hydrogen carbonate solution, followed by extraction with chloroform. The organic layer was washed with a saturated saline solution and dried with anhydrous sodium sulfate. After filtration, the solvent was distilled off under reduced pressure. The residue was purified through silica gel column chromatography (chloroform/methanol/water), thereby obtaining the subject compound (83.0 mg) as a brown solid.
MS(FAB,Pos.):m/z=398[M+H]$^+$

EXAMPLE 18-5

Synthesis of 2-(3-dipropylaminomethyl-phenyl)-3-methyl-3H-benzimidazol-5-carboxylic acid methyl ester The compound (83.0 mg) obtained in Example 18-4 was dissolved in methanol (1.0 ml) and added with a 4 mol/l hydrogen chloride/dioxane solution (1.0 ml) and the whole was stirred at room temperature for 6 hours. After completion of the reaction, the solvent was distilled off under reduced pressure. The residue was dissolved in methanol to generate a free compound therefrom through an anion-exchange resin (Amberlite IRA-410). The resin was separated by filtration and the filtrate subjected to distillation of the solvent under reduced pressure. The residue was purified through silica gel column chromatography (chloroform/ethyl acetate), thereby obtaining the subject compound (44.0 mg) as a brown solid.
MS(FAB,Pos.):m/z=380[M+H]$^+$

EXAMPLE 18-6

Synthesis of 2-(3-dipropylaminomethyl-phenyl)-3-methyl-3H-benzimidazol-5-carbaldehyde Lithium aluminum hydride (16.5 mg) was suspended in THF (1.2 ml) and then the whole was cooled to 0° C. After that, a THF solution (1.0 ml) containing the compound (44.0 mg) obtained in Example 18-5 was dropped in the suspension. The whole was stirred at 0° C. for 2 hours. After completion of the reaction, sodium sulfate decahydrate was gradually added to the solution until bubbling was stopped, and a 1 mol/l sodium hydroxide aqueous solution was then added to the mixture until a white precipitate was generated. A solid was separated by filtration and the filtrate was then subjected to distillation of the solvent under reduced pressure.

The resultant was dissolved in dichloromethane (1.0 ml) and added with manganese dioxide (chemically processed product) (105 mg) and the whole was stirred at room temperature for 19 hours. After completion of the reaction, the resultant was subjected to filtration through Celite and the filtrate was subjected to distillation of the solvent under reduced pressure. The residue was purified through silica gel column chromatography (chloroform/methanol), thereby obtaining the subject compound (28.0 mg) as a brown solid.

MS(FAB,Pos.):m/z=350[M+H]$^+$

EXAMPLE 18-7

Synthesis of [3-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropyl-amine [Compound No. 18]

The compound (31.2 mg) obtained in Example 18-6 was dissolved in methanol (1.0 ml) and added with acetic acid (30 µl) and 1-methyl-2-aminomethylimidazole (15.4 mg), and the whole was stirred at room temperature for 2 hours. Sodium cyanoborohydride (22.7 mg) was added thereto and the whole was stirred at room temperature for 15 hours. Furthermore, 2-imidazole carboxaldehyde (18.0 mg) was added thereto and the whole was stirred at room temperature for 18 hours. After completion of the reaction, the solvent was distilled off under reduced pressure. The residue was dissolved in chloroform, washed with a saturated aqueous sodium hydrogen carbonate solution and a saturated saline solution, and dried with anhydrous sodium sulfate. After filtration, the solvent was distilled off under reduced pressure. The residue was purified through silica gel column chromatography (chloroform/methanol) and treated with hydrochloric acid, thereby obtaining a hydrochloride (25.6 mg) of the subject compound as a white solid.

MS(FAB,Pos.):m/z=525[M+H]$^+$
$^1$H-NMR(500 MHz,DMSO-$d_6$):δ=0.88(6H,t,J=7.3 Hz), 1.70-1.83(4H,m),2.97-3.07(4H,br),3.75(3H,s),3.93(2H,s), 4.15(2H,s),4.17(3H,s),4.23(2H,s),4.47(2H,d,J=4.9 Hz), 7.54-7.55(2H,m),7.57(1H,d,J=8.3 Hz),7.65(2H,s),7.74(1H, d,J=8.3 Hz),7.81(1H,t,J=8.1 Hz),7.99(1H,d,J=8.1 Hz),8.03 (1H,d,J=7.8 Hz),8.32(1H,s),8.40(1H,s).

EXAMPLE 19

Production Example 19

Synthesis of 6-{[(1H-imidazol-2-ylmethyl)-(1-methyl-1H-imidazol-2-ylmethyl)-amino]-methyl}-5,6,7,8-tetrahydro-imidazo[1,2-a]pyridine-2-carboxylic acid-(4-dipropylamino-butyl)-amide [Compound No. 19]

EXAMPLE 19-1

Synthesis of 6-cyano-imidazo[1,2-a]pyridine-2-carboxylic acid ethyl ester

In ethanol (30 ml), 2-amino-5-cyanopyridine (2.45 g) was dissolved. The solution was added with 3-bromo-2-oxo-propionic acid ethyl ester (3.90 g) and the whole was refluxed under heating for 7 hours. The concentrated residue was dissolved in a minimum amount of a 10% hydrogen chloride/methanol solution and the solution was adjusted to pH 8 with a saturated aqueous sodium hydrogen carbonate solution. The precipitate was collected by filtration, thereby obtaining the subject compound (3.81 g) as a pale-yellow solid.

MS(FAB,Pos.):m/z=216[M+H]$^+$
$^1$H-NMR(500 MHz,CDCl$_3$):δ=1.33(3H,t,J=7.1 Hz),4.33 (2H,q,J=7.1 Hz),7.61(1H,dd,J=1.7,9.6 Hz),7.81(1H,ddc, J=0.7,1.0,9.6 Hz),8.61(1H,d,J=0.7 Hz),9.36(1H,dd,J=1.0, 1.7 Hz).

EXAMPLE 19-2

Synthesis of 6-cyano-imidazo[1,2-a]pyridine-2-carboxylic acid-(4-dipropylamino-butyl)-amide The compound (263 mg) obtained in Example 1-2 was dissolved in dichloromethane (4.0 ml) and a 15% trimethyl aluminum/hexane solution (1.08 ml) was dropped thereto. The whole was stirred at room temperature for 15 minutes. The solution was added with the compound (300 mg) obtained in Example 19-1 and stirred for additional 20 hours. The resultant was heated to 40° C. and stirred for additional 7 hours, and then 1 mol/l hydrochloric acid was added to stop the reaction, followed by extraction with chloroform. The organic layer was washed with a saturated aqueous sodium hydrogen carbonate solution, water, and a saturated saline solution and dried with anhydrous sodium sulfate. The residue obtained by distilling the solvent off was purified through silica gel column chromatography (chloroform/methanol), thereby obtaining the subject compound (237 mg) as a yellow solid.

MS(FAB,Pos.):m/z=342[M+H]$^+$
$^1$H-NMR(500 MHz,CDCl$_3$):δ=0.87(6H,t,J=3.7 Hz),1.43-1.73(8H,m),2.39-2.50(6H,m),3.50(2H,dd,J=6.3,6.8 Hz), 7.35(1H,dd,J=1.7,9.6 Hz),7.51(1H,br),7.66(1H,ddc,J=0.7, 1.0,9.6 Hz),8.26(1H,d,J=0.5 Hz),8.64(1H,dd,J=1.0,1.7 Hz).

EXAMPLE 19-3

Synthesis of 6-aminomethyl-5,6,7,8-tetrahydro-imidazo[1,2-a]pyridine-2-carboxylic acid-(4-dipropylamino-butyl)-amide An ethanol solution (20 ml) containing the compound (40.2 mg) obtained in Example 19-2 was added with an ethanol suspension of Raney nickel and a 1 mol/l sodium hydroxide aqueous solution (2.0 ml), and the whole was stirred at room temperature for 14 hours under a hydrogen atmosphere. The catalyst was removed by filtration through Celite. The residue obtained by distilling the solvent off under reduced pressure was dissolved in chloroform, washed with water and a saturated saline solution, and dried with anhydrous sodium sulfate. The solvent was distilled off, thereby obtaining the subject compound (40.1 mg) as a yellow oily substance.

MS(FAB,Pos.):m/z=350[M+H]$^+$
$^1$H-NMR(500 MHz,CDCl$_3$):δ=0.86(6H,t,J=7.5 Hz),2.03-2.13(2H,br),2.34-2.38(4H,m),2.44(2H,t,J=7.2 Hz),2.75-2.82 (2H,m),2.85(2H,dd,J=6.2,12.4 Hz),2.97(1H,ddc,J=3.5,5.5, 16.9 Hz),3.40(2H,dd,J=6.8,13.4 Hz),3.67(1H,dd,J=10.3, 12.2 Hz),4.18,(1H,ddc,J=1.1,5.2,12.4 Hz),7.06(1H,br),7.40 (1H,s).

EXAMPLE 19-4

6-{[(1H-imidazol-2-ylmethyl)-amino]-methyl}-5,6, 7,8-tetrahydro-imidazo[1,2-a]pyridine-2-carboxylic acid-(4-dipropylamino-butyl)-amide The compound (28.3 mg) obtained in Example 19-3 was dissolved in methanol (1.0 ml) and added with trimethyl orthoformate (0.030 ml) and 2-imidazole carboxaldehyde (11.7 mg), and the whole was stirred at room temperature for 3 hours. After having been cooled to 0° C., the solution was added with sodium borohydride (4.6 mg) and the whole was warmed to room temperature and stirred for additional 15 minutes. The resultant was added with water to stop the reaction and subjected to extraction with chloroform. The organic layer was washed with water and a saturated saline solution and dried with anhydrous sodium sulfate. The solvent was distilled off. The residue was purified through silica gel column chromatography (chloroform/ethyl acetate), thereby obtaining the subject compound (30.5 mg) as a colorless oily substance.

MS(FAB,Pos.):m/z=430[M+H]$^+$
$^1$H-NMR(500 MHz,CDCl$_3$):δ=0.85(6H,t,J=7.2 Hz),1.41-1.48(6H,m),1.50-1.52(2H,m),1.56-1.59(2H,m),2.04-2.11 (2H,br),2.33-2.36(4H,m),2.41(2H,t,J=7.3 Hz),2.61(1H,dd, J=8.1,12.0 Hz),2.70-2.76(2H,m),2.91(1H,ddd,J=3.6,5.5, 16.9 Hz),3.38(2H,dd,J=6.8,13.4 Hz),3.61(1H,dd,J=10.0, 12.4 Hz),3.91(2H,d,J=2.2 Hz),4.12(1H,dd,J=5.0,12.4 Hz), 7.00(2H,s),7.14(1H,br),7.31(1H,s).

EXAMPLE 19-5

Synthesis of 6-{[(1H-imidazol-2-ylmethyl)-(1-methyl-1H-imidazol-2-ylmethyl)-amino]-methyl}-5,6,7, 8-tetrahydro-imidazo[1,2-a]pyridine-2-carboxylic acid-(4-dipropylamino-butyl)-amide [Compound No. 19]

The compound (19.6 mg) obtained in Example 19-4 was dissolved in methanol (2.0 ml) and added with 1-methyl-2-imidazole carboxaldehyde (6.2 mg) and sodium cyanoborohydride (5.9 mg). The solution was adjusted to pH 4 with acetic acid and stirred at room temperature for 3 hours. The resultant was added with a saturated sodium hydrogen carbonate aqueous solution to stop the reaction and subjected to extraction with chloroform. The organic layer was washed with water and a saturated saline solution and dried with anhydrous sodium sulfate. The solvent was distilled off. The residue was purified through silica gel column chromatography (chloroform/ethyl acetate) and treated with hydrochloric acid, thereby obtaining a hydrochloride (22.0 mg) of the subject compound as a white solid.

MS(FAB,Pos.):m/z=524[M+H]$^+$
$^1$H-NMR(500 MHz,CDCl$_3$):δ=0.87(6H,t,J=7.3 Hz),1.40-1.69(9H,m),2.05(4H,br),2.13-2.18(1H,m),2.35(2H,d,J=4.5 Hz),2.35(2H,t,J=7.8 Hz),2.42(2H,t,J=7.3 Hz),2.50-2.60(3H, m),2.80-2.84(1H,m),2.93-2.97(1H,m),3.40(2H,dd,J=6.6, 13.4 Hz),3.47-3.49(2H,m),3.56(2H,d,J=2.7 Hz),3.62-3.66 (2H,m),3.73(3H,s),4.18(1H,dd,J=4.0,12.5 Hz),6.95(1H,d, J=1.2 Hz),7.03-7.04(3H,m),7.39(1H,s),12.39(1H,br).

EXAMPLE 20

Production Example 20

Synthesis of N-(4-dipropylamino-butyl)-4-{[(1-methyl-1H-imidazo-2-ylmethyl) -(5-methyl-pyridin-2-ylmethyl)-amino]-methyl}-benzamide [Compound No. 20]

EXAMPLE 20-1

Synthesis of t-butyl-4-(4-{dipropylaminolbutylcarbamoyl)benzyl carbamate 4-(t-butoxycarbonylamino-methyl)-benzoic acid (558 mg) was dissolved in chloroform (9.0 ml) and then added with WSCI hydrochloride (728 mg) and HOBt (503 mg) under ice-cooling, followed by stirring for 15 minutes. Then, a chloroform solution (3.0 ml) containing the compound (652 mg) obtained in Example 1-2 was gradually added thereto and the whole was stirred at room temperature for 12 hours. After completion of the reaction, a 1 mol/l hydrochloric acid (7.0 ml) was added thereto and the aqueous layer was extracted with chloroform. The organic layer was washed with a 1 mol/l sodium hydroxide aqueous solution and a saturated saline solution and dried with anhydrous sodium sulfate. The solvent was distilled off. The residue was then purified through silica gel column chromatography (hexane/ethyl acetate), thereby obtaining the subject compound (715 mg) as a yellow oily substance.

EXAMPLE 20-2

Synthesis of 4-(aminomethyl)-N-(4-{dipropylamino}butyl)benzamide

The compound (715 mg) obtained in Example 20-1 was dissolved in methanol (7.0 ml) and added with a 4 mol/l hydrogen chloride/dioxane solution (7.0 ml) at room temperature and the whole was stirred for 2 hours. After completion of the reaction, the solvent was distilled off and the residue was dissolved in chloroform and washed with a 1 mol/l sodium hydroxide aqueous solution. The organic layer was washed with a saturated saline solution and dried with anhydrous sodium sulfate. The solvent was distilled off, thereby obtaining the subject compound (559 mg) as a yellow oily substance.

EXAMPLE 20-3

Synthesis of N-(4-dipropylamino-butyl)-4-{[(1-methyl-1H-imidazol-2-ylmethyl)-amino]-methyl}-benzamide The compound (538 mg) obtained in Example 20-2 was dissolved in anhydrous methanol (10 ml), added with trimethyl orthoformate (600 μl) at room temperature under a nitrogen atmosphere, and then added with a methanol solution (2.0 ml) containing 1-methyl-2-imidazole carboxaldehyde (240 mg). The whole was stirred at room temperature for 36 hours and then added with sodium borohydride (140 mg) under ice-cooling. The whole was warmed to room temperature and stirred for 1 hour. After completion of the reaction, the resultant was added with water under ice-cooling while the whole was stirred. The solvent was distilled off under reduced pressure and the residue was dissolved in chloroform and added with water, followed by extraction of the aqueous layer with chloroform. The organic layer was washed with a saturated saline solution and dried with anhydrous sodium sulfate. After filtration, the solvent was distilled off under reduced pressure. The residue was purified through silica gel column chromatography (chloroform/methanol), thereby obtaining the subject compound (782 mg) as a yellow oily substance.

MS(FAB,Pos.):m/z=400[M+H]$^+$
$^1$H-NMR(500 MHz,CDCl$_3$):δ=0.85(6H,t,J=7.4 Hz),1.39-1.45(4H,m),1.56(2H,quint.,J=6.9 Hz),1.65(2H,quint,J=6.9 Hz),2.36(4H,t,J=2.2 Hz), 2.44(2H,t,J=6.9 Hz),3.45(2H,dt, J=6.6,6.6 Hz),3.63(3H,s),3.83(2H,s),3.87(2H,s),6.78(1H, brs),6.82(1H,d,J=1.2 Hz),6.94(1H,d,J=1.2 Hz),7.40(2H,d, J=8.1 Hz),7.71(1H,dd,J=1.7,3.8 Hz),7.28(1H, dd,J=1.7,3.8 Hz).

EXAMPLE 20-4

Synthesis of 5-methyl-2-pyridine aldehyde

The subject compound (439 mg) was obtained in a similar manner as in Example 15-6 except for using 2,5-lutidine as a raw material.
MS(FAB,Pos.):m/z=122[M+H]$^+$
$^1$H-NMR(500 MHz,CDCl$_3$):δ=2.46(3H,s),7.67(1H,dd, J=1.4,7.9 Hz),7.89(1H,d,J=7.9 Hz),8.62(1H,d,J=1.4 Hz), 10.05(1H,s).

EXAMPLE 20-5

Synthesis of N-(4-dipropylamino-butyl)-4-{[(1-methyl-1H-imidazol-2-ylmethyl)-(5-methyl-pyridin-2-ylmethyl)-amino]-methyl}-benzamide [Compound No. 20]

The compound (782 mg) obtained in Example 20-3 was dissolved in anhydrous methanol (12 ml) and then added with sodium cyanoborohydride (380 mg) and acetic acid (1.5 ml). Then, the solution was added with a methanol solution (2.0 ml) containing the compound (289 mg) obtained in Example 20-4 at −10° C. and then stirred at room temperature for 12 hours under a nitrogen atmosphere. After completion of the reaction, water was added thereto to stop the reaction. The solvent was distilled off under reduced pressure and chloroform and a 1 mol/l sodium hydroxide aqueous solution were added to the residue to make the pH of the aqueous layer about 10, followed by extraction of the aqueous layer with chloroform. The organic layer was washed with a saturated saline solution and dried with anhydrous sodium sulfate. The resultant was then concentrated under reduced pressure. The residue was purified through silica gel column chromatography (chloroform/ethyl acetate) and then treated with hydrochloric acid, thereby obtaining a hydrochloride (316 mg) of the subject compound as a white solid.
MS(FAB,Pos.):m/z=505[M+H]$^+$
$^1$H-NMR(500 MHz,CDCl$_3$):δ=0.83(6H,t,J=7.3 Hz),1.41 (4H,qt,J=2.4,6.4 Hz),1.55(2H,quint.,J=7.1 Hz),1.65(2H, quint.,J=7.3 Hz),2.32(3H,s),2.35(4H,t,J=2.4 Hz),2.44(2H,t, J=7.1 Hz),3.45(2H,dt,J=5.6,6.8 Hz),3.49(3H,s),3.65(3H,s), 3.69(2H,s),3.70(2H,s),6.94(1H,brt,J=5.0 Hz),6.77(1H,d, J=1.2 Hz),6.90(1H,d,J=1.2 Hz),7.24(1H,d,J=7.8 Hz),7.38 (2H,d,J=8.3 Hz),7.46(1H,dd,J=1.7,8.0 Hz),7.69(2H,d,J=8.6 Hz),8.37(1H,d,J=1.5 Hz).

EXAMPLE 21

Production Example 21

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-methanesulfonamide [Compound No. 21]

EXAMPLE 21-1

Synthesis of 4-{[t-butoxycarbonyl-(1-methyl-1H-imidazol-2-ylmethyl)-amino]-methyl}-benzoic acid methyl ester In DMF (150 ml), 4-{[t-butoxycarbonyl-(1H-imidazol-2-ylmethyl)-amino]-methyl}benzoic acid (5.0 g) obtained by a known technique is dissolved. The solution was added with 60% sodium hydride (1.45 g) and methyl iodide (2.70 ml), and the whole was stirred at room temperature for 18 hours. The reaction solution was added to a saturated ammonium chloride aqueous solution and the whole was subjected to extraction with chloroform. The organic layer was dried with anhydrous sodium sulfate and concentrated under reduced pressure. The residue was purified through silica gel column chromatography (chloroform/methanol), thereby obtaining the subject compound (2.31 g) as a brown solid.
MS(FAB,Pos.):m/z=360[M+H]$^+$

EXAMPLE 21-2

Synthesis of (4-hydroxymethylbenzyl)-(1-methyl-1H-imidazol-2-ylmethyl)-carbamic acid t-butyl ester Lithium aluminum hydride (1.0 g) was suspended in THF (95 ml). After that, a THF solution (95.1 ml) containing the compound (3.17 g) obtained in Example 21-1 was gradually dropped therein at room temperature. Then, the whole was stirred for additional 1 hour. The reaction solution was added with ethyl acetate, methanol, and a 10% aqueous sodium potassium tartrate solution and the whole was stirred for 1 hour, followed by extraction with chloroform. The organic layer was dried with anhydrous sodium sulfate and concentrated under reduced pressure. The residue was purified through silica gel column chromatography (chloroform/methanol), thereby obtaining the subject compound (1.37 g) as a brown oily substance.
MS(FAB,Pos.):m/z=360[M+H]$^+$

EXAMPLE 21-3

Synthesis of (4-formyl-1-benzyl)-(1-methyl-1H-imidazol-2-ylmethyl)-carbamic acid t-butyl ester The compound (1.37 g) obtained in Example 21-2 was dissolved in ethyl acetate (68.5 ml) and then added with manganese dioxide (chemically processed product) (13.7 g) and the whole was stirred at room temperature for 1 hour. The reaction solution was filtrated through Celite. The filtrate was concentrated under reduced pressure. The residue was then purified through silica gel column chromatography (chloroform/methanol), thereby obtaining the subject compound (1.37 g) as a brown oily substance.
MS(FAB,Pos.):m/z=485[M+H]$^+$

EXAMPLE 21-4

Synthesis of {4-[(4-dipropylaminobutylamino)-methyl]-benzyl}-(1-methyl-1H-imidazol-2-ylmethyl)-carbamic acid t-butyl ester The compound (1.28 g) obtained in Example 21-3 was dissolved in methanol (38.6 ml). Then, the solution was added with the compound (0.669 g) obtained in Example 1-2 and trimethyl orthoformate (1.28 ml) and the whole was stirred at room temperature for 2.5 hours. The resultant was added with sodium borohydride (0.441 g) under ice-cooling and stirred at room temperature for 0.5 hours. The reaction solution was concentrated under reduced pressure. The residue was added with water and subjected to extraction with chloroform. The organic layer was washed with a saturated saline solution, dried with anhydrous sodium sulfate, and concentrated under reduced pressure. The residue was purified through silica gel column chromatography (chloroform/ethyl acetate), thereby obtaining the subject compound (1.71 g) as a brown oily substance.
MS(FAB,Pos.):m/z=486[M+H]$^+$

EXAMPLE 21-5

Synthesis of (4-{[(4-dipropylamino-butyl)-methane-sulfonyl-amino]-methyl}-benzyl)-(1-methyl-1H-imidazol-2-ylmethyl)-carbamic acid t-butyl ester The compound (182.6 mg) obtained in Example 21-4 was dissolved in dichloromethane (5.3 ml) and added with triethylamine (0.105 ml) and methanesulfonyl chloride (43.6 µl), and the whole was stirred at room temperature for 0.5 hours. The reaction solution was added with water, subjected to extraction with chloroform, dried with anhydrous sodium sulfate, and concentrated under reduced pressure. The residue was purified through silica gel column chromatography (chloroform/ethyl acetate), thereby obtaining the subject compound (148.0 mg) as a colorless oily substance.
MS(FAB,Pos.):m/z=564[M+H]$^+$

EXAMPLE 21-6

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-methanesulfonamide [Compound No. 21]

The compound (148.0 mg) obtained in Example 21-5 was dissolved in methanol (2.9 ml) and added with a 4 mol/l hydrogen chloride/dioxane solution (2.9 ml) and the whole was stirred at room temperature for 1 hour. The reaction solution was concentrated under reduced pressure. The residue was added with a 1 mol/l sodium hydroxide aqueous solution, subjected to extraction with chloroform, dried with anhydrous sodium sulfate, and concentrated under reduced pressure, followed by drying under vacuum.

The resultant was dissolved in methanol (6.09 ml) and added with 2-imidazole carboxaldehyde (43.4 mg) and sodium cyanoborohydride (33.0 mg). The solution was adjusted to pH 5 with acetic acid and stirred at room temperature for 15 hours. The reaction solution was concentrated under reduced pressure. The residue was added with a saturated sodium hydrogen carbonate aqueous solution, subjected to extraction with chloroform, dried with anhydrous sodium sulfate, and concentrated under reduced pressure. The residue was purified through silica gel column chromatography (chloroform/ethyl acetate) and treated with hydrochloric acid, thereby obtaining a hydrochloride (102.4 mg) of the subject compound as a white solid.
MS(FAB,Pos.):m/z=544[M+H]$^+$
$^1$H-NMR(500 Mz,DMSO-d$_6$+D$_2$O):δ=0.89(6H,t,J=7.3 Hz),1.43-1.62(8H,m),2.90-3.11(8H,m),2.96(3H,s),3.69(5H,s),4.06(2H,s),4.13(2H,s),4.27(2H,s),7.27(2H,d,J=8.1 Hz),7.33(2H,d,J=8.1 Hz),7.50(2H,s),7.61(2H,s).

EXAMPLE 22

Production Example 22

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-4-methyl-benzenesulfonamide [Compound No. 22]

EXAMPLE 22-1

Synthesis of (4-{[(4-dipropylamino-butyl)-(toluene-4-sulfonyl)-amino]-methyl}-benzyl)-(1-methyl-1H-imidazol-2-ylmethyl)-carbamic acid t-butyl ester The compound (182.0 mg) obtained in Example 21-4 was dissolved in dichloromethane (5.3 ml) and added with triethylamine (0.104 ml) and p-toluenesulfonyl chloride (107.2 mg), and the whole was stirred at room temperature for 0.5 hours.

The reaction solution was added with water, subjected to extraction with chloroform, dried with anhydrous sodium sulfate, and concentrated under reduced pressure. The residue was purified through silica gel column chromatography (chloroform/ethyl acetate), thereby obtaining the subject compound (219 mg) as a colorless oily substance.
MS(FAB,Pos.):m/z=640[M+H]$^+$

EXAMPLE 22-2

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-4-methyl-benzenesulfonamide [Compound No. 22]

The compound (219.5 mg) obtained in Example 22-1 was dissolved in methanol (4.3 ml) and added with a 4 mol/l hydrogen chloride/dioxane solution (4.3 ml) and the whole was stirred at room temperature for 1 hour. The reaction solution was concentrated under reduced pressure. The residue was added with a 1 mol/l sodium hydroxide aqueous solution, subjected to extraction with chloroform, dried with anhydrous sodium sulfate, and concentrated under reduced pressure, followed by drying under vacuum.

The resultant was dissolved in methanol (9.2 ml) and added with 2-imidazole carboxaldehyde (56.7 mg) and sodium cyanoborohydride (43.1 mg). The solution was adjusted to pH 5 with acetic acid and stirred at room temperature for 15 hours. The reaction solution was concentrated under reduced pressure. The residue was added with a saturated sodium hydrogen carbonate aqueous solution, subjected to extraction with chloroform, dried with anhydrous sodium sulfate, and concentrated under reduced pressure. The residue was purified through silica gel column chromatography (chloroform/ethyl acetate) and treated with hydrochloric acid, thereby obtaining a hydrochloride (164.4 mg) of the subject compound as a white solid.
MS(FAB,Pos.):m/z=620[M+H]$^+$
$^1$H-NMR(500 Mz,DMSO-d$_6$+D$_2$O):δ=0.88(6H,t,J=7.3 Hz),1.26-1.60(8H,m),2.42(3H,s),2.83-3.06(8H,m),3.63(3H,s),3.69(2H,s),4.05(2H,s),4.13(2H,s),4.23(2H,s),7.21(2H,d,J=8.3 Hz),7.31(2H,d,J=8.0 Hz),7.46(2H,d,J=8.0 Hz),7.50 (2H,s),7.61(2H,s),7.75(2H,d,J=8.3 Hz).

EXAMPLE 23

Production Example 23

Synthesis of N-ethyl-N-(4-{[(1H-imidazol-2-ylmethyl)-(1-methyl-1H-imidazol-2-ylmethyl)-amino]-methyl}-benzyl)-N',N'-dipropyl-butane-1,4-diamine [Compound No. 23]

EXAMPLE 23-1

Synthesis of 4-(t-butoxycarbonylamino-methyl)-benzoic acid methyl ester 4-aminomethylbenzoic acid methyl ester hydrochloride was subjected to desalting, thereby obtaining a free compound (20.2 g). The free compound was dissolved in anhydrous chloroform (400 ml) and added with triethylamine (34.1 ml) and di-t-butylcarbonate (32.0 g), and the whole was stirred overnight at room temperature under a nitrogen atmosphere. After completion of the reaction, the solvent was distilled off. The resultant was dissolved in chloroform and added with distilled water, and the whole was stirred for a while. The resultant was subjected to extraction with chloroform and washed with a saturated saline solution. The organic layer was dried with anhydrous sodium sulfate. The solvent was distilled off, thereby obtaining the subject compound (35.7 g) as a colorless crystal.

MS(FAB,Pos.):m/z=266[M+H]$^+$

EXAMPLE 23-2

Synthesis of (4-hydroxymethyl-benzyl)-carbamic acid t-butyl ester

The compound (35.7 g) obtained in Example 23-1 was dissolved in anhydrous THF (800 ml) and added with Lithium aluminum hydride (10.2 g) in an ice bath and the whole was stirred for 2 days under a nitrogen atmosphere. After completion of the reaction, methanol and then an aqueous sodium potassium tartrate solution were added thereto and the whole was stirred overnight. The resultant was subjected to extraction with chloroform and washed with saturated saline solution. The organic layer was dried with anhydrous sodium sulfate. The solvent was distilled off, thereby obtaining the subject compound (29.2 g) as a colorless crystal.

EXAMPLE 23-3

Synthesis of (4-formyl-benzyl)-carbamic acid t-butyl ester

The compound (17.6 g) obtained in Example 23-2 was dissolved in chloroform (400 ml) and then added with manganese dioxide (chemically processed product) (88.2 g) and the whole was stirred overnight at room temperature. After completion of the reaction, the resultant was filtrated through Celite. The solvent was distilled off, thereby obtaining the subject compound (20.4 g) as a colorless crystal.

EXAMPLE 23-4

Synthesis of {4-[(4-dipropylamino-butylamino)-methyl]-benzyl}-carbamic acid t-butyl ester The compound (9.25 g) obtained in Example 1-2 was dissolved in anhydrous methanol (200 ml) and then added with trimethyl orthoformate (8.81 ml) and the compound (12.6 g) obtained in Example 23-3. The whole was stirred at room temperature for 1.5 hours under a nitrogen atmosphere. Then, sodium borohydride (2.03 g) was added thereto in an ice bath and the whole was stirred at room temperature for 2 hours. After completion of the reaction, distilled water was added thereto and the whole was stirred for a while. The solution was subjected to extraction with chloroform and washed with a saturated saline solution. The organic layer was dried with anhydrous sodium sulfate. The solvent was distilled off, thereby obtaining the subject compound (19.3 g) as a colorless oily substance.

EXAMPLE 23-5

Synthesis of (4-{[(4-dipropylamino-butyl)-ethyl-amino]-methyl}-benzyl)-carbamic acid t-butyl ester The compound (289 mg) obtained in Example 23-4 was dissolved in anhydrous methanol (6.0 ml) and added with sodium cyanoborohydride (92.8 mg), acetic acid (1.00 ml), and acetaldehyde (61.3 µl). The whole was stirred overnight at room temperature under a nitrogen atmosphere. After completion of the reaction, the solvent was distilled off. The resultant was dissolved in chloroform and added with a 1 mol/l sodium hydroxide aqueous solution, followed by stirring for a while. The resultant was subjected to extraction with chloroform, washed with a saturated aqueous sodium hydrogen carbonate solution and a saturated saline solution. The organic layer was dried with anhydrous sodium sulfate. The solvent was distilled off, thereby obtaining the subject compound (311 mg) as a pale-yellow oily substance.

EXAMPLE 23-6

Synthesis of N-(4-aminomethyl-benzyl)-N-ethyl-N', N'-dipropyl-butane-1,4-diamine The compound (311 mg) obtained in Example 23-5 was dissolved in anhydrous methanol (1.0 ml) and added with a 4 mol/l hydrogen chloride/dioxane solution (3.0 ml) and the whole was stirred at room temperature for 1 hour. After completion of the reaction, the solvent was distilled off. The resultant was added with a 1 mol/l sodium hydroxide aqueous solution, subjected to extraction with chloroform, and washed with a saturated saline solution. The organic layer was dried with anhydrous sodium sulfate. The solvent was distilled off, thereby obtaining the subject compound (219 mg) as a pale-yellow oily substance.

MS(FAB,Pos.):m/z=320[M+H]$^+$

EXAMPLE 23-7

Synthesis of N-ethyl-N-(4-{[(1H-imidazol-2-ylm-ethyl)amino]methyl}benzyl)-N',N'-dipropyl-butane-1,4-diamine The compound (219 mg) obtained in Example 23-6 was dissolved in anhydrous methanol (5.0 ml) and added with trimethyl orthoformate (112 µl) and 2-imidazole carboxaldehyde (72.4 mg) and the whole was stirred overnight at room temperature, under a nitrogen atmosphere. Subsequently, sodium borohydride (12.3 mg) was added thereto in an ice bath, and the whole was stirred at room temperature for 1 hour. After completion of the reaction, distilled water was added thereto and the whole was stirred for a while. The resultant was subjected to extraction with chloroform and washed with a saturated aqueous sodium hydrogen carbonate solution and a saturated saline solution. The organic layer obtained was dried with anhydrous sodium sulfate. The solvent was distilled off, thereby obtaining the subject compound (317 mg) as a yellow oily substance.

EXAMPLE 23-8

Synthesis of N-ethyl-N-(4-{[(1H-imidazol-2-ylm-ethyl)-(1-methyl-1H-imidazol-2-ylmethyl)-amino]-methyl}-benzyl)-N',N'-dipropyl-butane-1,4-diamine [Compound No. 23]

The compound (317 mg) obtained in Example 23-7 was dissolved in anhydrous methanol (6.0 ml) and added with sodium cyanoborohydride (74.8 mg), acetic acid (1.00 ml), and 1-methyl-2-imidazole carboxaldehyde (105 mg) and the whole was stirred overnight at room temperature under a nitrogen atmosphere. After completion of the reaction, the solvent was distilled off and the resultant was dissolved in chloroform and added with a 1 mol/l sodium hydroxide aqueous solution. The whole was stirred for a while and subjected to extraction with chloroform, followed by washing with a saturated aqueous sodium hydrogen carbonate solution and a saturated saline solution. The organic layer obtained was dried with anhydrous sodium sulfate. The solvent was distilled off. The residue was purified through silica gel column chromatography (chloroform/ethyl acetate) and treated with hydrochloric acid, thereby obtaining a hydrochloride (318 mg) of the subject compound as a white solid.

MS(FAB,Pos.):m/z=494[M+H]$^+$ $^1$H-NMR(500 MHz,DMSO-d$_6$+D$_2$O):δ=0.92(6H,t,J=7.2 Hz),1.24(3H,t,J=7.3 Hz),1.62-1.68(6H,m),1.76-1.78(2H,m), 2.92-3.02(4H,m),3.05-3.08(2H,m),3.62(2H,s),3.69(2H,s), 3.71(3H,s),3.74(2H,s),4.10(2H,s),4.17(2H,s),4.17-4.19(1H, m),4.26-4.29(1H,m),7.41(2H,d,J=7.9 Hz),7.48(2H,d,J=8.7 Hz),7.49(2H,s),7.61(2H,s).

EXAMPLE 24

Production Example 24

Synthesis of N-(4-{[(1H-imidazol-2-ylmethyl)-(1-methyl-1H-imidazol-2-ylmethyl)-amino]-methyl}-benzyl)-N-phenyl-N',N'-dipropyl-butane-1,4-diamine [Compound No. 24]

EXAMPLE 24-1

Synthesis of N'-phenyl-N,N-dipropyl-butane-1,4-diamine

The compound (357.7 mg) obtained in Example 17-5 was dissolved in anhydrous methanol (14 ml) and added with aniline (0.209 ml) and trimethyl orthoformate (0.686 ml) and the whole was stirred at room temperature for 3 hours. Sodium borohydride (237.2 mg) was added thereto and the whole was stirred at room temperature for 1 hour. After completion of the reaction, the solvent was distilled off. The resultant was added with water, subjected to extraction with chloroform, and dried with magnesium sulfate. The solvent was distilled off. The residue was purified through silica gel column chromatography (hexane/ethyl acetate), thereby obtaining the subject compound (165.2 mg) as a colorless oily substance.

MS(FAB,Pos.):m/z=249[M+H]$^+$ $^1$H-NMR(500 MHz,CDCl$_3$):δ=0.87(6H,t,J=7.3 Hz),1.41-1.49(4H,m),1.52-1.58(2H,m),1.63(2H,quint.,J=7.1 Hz), 2.35-2.39(4H,m),2.44(2H,t,J=7.1 Hz),3.12(2H,t,J=6.8 Hz), 6.60(2H,dd,J=1.0,8.5 Hz),6.68(1H,t,J=7.3 Hz),7.17(2H,t, J=7.3 Hz).

EXAMPLE 24-2

Synthesis of 4-{[(4-dipropylamino-butyl)-phenyl-amino]-methyl}-benzonitrile

The compound (152.5 mg) obtained in Example 24-1 was dissolved in anhydrous DMF (6.1 ml) and added with cesium carbonate (299.0 mg) and 4-bromomethyl-benzonitrile (manufactured by Tokyo Kasei Kogyo Co., Ltd.) (184.0 mg). The whole was stirred overnight at 60° C. and then stirred at 80° C. for additional 24 hours. After completion of the reaction, the solvent was distilled off. The resultant was added with water, subjected to extraction with chloroform, and dried with magnesium sulfate. The solvent was distilled off. The residue was purified through silica gel column chromatography (hexane/ethyl acetate), thereby obtaining the subject compound (88.8 mg) as a colorless oily substance.

MS(FAB,Pos.):m/z=363[M+H]$^+$

EXAMPLE 24-3

Synthesis of N-(4-{[(1H-imidazol-2-ylmethyl)-amino]-methyl}-benzyl)-N-phenyl-N',N'-dipropyl-butane-1,4-diamine The compound (88.8 mg) obtained in Example 24-2 was dissolved in anhydrous THF (3.5 ml) and added with Lithium aluminum hydride (36.4 mg). The whole was stirred at room temperature for 4 hours and then stirred at 60° C. for additional 2 hours. After completion of the reaction, ethyl acetate was added thereto. The resultant was added with an aqueous sodium potassium tartrate solution and stirred, followed by extraction with chloroform. The resultant was dried with magnesium sulfate and the solvent was distilled off under reduced pressure.

The resultant was dissolved in anhydrous methanol (3.5 ml) and added with 2-imidazole carboxaldehyde (34.6 mg) and trimethyl orthoformate (0.079 ml) and the whole was stirred at room temperature for 13 hours. The resultant was added with sodium borohydride (27.2 mg) and stirred at room temperature for 2 hours. The resultant was added with water, subjected to extraction with chloroform, and dried with magnesium sulfate. The solvent was distilled off. The residue was purified through silica gel column chromatography (chloroform/methanol), thereby obtaining the subject compound (45.5 mg) as a colorless oily substance.

MS(FAB,Pos.):m/z=448[M+H]$^+$.

EXAMPLE 24-4

Synthesis of N-(4-{[(1H-imidazol-2-ylmethyl)-(1-methyl-1H-imidazol-2-ylmethyl)-amino]-methyl}-benzyl)-N-phenyl-N',N'-dipropyl-butane-1,4-diamine [Compound No. 24]

The compound (45.5 mg) obtained in Example 24-3 was dissolved in anhydrous methanol (1.8 ml) and added with 1-methyl-2-imidazole carboxaldehyde (16.5 mg) and sodium cyanoborohydride (18.9 mg). The solution was adjusted to pH 5 with acetic acid and stirred at room temperature for 24 hours. After completion of the reaction, the solvent was distilled off and the resultant was added with a 1 mol/l sodium hydroxide aqueous solution and subjected to extraction with chloroform. The resultant was dried with magnesium sulfate and the solvent was distilled off. The residue was purified through silica gel column chromatography (chloroform/ethyl acetate) and treated with hydrochloric acid, thereby obtaining a hydrochloride (32.7 mg) of the subject compound as a white solid.

MS(FAB,Pos.):m/z=542[M+H]$^+$ $^1$H-NMR(500 MHz,DMSO-d$_6$+D$_2$O):δ=0.90(6H,t,J=7.1 Hz),1.60-1.67(8H,m),2.96-2.99(4H,m),3.04-3.07(2H,m), 3.43(2H,t,J=7.1 Hz),4.03(2H,s),4.11(2H,s),4.49(2H,s),6.66 (3H,br),7.10(2H,d,J=7.9 Hz),7.15(2H,t,J=7.9 Hz),7.23(2H, d,J=7.9 Hz),7.45(2H,s),7.58(2H,s).

EXAMPLE 25

Production Example 25

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-acetamide [Compound No. 25]

EXAMPLE 25-1

Synthesis of (4-{[(4-dipropylamino-butyl)-acetamino]-methyl}-benzyl)-(1-methyl-1H-imidazol-2-ylmethyl)-carbamic acid t-butyl ester The compound (182.6 mg) obtained in Example 21-4 was dissolved in chloroform (7.0 ml) and added with triethylamine (0.133 ml) and acetic anhydride (73.5 mg) and the whole was stirred at room temperature for 24 hours. The reaction solution was added with water, subjected to extraction with chloroform, dried with anhydrous sodium sulfate, and concentrated under reduced pressure. The residue was purified through silica gel column chromatography (chloroform/ethyl acetate), thereby obtaining the subject compound (253.2 mg) as a colorless oily substance.

MS(FAB,Pos.):m/z=528[M+H]$^+$

EXAMPLE 25-2

Synthesis of N-(4-dipropylamino-butyl)-N-(4-{[(1H-imidazol-2-ylmethyl)-(1-methyl-1H-imidazol-2-ylmethyl)-amino]-methyl}-benzyl)-acetamide [Compound No. 25]

The compound (237.9 mg) obtained in Example 25-1 was dissolved in methanol (4.7 ml) and added with a 4 mol/l hydrogen chloride/dioxane solution (4.7 ml) and the whole was stirred at room temperature for 1 hour. The reaction solution was concentrated under reduced pressure. The residue was added with a 1 mol/l sodium hydroxide aqueous solution, subjected to extraction with chloroform, dried with anhydrous sodium sulfate, and concentrated under reduced pressure, followed by drying under vacuum.

The resultant was dissolved in methanol (9.6 ml) and added with 2-imidazole carboxaldehyde (74.5 mg) and sodium cyanoborohydride (56.7 mg). The solution was adjusted to pH 5 with acetic acid and stirred at room temperature for 20 hours. The reaction solution was concentrated under reduced pressure. The residue was added with a saturated sodium hydrogen carbonate aqueous solution, subjected to extraction with chloroform, dried with anhydrous sodium sulfate, and concentrated under reduced pressure. The residue was purified through silica gel column chromatography (chloroform/methanol) and treated with hydrochloric acid, thereby obtaining a hydrochloride (186.1 mg) of the subject compound as a white solid.

MS(FAB,Pos.):m/z=508[M+H]$^+$ $^1$H-NMR(500 Mz, DMSO-d$_6$+D$_2$O):δ=0.90(6H,t,J=7.3 Hz),1.49-1.67(8H,m),2.00(3H,s),2.95-3.04(6H,m),3.17-3.24(2H,m),3.67(3H,s),3.70(2H,s),4.07(2H,m),4.15(2H,m),4.43(2H,s),4.49(2H,s),7.08(1H,d,J=8.1 Hz),7.11(1H,d,J=8.1 Hz),7.29(1H,d,J=8.1 Hz),7.34(1H,d,J=8.1 Hz),7.49(2H,s),7.60(2H,s).

EXAMPLE 26

Production Example 26

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-1-methyl-urea [Compound No. 26]

EXAMPLE 26-1

Synthesis of 3-(4-cyano-phenyl)-1-(4-dipropylamino-butyl)-1-methyl-urea

Acetic anhydride (1.23 ml) was cooled with ice and then added with formic acid (0.604 ml) and the whole was stirred at 50° C. for 2 hours. After completion of the reaction, the solution was left standing for cooling and anhydrous THF (1.0 ml) was added thereto. The whole was cooled with ice and a THF solution (2.0 ml) containing the compound (896.0 mg) obtained in Example 1-2 was added thereto, followed by stirring at room temperature for 30 minutes. After completion of the reaction, the solvent was distilled off.

The resultant was dissolved in anhydrous THF (30 ml) and added with Lithium aluminum hydride (592 mg) and the whole was stirred at room temperature for 1 hour and then refluxed under heating for 2 hours. After ethyl acetate was added thereto, the resultant was added with an aqueous sodium potassium tartrate solution and was stirred at room temperature, followed by extraction with chloroform. The resultant was dried with magnesium sulfate and the solvent was distilled off.

The resultant was dissolved in toluene (30 ml) and added with 4-isocyanat-benzonitrile (manufactured by Aldrich Corporation) (910.9 mg) and the whole was stirred at room temperature for 14 hours. After completion of the reaction, the solvent was distilled off. The residue was purified through silica gel column chromatography (hexane/ethyl acetate), thereby obtaining the subject compound (97.6 mg) as a colorless oily substance.

MS(FAB,Pos.):m/z=331[M+H]$^+$ $^1$H-NMR(500 MHz,CDCl$_3$):δ=0.86(6H,t,J=7.3 Hz),1.41-1.53(6H,m),1.61-1.68(4H,m),2.36-2.40(4H,m),2.45(2H,t,J=7.1 Hz),3.03(3H,s),3.36(2H,t,J=7.6 Hz),6.78(1H,br),7.50-7.53(2H,m),7.55-7.57(2H,m).

EXAMPLE 26-2

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-1-methyl-urea [Compound No. 26]

The compound (97.6 mg) obtained in Example 26-1 was dissolved in ethanol (4.0 ml), and a 1 mol/l sodium hydroxide aqueous solution (1.0 ml) and Raney nickel (10 mg) were added thereto. The whole was stirred at room temperature for 16 hours under a hydrogen atmosphere. After completion of the reaction, the resultant was subjected to filtration through Celite. The filtrate was added with water, subjected to extraction with chloroform, and dried with magnesium sulfate, thereby distilling the solvent off under reduced pressure.

The resultant was dissolved in methanol (3.4 ml) and added with 2-imidazole carboxaldehyde (36.5 mg) and trimethyl orthoformate (0.082 ml), followed by stirring at room temperature for 16.5 hours. The resultant was added with sodium borohydride (28.4 mg) and the whole was stirred at room temperature for 3 hours. After completion of the reaction, the solvent was distilled off. The resultant was added with water, subjected to extraction with chloroform, and dried with magnesium sulfate. The solvent was distilled off.

The resultant was dissolved in methanol (4.0 ml) and added with 1-methyl-2-imidazole carboxaldehyde (39.6 mg) and sodium cyanoborohydride (45.2 mg). The solution was adjusted to pH 5 with acetic acid and stirred at room temperature for 22 hours. After completion of the reaction, the solvent was distilled off. The resultant was added with a 1 mol/l sodium hydroxide aqueous solution, subjected to extraction with chloroform, and dried with magnesium sulfate. The solvent was distilled off. The residue was purified through silica gel column chromatography (chloroform/ethyl acetate) and treated with hydrochloric acid, thereby obtaining a hydrochloride (76.8 mg) of the subject compound as a white solid.

MS(FAB,Pos.):m/z=509[M+H]$^+$ $^1$H-NMR(500 MHz,DMSO-d$_6$):δ=0.88(6H,t,J=7.3 Hz), 1.51-1.55(2H,m),1.60-1.70(6H,m),2.92-2.96(4H,m),2.94 (3H,s),3.03-3.06(2H,m),3.32(2H,t,J=7.2 Hz),3.58(2H,s), 3.69(3H,s),4.04(2H,s),4.11(2H,s),7.25(2H,d,J=8.7 Hz),7.42 (2H,d,J=8.5 Hz),7.56(2H,dd,J=2.0,7.1 Hz),7.64(2H,s),8.30 (1H,s)10.24(1H,s),14.79(2H,br).

EXAMPLE 27

Production Example 27

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-1,3-dimethyl-urea [Compound No. 27]

EXAMPLE 27-1

Synthesis of 1-(4-cyano-phenyl)-3-(4-dipropyl-butyl)-1,3-dimethyl-urea

The compound (197.3 mg) obtained in Example 26-1 was dissolved in anhydrous THF (6.0 ml) and added with 60% sodium hydride (27.5 mg) and the whole was stirred at room temperature for 1.5 hours. The resultant was added with methyl iodide (0.045 ml) and stirred at room temperature for 2 hours. After completion of the reaction, the solvent was distilled off. The resultant was added with water, subjected to extraction with chloroform, and dried with magnesium sulfate. The solvent was distilled off. The residue was purified through silica gel column chromatography (hexane/ethyl acetate), thereby obtaining the subject compound (37.8 mg) as a colorless oily substance.

MS(FAB,Pos.):m/z=345[M+H]$^+$

EXAMPLE 27-2

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-1,3-dimethyl-urea [Compound No. 27]

The compound (37.8 mg) obtained in Example 27-1 was dissolved in ethanol (1.5 ml), and a 1 mol/l sodium hydroxide aqueous solution (0.4 ml) and Raney nickel (3.8 mg) were added thereto. The whole was stirred at room temperature for 4 hours under a hydrogen atmosphere. After completion of the reaction, the resultant was subjected to filtration through Celite. The solvent was distilled off. Then the resultant was subjected to extraction with chloroform, and the solvent was distilled off.

The resultant was dissolved in methanol (1.2 ml) and added with 2-imidazole carboxaldehyde (12.9 mg) and trimethyl orthoformate (0.029 ml), followed by stirring at room temperature for 3 days. The resultant was added with sodium borohydride (10.1 mg) and the whole was stirred at room temperature for 4 hours. After completion of the reaction, the solvent was distilled off. The resultant was added with water, subjected to extraction with chloroform, and dried with magnesium sulfate. The solvent was distilled off.

The resultant was dissolved in methanol (1.6 ml) and added with 1-methyl-2-imidazole carboxaldehyde (14.8 mg) and sodium cyanoborohydride (16.8 mg). The solution was adjusted to pH 5 with acetic acid and stirred overnight at room temperature. After completion of the reaction, the solvent was distilled off. The resultant was added with a 1 mol/l sodium hydroxide aqueous solution, subjected to extraction with chloroform, and dried with magnesium sulfate. The solvent was distilled off. The residue was purified through silica gel column chromatography (chloroform/ethyl acetate) and treated with hydrochloric acid, thereby obtaining a hydrochloride (39.5 mg) of the subject compound as a white solid.

MS(FAB,Pos.):m/z=523[M+H]$^+$ $^1$H-NMR(500 MHz,DMSO-d$_6$):δ=0.90(6H,t,J=7.3 Hz), 1.43-1.48(2H,m),1.54-1.57(2H,m),1.63-1.71(4H,m),2.47 (3H,s),2.89-3.06(6H,m),3.00(3H,s),3.11(2H,t,J=7.3 Hz), 3.65(3H,s),3.70(3H,s),4.11(2H,s),4.19(2H,s),7.06(2H,d, J=8.4 Hz),7.35(2H,d,J=8.5 Hz),7.53(2H,dd,J=2.0,6.8 Hz), 7.63(2H,s),10.45(1H,br),14.80(1H,br),14.92(1H, br).

EXAMPLE 28

Production Example 28

Synthesis of N-methyl-N-[4-({(1-methyl-1H-imidazol-2-ylmethyl)-[1-(toluene-4-sulfonyl)-1H-imidazol-2-ylmethyl]-amino}-methyl)-benzyl]-N",N"-dipropyl-butane-1,4-diamine [Compound No. 28]

EXAMPLE 28-1

Synthesis of N-methyl-N",N"-dipropyl-N-[4-({[1-(toluene-4-sulfonyl)-1H-imidazol-2-ylmethyl]-amino}-methyl)-benzyl]-butane-1,4-diamine The compound (568 mg) obtained in Example 9-2 was dissolved in anhydrous THF (11 ml) and the whole was added 60% sodium hydride (157 mg) while being stirred under ice-cooling under a nitrogen atmosphere. The whole was then warmed back to room temperature and stirred for 1 hour. Under ice-cooling, a THF solution (2.0 ml) containing p-toluenesulfonyl chloride (315 mg) was gradually dropped therein and the whole was stirred for 30 minutes while being kept under ice-cooling. After completion of the reaction, acetic acid (220 μl) was added to neutralize the resultant while the whole was stirred under ice-cooling, and water was added thereto to stop the reaction. The resultant was warmed back to room temperature. The solvent was distilled off under reduced pressure. The residue was dissolved in chloroform and added with a 1 mol/l sodium hydroxide aqueous solution to make the pH of the aqueous layer about 10. The aqueous layer was extracted with chloroform. The organic layer was washed with a saturated saline solution and then dried with anhydrous sodium sulfate. After filtration, the resultant was concentrated and evaporated to dryness under reduced pressure, thereby obtaining the subject compound (678 mg) as a yellow oily substance.

MS(FAB,Pos.):m/z=540[M+H]$^+$ $^1$H-NMR(500 MHz,CDCl$_3$):δ=0.86(6H,t,J=6.3 Hz),1.42-1.52(8H,m),2.16(3H,s),2.18-2.41(8H,m),2.42(3H,s),3.46 (2H,s),3.76(2H,s),4.03(2H,s),6.98(1H,d,J=1.7 Hz),7.22(1H, dd,J=2.0,6.3 Hz),7.25(1H,dd,J=2.0,4.2 Hz),7.29(2H,dd, J=0.7,2.0 Hz),7.30(2H,dd,J=0.7,2.0 Hz),7.42(1H,d,J=1.7 Hz),7.76(1H,dd,J=2.0,2.0 Hz),7.79(1H,dd,J=2.0,2.0 Hz).

EXAMPLE 28-2

Synthesis of N-methyl-N-[4-({(1-methyl-1H-imidazol-2-ylmethyl)-[1-(toluene-4-sulfonyl)-1H-imidazol-2-ylmethyl]-amino}-methyl)-benzyl]-N'',N''-dipropyl-butane-1,4-diamine [Compound No. 28]

The compound (307 mg) obtained in Example 28-1 was dissolved in anhydrous DMF (6.0 ml), added with potassium carbonate (175 mg) at room temperature under a nitrogen atmosphere, and added with the compound (107 mg) obtained in Example 10-2 under ice-cooling. The whole was stirred at room temperature for 2 hours and stirred at 60° C. for additional 22 hours. The resultant was left standing for cooing and then added with water under ice-cooling to stop the reaction. The solvent was distilled off under reduced pressure. The residue was dissolved in chloroform and added with water. The aqueous layer was extracted with chloroform. The organic layer was washed with a saturated saline solution and then dried with anhydrous sodium sulfate.

After filtration, the solvent was distilled off under reduced pressure. The residue was purified through silica gel column chromatography (chloroform/ethyl acetate), thereby obtaining the subject compound (49.3 mg) as a brown oily substance.

MS(FAB,Pos.):m/z=634[M+H]$^+$ $^1$H-NMR(500 MHz,CDCl$_3$):δ=0.86(6H,t,J=7.3 Hz),1.41-1.51(8H,m),2.15(3H,s),2.33-2.39(8H,m),2.41(3H,s),3.43 (3H,s),3.45(2H,s),3.70(2H,s),3.71(2H,s),3.85(2H,s),6.79 (1H,d,J=1.2 Hz),6.92(1H,d,J=1.2 Hz),6.98(1H,d,J=1.7 Hz), 7.23(1H,dd,J=7.0,8.2 Hz),7.26(1H,dd,J=0.6,2.9 Hz),7.27 (2H,dd,J=0.6,0.6 Hz),7.27(2H,dd,J=0.6,4.1 Hz),7.40(1H,d, J=1.7 Hz),7.57(1H,dd,J=1.8,2.0 Hz),7.79(1H,dd,J=1.7,2.0 Hz).

EXAMPLE 29

Production Example 29

Synthesis of [4-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropylamine [Compound No. 29]

EXAMPLE 29-1

Synthesis of 3,4-diaminobenzonitrile

3-Nitro-4-aminobenzonitrile (3.00 g) was dissolved in ethanol (300 ml) and added with stannous chloride dihydrate (20.7 g) and the whole was heated to 60° C. Sodium borohydride (348 mg) was gradually added thereto and the whole was stirred overnight at 60° C. After completion of the reaction, the resultant was added with water (300 ml) and neutralized with a 5 mol/l sodium hydroxide aqueous solution. After ethanol was distilled off under reduced pressure, the aqueous layer was added with ethyl acetate for extraction. The organic layer was washed with a saturated saline solution and then dried with anhydrous sodium sulfate. After filtration, the solvent was distilled off under reduced pressure. The residue was recrystallized, thereby obtaining the subject compound (1.11 g) as a brown crystal.

MS(EI):m/z=133[M]$^+$ $^1$H-NMR(500 MHz,CDCl$_3$):δ=6.68(1H,d,J=8.1 Hz),6.95 (1H,s),7.05(1H,d,J=8.1 Hz).

EXAMPLE 29-2

Synthesis of 4-dipropylaminomethyl-benzoic acid methyl ester

4-Bromomethylbenzoic acid methyl ester (831 mg) was dissolved in DMF (12.5 ml) and added with dipropylamine (971 μl) and the whole was stirred at room temperature for 2 hours. After completion of the reaction, the solvent was distilled off under reduced pressure. The residue was dissolved in chloroform, washed with a saturated aqueous sodium hydrogen carbonate solution, and subjected to extraction with chloroform. The organic layer was washed with a saturated saline solution and dried with anhydrous sodium sulfate. After filtration, the solvent was distilled off, thereby obtaining the subject compound (883 mg) as a brown solid.

EXAMPLE 29-3

Synthesis of 4-dipropylaminomethyl-benzoic acid

The compound (883 mg) obtained in Example 29-2 was dissolved in methanol (18 ml) and added with a 1 mol/l sodium hydroxide aqueous solution (9.0 ml) and the whole was stirred overnight at room temperature. After completion of the reaction, the solvent was distilled off under reduced pressure. The residue was dissolved in 1 mol/l hydrochloric acid, subjected to extraction with chloroform, and dried with anhydrous sodium sulfate. After filtration, the solvent was distilled off and the residue was dried under vacuum, thereby obtaining the subject compound (820 mg) as a white solid.

MS(FAB,Pos.):m/z=236[M+H]$^+$ $^1$H-NMR(500 MHz,DMSO-d$_6$):δ=0.86(6H,t,J=7.3 Hz), 1.74(4H,sext.,J=7.3 Hz),2.92(4H,br),4.38(2H,d,J=4.6 Hz), 7.78(2H,d,J=8.0 Hz),8.00(1H,d,J=8.0 Hz),10.85(1H,br).

EXAMPLE 29-4

Synthesis of N-(2-amino-5-cyano-phenyl)-4-dipropylaminomethyl-benzamide

The compound (1.01 g) obtained in Example 29-3, WSCI hydrochloride (973 mg), and HOBt (894 mg) were dissolved in chloroform (30 ml), and the whole was stirred for 2 hours. Then, the compound (445 mg) obtained in Example 29-1 was added thereto and the whole was stirred at room temperature for 3 hours. After completion of the reaction, the solvent was distilled off under reduced pressure. Then, the residue was dissolved in chloroform and washed with a saturated ammonium chloride aqueous solution, a saturated aqueous sodium hydrogen carbonate solution, and a saturated saline solution. After that, the resultant was dried with anhydrous sodium sulfate. After filtration, the solvent was distilled off under reduced pressure. The residue was purified through silica gel column chromatography (chloroform/ethyl acetate), thereby obtaining the subject compound (613 mg) as an orange solid.

MS(FAB,Pos.):m/z=351[M+H]$^+$
$^1$H-NMR(500 MHz,CDCl$_3$):δ=0.87(6H,t,J=7.3 Hz),1.48 (4H,sext.,J=7.3 Hz),2.38(4H,t,J=7.3 Hz),3.62(2H,s),4.43 (3H,br),6.83(1H,d,J=8.3 Hz),7.37(1H,d,J=8.3 Hz),7.49(2H, d,J=8.1 Hz),7.52(1H,s),7.80(1H,br),7.84(1H,d,J=8.1 Hz).

EXAMPLE 29-5

Synthesis of 2-(4-dipropylaminomethyl-phenyl)-3-methyl-3H-benzimidazol-5-carbonitrile The compound (613 mg) obtained in Example 29-4 was dissolved in THF (18 ml) and added with 60% sodium hydride (105 mg). After that, the whole was gradually added with methyl iodide (373 mg) and stirred at room temperature for 16 hours. After completion of the reaction, the solvent was distilled off under reduced pressure. The residue was dissolved in chloroform, washed with water, and subjected to extraction with chloroform. The organic layer was washed with a saturated saline solution and dried with anhydrous sodium sulfate. After filtration, the solvent was distilled off. The residue was purified through silica gel column chromatography (hexane/ethyl acetate), thereby obtaining the subject compound (160 mg) as a brown solid.

MS(FAB,Pos.):m/z=347[M+H]$^+$
$^1$H-NMR(500 MHz,CDCl$_3$):δ=0.88(6H,t,J=7.3 Hz),1.50 (4H,sext.,J=7.3 Hz),2.41(4H,t,J=7.3 Hz),3.64(2H,s),3.93 (3H,s),7.55(2H,d,J=8.3 Hz),7.57(1H,d,J=8.3 Hz),7.72(2H,d, J=8.3 Hz),7.74(1H,s),7.86(1H,d,J=8.3 Hz).

EXAMPLE 29-6

Synthesis of [4-(6-aminomethyl-1-methyl-1H-benzimidazol-2-yl)-benzyl]-dipropyl-amine Lithium aluminum hydride (64.0 mg) was suspended in THF (5.0 ml) and the whole was cooled to 0° C. A THF solution (5.0 ml) containing the compound (155 mg) obtained in Example 29-5 was dropped therein and the whole was stirred at 0° C. for 1 hour. After completion of the reaction, sodium sulfate decahydrate was added thereto until bubbling was stopped, and a 1 mol/l sodium hydroxide aqueous solution was then added thereto until a white precipitate was generated. A solid was separated by filtration and the solvent in the filtrate was then distillated off under reduced pressure, and the residue was dried under vacuum, thereby obtaining the subject compound (93.5 mg) as a yellow oily substance.

MS(FAB,Pos.):m/z=351[M+H]$^+$
$^1$H-NMR(500 MHz,DMSO-d$_6$):δ=0.94(6H,t,J=7.3 Hz), 1.71-1.89(4H,m),2.98(2H,s),3.13-3.20(2H,m),3.23-3.30 (2H,m),3.99(3H,s),4.64(2H,s),7.67(1H,d,J=8.3 Hz),7.78 (2H,d,J=8.3 Hz),7.87(1H,d,J=8.3 Hz),8.05(2H,d,J=8.3 Hz), 8.35(1H,s).

EXAMPLE 29-7

Synthesis of [4-(6-{[(1H-imidazol-2-ylmethyl)-(1-methyl-1H-imidazol-2-ylmethyl)-amino]-methyl}-1-methyl-1H-benzimidazol-2-yl)-benzyl]-dipropyl-amine [Compound No. 29]

The compound (93.5 mg) obtained in Example 29-6 was dissolved in methanol (4.0 ml) and added with trimethyl orthoformate (100 μl) and 2-imidazole carboxaldehyde (31.7 mg) and the whole was stirred at room temperature for 1 hour. After having been cooled to 0° C., the solution was added with sodium borohydride (13.2 mg). The whole was warmed back to room temperature and stirred for 30 minutes.

After completion of the reaction, the solvent was distilled off under reduced pressure. The residue was dissolved in chloroform, washed with a saturated aqueous sodium hydrogen carbonate solution, and subjected to extraction with chloroform. The organic layer was washed with a saturated saline solution and dried with anhydrous sodium sulfate. After filtration, the solvent was distilled off under reduced pressure.

The resultant was dissolved in methanol (4.0 ml) and added with acetic acid (100 μl) and 1-methyl-2-imidazole carboxaldehyde (61.0 mg), followed by stirring at room temperature for 30 minutes. The resultant was added with sodium cyanoborohydride (53.6 mg) and the whole was stirred at room temperature for 3 hours. After completion of the reaction, the solvent was distilled off under reduced pressure. The residue was dissolved in chloroform, washed with a saturated aqueous sodium hydrogen carbonate solution, and subjected to extraction with chloroform. The organic layer was washed with a saturated saline solution and dried anhydrous with sodium sulfate. After filtration, the solvent was distilled off under reduced pressure. The residue was purified through silica gel column chromatography (chloroform/ethyl acetate) and treated with hydrochloric acid, thereby obtaining a hydrochloride (38.4 mg) of the subject compound as a white solid.

MS(FAB,Pos.):m/z=525[M+H]$^+$
$^1$H-NMR(500 MHz,DMSO-d$_6$):δ=0.89(6H,t,J=7.3 Hz), 1.72-1.82(4H,m),2.94-3.02(4H,m),3.75(3H,s),3.94(2H,s), 4.13(3H,s),4.16(2H,s),4.24(2H,s),4.48(2H,d,J=5.6 Hz), 7.53-7.54(2H,m),7.59(1H,d,J=8.5 Hz),7.64(2H,s),7.75(1H, d,J=8.5 Hz),8.04(2H,d,J=8.7 Hz),8.07(2H,d,J=8.7 Hz),8.33 (1H,s).

EXAMPLE 30

Production Example 30

Synthesis of 6-{[(1H-imidazol-2-ylmethyl)-(1-methyl-1H-imidazol-2-ylmethyl)-amino]-methyl}-imidazo[1,2-a]pyridine-2-carboxylic acid-(4-dipropyl)-amino-butyl)-amide [Compound No. 30]

EXAMPLE 30-1

Synthesis of 6-amino-pyridine-3-carboxaldehyde

2-Amino-5-cyanopyridine (1.02 g) was dissolved in THF (40 ml) and added with Lithium aluminum hydride (637 mg) and the whole was stirred at room temperature for 2 hours. Water was added thereto to stop the reaction, and the whole was added with a saturated sodium sulfate aqueous solution and subjected to filtration through Celite. The residue obtained by concentration of the filtrate was purified through silica gel column chromatography (chloroform/methanol), thereby obtaining the subject compound (1.04 g) as a yellow solid.

MS(EI):m/z=122[M]$^+$
$^1$H-NMR(500 MHz,DMSO-d$_6$):δ=6.51(1H,dd,J=0.7,8.9 Hz),7.19(2H,br),7.75(1H,dd,J=2.4,8.9 Hz),8.43(1H,dd, J=0.5,2.2 Hz),9.66(1H,s).

EXAMPLE 30-2

Synthesis of 6-formyl-imidazo[1,2-a]pyridine-2-carboxylic acid ethyl ester

An ethanol solution (8.0 ml) containing the compound (318 mg) obtained in Example 30-1 was added with 3-bromo- 2-oxo-propionic acid ethyl ester (0.33 ml) and the whole was stirred at room temperature for 18 hours. The solvent was distilled off. The residue was purified through silica gel column chromatography (chloroform/methanol), thereby obtaining the subject compound (230 mg) as a yellow solid.

MS(FAB,Pos.):m/z=219[M+H]$^+$ $^1$H-NMR(500 MHz,CDCl$_3$):δ=1.46(3H,t,J=7.0 Hz),4.49 (2H,q,J=7.0 Hz), 7.73-7.79(2H,m),8.33(1H,d,J=0.5 Hz),8.72 (1H,dd,J=1.0,1.7 Hz),9.99(1H,s).

EXAMPLE 30-3

Synthesis of 6-{[(1-methyl-1H-imidazol-2-ylmethyl)-amino]-methyl}-imidazo[1,2-a]pyridine-2-carboxylic acid-(4-dipropylamino-butyl)-amide A 15% trimethyl aluminum/hexane solution (0.32 ml) was dropped into a dichloromethane solution (2.0 ml) containing the compound (72.0 mg) obtained in Example 1-2 and the whole was stirred at room temperature for 15 minutes. A dichloromethane solution (2.0 ml) containing the compound (41.8 mg) obtained in Example 30-2 was dropped thereto and the whole was stirred at room temperature for 20 hours. To this solution, 1 mol/l hydrochloric acid was dropped to stop the reaction, and the whole was neutralized with a saturated aqueous sodium hydrogen carbonate solution and then subjected to extraction with chloroform. The organic layer was washed with a saturated aqueous sodium hydrogen carbonate solution and a saturated saline solution and dried with anhydrous sodium sulfate.

Of the resultant residue (65.2 mg), 40.2 mg thereof was dissolved in methanol (2.0 ml) and added with trimethyl orthoformate (0.040 ml). A methanol solution (1.0 ml) containing the compound (20.0 mg) obtained in Example 14-7 was dropped thereto and the whole was stirred at room temperature for 4 hours. After having been cooled to 0° C., the resultant was added with sodium borohydride (6.8 mg), warmed to room temperature, and stirred for 30 minutes. Water was added thereto to stop the reaction and the concentrated residue was extracted with chloroform. The organic layer was washed with water and a saturated saline solution and dried with anhydrous sodium sulfate.

The solvent was distilled off. The residue was purified through silica gel column chromatography (chloroform/methanol) thereby obtaining the subject compound (34.7 mg) as a pale-yellow oily substance.

MS(FAB,Pos.):m/z=440[M+H]$^+$ $^1$H-NMR(500 MHz,CDCl$_3$):δ=0.86(6H,t,J=7.3 Hz),1.43-1.48(4H,m),1.55-1.57(2H,m),1.63-1.66(2H,m),2.37(4H,t,J=7.3 Hz),2.46(2H,br),3.48(2H,tt,J=6.3,6.9 Hz),3.64(3H,s), 3.85(2H,s),3.89(2H,s),6.82(1H,d,J=1.2 Hz),6.94(1H,d,J=1.2 Hz),7.26(1H,dd,J=1.7,9.3 Hz),7.41(1H,t,J=5.8 Hz),7.50(1H, d,J=9.3 Hz),8.08(1H,d,J=0.6 Hz),8.10(1H,d,J=1.1 Hz).

EXAMPLE 30-4

Synthesis of 6-{[(1H-imidazol-2-ylmethyl)-(1-methyl-1H-imidazol-2-ylmethyl)-amino]-methyl}-imidazo[1,2-a]pyridine-2-carboxylic acid-(4-dipropyl)-amino-butyl)-amide [Compound No. 30]

The compound (34.7 mg) obtained in Example 30-3 was dissolved in methanol (3.0 ml) and added with 2-imidazole carboxaldehyde (9.1 mg) and sodium cyanoborohydride (9.9 mg). The solution was adjusted to pH 4 with acetic acid and stirred at room temperature for 45 hours. A saturated aqueous sodium hydrogen carbonate solution was added thereto to stop the reaction and the whole was subjected to extraction with chloroform. The organic layer was washed with water and a saturated saline solution and dried with anhydrous sodium sulfate. The residue obtained by distilling the solvent off was purified through silica gel column chromatography (chloroform/ethyl acetate) and treated with hydrochloric acid, thereby obtaining a hydrochloride (23.6 mg) of the subject compound as a pale-yellow solid.

MS(FAB,Pos.):m/z=520[M+H]$^+$ $^1$H-NMR(500 MHz,CDCl$_3$):δ=0.86(6H,t,J=7.3 Hz),1.26-1.48(4H,m),1.51-1.56(2H,m),1.61-1.67(2H,m),2.34-2.37 (4H,m),2.44(2H,t,J=7.3 Hz),3.48(2H,tt,J=6.4,6.9 Hz),3.56 (2H,s),3.57(2H,s),3.65(3H,s),3.66(2H,s),6.92(1H,d,J=1.2 Hz),7.03(1H,d,J=1.2 Hz),7.08(1H,s),7.14(1H,s),7.39(1H, br),7.39(1H,dd,J=1.5,9.5 Hz),7.54(1H,d,J=9.3 Hz),8.11(1H, d,J=0.7 Hz),8.23(1H,d,J=0.7 Hz),12.41(1H,br).

EXAMPLE 31

Production Example 31

Synthesis of N-(4-{[(1H-imidazol-2-ylmethyl)-(1-methyl-1H-imidazol-2-ylmethyl)-amino]-methyl}-benzyl)-N',N'-dipropyl-N-(2,2,2-trifluoro-ethyl)-butane-1,4-diamine [Compound No. 31]

EXAMPLE 31-1

Synthesis of (4-{[(4-dipropylaminobutyl)-(2,2,2-trifluoroacetyl)-amino]-methyl}-benzyl)-(1-methyl-1H-imidazol-2-ylmethyl)-carbamic acid t-butyl ester The compound (222 mg) obtained in Example 21-4 was dissolved in anhydrous dichloromethane (4.4 ml) and added with triethylamine (0.071 ml). The whole was cooled with ice and added with trifluoroacetic anhydride (0.072 ml), followed by stirring at room temperature for 1.5 hours. After completion of the reaction, the resultant was washed with water and dried with magnesium sulfate. The solvent was distilled off. The residue was purified through silica gel column chromatography (chloroform/ethyl acetate), thereby obtaining the subject compound (178.6 mg) as a colorless oily substance.

MS(FAB,Pos.):m/z=582[M+H]$^+$

EXAMPLE 31-2

Synthesis of N-(4-{[(1H-imidazol-2-ylmethyl)-(1-methyl-1H-imidazol-2-ylmethyl)-amino]-methyl}-benzyl)-N',N'-dipropyl-N-(2,2,2-trifluoro-ethyl)-butane-1,4-diamine [Compound No. 31]

The compound (178.6 mg) obtained in Example 31-1 was dissolved in anhydrous THF (0.9 ml) and added with a 1 mol/l borane-THF complex/THF solution (1.72 ml). The whole was refluxed under heating for 18.5 hours. After completion of the reaction, methanol was added thereto and the solvent was distilled off. The resultant was added with 1 mol/l hydrochloric acid and the whole was refluxed under heating for 3 hours. The solution was neutralized with a 1 mol/l sodium hydroxide aqueous solution and subjected to extraction with chloroform. The resultant was dried with magnesium sulfate and the solvent was distilled off.

The resultant was dissolved in anhydrous methanol (5.2 ml) and added with 2-imidazole carboxaldehyde (40.4 mg) and sodium cyanoborohydride (52.8 mg). The solution was adjusted to pH 5 with acetic acid and stirred at room temperature for 18 hours. After completion of the reaction, the solvent was distilled off. The resultant was added with a 1 mol/l sodium hydroxide aqueous solution, subjected to extraction with chloroform, and dried with magnesium sulfate. The solvent was distilled off. The residue was purified through silica gel column chromatography (chloroform/ethyl acetate) and treated with acetic acid, thereby obtaining a hydrochloride (138.7 mg) of the subject compound as a white solid.

MS(FAB,Pos.):m/z=548[M+H]$^+$ $^1$H-NMR(500 MHz,DMSO-d$_6$+D$_2$O):δ=0.90(6H,t,J=7.3 Hz),1.47-1.48(2H, m),1.57-1.64(6H,m),2.94-3.00(6H,m),3.21-3.23(2H,m),3.69(6H,s),3.74(3H,s),4.06(2H,s),4.14 (2H,s),7.20(2H,d,J=8.1 Hz),7.28(2H,d,J=8.1 Hz),7.48(2H,s),7.59(2H,s).

EXAMPLE 32

Production Example 32

Synthesis of N-(4-{[(1-methanesulfonyl-1H-imidazol-2-ylmethyl)-(1-methyl-1H-imidazol-2-ylmethyl)-amino]-methyl}-benzyl)-N-methyl-N'',N''-dipropyl-butane-1,4-diamine [Compound No. 32]

EXAMPLE 32-1

Synthesis of N-[4-{[(1H-imidazol-2-ylmethyl)-(1-methyl-1H-imidazol-2-ylmethyl)-amino]-methyl}-benzyl]-N-methyl-N'',N''-dipropyl-butane-1,4-diamine The compound (26.7 mg) obtained in Example 9-2 was dissolved in anhydrous THF (0.35 ml) and added with triethylamine (350 µl) and a THF solution (50 µl) containing 1-methyl-2-imidazole carboxaldehyde (9.20 mg). The solution was added with sodium triacetoxyborohydride (31.3 mg) and the whole was stirred at room temperature for 24 hours under a nitrogen atmosphere. After completion of the reaction, water was added thereto and the solvent was distilled off under reduced pressure. The residue was added with chloroform and a 1 mol/l sodium hydroxide aqueous solution to make the pH of the aqueous layer 10, and the aqueous layer was extracted with chloroform. The organic layer was washed with a saturated saline solution and dried with anhydrous sodium sulfate. After filtration, the resultant was concentrated and evaporated to dryness under reduced pressure. The residue was purified through silica gel column chromatography (chloroform/ethyl acetate), thereby obtaining the subject compound (23.1 mg) as a yellow oily substance.

MS(FAB,Pos.):m/z=480[M+H]$^+$ $^1$H-NMR(500 MHz,CDCl$_3$):δ=0.86(6H,t,J=7.3 Hz),1.41-1.52(8H,m),2.16(3H,s),2.36-2.44(8H,m),3.46(2H,s),3.55 (5H,s),3.62(2H,s),3.67(2H,s),6.87(1H,d,J=1.2 Hz),6.99(1H,d,J=1.2 Hz),7.10(2H,s),7.27(2H,d,J=8.0 Hz),7.35(1H,d,J=8.0 Hz).

EXAMPLE 32-2

Synthesis of N-(4-{[(1-methanesulfonyl-1H-imidazol-2-ylmethyl)-(1-methyl-1H-imidazol-2-ylmethyl)-amino]-methyl}-benzyl)-N-methyl-N'',N''-dipropyl-butane-1,4-diamine [Compound No. 32]

The compound (125 mg) obtained in Example 32-1 was dissolved in anhydrous chloroform, added with triethylamine (60 µl) at room temperature under a nitrogen atmosphere, and added with methanesulfonyl chloride (25 µl) and the whole was stirred. After completion of the reaction, water and methanol were added thereto to stop the reaction. Water was added thereto and the aqueous layer was extracted with chloroform. The organic layer was washed with a saturated saline solution and dried with anhydrous sodium sulfate. After filtration, the resultant was concentrated and evaporated to dryness under reduced pressure. The residue was purified through silica gel column chromatography (chloroform/ethyl acetate), thereby obtaining the subject compound (87.7 mg) as a yellow oily substance.

MS(FAB,Pos.):m/z=558[M+H]$^+$ $^1$H-NMR(500 MHz,CDCl$_3$):δ=0.86(6H,t,J=7.3 Hz),1.32-1.51(8H,m),2.15(3H,s),2.33-2.41(8H,m),3.39(3H,s),3.44 (2H,s),3.45(3H,s),3.76(2H,s),3.89(2H,s),4.05(2H,s),6.79 (1H,d,J=1.2 Hz),6.91(1H,d,J=1.2 Hz),6.98(1H,d,J=1.7 Hz),7.16(2H,d,J=8.0 Hz),7.24(2H,d,J=8.0 Hz),7.30(1H,d,J=1.7 Hz).

EXAMPLE 33

Production Example 33

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionitrile [Compound No. 33]

EXAMPLE 33-1

Synthesis of (4-{[(2-cyano-ethyl)-(4-dipropylamino-butyl)-amino]-methyl}-benzyl)-carbamic acid t-butyl ester The compound (260 mg) obtained in Example 23-4 was dissolved in methanol (5.0 ml) and added with distilled water (1.0 ml) and acrylonitrile (87.4 µl) and the whole was stirred overnight at room temperature. After completion of the reaction, the solvent was distilled off and the resultant was subjected to extraction with chloroform and washed with a saturated saline solution. The organic layer was dried with anhydrous sodium sulfate. The solvent was distilled off, thereby obtaining the subject compound (332 mg) as a colorless oily substance.

MS(FAB,Pos.):m/z=445[M+H]$^+$

EXAMPLE 33-2

Synthesis of 3-[(4-(aminomethyl-benzyl)-(4-dipropylamino-butyl)-amino)-propionitrile The compound (331 mg) obtained in Example 33-1 was dissolved in anhydrous THF (1.0 ml) and added with a 4 mol/l hydrogen chloride/dioxane solution (6.0 ml) and the whole was stirred at room temperature for 20 minutes. After completion of the reaction, the solvent was distilled off. The resultant was added with a 1 mol/l sodium hydroxide aqueous solution, subjected to extraction with chloroform, and washed with a saturated saline solution. The organic layer was dried with anhydrous sodium sulfate. The solvent was distilled off, thereby obtaining the subject compound (235 mg) as a pale-yellow oily substance.

MS(FAB,Pos.):m/z=345[M+H]$^+$

EXAMPLE 33-3

Synthesis of 3-[(4-(dipropylamino-butyl)-(4-{[(1H-imidazol-2-ylmethyl)-amino]-methyl}-benzyl) amino]-propionitrile The compound (235 mg) obtained in Example 33-2 was dissolved in anhydrous methanol (5.0 ml) and added with trimethyl orthoformate (112 µl) and 2-imidazole carboxaldehyde (72.1 mg) and the whole was stirred overnight at room temperature under a nitrogen atmosphere. Subsequently, sodium borohydride (25.8 mg) was added thereto in an ice bath and the whole was stirred at room temperature for 2 hours. After completion of the reaction, the resultant was added with distilled water and stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off, thereby obtaining the subject compound (309 mg) as a pale-yellow oily substance.

MS(FAB,Pos.):m/z=425[M+H]$^+$

EXAMPLE 33-4

Synthesis of 3-[(4-(dipropylamino-butyl)-(4-{[(1H-imidazol-2-ylmethyl)-(5-methyl-cyanopenta-1,3-dienylmethyl)-amino]-methyl}-benzyl)-amino]-propionitrile The compound (141 mg) obtained in Example 33-3 was dissolved in anhydrous methanol (3.0 ml) and added with sodium cyanoborohydride (31.3 mg), acetic acid (1.00 ml), and 1-methyl-2-imidazole carboxaldehyde (40.2 mg) and the whole was stirred at room temperature for 4 days under a nitrogen atmosphere. After completion of the reaction, the solvent was distilled off and the resultant was dissolved in chloroform and added with a 1 mol/l sodium hydroxide aqueous solution, followed by stirring for a while. The resultant was subjected to extraction with chloroform and washed with a saturated aqueous sodium hydrogen carbonate solution and a saturated saline solution. The organic layer was dried with anhydrous sodium sulfate. The solvent was distilled off. The residue was purified through silica gel column chromatography (chloroform/ethyl acetate) and treated with tartaric acid, thereby obtaining a tartrate (159 mg) of the subject compound as a white solid.

MS(FAB,Pos.):m/z=519[M+H]$^+$
$^1$H-NMR(500 MHz,DMSO-d$_6$+D$_2$O):δ=0.89(6H,t,J=7.3 Hz),1.43-1.46(2H,m),1.55-1.61(6H,m),2.42(2H,t,J=6.7 Hz), 2.64-2.66(4H,m),2.92-2.97(6H,m),3.51(3H,s),3.53(2H,s), 3.55(2H,s),3.61(4H,s),4.22(6H,s),6.86(1H,d,J=1.2 Hz),7.05 (2H,s),7.11(1H,d,J=1.2 Hz),7.28(2H,d,J=8.4 Hz),7.31(2H,d, J=8.4 Hz).

EXAMPLE 34

Production Example 34

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid methyl ester [Compound No. 34]

EXAMPLE 34-1

Synthesis of 3-[(4-amino-methyl-benzyl)-(4-dipropylamino-butyl)-amino]-propionic acid methyl ester The compound (128 mg) obtained in Example 33-1 was dissolved in anhydrous methanol (1.0 ml) and added with a 4 mol/l hydrogen chloride/dioxane solution (3.0 ml) and the whole was stirred at room temperature for 2.5 hours. After completion of the reaction, the solvent was distilled off. The resultant was added with a 1 mol/l sodium hydroxide aqueous solution, subjected to extraction with chloroform, and washed with a saturated saline solution. The organic layer was dried with anhydrous sodium sulfate. The solvent was distilled off. The residue was purified through silica gel column chromatography (chloroform/ethyl acetate), thereby obtaining the subject compound (40.6 mg) as a colorless oily substance.

MS(FAB,Pos.):m/z=378[M+H]$^+$

EXAMPLE 34-2

Synthesis of 3-[(4-dipropylamino-butyl)-(4-{[(1H-imidazol-2-ylmethyl)-amino]-methyl}-benzyl)-amino]-propionic acid methyl ester The compound (40.0 mg) obtained in Example 34-1 was dissolved in anhydrous methanol (1.0 ml) and added with trimethyl orthoformate (17.4 µl) and 2-imidazole carboxaldehyde (11.2 mg) and the whole was stirred overnight at room temperature under a nitrogen atmosphere. Subsequently, sodium borohydride (4.00 mg) was added thereto in an ice bath and the whole was stirred at room temperature for 2 hours.

After completion of the reaction, distilled water was added thereto and the whole was stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off, thereby obtaining the subject compound (48.2 mg) as a colorless oily substance.

EXAMPLE 34-3

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid methyl ester [Compound No. 34]

The compound (48.2 mg) obtained in Example 34-2 was dissolved in anhydrous methanol (1.0 ml) and added with sodium cyanoborohydride (9.90 mg), acetic acid (100 µl), and 1-methyl-2-imidazole carboxaldehyde (12.8 mg) and the whole was stirred at room temperature for 3 days under a nitrogen atmosphere. After completion of the reaction, the solvent was distilled off. The resultant was dissolved in chloroform and added with a 1 mol/l sodium hydroxide aqueous solution, and the whole was stirred for a while. The solution was subjected to extraction with chloroform, and washed with a saturated aqueous sodium hydrogen carbonate solution and a saturated saline solution. The organic layer was dried with anhydrous sodium sulfate. The solvent was distilled off. The residue was purified through silica gel column chromatography (chloroform/ethyl acetate) and treated with hydrochloric acid, thereby obtaining a hydrochloride (56.1 mg) of the subject compound as a white solid.

MS(FAB,Pos.):m/z=552[M+H]$^+$
$^1$H-NMR(500 MHz,DMSO-d$_6$+D$_2$O):δ=0.92(6H,t,J=7.3 Hz),1.62-1.69(6H,m),1.74-1.83(2H,m),2.92-3.06(10H,m), 3.17-3.22(2H,m),3.64(3H,s),3.72(3H,s),3.75(2H,s),4.10 (2H,s),4.19(2H,s),4.26-4.34(2H,m),7.41(2H,d,J=8.2 Hz), 7.465(1H,s),7.467(1H,s),7.50(2H,d,J=8.1 Hz),7.60(2H,s).

EXAMPLE 35

Production Example 35

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-thiourea [Compound No. 35]

EXAMPLE 35-1

Synthesis of 1-(4-cyano-phenyl)-3-(4-dipropylamino-butyl)-thiourea

The compound (656.8 mg) obtained in Example 1-2 was dissolved in anhydrous toluene (19.7 ml) and added with 4-isothiocyanate-benzonitrile (manufactured by Aldrich Corporation) (793.0 mg) and the whole was refluxed under heating for 18.5 hours. After having been left for cooling, the solvent was distilled off. The resultant was added with water and subjected to extraction with chloroform. The resultant was dried with magnesium sulfate and the solvent was distilled off. The residue was purified through silica gel column chromatography (chloroform/ethyl acetate), thereby obtaining the subject compound (314.4 mg) as a colorless oily substance.

MS(FAB,Pos.):m/z=333[M+H]$^+$ $^1$H-NMR(500 MHz,CDCl$_3$):δ=0.83(6H,t,J=7.3 Hz),1.34-1.41(4H,m),1.55 (2H,quint.,J=6.8 Hz),1.71(2H,quint.,J=6.6 Hz),2.28(4H,t,J=7.8 Hz),2.42(2H,t,J=6.3 Hz),3.62(2H,br), 7.39(2H,br),7.65(2H,d,J=8.8 Hz).

EXAMPLE 35-2

Synthesis of 1-(4-dipropylamino-butyl)-3-(4-{[(1H-imidazol-2-ylmethyl)-amino]-methyl}-phenyl)-thiourea The compound (314.4 mg) obtained in Example 35-1 was dissolved in anhydrous THF (12.6 ml) and added with Lithium aluminum hydride (144 mg) and the whole was stirred overnight at room temperature. Then, the solution was refluxed under heating for 2 hours. After completion of the reaction, ethyl acetate was added thereto. An aqueous sodium potassium tartrate solution was added thereto and the whole was stirred overnight. The resultant was subjected to extraction with chloroform.

The resultant was dried with magnesium sulfate and the solvent was distilled off.

The resultant was dissolved in methanol (6.4 ml) and added with 2-imidazole carboxaldehyde (137.4 mg) and trimethyl orthoformate (0.312 ml) and the whole was stirred at room temperature for 2 hours. Sodium borohydride (107.8 mg) was added thereto and the whole was stirred at room temperature for 1 hour. After completion of the reaction, the solvent was distilled off. The resultant was added with water, subjected to extraction with chloroform, and dried with magnesium sulfate. The solvent was distilled off. The residue was purified through silica gel column chromatography (chloroform/methanol), thereby obtaining the subject compound (93.8 mg) as a colorless oily substance.

MS(FAB,Pos.):m/z=417[M+H]$^+$

EXAMPLE 35-3

Synthesis of 1-(4-dipropylamino-butyl)-3-(4-{[(1H-imidazol-2-ylmethyl)-(1-methyl-1H-imidazol-2-ylmethyl)-amino]-methyl}-phenyl)-thiourea [Compound No. 35]

The compound (93.8 mg) obtained in Example 35-2 was dissolved in anhydrous methanol (3.8 ml) and added with 1-methyl-2-imidazole carboxaldehyde (38.5 mg) and sodium cyanoborohydride (43.4 mg). The solution was adjusted to pH 5 with acetic acid and stirred at room temperature for 13.5 hours. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off under reduced pressure. The residue was purified through silica gel column chromatography (chloroform/methanol) and treated with hydrochloric acid, thereby obtaining hydrochloride (86.6 mg) of the subject compound as a white solid.

MS(FAB,Pos.):m/z=511[M+H]$^+$ $^1$H-NMR(500 MHz,DMSO-d$_6$+D$_2$O):δ=0.91(6H,t,J=7.3 Hz),1.56-1.68(8H, m),2.99-3.02(4H,m),3.06-3.09(2H,m), 3.50(2H,br),3.66(2H,s),3.70(3H,s),4.04(2H,s),4.12(2H,s), 7.26(2H,d,J=8.5 Hz),7.40(2H,d, J=8.3 Hz),7.50(2H,s),7.61 (2H,s).

EXAMPLE 36

Production Example 36

Synthesis of {3-[6-(4-{[(1H-imidazol-2-ylmethyl)-(1-methyl-1H-imidazol-2-ylmethyl)-amino]-methyl}-phenyl)-pyridin-2-yl]-propyl}-dipropyl-amine [Compound No. 36]

EXAMPLE 36-1

Synthesis of 2-chloro-6-p-tolylpyridine

4-Methylphenylboronic acid (1.00 g), 2,6-dichloropyridine (3.27 g), tetrakis(triphenylphosphine)palladium(0) (0.255 g) and potassium phosphate (3.12 g) were dissolved in toluene (35 ml) and water (6.0 ml). The mixture was stirred at 80° C. for 15 hours under a nitrogen atmosphere. The organic layer was separated, washed with a saturated aqueous sodium hydrogen carbonate solution, and dried with anhydrous magnesium sulfate and the solvent was distilled off. The resultant was crudely purified through silica gel column chromatography (chloroform), thereby obtaining a mixture (4.02 g) containing the subject compound.

EXAMPLE 36-2

Synthesis of 2-(4-bromomethyl-phenyl)-6-chloro-pyridine

The mixture (4.02 g) obtained in Example 36-1 in a carbon tetrachloride solution (45 ml) was added with N-bromosuccinimide (1.31 g) and 2,2'-azobisisobutyronitrile (0.121 g) and the whole was refluxed for 30 minutes. After that, the solution was cooled to room temperature and a solid component was separated by filtration. The organic layer was washed with a 1 mol/l sodium hydroxide aqueous solution and a saturated saline solution in the stated order, and dried with anhydrous magnesium sulfate. The solvent was distilled off and dried under reduced pressure, thereby obtaining a mixture (5.72 g) containing the subject compound.

EXAMPLE 36-3

Synthesis of 2-[4-(6-chloro-pyridin-2-yl)-benzyl]-isoindol-1,3-dione

The mixture (5.72 g) obtained in Example 36-2 and potassium phthalimide (2.04 g) were dissolved in DMF (30 ml) and the whole was stirred at room temperature for 24 hours. Then, a solid component was separated by filtration. After the solvent was distilled off, the resultant was dissolved in chloroform and washed with a aqueous sodium hydrogen carbonate solution. The aqueous layer was extracted with chloroform and dried with anhydrous magnesium sulfate. The solvent was distilled off. The resultant residue was purified through silica gel column chromatography (chloroform), thereby obtaining the subject compound (1.56 g) as a colorless solid.
MS(FAB,Pos.):m/z=349[M+H]$^+$
$^1$H-NMR(500 MHz,CDCl$_3$):δ=4.90(2H,s),7.25(1H,d,J=7.8 Hz),7.53(2H,d,J=8.5 Hz),7.60(1H,d,J=7.8 Hz),7.68(1H,t,J=7.8 Hz),7.72(2H,dd,J=3.2,5.4 Hz),7.86(2H,dd,J=2.9,5.4 Hz),7.94(2H,d,J=8.3 Hz).

EXAMPLE 36-4

Synthesis of 2-{4-[6-(3-dipropylamino-propyl)-pyridin-2-yl]-benzyl}-isoindol-1,3-dione An anhydrous THF solution (1.0 ml) containing 2-propenyl dipropylamine (158 mg) was cooled with ice and a 0.5 mol/l 9-borabicyclo-[3,3,1]-nonane(9-BBN)/THF solution (2.06 ml) was dropped thereto. The whole was gradually warmed to room temperature and stirred for 5 hours. After that, a 1,1'-bis(diphenylphosphino)ferrocene-palladium(II) dichloride dichloromethane complex (PdCl$_2$ (dppf)) (210 mg) and the compound (300 mg) obtained in Example 36-3 were added thereto together with DMF (3.0 ml), and a 3 mol/l aqueous solution (0.86 ml) of cesium fluoride was added thereto. The whole was stirred at 80° C. for 23 hours and then heated to 100° C. and stirred for 2 hours. After the resultant was cooled to room temperature, a solid component was separated by filtration and the solvent was distilled off. The concentrate was dissolved in chloroform, washed with saturated aqueous sodium hydrogen carbonate solution, extracted with chloroform, and dried with anhydrous magnesium sulfate, followed by distillating off the solvent. The resultant residue was purified through silica gel column chromatography (chloroform/methanol), thereby obtaining the subject compound (44.0 mg) as a pale-brown liquid.
MS(FAB,Pos.):m/z=456[M+H]$^+$
$^1$H-NMR(500 MHz,CDCl$_3$):δ=0.87(6H,t,J=7.3 Hz),1.42-1.70(4H,m),1.98-2.16(2H,m),2.40-2.80(6H,m),2.86(2H,t,J=7.6 Hz),4.90(2H,s),7.08(1H,d,J=7.3 Hz),7.50(1H,d,J=7.8 Hz),7.52(2H,d,J=8.5 Hz),7.63(1H,t,J=7.8 Hz),7.72(2H,dd,J=3.2,5.6 Hz),7.86(2H,dd,J=3.2,5.4 Hz), 7.93(2H,d,J=8.3 Hz).

EXAMPLE 36-5

Synthesis of {3-[6-(4-aminomethyl-phenyl)-pyridin-2-yl]-propyl}-dipropyl-amine

A methanol solution (2.0 ml) containing the compound (40.0 mg) obtained in Example 36-4 was added with hydrazine monohydrate (44 mg) and the whole was stirred at 60° C. for 1.5 hours, followed by distillating off the solvent. The residue was dissolved in chloroform and filtrated through Celite, the solvent was distilled off, thereby obtaining the subject compound (30.1 mg) as an amber liquid.

EXAMPLE 36-6

Synthesis of {3-[6-(4-{[(1H-imidazol-2-ylmethyl)-amino]-methyl}-phenyl)-pyridin-2-yl]-propyl}-dipropyl-amine An anhydrous methanol solution (0.50 ml) containing the compound (30.1 mg) obtained in Example 36-5 and 2-imidazole carboxaldehyde (10.1 mg) was added with trimethyl orthoformate (0.029 ml), and the whole was stirred at room temperature for 14 hours. Sodium borohydride (17.0 mg) was added thereto and the whole was stirred for 30 minutes. The solvent was distilled off. The residue was dissolved in chloroform, washed with a saturated aqueous sodium hydrogen carbonate solution, and dried with anhydrous sodium sulfate, and the solvent was distilled off, thereby obtaining the subject compound (30.4 mg).

EXAMPLE 36-7

Synthesis of {3-[6-(4-{[(1H-imidazol-2-ylmethyl)-(1-methyl-1H-imidazol-2-ylmethyl)-amino]-methyl}-phenyl)-pyridin-2-yl]-propyl}-dipropyl-amine [Compound No. 36]

An anhydrous methanol solution (0.50 ml) containing the compound (30.4 mg) obtained in Example 36-6 and 1-methyl-2-imidazole carboxaldehyde (11.6 mg) was added with 4 drops of acetic acid. Then, sodium cyanoborohydride (17 mg) was added thereto and the whole was stirred at room temperature for 29 hours. After completion of the reaction, the solvent was distilled off. The residue was dissolved in chloroform, washed with a saturated aqueous sodium hydrogen carbonate solution, and dried with anhydrous sodium sulfate, and the solvent was distilled off. The resultant residue was purified through silica gel column chromatography (chloroform), thereby obtaining the subject compound (23.0 mg) as a pale-yellow viscous liquid. The liquid was treated with hydrochloric acid, thereby obtaining a hydrochloride (28.3 mg) of the subject compound as a colorless solid.
MS(FAB,Pos.):m/z=500[M+H]$^+$
$^1$H-NMR(500 MHz,CDCl$_3$):δ=0.88(6H,t,J=7.3 Hz),1.46(4H,sext.,J=7.6 Hz),1.97(2H,quint.,J=7.6 Hz),2.40(4H,t,J=7.6 Hz),2.53(2H,t,J=7.3 Hz),2.86(2H,t,J=7.6 Hz),3.49(2H,s),3.59(3H,s),3.66(2H,s),3.75(2H,s),6.89(1H,d,J=2.2 Hz),7.01(1H,d,J=2.0 Hz),7.10(1H,d,J=7.1 Hz),7.10(1H,br),7.15(1H,br),7.51(2H,d,J=8.3 Hz),7.53(1H,d,J=7.8 Hz),7.65(1H,t,J=7.8 Hz),7.99(2H,d,J=8.3 Hz),12.40(1H,s).

EXAMPLE 37

Production Example 37

Synthesis of N-(4-dipropylamino-butyl)-2,2,2-trifluoro-N-(4-{[(1H-imidazol-2-ylmethyl)-(1-methyl-1H-imidazol-2-ylmethyl)-amino]-methyl}-benzyl)-acetamide [Compound No. 37]

EXAMPLE 37-1

Synthesis of N-(4-dipropylamino-butyl)-2,2,2-trifluoro-N-(4-{[(1H-imidazol-2-ylmethyl)-(1-methyl-1H-imidazol-2-ylmethyl)-amino]-methyl}-benzyl)-acetamide [Compound No. 37]

The compound (166.6 mg) obtained in Example 21-4 was dissolved in anhydrous dichloromethane (5.0 ml) and added with triethylamine (0.052 ml). The whole was cooled with ice and added with trifluoroacetic anhydride (0.052 ml), followed by stirring at room temperature for 1 hour. After completion of the reaction, the resultant was washed with water and dried with magnesium sulfate. The solvent was distilled off.

The resultant was dissolved in methanol (2.4 ml) and added with a 4 mol/l hydrogen chloride/dioxane solution (2.4 ml) and the whole was stirred at room temperature for 1 hour. After completion of the reaction, the solvent was distilled off. A 1 mol/l sodium hydroxide aqueous solution was added thereto and the whole was subjected to extraction with chloroform and dried with magnesium sulfate. The solvent was distilled off.

The resultant was dissolved in anhydrous methanol (6.5 ml) and added with 2-imidazole carboxaldehyde (49.0 mg) and sodium cyanoborohydride (64.1 mg). The solution was adjusted to pH 5 with acetic acid and stirred at room temperature for 3 days. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off. The residue was purified through silica gel column chromatography (chloroform/ethyl acetate) and treated with hydrochloric acid, thereby obtaining hydrochloride (84.9 mg) of the subject compound as a white solid.

MS(FAB,Pos.):m/z=562[M+H]$^+$
$^1$H-NMR(500 MHz,DMSO-d$_6$+D$_2$O):δ=0.90(6H,dt,J=3.1,7.3 Hz),1.57-1.67(8H,m),2.95-3.03(6H,m),3.24(1H,m),3.35(1H,m),3.69(3H,s),3.71(2H,s),4.07(2H,d,J=5.8 Hz),4.15(2H,d,J=8.7 Hz),4.57(1H,s),4.63(1H,s),7.12-7.17(2H,m),7.31-7.35(2H,m),7.45(2H,s),7.58(2H,s).

EXAMPLE 38

Production Example 38

Synthesis of [4-(5-{[(1H-imidazol-2-ylmethyl)-(1-methyl-1H-imidazol-2-ylmethyl)-amino]-methyl}-1,3-dihydro-isoindol-2-yl)-butyl]-dipropyl-amine [Compound No. 38]

EXAMPLE 38-1

Synthesis of [4-(5-{[(1H-imidazol-2-ylmethyl)-amino]-methyl}-1,3-dihydro-isoindol-2-yl)-butyl]-dipropyl-amine A THF solution (2.0 ml) containing the compound (24.3 mg) obtained in Example 7-7 was added with a 1 mol/l borane-THF complex/THF solution (0.41 ml). The whole was refluxed under heating for 16 hours. After having been cooled to 0° C., the solution was added with methanol to stop the reaction and concentrated. The residue was added with a 1 mol/l hydrochloric acid (4.0 ml) and the whole was refluxed under heating for 3 hours. After having been left standing for cooling, the resultant was added with a 1 mol/l sodium hydroxide aqueous solution (5 ml) and the whole was subjected to extraction with chloroform. The organic layer was washed with a saturated aqueous sodium hydrogen carbonate solution and dried with anhydrous sodium sulfate. The residue obtained by distilling the solvent off was purified through silica gel column chromatography (chloroform/methanol), thereby obtaining the subject compound (12.5 mg) as a colorless oily substance.

MS(FAB,Pos.):m/z=384[M+H]$^+$
$^1$H-NMR(500 MHz,CDCl$_3$):δ=0.88(6H,t,J=7.3 Hz),1.42-1.48(4H,m),1.49-1.60(4H,m),2.36-2.39(4H,m),2.45(2H,t,J=7.3 Hz),2.72(2H,t,J=7.3 Hz),3.76(2H,s),3.88-3.90(6H,m),6.98(2H,s),7.10-7.15(3H,m).

EXAMPLE 38-2

Synthesis of [4-(5-{[(1H-imidazol-2-ylmethyl)-(1-methyl-1H-imidazol-2-ylmethyl)-amino]-methyl}-1,3-dihydro-isoindol-2-yl)-butyl]-dipropyl-amine [Compound No. 38]

The compound (12.5 mg) obtained in Example 38-1 was dissolved in methanol (2.0 ml) and added with 1-methyl-2-imidazole carboxaldehyde (4.4 mg) and sodium cyanoborohydride (4.2 mg). The solution was adjusted to pH 4 with acetic acid and stirred at room temperature for 8 hours. The residue obtained by concentration of the solution was added with a saturated aqueous sodium hydrogen carbonate solution to neutralize the solution and the whole was subjected to extraction with chloroform. The organic layer was washed with a saturated aqueous sodium hydrogen carbonate solution and dried with anhydrous sodium sulfate. The residue obtained by distilling the solvent off was purified through silica gel column chromatography (chloroform/methanol), thereby obtaining the subject compound (7.7 mg) as a colorless oily substance.

MS(FAB,Pos.):m/z=478[M+H]$^+$
$^1$H-NMR(500 MHz,CDCl$_3$):δ=0.87(6H,t,J=7.4 Hz),1.42-1.48(4H,m),1.49-1.60(4H,m),2.35(4H,m),2.45(2H,t,J=7.3 Hz),2.72(2H,t,J=7.3 Hz),3.43(2H,s),3.54(3H,s),3.62(2H,s),3.67(2H,s),3.90(4H,s),6.87(1H,d,J=1.5 Hz),7.00(1H,d,J=1.2 Hz),7.08(1H,s),7.12(1H,s),7.15(1H,d,J=8.0 Hz),7.23-7.24(3H,m),12.38(1H,br).

EXAMPLE 39

Production Example 39

Synthesis of {4-(1E)-[2-(4-{[(1H-imidazol-2-ylmethyl)-(1-methyl-1H-imidazol-2-ylmethyl)-amino]-methyl}-phenyl)-vinyl]-benzyl}-dipropyl-amine [Compound No. 39]

EXAMPLE 39-1

Synthesis of methylen-triphenyl-λ$^5$-phosphane

Methyl triphenyl phosphiniumbromide (6.00 g) was suspended in THF (50 ml). After having been cooled to 0° C., the reaction solution was added with sodium amide (1.46 g) and the whole was refluxed under heating for 3 hours. The reaction solution was cooled to room temperature and then filtrated through Celite. The filtrate was concentrated under reduced pressure, thereby obtaining the subject compound (1.92 g) as a yellow-red solid.

EXAMPLE 39-2

Synthesis of 2-(4-vinyl-benzyl-isoindol)-1,3-dione

The compound (0.99 g) obtained in Example 1-1 was dissolved in THF (30 ml). The reaction solution was cooled to 0° C. and added with the compound (1.66 g) obtained in Example 39-1 and the whole was stirred at room temperature for 1.5 hours. The reaction solution was concentrated under reduced pressure and the solvent was distilled off. The resultant residue was purified through silica gel column chromatography (hexane/ethyl acetate), thereby obtaining the subject compound (0.78 g) as a white solid.

$^1$H-NMR(500 MHz,CDCl$_3$):δ=4.83(2H,s),5.23(1H,dd, J=1.0,10.0 Hz),5.71(1H,dd,J=1.0,16.6 Hz),6.67(1H,dd, J=6.8,10.7 Hz),7.35-7.40(4H,m),7.70-7.72(2H,m),7.83-7.85 (2H,m).

EXAMPLE 39-3

Synthesis of 4-{2-[4-(1E)-(1,3-dioxo-1,3-dihydro-isoindol-2-ylmethyl)-phenyl]-vinyl}-benzaldehyde The compound (760 mg) obtained in Example 39-2, p-bromobenzaldehyde (690 mg), tri-o-tolylphosphine (103 mg), and palladium acetate (39 mg) were suspended in xylene (15 ml) and triethylamine (15 ml) and the whole was stirred at 130° C. for 63 hours. The reaction solution was cooled to room temperature and then concentrated under reduced pressure. The resultant residue was added with distilled water and the whole was subjected to extraction with dichloromethane. The organic layer was dried with anhydrous magnesium sulfate. The drying agent was filtrated out and the organic layer was then concentrated under reduced pressure. The residue was purified through silica gel column chromatography (hexane/dichloromethane), thereby obtaining a yellow-white solid (0.91 g).

MS(FAB,Pos.):m/z=368[M+H]$^+$ $^1$H-NMR(500 MHz,CDCl$_3$):δ=4.86(2H,s),7.11(1H,d, J=16.2 Hz),7.22(1H, d,J=16.2 Hz),7.45(2H,d,J=8.3 Hz),7.50 (2H,d,J=8.3 Hz),7.64(2H,d,J=8.5 Hz),7.71-7.73(2H,m), 7.85-7.87(4H,m),9.99(1H,s).

EXAMPLE 39-4

Synthesis of 2-{4-(1E)-[2-(4-dipropylaminomethyl-phenyl)-vinyl]-benzyl}-isoindol-1,3-dione The compound (650 mg) obtained in Example 39-3 was dissolved in 1,2-dichloroethane (40 ml). The reaction solution was added with n-dipropylamine (0.29 ml) and sodium triacetoxyborohydride (600 mg) and the whole was stirred at room temperature for 18 hours. After that, n-dipropylamine (0.29 ml) was added thereto and the whole was stirred at 50° C. for 1 hour. Then, sodium triacetoxyborohydride (600 mg) was added thereto and the whole was stirred at 50° C. for 20 hours. The reaction solution was cooled to room temperature and then concentrated under reduced pressure. The resultant residue was added with a 1 mol/l sodium hydroxide aqueous solution and the whole was subjected to extraction with chloroform. The organic layer was dried with anhydrous magnesium sulfate. The drying agent was filtrated out and the organic layer was then concentrated under reduced pressure. The residue was purified through silica gel column chromatography (chloroform/ethyl acetate), thereby obtaining the subject compound (646 mg) as a white solid.

$^1$H-NMR(500 MHz,CDCl$_3$):δ=0.86(6H,t,J=7.3 Hz),1.44-1.51(4H,m),2.35-2.38(4H,m),3.54(2H,s),4.85(2H,s),7.05 (2H,d,J=1.7 Hz),7.30-7.46(8H,m),7.70-7.73(2H,m),7.84-7.86(2H,m).

EXAMPLE 39-5

Synthesis of {4-(1E)-[2-(4-{[(1H-imidazol-2-ylmethyl)-(1-methyl-1H-imidazol-2-ylmethyl)-amino]-methyl}-phenyl)-vinyl]-benzyl}-dipropyl-amine [Compound No. 39]

The compound (630 mg) obtained in Example 39-4 was dissolved in chloroform (5.0 ml) and methanol (10 ml). The reaction solution was added with hydrazine monohydrate (1.0 ml) and refluxed under heating for 1 hour. The reaction solution was cooled to room temperature and then the precipitated solid was filtrated out. The filtrate was concentrated under reduced pressure. The residue was added with distilled water and the whole was subjected to extraction with chloroform. The organic layer was dried with anhydrous magnesium sulfate. The drying agent was filtrated out and the organic layer was then concentrated under reduced pressure.

The resultant was dissolved in methanol (12 ml). The reaction solution was added with 2-imidazole carboxaldehyde (219 mg) and trimethyl orthoformate (0.39 ml) and the whole was stirred at room temperature for 16 hours. After having been cooled to 0° C., the reaction solution was added with sodium borohydride (135 mg) and the whole was stirred at room temperature for 3 hours. The reaction solution was concentrated under reduced pressure. The resultant residue was added with distilled water and the whole was subjected to extraction with chloroform. The organic layer was washed with a saturated saline solution and dried with anhydrous magnesium sulfate. The drying agent was filtrated out and the organic layer was then concentrated under reduced pressure.

The resultant was dissolved in methanol (12 ml). The reaction solution was added with 1-methyl-2-imidazole carboxaldehyde (156 mg) and trimethyl orthoformate (0.24 ml) and the whole was stirred at room temperature for 15 hours. After having been cooled to 0° C., the reaction solution was added with sodium borohydride (83 mg) and the whole was stirred at room temperature for 2 hours. The reaction solution was concentrated under reduced pressure. The resultant residue was added with distilled water and the whole was subjected to extraction with chloroform. The organic layer was washed with a saturated saline solution and dried with anhydrous magnesium sulfate. The drying agent was filtrated out and the organic layer was then concentrated under reduced pressure. The residue was purified through silica gel column chromatography (chloroform/ethyl acetate), thereby obtaining the subject compound (449 mg) as a white solid.

MS(FAB,Pos.):m/z=497[M+H]$^+$ $^1$H-NMR(500 MHz,DMSO-d$_6$):δ=0.88(6H,t,J=7.3 Hz), 1.70(4H,tq,J=7.3,7.6 Hz),2.96(4H,t,J=7.6 Hz),3.17(2H,s), 3.72(3H,s),4.07(2H,s),4.15(2H,s),4.31(2H,s),7.28(2H,d, J=9.9 Hz),7.35(2H,d,J=8.1 Hz),7.50(2H,s),7.52-7.57(4H, m),7.62(2H,s),7.69(2H,d,J=8.2 Hz).

EXAMPLE 40

Production Example 40

Synthesis of {[4-((1Z)-2-{4-[(dipropylamino)-methyl]-phenyl}-vinyl)-phenyl]-methyl}-(imidazol-2-ylmethyl)-[(1-methylimidazol-2-yl)-methyl]-amine [Compound No. 40]

EXAMPLE 40-1

Synthesis of 4-((1Z)-2-{4-[(1,3-dioxo[c]azolin-2-yl)-methyl]-phenyl}-vinyl)-benzaldehyde The compound (0.76 g) obtained in Example 39-3, p-bromobenzaldehyde (0.69 g), tri-o-tolylphosphine (103 mg), and palladium acetate (39 mg) were suspended in xylene (15 ml) and triethylamine (15 ml) and the whole was stirred at 130° C. for 63 hours. The reaction solution was cooled to room temperature and then concentrated under reduced pressure. The resultant residue was added with distilled water and the whole was subjected to extraction with dichloromethane. The organic layer was dried with anhydrous magnesium sulfate. The drying agent was filtrated out and the organic layer was then concentrated under reduced pressure. The resultant residue was purified through silica gel column chromatography (hexane/dichloromethane), thereby obtaining the subject compound (25 mg) as a colorless oily substance.
$^1$H-NMR(500 MHz,CDCl$_3$):δ=4.87(2H,s),5.55(2H,m), 7.72-7.88(8H,m), 7.25-7.48(4H,m),10.02(1H,s).

EXAMPLE 40-2

Synthesis of 2-{[4-((1Z)-2-{4-[(dipropylamino)-methyl]-phenyl}-vinyl)-phenyl]-methyl}-benzo[c]azolin-1,3-dione The compound (25 mg) obtained in Example 40-1 was dissolved in 1,2-dichloroethane (3.0 ml). The reaction solution was added with n-dipropylamine (0.019 ml) and sodium triacetoxyborohydride (36 mg) and the whole was stirred at room temperature for 62 hours. After that, n-dipropylamine (0.019 ml) and sodium triacetoxyborohydride (36 mg) were added thereto and the whole was stirred at 50° C. for 3 hours. Then, n-dipropylamine (0.019 ml) and sodium triacetoxyborohydride (36 mg) were added thereto and the whole was refluxed under heating for 3 hours. The reaction solution was cooled to room temperature and then concentrated under reduced pressure. The resultant residue was added with a 1 mol/l sodium hydroxide aqueous solution and the whole was subjected to extraction with chloroform. The organic layer was dried with anhydrous magnesium sulfate. The drying agent was filtrated out and the organic layer was then concentrated under reduced pressure. The resultant residue was purified through silica gel column chromatography (chloroform/ethyl acetate), thereby obtaining the subject compound (27.0 mg) as a colorless oily substance.
$^1$H-NMR(500 MHz,CDCl$_3$):δ=0.86(6H,t,J=7.3 Hz),1.44-1.50(4H,m),2.36-2.39(4H,m),3.55(2H,s),4.86(2H,s),5,37 (1H,d,J=1.2 Hz),5.44(1H,d,J=1.2 Hz),7.22-7.47(6H,m), 7.70-7.74(2H,m),7.84-7.87(2H,m).

EXAMPLE 40-3

Synthesis of {[4-((1Z)-2-{4-[(dipropylamino)-methyl]-phenyl}-vinyl)-phenyl]-methyl}-(imidazol-2-ylmethyl)-[(1-methylimidazol-2-yl)-methyl]-amine [Compound No. 40]

The compound (110 mg) obtained in Example 40-2 was dissolved in methanol (6.0 ml). The reaction solution was added with hydrazine monohydrate (0.5 ml) and refluxed under heating for 1 hour. The reaction solution was cooled to room temperature and then concentrated under reduced pressure. The resultant residue was added with distilled water and the whole was subjected to extraction with chloroform. The organic layer was dried with anhydrous magnesium sulfate. The drying agent was filtrated out and the organic layer was then concentrated under reduced pressure.

The resultant was dissolved in methanol (3.0 ml). 2-Imidazole carboxaldehyde (16.4 mg) and trimethyl orthoformate (28 μl) were added thereto, and the whole was stirred at room temperature for 16.5 hours. After having been cooled to 0° C., the reaction solution was added with sodium borohydride (9.7 mg) and the whole was stirred at room temperature for 1 hour. The reaction solution was concentrated under reduced pressure. The resultant residue was added with distilled water and the whole was subjected to extraction with chloroform. The organic layer was dried with anhydrous magnesium sulfate. The drying agent was filtrated out and the organic layer was then concentrated under reduced pressure.

The resultant was dissolved in methanol (2.0 ml) and added with 1-methyl-2-imidazole carboxaldehyde (9.5 mg) and trimethyl orthoformate (14 μl), and the whole was stirred at room temperature for 65 hours. After having been cooled to 0° C., the reaction solution was added with sodium borohydride (4.1 mg) and the whole was stirred at room temperature for 2 hours. The reaction solution was concentrated under reduced pressure. The resultant residue was added with distilled water and the whole was subjected to extraction with chloroform. The organic layer was dried with anhydrous magnesium sulfate. The drying agent was filtrated out and the organic layer was then concentrated under reduced pressure. The residue was purified through silica gel column chromatography (chloroform/ethyl acetate), thereby obtaining the subject compound (3.9 mg) as a yellow oily substance.
MS(FAB,Pos.):m/z=497[M+H]$^+$
$^1$H-NMR(500 MHz,CDCl$_3$):δ=0.87(6H,t,J=7.3 Hz),1.49 (4H,tq,J=7.3,7.6 Hz),2.39(4H,t,J=7.6 Hz),3.50(2H,s),3.56 (3H,s),3.59(2H,s),3.63(2H,s),3.71(2H,s),5.42(1H,d,J=1.2 Hz),5.44(1H,d,J=1.2 Hz),6.88-7.47(12H,m).

EXAMPLE 41

Production Example 41

Synthesis of {[4-((1E)-2-{4-[2-(dipropylamino)-ethyl]-phenyl}-vinyl)-phenyl]-methyl}-(imidazol-2-ylmethyl)-[(1-methylimidazol-2-yl)-methyl]-amine [Compound No. 41]

EXAMPLE 41-1

Synthesis of 2-{[4-((1E)-2-{4-[2-(dipropylamino)-ethyl]-phenyl}-vinyl)-phenyl]-methyl}-benzo[c]azolin-1,3-dione Under a nitrogen atmosphere, methoxymethyl triphenylphosphonium chloride (1.05 g) was suspended in THF (25 ml). After having been cooled to 0° C., the reaction solution was added with a 2 mol/l lithium diisopropylamide/heptane/THF/ethylbenzene solution (1.52 ml) and the whole was stirred at room temperature for 1.5 hours to control ylide. Under a nitrogen atmosphere, the compound (400 mg) obtained in Example 39-4 was suspended in THF (20 ml). After having been cooled to 0° C., the reaction solution was added with ylide and the whole was stirred at room temperature for 14 hours. The reaction solution was concentrated under reduced pressure and then the residue was purified through column chromatography (chloroform/ethyl acetate).

The resultant was dissolved in 1,4-dioxane (10 ml). The reaction solution was added with 1 mol/l hydrochloric acid (3.0 ml) and the whole was refluxed under heating for 2 hours. The reaction solution was cooled to room temperature and then concentrated under reduced pressure. A 1 mol/l sodium hydroxide aqueous solution was added thereto and the whole was subjected to extraction with chloroform. After that, the organic layer was washed with a saturated saline solution and the organic layer was dried with anhydrous magnesium sulfate. The drying agent was filtrated out and the organic layer was then concentrated under reduced pressure.

The resultant was dissolved in 1,2-dichloroethane (6.0 ml). The reaction solution was added with n-dipropylamine (0.057 ml) and sodium triacetoxyborohydride (106 mg), and the whole was stirred at room temperature for 66 hours. After having been concentrated under reduced pressure, the reaction solution was added with a 1 mol/l sodium hydroxide aqueous solution and the whole was subjected to extraction with chloroform.

The organic layer was dried with anhydrous magnesium sulfate. The drying agent was filtrated out and the organic layer was then concentrated under reduced pressure. The resultant residue was purified through silica gel column chromatography (chloroform/ethyl acetate), thereby obtaining the subject compound (55 mg) as a white solid.

$^1$H-NMR(500 MHz,CDCl$_3$):δ=0.82-0.94(6H,m),1.44-1.65(4H,m),2.48(4H,t,J=7.6 Hz),4.85(2H,s),7.04(2H,d,J=3.9 Hz),7.16-7.49(8H,m),7.65-7.73(2H,m),7.84-7.86(2H,m).

EXAMPLE 41-2

Synthesis of {[4-((1E)-2-{4-[2-(dipropylamino)-ethyl]-phenyl}-vinyl)-phenyl]-methyl}-(imidazol-2-ylmethyl)-[(1-methylimidazol-2-yl)-methyl]-amine [Compound No. 41]

The compound (113 mg) obtained in Example 41-1 was dissolved in chloroform (5.0 ml) and methanol (5.0 ml).

The reaction solution was added with hydrazine monohydrate (0.5 ml) and refluxed under heating for 2 hours. The reaction solution was cooled to room temperature and then the solvent was concentrated under reduced pressure. The resultant residue was added with distilled water and the whole was subjected to extraction with chloroform. The organic layer was dried with anhydrous magnesium sulfate. The drying agent was filtrated out and the organic layer was then concentrated under reduced pressure.

The reaction solution was added with hydrazine monohydrate (0.5 ml) and refluxed under heating for 2 hours. The reaction was cooled to room temperature and then concentrated under reduced pressure. The resultant residue was added with distilled water and the whole was subjected to extraction with chloroform. The organic layer was dried with anhydrous magnesium sulfate. The drying agent was filtrated out and the organic layer was then concentrated under reduced pressure.

The drying agent was filtrated out and the organic layer was then concentrated under reduced pressure.

The resultant was dissolved in methanol (37 ml). 1-Methyl-2-imidazole carboxaldehyde (9.5 mg) and trimethyl orthoformate (0.051 ml) were added thereto and the whole was stirred at room temperature for 16 hours. After having been cooled to 0° C., the reaction solution was added with sodium borohydride (18 mg) and the whole was stirred at room temperature for 3 hours. The reaction solution was concentrated under reduced pressure. The resultant was added with distilled water and the whole was subjected to extraction with chloroform. The organic layer was dried with anhydrous magnesium sulfate. The drying agent was filtrated out and the organic layer was then concentrated under reduced pressure. The residue was purified through silica gel column chromatography (chloroform/ethyl acetate) and treated with hydrochloric acid, thereby obtaining a hydrochloride (65.4 mg) of the subject compound as a white solid.

MS(FAB,Pos.):m/z=511[M+H]$^+$ $^1$H-NMR(500 MHz,DMSO-d$_6$):δ=0.92(6H,t,J=7.3 Hz), 1.71(4H,sext.,J=7.3 Hz),3.02-3.08(6H,m),3.20-3.26(2H,m), 3.64-3.72(2H,m),3.71(3H,s),4.09(2H,s),4.16(2H,s),7.21 (2H,s),7.32(2H,d,J=8.2 Hz),7.40(2H,d,J=8.2 Hz),7.49(2H,d, J=8.4 Hz),7.52-7.56(4H,m),7.65(2H,s),10.45(1H,br).

EXAMPLE 42

Production Example 42

Synthesis of {[4-((1E)-2-{4-[(dipropylamino)-methyl]-phenyl}-vinyl)-phenyl]-methyl}-bis-(imidazol-2-ylmethyl)-amine [Compound No. 42]

EXAMPLE 42-1

Synthesis of {[4-((1E)-2-{4-[(dipropylamino)-methyl]-phenyl}-vinyl)-phenyl]-methyl}-bis-(imidazol-2-ylmethyl)-amine [Compound No. 42]

The compound (311 mg) obtained in Example 39-4 was dissolved in chloroform (5.0 ml) and methanol (5.0 ml).

The reaction solution was added with hydrazine monohydrate (0.5 ml) and refluxed under heating for 2 hours. The reaction solution was cooled to room temperature and then concentrated under reduced pressure. The resultant was added with distilled water and the whole was subjected to extraction with chloroform. The organic layer was dried with anhydrous magnesium sulfate. The drying agent was filtrated out and the organic layer was then concentrated under reduced pressure.

The resultant was dissolved in methanol (8.0 ml). After having been cooled to 0° C., the reaction solution was added with 2-imidazole carboxaldehyde (128 mg), trimethyl orthoformate (0.146 ml), and sodium cyanoborohydride (107 mg) and the whole was stirred at room temperature for 38 hours. The reaction solution was concentrated under reduced pressure. The resultant residue was added with a 1 mol/l sodium hydroxide aqueous solution and the whole was subjected to extraction with chloroform. The organic layer was dried with anhydrous magnesium sulfate. The drying agent was filtrated out and the organic layer was then concentrated under reduced pressure. The residue was purified through silica gel column chromatography (chloroform/ethyl acetate) and treated with hydrochloric acid, thereby obtaining a hydrochloride (50 mg) of the subject compound as a yellow-white solid.

MS(FAB,Pos.):m/z=483[M+H]$^+$ $^1$H-NMR(500 MHz,DMSO-d$_6$):δ=0.87(6H,t,J=7.3 Hz), 1.72(4H,br),2.93(4H,br),4.13(2H,s),4.30(4H,br),4.48(2H, br),7.28(1H,d,J=7.3 Hz), 7.38(1H,s),7.43(1H,d,J=8.1 Hz), 7.50(1H,d,J=8.2 Hz),7.59-7.71(10H,m).

EXAMPLE 43

Production Example 43

Synthesis of [4-(6-{[(1H-imidazol-2-yl-methyl.)-(1-methyl-imidazol-2-yl-methyl)-amino]-methyl}-benzothiazol-2-yl)-benzyl]-dipropyl-amine [Compound No. 43]

EXAMPLE 43-1

Synthesis of N-(4-cyano-phenyl)-4-methyl-benzamide

4-Aminobenzonitrile (1.10 g) was dissolved in chloroform (30 ml). After having been cooled to 0° C., the reaction solution was added with 4-dimethylaminopyridine (1.70 g) and p-toluic acid chloride (1.95 g). The reaction solution was warmed back to room temperature and stirred overnight. The reaction solution was added with distilled water and subjected to extraction with chloroform. The organic layer was washed with a saturated saline solution and dried with anhydrous sodium sulfate. The organic layer was concentrated under reduced pressure. The resultant residue was purified through silica gel column chromatography (chloroform/ethyl acetate) and then purified by recrystallization (hexane/ethanol), thereby obtaining the subject compound (1.26 g) as a white solid.

MS(FAB,Pos.):m/z=237[M+H]$^+$

EXAMPLE 43-2

Synthesis of N-(4-cyano-phenyl)-4-methyl-thiobenzamide

The compound (1.26 g) obtained in Example 43-1 was dissolved in toluene (20 ml) and added with a Lawesson's reagent (1.29 g) and the whole was refluxed under heating for 2 hours. The reaction solution was cooled to room temperature and the precipitated solid was filtrated out. The resultant solid was subjected to recrystallization (methanol), thereby obtaining the subject compound (1.09 g) as a yellow solid.

MS(FAB,Pos.):m/z=253[M+H]$^+$

EXAMPLE 43-3

Synthesis of 2-p-toluyl-benzothiazol-6-carbonitrile

Potassium ferricyanide (5.78 g) was dissolved in distilled water (40 ml) and the whole was heated to 90° C. A suspension containing the compound (1.09 g) obtained in Example 43-2, ethanol (1.0 ml), and a 30% sodium hydroxide aqueous solution (3.2 ml) was dropped to the reaction solution for 5 minutes. The whole was stirred at 90° C. for 3 hours and then cooled to room temperature. The precipitated solid was filtrated out and purified by recrystallization (methanol), thereby obtaining the subject compound (0.53 g) as a white solid.

MS(FAB,Pos.):m/z=251[M+H]$^+$

EXAMPLE 43-4

Synthesis of 2-(4-dipropyl-amino-methyl-phenyl)-benzothiazol-6-carbonitrile

The compound (0.53 g) obtained in Example 43-3 and N-bromosuccinimide (0.43 g) were weighed and carbon tetrachloride (15 ml) was added thereto. The reaction solution was added with 2,2'-azobisisobutyronitrile (13.2 ml) and refluxed under heating for 1.5 hours. The reaction solution was cooled to room temperature and then subjected to filtration through Celite. The filtrate was concentrated under reduced pressure.

The resultant was dissolved in dichloromethane (18 ml) and added with 4-dimethylaminopyridine (0.55 g) and n-dipropylamine (0.5 ml) and the whole was stirred at room temperature for 2 hours. The reaction solution was added with distilled water and the whole was subjected to extraction with chloroform. The organic layer was washed with a saturated saline solution and dried with anhydrous sodium sulfate. The organic layer was then concentrated under reduced pressure. The resultant residue was purified through silica gel column chromatography (chloroform/ethyl acetate), thereby obtaining the subject compound (110.2 mg) as a pale-yellow solid.

MS(FAB,Pos.):m/z=350[M+H]$^+$

EXAMPLE 43-5

Synthesis of [4-(6-amino-methyl-benzothiazol-2-yl)-benzyl]-dipropyl-amine

The compound (99.8 mg) obtained in Example 43-4 was dissolved in chloroform (1.0 ml) and methanol (10 ml).

The reaction solution was added with platinum oxide (7.3 mg) and the whole was stirred overnight at room temperature under a hydrogen atmosphere. The catalyst was filtrated out through Celite and the filtrate was concentrated under reduced pressure. The resultant residue was purified through silica gel column chromatography (chloroform/ethyl acetate), thereby obtaining the subject compound (52.5 mg) as a pale-yellow solid.

MS(FAB,Pos.):m/z=354[M+H]$^+$

EXAMPLE 43-6

Synthesis of [4-(6-{[(1H-imidazol-2-yl-methyl)-(1-methyl-imidazol-2-yl-methyl)-amino]-methyl}-benzothiazol-2-yl)-benzyl]-dipropyl-amine [Compound No. 43]

The compound (52.5 mg) obtained in Example 43-5 was dissolved in methanol (1.0 ml). The reaction solution was added with 2-imidazole carboxaldehyde (15.2 mg) and trimethyl orthoformate (40 µl) and the whole was stirred at room temperature for 2 hours. Subsequently, sodium borohydride (15.3 mg) was added thereto and the whole was stirred at room temperature for 40 minutes. The reaction solution was added with a saturated aqueous ammonium chloride solution (2.0 ml) and the whole was stirred at room temperature for 30 minutes. The whole was subjected to extraction with chloroform. The organic layer was washed with a saturated saline solution and dried with anhydrous sodium sulfate. The reaction solution was concentrated under reduced pressure.

The resultant was dissolved in methanol (1.5 ml) and added with 1-methyl-2-imidazole carboxaldehyde (37.0 mg) and sodium cyanoborohydride (47.4 mg). The reaction solution was added with acetic acid to adjust to pH 5 and the whole was stirred at room temperature for 20 hours. The reaction solution was added with a 1 mol/l sodium hydroxide aqueous solution and the whole was subjected to extraction with chloroform. The organic layer was washed with a saturated saline solution and dried with anhydrous sodium sulfate.

After the organic layer was concentrated under reduced pressure, the residue was purified through silica gel column chromatography (chloroform/ethyl acetate) and treated with hydrochloric acid, thereby obtaining a hydrochloride (44.8 mg) of the subject compound as a pale-yellow solid.

MS(FAB,Pos.):m/z=528[M+H]$^+$ $^1$H-NMR(500 MHz,DMSO-d$_6$):δ=0.87(6H,t,J=7.3 Hz), 1.75(4H,br),2.96 ( 4H,br),3.72(3H,s),3.86(2H,s),4.14(2H,s), 4.21(2H,s),4.40(2H,br), 7.51(2H,s),7.57(1H,d,J=8.3 Hz), 7.63(2H,s),7.83(2H,d,J=8.4 Hz), 7.95(1H,d,J=8.3 Hz),8.16 (2H,d,J=8.4 Hz),8.30(1H,s).

EXAMPLE 44

Production Example 44

Synthesis of (4-{[(1H-imidazol-2-ylmethyl)-(1-methyl-1H-imidazol-2-ylmethyl)-amino]-methyl}-benzyl)-methyl-(4-piperidin-1-ylbutyl)amine [Compound No. 44]

EXAMPLE 44-1

Synthesis of 4-[(4,4-diethoxybutylamino)methyl]-benzonitrile

4-Formylbenzonitrile (612.0 mg) was dissolved in methanol (18.4 ml), and 4,4-diethoxybutylamine (752.5 mg) and trimethyl orthoformate (1.53 ml) were added thereto. The whole was stirred at room temperature for 18 hours. Subsequently, the solution was added with sodium borohydride (529.7 mg) under ice-cooling and stirred at room temperature for additional 30 minutes. The reaction solution was concentrated under reduced pressure. The residue was added with water and the whole was subjected to extraction with chloroform. The organic layer was washed with a saturated saline solution and dried with anhydrous sodium sulfate, followed by concentration under reduced pressure. The residue was purified through silica gel column chromatography (chloroform/methanol), thereby obtaining the subject compound (1.16 g) as a yellow oily substance.
MS(FAB,Pos.):m/z=277[M+H]$^+$

EXAMPLE 44-2

Synthesis of 4-{[(4,4-diethoxybutyl)methylamino]methyl}benzonitrile

The compound (1.16 g) obtained in Example 44-1 was dissolved in methanol (34.8 ml) and added with sodium cyanoborohydride (1.21 g) and a 36% formaldehyde aqueous solution (0.648 ml). The solution was adjusted to pH 4 with acetic acid and stirred at room temperature for 18 hours. The reaction solution was concentrated under reduced pressure. The residue was dissolved in chloroform and washed with a 1 mol/l sodium hydroxide aqueous solution and dried with anhydrous sodium sulfate, followed by concentration under reduced pressure. The residue was purified through silica gel column chromatography (chloroform/methanol), thereby obtaining the subject compound (1.22 g) as a yellow oily substance.
MS(FAB,Pos.):m/z=291[M+H]$^+$

EXAMPLE 44-3

Synthesis of 4-{[methyl-(4-oxobutyl)-amino]-methyl}-benzonitrile

The compound (1.22 g) obtained in Example 44-2 was dissolved in THF (12.2 ml) and added with 1 mol/l hydrochloric acid (12.2 ml). The whole was stirred at room temperature for 19 hours. The reaction solution was concentrated under reduced pressure. The residue was added with a 1 mol/l sodium hydroxide aqueous solution and the whole was subjected to extraction with chloroform. The organic layer was washed with a saturated saline solution and dried with anhydrous sodium sulfate, followed by concentration under reduced pressure. The residue was purified through silica gel column chromatography (chloroform/methanol), thereby obtaining the subject compound (0.790 g) as a yellow oily substance.
MS(FAB,Pos.):m/z=217[M+H]$^+$

EXAMPLE 44-4

Synthesis of 4-{methyl-(4-piperidin-1-ylbutyl)-amino]-methyl}-benzonitrile

The compound (0.790 g) obtained in Example 44-3 was dissolved in methanol (23.7 ml) and added with piperidine (0.542 ml) and sodium cyanoborohydride (459.3 mg). The solution was adjusted to pH 4 with acetic acid and stirred at room temperature for 5 days. The reaction solution was concentrated under reduced pressure. The residue was dissolved in chloroform, washed with a 1 mol/l sodium hydroxide aqueous solution and a saturated saline solution, and dried anhydrous sodium sulfate, followed by concentration under reduced pressure. The residue was purified through silica gel column chromatography (chloroform/ethyl acetate), thereby obtaining the subject compound (0.905 g) as a yellow oily substance.
MS(FAB,Pos.):m/z=286[M+H]$^+$

EXAMPLE 44-5

Synthesis of (4-aminomethylbenzyl)-methyl-(4-piperidin-1-ylbutyl)-amine

Lithium aluminum hydride (360.8 mg) was suspended in THF (27 ml) and a THF solution (27 ml) in which the compound (904.6 mg) obtained in Example 44-4 was dissolved was gradually added thereto. The whole was stirred at room temperature for 1 hour. The reaction solution was added with ethyl acetate, methanol, and a 10% aqueous sodium potassium tartrate solution and the whole was stirred for 1 day. The solution was subjected to extraction with chloroform and washed with a saturated saline solution. After that, the resultant was dried with anhydrous sodium sulfate and concentrated under reduced pressure. The residue was purified through silica gel column chromatography (chloroform/ethyl acetate), thereby obtaining the subject compound (247.5 mg) as a yellow oily substance.

EXAMPLE 44-6

Synthesis of (4-{[(1H-imidazol-2-ylmethyl)-amino]-methyl)-benzyl}-methyl-(4-piperidin-1-ylbutyl)-amine The compound (248.5 mg) obtained in Example 44-5 was dissolved in methanol (12.4 ml) and added with 2-imidazole carboxaldehyde (123.7 mg) and trimethyl orthoformate (0.282 ml) and the whole was stirred at room temperature for 2.5 hours. Subsequently, sodium borohydride (97.4 mg) was added thereto under ice-cooling and the whole was stirred at room temperature for additional 30 minutes. The reaction solution was concentrated under reduced pressure. The residue was added with water and the whole was subjected to extraction with chloroform. The organic layer was washed with a saturated saline solution and dried with anhydrous sodium sulfate, followed by concentration under reduced pressure. The residue was purified through silica gel column chromatography (chloroform/methanol), thereby obtaining the subject compound (116.3 mg) as a yellow oily substance.
MS(FAB,Pos.):m/z=370[M+H]$^+$

EXAMPLE 44-7

Synthesis of (4-{[(1H-imidazol-2-ylmethyl)-(1-methyl-1H-imidazol-2-ylmethyl)-amino]-methyl}-benzyl)-methyl-(4-piperidin-1-ylbutyl)amine [Compound No. 44]

The compound (116.3 mg) obtained in Example 44-6 was dissolved in methanol (5.81 ml) and added with 1-methyl-2-imidazole carboxaldehyde (52.0 mg) and sodium cyanoborohydride (39.6 mg). The solution was adjusted to pH 4 with acetic acid and stirred at room temperature for 6 days. The reaction solution was concentrated under reduced pressure. The residue was dissolved in chloroform, washed with a 1 mol/l sodium hydroxide aqueous solution and a saturated saline solution, and dried with anhydrous sodium sulfate, followed by concentration under reduced pressure. The residue was purified through silica gel column chromatography (chloroform/methanol) and treated with hydrochloric acid, thereby obtaining a hydrochloride (163.4 mg) of the subject compound as a white solid.
MS(FAB,Pos.):m/z=464[M+H]$^+$
$^1$H-NMR(500 Mz,DMSO-d$_6$+D$_2$O):δ=1.69-1.81(10H,m), 2.58(3H,m),2.82-3.17(6H,m),3.71(3H,s),3.74(2H,s),4.11 (2H,s),4.19(2H,s),4.31(2H,s),7.41(2H,d,J=8.1 Hz),7.47(2H, d,J=8.1 Hz),7.50(2H,s),7.62(2H,s).

EXAMPLE 45

Production Example 45

Synthesis of 2-(2-(4-dipropylamino-butyl)-6-{[(1H-imidazol-2-ylmethyl)-(1-methyl-1H-imidazol-2-ylmethyl)-amino]-methyl}-benzimidazol-1-yl)-ethanol [Compound No. 45]

EXAMPLE 45-1

Synthesis of 1-iodo-2-methoxymethoxy-ethane

2-Iodoethanol (0.637 g) was dissolved in dimethoxymethane (5.0 ml). The reaction solution was added with p-toluenesulfonic acid monohydrate (82 mg) and lithium bromide (42 mg), and stirred at room temperature for 18 hours. The reaction solution was concentrated under reduced pressure. The resultant residue was added with distilled water and the whole was subjected to extraction with chloroform. The organic layer was dried with anhydrous sodium sulfate. The drying agent was filtrated out and the organic layer was concentrated under reduced pressure, thereby obtaining the subject compound (0.547 g) as a brown oily substance.
MS(FAB,Pos.):m/z=217[M+H]$^+$

EXAMPLE 45-2

Synthesis of 3,4-diamino-benzonitrile

3-Nitro-4-amino-benzonitrile (4.38 g) was dissolved in ethanol (600 ml) and added with stannous chloride dihydrate (34.6 g) and the whole was heated to 60° C. Sodium borohydride (366 mg) was gradually added thereto and the whole was stirred overnight at 60° C. After completion of the reaction, the resultant was filtrated through Celite and the filtrate was subjected to distillation of the solvent under reduced pressure. The residue was dissolved in chloroform, washed with a saturated aqueous sodium hydrogen carbonate solution and a saturated saline solution, and then dried with anhydrous sodium sulfate. After filtration, the solvent was distilled off under reduced pressure. The residue was allowed to recrystallize (hexane/ethyl acetate), thereby obtaining the subject compound (2.56 g) as a brown crystal.
MS(EI):m/z=133[M]$^+$
$^1$H-NMR(500 MHz,CDCl$_3$):δ=6.68(1H,d,J=8.1 Hz),6.95 (1H,s),7.05(1H, d,J=8.1 Hz).

EXAMPLE 45-3

Synthesis of [4-(2-amino-5-cyano-phenylcarbamoyl)-butyl]-carbamic acid t-butyl ester In chloroform/DMF (60 ml/30 ml), t-butoxycarbonylamino valeric acid (3.91 g), WSCI hydrochloride (4.02 g), and HOBt (2.82 g) were dissolved and the whole was stirred for 1 hour. The solution was added with the compound (2.32 g) obtained in Example 39-2 and the whole was stirred overnight at room temperature. After completion of the reaction, the solvent was distilled off under reduced pressure. The residue was dissolved in chloroform, washed with a saturated aqueous ammonium chloride solution, a saturated aqueous sodium hydrogen carbonate solution, and a saturated saline solution, and then dried with anhydrous sodium sulfate. After filtration, the solvent was distilled off under reduced pressure. The residue was purified through silica gel column chromatography (hexane/ethyl acetate), thereby obtaining the subject compound (4.06 g) as a white solid.
MS(FAB,Pos.):m/z=333[M+H]$^+$
$^1$H-NMR(500 MHz,DMSO-d$_6$):δ=1.34-1.46(2H,m),1.38 (9H,s),1.56(2H,quint., J=7.3 Hz),2.33(2H,t,J=7.3 Hz),2.93 (2H,dt,J=6.1,6.8 Hz),5.93 (2H,br),6.76(1H,d,J=8.4 Hz),6.83 (1H,t,J=5.4 Hz),7.28(1H,d,J=8.4 Hz),7.61(1H,s),9.10(1H,s).

EXAMPLE 45-4

Synthesis of 2-(4-dipropylamino-butyl)-3-(2-hydroxy-ethyl)-3H-benzinidazol-5-carbonitrile The compound (175.1 mg) obtained in Example 45-3 was dissolved in DMF (4.0 ml). The reaction solution was cooled to 0° C. and added with 60% sodium hydride (45.2 mg) and the whole was stirred at room temperature for 40 minutes. Then, the compound (179.9 mg) obtained in Example 45-1 was added thereto and the whole was stirred at room temperature for 2 hours. The reaction solution was added with distilled water and subjected to extraction with diethylether. The organic layer was washed with a saturated saline solution and dried with anhydrous sodium sulfate. The drying agent was filtrated out and then the organic layer was concentrated under reduced pressure.
The resultant was dissolved in methanol (3.0 ml). The reaction solution was added with a 4 mol/l hydrogen chloride/dioxane solution (2.0 ml) and the whole was stirred at room temperature for 1.5 hours. The reaction solution was concentrated under reduced pressure and added with a 1 mol/l sodium hydroxide aqueous solution and the whole was subjected to extraction with chloroform. The organic layer was washed with a saturated saline solution and dried with anhydrous sodium sulfate. The drying agent was filtrated out and then the organic layer was concentrated under reduced pressure.

The resultant was dissolved in methanol (1.5 ml). The reaction solution was added with trimethyl orthoformate (76 μl) and the whole was cooled to 0° C. After that, a methanol solution (1.0 ml) in which propionaldehyde (40.1 mg) was dissolved was dropped thereto and the whole was stirred at room temperature for 20 minutes. Subsequently, the solution was added with sodium cyanoborohydride (43.7 mg) and the whole was stirred at room temperature for 14.5 hours. The reaction solution was concentrated under reduced pressure and added with a 1 mol/l sodium hydroxide aqueous solution and the whole was subjected to extraction with chloroform. The organic layer was washed with a saturated saline solution and dried with anhydrous sodium sulfate. The drying agent was filtrated out and then the organic layer was concentrated under reduced pressure. The resultant residue was purified through silica gel column chromatography (hexane/ethyl acetate), thereby obtaining the subject compound (41.8 mg) as a purple solid.

MS(FAB,Pos.):m/z=343[M+H]$^+$

EXAMPLE 45-5

Synthesis of 2-(2-(4-dipropylamino-butyl)-6-{[(1H-imidazol-2-ylmethyl)-(1-methyl-1H-imidazol-2-ylmethyl)-amino]-methyl}-benzimidazol-1-yl)-ethanol [Compound No. 45]

The compound (41.8 mg) obtained in Example 45-4 was dissolved in ethanol (1.5 ml). The reaction solution was added with a 1 mol/l sodium hydroxide aqueous solution (0.3 ml) and Raney nickel (4.3 mg). The whole was stirred at room temperature for 17 hours under a hydrogen atmosphere. Then, the resultant was filtrated through Celite and added with distilled water, followed by extraction with chloroform. The organic layer was washed with a saturated saline solution and dried with anhydrous sodium sulfate. The drying agent was filtrated out and then the organic layer was concentrated under reduced pressure.

The resultant was dissolved in methanol (1.2 ml). The reaction solution was added with 2-imidazole carboxaldehyde (11.0 mg) and trimethyl orthoformate (30 μl) and the whole was stirred at room temperature for 1.5 hours. After having been cooled to 0° C., the reaction solution was added with sodium borohydride (2.7 mg) and the whole was stirred at room temperature for 1.5 hours. The reaction solution was concentrated under reduced pressure and added with distilled water, and the whole was subjected to extraction with chloroform. The organic layer was washed with a saturated saline solution and dried with anhydrous sodium sulfate. The drying agent was filtrated out and then the organic layer was concentrated under reduced pressure.

The resultant was dissolved in methanol (1.0 ml) and added with 1-methyl-2-imidazole carboxaldehyde (14.8 mg) and sodium cyanoborohydride (15.4 mg). The solution was adjusted to pH 5 with acetic acid and stirred at room temperature for 15 hours. The reaction solution was concentrated under reduced pressure. The resultant residue was added with a 1 mol/l sodium hydroxide aqueous solution and subjected to extraction with chloroform. The organic layer was washed with a saturated saline solution and dried with anhydrous sodium sulfate. The drying agent was filtrated out and then the organic layer was concentrated under reduced pressure. The residue was purified through silica gel column chromatography (chloroform/methanol) and treated with hydrochloric acid, thereby obtaining a hydrochloride (32.4 mg) of the subject compound as a pale-yellow solid.

MS(FAB,Pos.):m/z=522[M+H]$^+$
$^1$H-NMR(500 MHz,DMSO-d$_6$):δ=0.91(6H,t,J=7.3 Hz), 1.65-1.73(4H,m),1.83(2H,m),1.93(2H,m),2.99(4H,br),3.11 (2H,br),3.29(2H,br),3.73(3H,s),3.88(2H,s),4.12(2H,s),4.20 (2H,s),4.66(2H,br),7.53-7.55(3H,m),7.64(2H,s),7.70(1H,d, J=8.2 Hz),8.33(1H,d,J=8.2 Hz),10.27(1H,br).

EXAMPLE 46

Production Example 46

Synthesis of [3-(6-{[(1H-imidazol-2-ylmethyl)-(1-methyl-1H-imidazol-2-ylmethyl)-amino]-methyl}-1-propyl-1H-benzimidazol-2-yl)-propyl]-dipropyl-amine [Compound No. 46]

EXAMPLE 46-1

Synthesis of 3,4-diaminobenzonitrile

An ethanol solution (300 ml) containing 4-amino-3-nitrobenzonitrile (3.00 g) was added with stannous chloride dihydrate (20.7 g) and then added with sodium borohydride (348 mg). The whole was stirred overnight at 60° C. After that, the resultant was subjected to distillation until the amount of the solution became about 100 ml. The resultant was added with water (100 ml) and a large amount of solid component was generated.

The resultant was added with a 5 mol/l sodium hydroxide aqueous solution (42 ml) to adjust to pH 7. The solvent was distilled off. The solid component was filtrated out through Celite and washed with methanol and ethyl acetate in the stated order. The filtrate was again filtrated through Celite and only organic solvent was distilled off under reduced pressure. The remaining aqueous layer was subjected to extraction with ethyl acetate and dried with anhydrous magnesium sulfate, and the solvent was distilled off, thereby obtaining the subject compound (2.29 g) as a khaki crystal.

EXAMPLE 46-2

Synthesis of [3-(2-amino-5-cyano-phenylcarbamoyl)-propyl]-carbamic acid t-butyl ester A DMF solution (30 ml) containing 4-(t-butoxycarbonylamino)-butyric acid (1.53 g) was added with HOBt (1.07 g) and WSCI hydrochloride (1.51 g) and the whole was stirred for 0.5 hours. The reaction solution was dropped to a DMF solution (12 ml) containing the compound (1.00 g) obtained in Example 46-1. The whole was stirred at room temperature for 12 hours and then the solvent was distilled off. The resultant was dissolved in chloroform, washed with a saturated aqueous ammonium chloride solution and a saturated aqueous sodium hydrogen carbonate solution in the stated order, and dried with anhydrous magnesium sulfate. The residue obtained by distilling the solvent off was purified through silica gel column chromatography (ethyl acetate/chloroform), thereby obtaining the subject compound (1.57 g) as a milky-white solid.

MS(FAB,Pos.):m/z=319[M+H]$^+$
$^1$H-NMR(500 MHz,CDCl$_3$):δ=1.38(9H,s),1.68(2H, quint.,J=7.1 Hz),2.32(2H,t,J=7.6 Hz),2.97(2H,q,J=6.6 Hz), 5.95(2H,s),6.75(1H,d,J=8.5 Hz),6.86(1H,t,J=5.6 Hz),7.28 (1H,dd,J=2.2,8.5 Hz),7.59(1H,d,J=1.7 Hz),9.08(1H,s).

EXAMPLE 46-3

Synthesis of {3-[(2-amino-5-cyano-phenyl)-propyl-carbamoyl]-propyl}-carbamic acid t-butyl ester A DMF solution (4.0 ml) containing the compound (0.501 g) obtained in Example 46-2 was added with 60% sodium hydride (76.0 mg) and the whole was stirred at room temperature for 30 minutes. The solution was cooled with ice and then 1-iodopropane (0.184 ml) was dropped thereto. The whole was stirred at room temperature for 23 hours. The solvent in the reaction solution was distilled off. The resultant was dissolved in chloroform, washed with a saturated aqueous sodium hydrogen carbonate solution, and dried with anhydrous magnesium sulfate. The residue obtained by distilling the solvent off was purified through silica gel column chromatography (ethyl acetate/chloroform), thereby obtaining the subject compound (0.378 g) as a colorless crystal.

MS(FAB,Pos.):m/z=343[M+H]$^+$
$^1$H-NMR(500 MHz,CDCl$_3$):δ=0.99(3H,t,J=7.3 Hz),1.42 (9H,s),1.85(2H, sext.,J=7.3 Hz),2.14(2H,quint.,J=7.3 Hz), 2.95(2H,t,J=7.3 Hz),3.30(2H,q,J=6.3 Hz),4.10(2H,t,J=7.3 Hz),4.86(1H,br),7.50(1H,dd,J=1.5,8.3 Hz),7.64(1H,dd, J=0.7,1.5 Hz),7.75(1H,dd,J=0.5,8.3 Hz).

EXAMPLE 46-4

Synthesis of 2-(3-aminopropyl)-3-propyl-3H-benzo[d]imidazol-5-carbonitrile

The compound (0.375 g) obtained in Example 46-3 was dissolved in ethyl acetate (4.0 ml) and added with a 4 mol/l hydrogen chloride/dioxane solution (1.09 ml). The whole was stirred for 20 minutes and added with methanol (8.0 ml), followed by distillating off the solvent. The concentrate was added with chloroform and washed with a 1 mol/l sodium hydroxide aqueous solution, and the aqueous layer was extracted with chloroform. The organic layer was dried with anhydrous sodium sulfate and the solvent was distilled off, thereby obtaining a crude product (0.314 g) containing the subject compound as an amber liquid.

EXAMPLE 46-5

Synthesis of 2-(3-(dipropylamino)propyl)-3-propyl-3H-benzo[d]imidazol-5-carbonitrile A methanol solution (8.0 ml) containing the crude product (0.314 g) of the compound obtained in Example 46-4 was added with acetic acid (100 μl) and added with sodium cyanoborohydride (0.275 g). Propionaldehyde (0.237 ml) was gradually dropped thereto. After the whole was stirred at room temperature for 13 hours, the solvent was distilled off. The resultant was added with ethyl acetate, washed with a saturated aqueous sodium hydrogen carbonate solution, and dried with anhydrous magnesium sulfate. The residue obtained by filtration and distilling the solvent off was purified through silica gel column chromatography (methanol/chloroform), thereby obtaining the subject compound (0.365 g) as a pale-yellow oily substance.

MS(FAB,Pos.):m/z=327[M+H]$^+$
$^1$H-NMR(500 MHz,CDCl$_3$):δ=0.92(6H,t,J=7.3 Hz),1.00 (3H,t,J=7.3 Hz), 1.54(4H,sext.,J=7.6 Hz),1.86(2H,sext., J=7.3 Hz),2.17(2H,quint.,J=6.3 Hz),2.58(4H,br),2.79(2H, br),3.01(2H,t,J=7.3 Hz),4.13(2H,t,J=7.3 Hz),7.50(1H,dd, J=1.5,8.3 Hz),7.65(1H,dd,J=0.7,1.5 Hz), 7.73(1H,dd,J=0.7, 8.3 Hz).

EXAMPLE 46-6

Synthesis of 3-[6-(aminomethyl)-1-propyl-1H-benzo[d]imidazol-2-yl]-N,N-dipropylpropan-1-amine An ethanol solution (12 ml) containing the compound (0.363 g) obtained in Example 46-5 was added with a 1 mol/l sodium hydroxide aqueous solution (3.6 ml) and added with Raney nickel (120 mg). The whole was stirred for 6 hours under a hydrogen atmosphere. The catalyst was removed by filtration through Celite and the solvent was distilled off. After that, the resultant was partitioned into chloroform and water. The solution was washed with a saturated aqueous sodium hydrogen carbonate solution, and dried with anhydrous magnesium sulfate. The residue obtained by distilling the solvent off was purified through silica gel column chromatography (chloroform), thereby obtaining the subject compound (0.244 g) as a colorless liquid.

MS(FAB,Pos.):m/z=331[M+H]$^+$
$^1$H-NMR(500 MHz,CDCl$_3$):δ=0.86(6H,t,J=7.3 Hz),0.99 (3H,t,J=7.6 Hz),1.44(4H,sext.,J=7.3 Hz),1.60(2H,br),1.84 (2H,sext.,J=7.6 Hz),2.04(2H,quint.,J=7.8 Hz),2.39(4H,t, J=7.8 Hz),2.56(2H,t,J=6.8 Hz),2.88(2H,t,J=7.6 Hz),4.00 (2H,s),4.08(2H,t,J=7.3 Hz),7.15(1H,dd,J=1.7,8.3 Hz),7.28 (1H,d,J=1.0 Hz),7.66(1H,d,J=8.3 Hz).

EXAMPLE 46-7

Synthesis of 3-(6-{[(1H-imidazol-2-yl)methylamino]methyl}-1-propyl-1H-benzo[d]imidazol-2-yl)-N,N-dipropylpropan-1-amine An anhydrous methanol solution (4.0 ml) containing the compound (0.244 g) obtained in Example 46-6 and 2-imidazole carboxaldehyde (85.0 mg) was added with trimethyl orthoformate (0.242 ml). The whole was stirred at room temperature for 14 hours and then added with sodium borohydride (0.140 g). After the solution was stirred for 2 hours, the solvent was distilled off. The resultant was dissolved in chloroform, washed with a saturated aqueous sodium hydrogen carbonate solution, and dried with anhydrous magnesium sulfate. The residue obtained by distilling the solvent off was purified through silica gel column chromatography (chloroform/methanol), thereby obtaining the subject compound (0.167 g) as a colorless oily substance.

MS(FAB,Pos.):m/z=411[M+H]$^+$
$^1$H-NMR(500 MHz,CDCl$_3$):δ=0.87(6H,t,J=7.3 Hz),0.98 (3H,t,J=7.6 Hz),1.45(4H,sext.,J=7.6 Hz),1.6-2.0(1H,br),1.83 (2H,sext.,J=6.6 Hz),2.04(2H,quint.,J=7.6 Hz),2.40(4H,t, J=7.3 Hz),2.57(2H,t,J=7.1 Hz),2.88(2H,t,J=7.6 Hz),3.93 (2H,s),3.97(2H,s),4.07(2H,t,J=7.6 Hz),6.99(2H,s),7.17(1H, d,J=8.3 Hz),7.23(1H,s),7.65(1H,d,J=8.3 Hz).

EXAMPLE 46-8

Synthesis of [3-(6-{[(1H-imidazol-2-ylmethyl)-(1-methyl-1H-imidazol-2-ylmethyl)-amino]-methyl}-1-propyl-1H-benzimidazol-2-yl)-propyl]-dipropyl-amine [Compound No. 46]

An anhydrous methanol solution (3.0 ml) containing the compound (0.166 g) obtained in Example 46-7 and 1-methyl-2-imidazole carboxaldehyde (53.0 mg) was added with 10 drops of acetic acid. The whole was added with sodium cyanoborohydride (76.0 mg) and stirred for 21 hours. After the solvent in the reaction solution was distilled off, the resultant was dissolved in chloroform, washed with a saturated aqueous sodium hydrogen carbonate solution, and dried with anhydrous magnesium sulfate. The residue obtained by distilling the solvent off was purified through silica gel column chromatography (chloroform), thereby obtaining the subject compound (86.0 mg) as a pale-yellow oily substance. The subject compound was treated with hydrochloric acid, thereby obtaining a hydrochloride (87.0 mg) of the subject compound as a colorless solid.

MS(FAB,Pos.):m/z=505[M+H]$^+$ $^1$H-NMR(500 MHz,CDCl$_3$):δ=0.87(6H,t,J=7.3 Hz),0.97 (3H,t,J=7.3 Hz), 1.44(4H,sext.,J=7.6 Hz),1.81(2H,sext., J=7.6 Hz),2.03(2H,quint.,J=7.6 Hz),2.38(4H,t,J=7.6 Hz), 2.56(2H,t,J=6.8 Hz),2.88(2H,t,J=7.6 Hz),3.43(2H,s),3.50 (3H,s),3.69(2H,s),3.82(2H,s),4.06(2H,t,J=7.3 Hz),6.86(1H, d,J=1.5 Hz),7.00(1H,d,J=1.2 Hz),7.10(1H,s),7.15(1H,s), 7.28(1H,s),7.33(1H,d,J=8.3 Hz),7.67(1H,d,J=8.1 Hz),12.4 (1H,br).

EXAMPLE 47

Production Example 47

Synthesis of [4-(6-{[(1H-imidazol-2-ylmethyl)-(1-methyl-1H-imidazol-2-ylmethyl)-amino]-methyl}-1-isopropyl-1H-benzimidazol-2-yl)-butyl]-dipropyl-amine [Compound No. 47]

EXAMPLE 47-1

Synthesis of {4-[(2-amino-5-cyano-phenyl)-isopropyl-carbamoyl]-butyl}-carbamic acid t-butyl ester The compound (242 mg) obtained in Example 45-3 was dissolved in DMF (5.0 ml). The solution was added with 60% sodium hydride (29.1 mg) and then 2-iodopropane (79.6 μl) in an ice bath. The whole was stirred overnight at room temperature. After completion of the reaction, the solvent was distilled off. The resultant was dissolved in chloroform and added with distilled water and the whole was stirred for a while. The solution was subjected to extraction with chloroform and washed with a saturated saline solution. The organic layer was dried with anhydrous sodium sulfate. The solvent was distilled off, and the residue was purified through silica gel column chromatography (hexane/ethyl acetate), thereby obtaining the subject compound (44.1 mg) as a pale-yellow oily substance.

MS(FAB. Pos.):m/z=375[M+H]$^+$ $^1$H-NMR(500 MHz,CDCl$_3$):δ=1.00(3H,d,J=6.6 Hz) 1.21 (3H,d,J=6.6 Hz),1.43(9H,s),1.53-1.65(4H,m),1.88-2.01(2H, m),3.00-3.07(2H,m),4.45(2H,brs),4.58(1H,brs),4.90(1H, sept.,J=6.6 Hz),6.80(1H,d,J=8.3 Hz),7.23(1H,d,J=2.0 Hz), 7.45(1H,dd,J=2.0,8.3 Hz).

EXAMPLE 47-2

Synthesis of 2-(4-amino-butyl)-3-isopropyl-3H-benzimidazol-5-carbonitrile

The compound (44.1 mg) obtained in Example 47-1 was dissolved in anhydrous methanol (1.0 ml) and added with a 4 mol/l hydrogen chloride/dioxane solution (1.0 ml) and the whole was stirred at room temperature for 3 hours. After completion of the reaction, the solvent was distilled off. The resultant was added with a 1 mol/l sodium hydroxide aqueous solution and the whole was subjected to extraction with chloroform and washed with a saturated saline solution. The organic layer was dried with anhydrous sodium sulfate. The solvent was distilled off, thereby obtaining the subject compound (26.0 mg) as a white crystal.

MS(FAB,Pos.):m/z=257[M+H]$^+$

EXAMPLE 47-3

Synthesis of 2-(4-dipropylamino-butyl)-3-isopropyl-3H-benzimidazol-5-carbonitrile The compound (26.0 mg) obtained in Example 47-2 was dissolved in anhydrous methanol (1.0 ml) and added with sodium cyanoborohydride (19.1 mg), trimethyl orthoformate (27.7 μl), and propionaldehyde (18.3 μl). The whole was stirred overnight at room temperature under a nitrogen atmosphere. After completion of the reaction, the solvent was distilled off. The resultant was dissolved in chloroform and added with a saturated aqueous sodium hydrogen carbonate solution and the whole was stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off, thereby obtaining the subject compound (34.0 mg) as a pale-yellow oily substance.

MS(FAB,Pos.):m/z=341[M+H]$^+$

EXAMPLE 47-4

Synthesis of [4-(6-aminomethyl-1-isopropyl-1H-benzimidazol-2-yl)-butyl]-dipropyl-amine The compound (34.0 mg) obtained in Example 47-3 was dissolved in ethanol (2.0 ml) and added with a 1 mol/l sodium hydroxide aqueous solution (340 μl) and Raney nickel (4.0 mg). The whole was stirred overnight at room temperature under a hydrogen atmosphere. After completion of the reaction, the solution was filtrated through Celite and the solvent was distilled off. The resultant was subjected to extraction with chloroform and washed with a saturated saline solution. The organic layer was dried with anhydrous sodium sulfate. The solvent was distilled off, thereby obtaining the subject compound (31.3 mg) as a pale-yellow oily substance.

MS(FAB,Pos.):m/z=345[M+H]$^+$

EXAMPLE 47-5

Synthesis of N-[4-({[(1H-imidazol-2-yl)methyl] amino}methyl)benzyl]-N-(1-cyanoethyl)-N',N'-dipropylbutane-1,4-diamine The compound (31.3 mg) obtained in Example 47-4 was dissolved in anhydrous methanol (1.0 ml) and added with trimethyl orthoformate (14.9 μl) and 2-imidazole carboxaldehyde (9.60 mg). The whole was stirred at room temperature for 2 hours under a nitrogen atmosphere. Subsequently, the solution was added with sodium borohydride (3.40 mg) in an ice bath and the whole was stirred at room temperature for 2 hours.

After completion of the reaction, the resultant was added with distilled water and the whole was stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off, thereby obtaining the subject compound (41.7 mg) as a colorless solid.

MS(FAB,Pos.):m/z=425[M+H]$^+$

EXAMPLE 47-6

Synthesis of [4-(6-{[(1H-imidazol-2-ylmethyl)-(1-methyl-1H-imidazol-2-ylmethyl)-amino]-methyl}-1-isopropyl-1H-benzimidazol-2-yl)-butyl]-dipropyl-amine [Compound No. 47]

The compound (41.7 mg) obtained in Example 47-5 was dissolved in anhydrous methanol (1.0 ml) and added with sodium cyanoborohydride (9.30 mg), acetic acid (100 μl), and 1-methyl-2-imidazole carboxaldehyde (11.9 mg). The whole was stirred overnight at room temperature under a nitrogen atmosphere. After completion of the reaction, the solvent was distilled off. The resultant was dissolved in chloroform and added with a 1 mol/l sodium hydroxide aqueous solution and the whole was stirred for a while. The resultant was subjected to extraction with chloroform and washed with a saturated aqueous sodium hydrogen carbonate solution and a saturated saline solution. The organic layer was dried with anhydrous sodium sulfate. The solvent was distilled off and the residue was purified through silica gel column chromatography (chloroform/ethyl acetate) and treated with hydrochloric acid, thereby obtaining a hydrochloride (26.4 mg) of the subject compound as a white solid.

MS(FAB,Pos.):m/z=519[M+H]$^+$
$^1$H-NMR(500 MHz,CDCl$_3$):δ=0.86(6H,t,J=7.3 Hz),1.43-1.45(4H,m),1.63(6H,d,J=6.8 Hz),1.62-1.65(2H,m),1.80-1.87(2H,m),2.36(4H,br), 2.48(2H,br),2.90(3H,t,J=7.8 Hz),3.43(2H,s),3.51(3H,s),3.70(2H, s),3.82(2H,s),4.67(1H,sept.,J=6.8 Hz),6.86(1H,d,J=1.2 Hz),7.00 (1H,d,J=1.2 Hz),7.13(2H,d,J=22.2 Hz),7.31(1H,dd,J=1.5,8.3 Hz),7.48(1H,s),7.66(1H,dd,J=3.9,8.3 Hz),12.4(1H,br).

EXAMPLE 48

Production Example 48

Synthesis of [5-(6-{[(1H-imidazol-2-ylmethyl)-(1-methyl-1H-imidazol-2-ylmethyl)-amino]-methyl}-1-propyl-1H-benzimidazol-2-yl)-pentyl]-dipropyl-amine [Compound No. 48]

EXAMPLE 48-1

Synthesis of [5-(2-amino-5-cyano-phenylcarbamoyl)-pentyl]-carbamic acid-benzyl ester The compound (510 mg) obtained in Example 46-1 was dissolved in DMF (20 ml). To this solution, a solution which was previously prepared by dissolving 6-benzyloxycarbonylamino-hexanoic acid (1.10 g) in DMF (10 ml), adding thereto WSCI hydrochloride (1.08 g) and HOBt (762 mg), and stirring the mixture for 30 minutes was dropped. The whole was stirred for 20 hours. The residue obtained by distilling the solvent off was subjected to extraction with chloroform. The organic layer was washed with water and a saturated saline solution, and dried with anhydrous sodium sulfate. The residue obtained by distilling the solvent off was purified through silica gel column chromatography (chloroform/methanol), thereby obtaining the subject compound (961 mg) as a white solid.

MS(FAB,Pos.):m/z=381[M+H]$^+$
$^1$H-NMR(500 MHz,DMSO):δ=1.30(2H,m),1.43(2H,tt,J=7.1,7.3 Hz),1.58(2H,m),2.32(2H,t,J=7.4 Hz),2.99(2H,dt,J=6.3,6.8 Hz),5.00(2H,s),5.93(2H,s),6.75(1H,d,J=8.3 Hz),7.26-7.38(6H,m),7.62(1H,d,J=2.0 Hz),9.08(1H,s).

EXAMPLE 48-2

Synthesis of {5-[(2-amino-5-cyano-phenyl)-propyl-carbamoyl]-pentyl}-carbamic acid-benzyl ester The compound (961 mg) obtained in Example 48-1 was dissolved in DMF (20 ml). After having been cooled to 0° C., the solution was added with 60% sodium hydride (72.9 mg) and warmed back to room temperature and the whole was stirred for 30 minutes. 1-Iodopropane (0.30 ml) was dropped to the solution and the whole was stirred for additional 3 hours. After having been cooled to 0° C., the solution was added with water to stop the reaction and concentrated. The residue was subjected to extraction with chloroform. The organic layer was washed with water and a saturated saline solution, and dried with anhydrous sodium sulfate. The residue obtained by distilling the solvent off was purified through silica gel column chromatography (chloroform/methanol), thereby obtaining the subject compound (317 mg) as a yellow oily substance.

MS(FAB,Pos.):m/z=423[M+H]$^+$
$^1$H-NMR(500 MHz,CDCl$_3$):δ=0.90(3H,t,J=7.3 Hz),1.22-1.27(2H,m),1.40-1.46(2H,m),1.49-1.63(2H,m),1.89-1.94(1H,m),2.01-2.07(1H,m),3.10-3.17(3H,m),3.86-3.92(1H,m),4.40(2H,s),4.79(1H,s),5.08 (2H,d,J=1.5 Hz),6.76(1H,d,J=8.5 Hz),7.25(1H,d,J=1.7 Hz),7.30-7.38(5H,m),7.41(1H,dd,J=1.7,8.5 Hz).

EXAMPLE 48-3

Synthesis of [5-(6-cyano-1-propyl-1H-benzimidazol-2-yl)-pentyl]-carbamic acid-benzyl ester The compound (317 mg) obtained in Example 48-2 was dissolved in methanol (5.0 ml) and added with a 4 mol/l hydrogen chloride/dioxane solution (2.0 ml) and the whole was stirred for 16 hours. The residue obtained by distilling the solvent off was dissolved in methanol and the solution was neutralized with an anion-exchange resin (Amberlite IRA-410). The resin was filtrated out and the solvent was distilled off, thereby obtaining the subject compound (291 mg) as a colorless oily substance.

MS(FAB,Pos.):m/z=405[M+H]$^+$
$^1$H-NMR(500 MHz,CDCl$_3$):δ=0.99(3H,t,J=7.3 Hz),1.48-1.54(2H,m),1.58-1.62(2H,m),1.84(2H,tq,J=7.3,7.6 Hz),1.95(2H,tt,J=7.3,7.6 Hz), 2.89(2H,t,J=7.6 Hz),3.27(2H,d,J=7.6 Hz),4.09(2H,t,J=7.4 Hz),5.09(2H,s),5.15(1H,s),7.32-7.50(5H,m),7.62(1H,t,J=0.7 Hz),7.72(1H,d,J=8.3 Hz).

EXAMPLE 48-4

Synthesis of 2-(5-amino-pentyl)-3-propyl-3H-benzimidazol-5-carbonitrile

The compound (107 mg) obtained in Example 48-3 was dissolved in ethanol (10 ml) and added with palladium carbon (20 mg) and the whole was stirred for 20 hours under a hydrogen atmosphere. After filtration through Celite, the solvent was distilled off. The residue was purified through silica gel column chromatography (chloroform/methanol), thereby obtaining the subject compound (25.6 mg) as a white solid.

MS(FAB,Pos.):m/z=271[M+H]$^+$
$^1$H-NMR(500 MHz,CDCl$_3$):δ=1.00(3H,t,J=7.4 Hz),1.48-1.58(4H,m),1.82-1.89(2H,m),1.93-1.99(2H,m),2.73(2H,t,

J=6.7 Hz),2.90(2H,t,J=7.8 Hz),4.10(2H,t,J=7.4 Hz),7.49 (1H,dd,J=1.7,8.3 Hz),7.64(1H,dd, J=0.7,1.5 Hz),7.76(1H, dd,J=0.5,8.3 Hz).

EXAMPLE 48-5

Synthesis of 2-(5-dipropylamino-pentyl)-3-propyl-3H-benzimidazol-5-carbonitrile

The compound (26.4 mg) obtained in Example 48-4 was dissolved in methanol (2.0 ml) and added with sodium cyanoborohydride (15.8 mg). After the solution was adjusted to pH 4 with acetic acid, propionaldehyde (0.020 ml) was added thereto and the whole was stirred at room temperature for 20 hours. After the solvent was distilled off, the resultant was neutralized with a saturated aqueous sodium hydrogen carbonate solution and the whole was subjected to extraction with chloroform. The organic layer was washed with a saturated aqueous sodium hydrogen carbonate solution and dried with anhydrous sodium sulfate. The solvent was distilled off, thereby obtaining the subject compound (29.4 mg) as a colorless oily substance.

MS(FAB,Pos.):m/z=355[M+H]$^+$
$^1$H-NMR(500 MHz,CDCl$_3$):δ=0.86(6H,t,J=7.4 Hz),1.00 (3H,t,J=7.3 Hz), 1.40-1.49(6H,m),1.51-1.56(2H,m),1.81-1.88(2H,m),1.91-1.97(2H,m),2.36(4H,t,J=7.7 Hz),2.41-2.44 (2H,m),2.89(2H,t,J=7.9 Hz),4.10(2H,t,J=7.4 Hz),7.48(1H, dd,J=1.7,8.3 Hz),7.63(1H,dd,J=1.5 Hz),7.76(1H,dd,J=0.5, 8.3 Hz).

EXAMPLE 48-6

Synthesis of [5-(6-{[(1H-imidazol-2-ylmethyl)-amino]-methyl}-1-propyl-1H-benzimidazol-2-yl)-pentyl]-dipropyl-amine The compound (29.8 mg) obtained in Example 48-5 was dissolved in ethanol (20 ml) and added with a 1 mol/l sodium hydroxide aqueous solution (4.0 ml). The solution was added with an ethanol suspension containing Raney nickel and the whole was stirred for 6 hours under a hydrogen atmosphere. After filtration through Celite, the solvent was distilled off and the resultant was subjected to extraction with chloroform.

The organic layer was washed with water and a saturated saline solution and then dried with anhydrous sodium sulfate. The solvent was distilled off.

The resultant was dissolved in methanol (2.0 ml) and added with 2-imidazole carboxaldehyde (13.4 mg) and trimethyl orthoformate (0.030 ml) and the whole was stirred at room temperature for 3 hours. After having been cooled to 0° C., the solution was added with sodium borohydride (10.5 mg) and warmed back to room temperature. The whole was stirred for 1 hour and added with water to stop the reaction. After that, the solvent was distilled off and the resultant was subjected to extraction with chloroform. The organic layer was washed with water and a saturated saline solution, and dried with anhydrous sodium sulfate. The solvent was distilled off. The residue was purified through silica gel column chromatography (chloroform/methanol), thereby obtaining the subject compound (26.0 mg) as a colorless oily substance.

MS(FAB,Pos.):m/z=439[M+H]$^+$
$^1$H-NMR(500 MHz,CDCl$_3$):δ=0.87(3H,t,J=7.4 Hz),1.01 (6H,t,J=7.1 Hz),1.40-1.49(4H,m),1.50-1.56(4H,m),1.78-1.86(2H,m),1.89-1.95(2H,m),2.25-2.38(2H,m),2.42(2H,t, J=7.4 Hz),2.52(2H,q,J=7.1 Hz),2.85(2H,t,J=7.8 Hz),3.92 (2H,s),3.96(2H,s),4.04(2H,t,J=7.4 Hz),6.99(2H,s),7.15(1H, d,J=8.3 Hz),7.22(1H,s),7.64(1H,d,J=8.1 Hz).

EXAMPLE 48-7

Synthesis of [5-(6-{[(1H-imidazol-2-ylmethyl)-(1-methyl-1H-imidazol-2-ylmethyl)-amino]-methyl}-1-propyl-1H-benzimidazol-2-yl)-pentyl]-dipropyl-amine [Compound No. 48]

The compound (8.8 mg) obtained in Example 48-6 was dissolved in methanol (2.0 ml) and added with 1-methyl-2-imidazole carboxaldehyde (2.6 mg) and sodium cyanoborohydride (2.5 mg). After the solution was adjusted to pH 4 with acetic acid, the whole was stirred at room temperature for 18 hours. After the solvent was distilled off, the resultant was neutralized with a saturated aqueous sodium hydrogen carbonate solution and the whole was subjected to extraction with chloroform. The organic layer was washed with a saturated aqueous sodium hydrogen carbonate solution and dried with anhydrous sodium sulfate. The solvent was distilled off. The residue was purified through silica gel column chromatography (chloroform/methanol) and treated with hydrochloric acid, thereby obtaining a hydrochloride (9.3 mg) of the subject compound as a white solid.

MS(FAB,Pos.):m/z=533[M+H]$^+$
$^1$H-NMR(500 MHz,CDCl$_3$):δ=0.90(6H,t,J=7.3 Hz),0.99 (3H,t,J=7.3 Hz),1.41-1.44(2H,m),1.65-1.70(4H,m),1.76-1.80(4H,m),1.90(2H,m),2.96-3.06(6H,m),3.22(2H,m),3.73 (3H,s),3.89(2H,s),4.12(2H,s),4.19(2H,s),4.53(2H,s),7.53 (1H,s),7.55(2H,s),7.64(2H,s),7.69(1H,d,J=8.4 Hz),8.41(1H, s),14.99(1H,br).

EXAMPLE 49

Production Example 49

Synthesis of N-(4-{[(1H-imidazol-2-ylmethyl)-(5,6,7,8-tetrahydro-quinolin-8-yl)-amino]-methyl}-benzyl)-N-methyl-N',N'-dipropyl-butane-1,4-diamine [Compound No. 49]

EXAMPLE 49-1

Synthesis of N-(4-{[(1H-imidazol-2-ylmethyl)-(5,6,7,8-tetrahydro-quinolin-8-yl)-amino]-methyl}-benzyl)-N-methyl-N',N'-dipropyl-butane-1,4-diamine [Compound No. 49]

The compound (203.5 mg) obtained in Example 9-2 was dissolved in anhydrous methanol (8.1 ml) and added with 6,7-dihydro-5H-quinolin-8-one (117.7 mg) which was synthesized by a known method and sodium cyanoborohydride (99.9 mg). After the solution was adjusted to pH 5 with acetic acid, the whole was stirred at room temperature for 2 days. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off. The residue was purified through silica gel column chromatography (chloroform/ethyl acetate) and treated with hydrochloric acid, thereby obtaining a hydrochloride (69.5 mg) of the subject compound as a pale-yellow solid.

MS(FAB,Pos.):m/z=517[M+H]$^+$
$^1$H-NMR(500 MHz,DMSO-d$_6$+D$_2$O):δ=0.92(6H,t,J=7.3 Hz),1.63-1.76(6H,m),1.78-1.84(4H,m),1.92-1.98(4H,m), 2.57(3H,s),2.98-3.07(10H,m),3.83(2H,s),4.10-4.16(2H,m), 4.29-4.31(2H,m),4.50(1H,m),7.41(2H,d,J=7.8 Hz),7.49(2H, s),7.55(2H,t,J=7.0 Hz)8.39(2H,d,J=1.4 Hz),8.83(1H,d,J=5.6 Hz).

EXAMPLE 50

Production Example 50

Synthesis of N-(4-dipropylamino-butyl)-N-(4-{[(1H-imidazol-2-ylmethyl)-(5,6,7,8-tetrahydro-quinolin-8-yl)-amino]-methyl}-benzyl)-methanesulfonamide [Compound No. 50]

EXAMPLE 50-1

Synthesis of (4-{[(4-dipropylamino-butyl)-methane-sulfonyl-amino]-methyl}-benzyl)-carbamic acid t-butyl ester The compound (198.3 mg) obtained in Example 23-4 was dissolved in anhydrous dichloromethane (4.0 ml) and added with triethylamine (0.142 ml) and methanesulfonyl chloride (0.060 ml), and the whole was stirred at room temperature for 1 hour. After completion of the reaction, the resultant was washed with water and dried with anhydrous magnesium sulfate. The solvent was distilled off. The residue was purified through silica gel column chromatography (chloroform/ethyl acetate), thereby obtaining the subject compound (192.0 mg) as a colorless oily substance.

MS(FAB,Pos.):m/z=469[M+H]$^+$

EXAMPLE 50-2

Synthesis of N-(4-dipropylamino-butyl)-N-(4-{[(1H-imidazol-2-ylmethyl)-amino]-methyl}-benzyl)-methanesulfonamide The compound (192 mg) obtained in Example 50-1 was dissolved in methanol (2.0 ml) and added with a 4 mol/l hydrogen chloride/dioxane solution (2.0 ml) and the whole was stirred at room temperature for 1 hour. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off.

The resultant was dissolved in anhydrous methanol (7.0 ml) and added with 2-imidazole carboxaldehyde (59.6 mg) and trimethyl orthoformate (0.135 ml) and the whole was stirred at room temperature for 14.5 hours. The solution was added with sodium borohydride (46.5 mg) and the whole was stirred at room temperature for 30 minutes. After completion of the reaction, the solvent was distilled off. The resultant was added with water and subjected to extraction with chloroform. The resultant was dried with magnesium sulfate and the solvent was distilled off. The residue was purified through silica gel column chromatography (chloroform/methanol), thereby obtaining the subject compound (154 mg) as a colorless oily substance.

MS(FAB,Pos.):m/z=450[M+H]$^+$

EXAMPLE 50-3

Synthesis of N-(4-dipropylamino-butyl)-N-(4-{[(1H-imidazol-2-ylmethyl)-(5,6,7,8-tetrahydro-quinolin-8-yl)-amino]-methyl}-benzyl)-methanesulfonamide [Compound No. 50]

The compound (154 mg) obtained in Example 50-2 was dissolved in anhydrous methanol (6.2 ml) and added with 6,7-dihydro-5H-quinolin-8-one (75.1 mg) which was synthesized by a known method and sodium cyanoborohydride (64.1 mg). After the solution was adjusted to pH 5 with acetic acid, the whole was stirred at room temperature for 2 days. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off. The residue was purified through silica gel column chromatography (chloroform/ethyl acetate) and treated with hydrochloric acid, thereby obtaining a hydrochloride (69 mg) of the subject compound as a pale-yellow solid.

MS(FAB,Pos.):m/z=581[M+H]$^+$ $^1$H-NMR(500 MHz,DMSO-d$_6$):δ=0.87(6H,t,J=7.3 Hz), 1.40-1.52(4H,m),1.59-1.66(4H,m),2.10-2.15(4H,m),2.87-2.90(6H,m),2.96(3H,s),3.05-3.08(4H,m),4.11(2H,d,J=15.5 Hz),4.24(2H,s),4.29-4.43(1H,m),4.92(2H,brs),7.21(2H,d, J=7.8 Hz),7.56(2H,s),7.90(1H,t,J=6.1 Hz),8.20(2H,d,J=7.6 Hz),8.36(1H,t,J=6.3 Hz),8.86(1H,d,J=5.3 Hz).

EXAMPLE 51

Production Example 51

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid [Compound No. 51]

EXAMPLE 51-1

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid [Compound No. 51]

The compound (129 mg) obtained in Example 34-3 was dissolved in anhydrous methanol (1.0 ml) and added with concentrated hydrochloric acid (10.0 ml) and the whole was refluxed under heating. After completion of the reaction, the solvent was distilled off, thereby obtaining a hydrochloride (71.4 mg) of the subject compound as a pale-yellow solid.

MS(FAB,Pos.):m/z=538[M+H]$^+$ $^1$H-NMR(500 MHz,DMSO-d$_6$+D$_2$O):δ=0.92(6H,t,J=7.5 Hz),1.63-1.69(6H,m),1.79(2H,br),2.85-3.08(10H,m),3.16-3.22(2H,m),3.64(2H,s),3.75(3H,s),4.11(2H,s),4.19(2H,s), 4.27-4.37(2H,m),7.31(2H,d,J=8.1 Hz),7.46-7.51(3H,m), 7.60(2H,s),7.56-7.63(1H,m).

EXAMPLE 52

Production Example 52

Synthesis of (4-dipropylamino-butyl)-(4-{[(1H-imidazol-2-ylmethyl)-(1-methyl-1H-imidazol-2-ylmethyl)-amino]-methyl}-benzyl)-cyanamide [Compound No. 52]

EXAMPLE 52-1

Synthesis of (4-cyano-benzyl)-(4-dipropylamino-butyl)-carbamic acid t-butyl ester The compound (236 mg) obtained in Example 1-2 was dissolved in methanol (4.0 ml) and added with trimethyl orthoformate (380 µl) and 4-cyanobenzaldehyde (159 mg) at room temperature and the whole was stirred at room temperature for 16 hours under a nitrogen atmosphere. After that, the solution was added with sodium borohydride (103 mg) under ice-cooling and the whole was stirred at room temperature for 30 minutes. After completion of the reaction, the solution was added with water and the solvent was distilled off under reduced pressure. The residue was dissolved in chloroform and added with water, and the aqueous layer was extracted with chloroform. The organic layer was washed with a saturated saline solution and dried with anhydrous sodium sulfate. The solvent was distilled off, thereby obtaining a yellow oily substance (384 mg). 293 mg of the substance was dissolved in chloroform (6.0 ml) and added with di-t-butyldicarbonate (334 mg) and the whole was stirred at room temperature for 10 hours under a nitrogen atmosphere. After completion of the reaction, the resultant was added with a saturated sodium hydrogen carbonate aqueous solution (3.0 ml) and the aqueous layer was extracted with chloroform. The organic layer was washed with a saturated saline solution and dried with anhydrous sodium sulfate. The solvent was distilled off and the residue was purified through silica gel column chromatography (hexane/ethyl acetate), thereby obtaining the subject compound (331 mg) as a yellow oily substance.

MS(FAB,Pos.):m/z=388[M+H]$^+$

EXAMPLE 52-2

Synthesis of (4-dipropylamino-butyl)-(4-{[(1H-imidazol-2-ylmethyl)-(1-methyl-1H-imidazol-2-ylmethyl)-amino]-methyl}-benzyl)-carbamic acid t-butyl ester The compound (331 mg) obtained in Example 52-1 was dissolved in ethanol (13 ml) and added with a 1 mol/l sodium hydroxide aqueous solution (3.0 ml) and an ethanol suspension containing Raney nickel and the whole was stirred for 3 hours at room temperature under a hydrogen atmosphere. After completion of the reaction, the solution was filtrated through Celite and the solvent was distilled off. The residue was dissolved in chloroform and the aqueous layer was extracted with chloroform. The organic layer was washed with a saturated saline solution and then dried with anhydrous sodium sulfate. The solvent was distilled off, thereby obtaining a colorless oily substance (283 mg).

The substance was dissolved in methanol (6.0 ml) and added with trimethyl orthoformate (240 µl) and 2-imidazole carboxaldehyde (83.7 mg) at room temperature and the whole was stirred at room temperature for 15 hours under a nitrogen atmosphere. After that, the solution was added with sodium borohydride (59.0 mg) under ice-cooling and the whole was stirred for 30 minutes at room temperature. After completion of the reaction, the solution was added with water and the solvent was distilled off under reduced pressure. The residue was dissolved in chloroform and added with water, and then the aqueous layer was extracted with chloroform. The organic layer was washed with a saturated saline solution and dried with anhydrous sodium sulfate. The solvent was distilled off.

The resultant was dissolved in ethanol (7.0 ml) and added with 1-methyl-2-imidazole carboxaldehyde (117 mg) and sodium triacetoxyborohydride (326 mg) and the whole was stirred at room temperature for 17 hours under a nitrogen atmosphere. After completion of the reaction, a saturated aqueous sodium hydrogen carbonate solution (20 ml) was poured to the resultant and the solvent was distilled off. The residue was dissolved in chloroform and then the aqueous layer was extracted with chloroform. The organic layer was washed with a saturated saline solution and dried with anhydrous sodium sulfate. The solvent was distilled off. The residue was purified through silica gel column chromatography (chloroform/methanol), thereby obtaining the subject compound (360 mg) as a yellow oily substance.

MS(FAB,Pos.):m/z=566[M+H]$^+$

EXAMPLE 52-3

Synthesis of N-(4-{[(1H-imidazol-2-ylmethyl)-(1-methyl-1H-imidazol-2-ylmethyl)-amino]-methyl}-benzyl)-N',N'-dipropyl-butane-1,4-diamine The compound (360 mg) obtained in Example 52-2 was dissolved in methanol (3.6 ml) and added with a 4 mol/l hydrogen chloride/dioxane solution (3.6 ml) and the whole was stirred at room temperature for 13 hours under a nitrogen atmosphere. After completion of the reaction, the solvent was distilled off.

The residue was admixed with a 1 mol/l sodium hydroxide aqueous solution and the whole mixture was subjected to extraction with chloroform. The organic layer was washed with a saturated saline solution and dried with anhydrous sodium sulfate. The solvent was distilled off. The residue was purified through silica gel column chromatography (chloroform/methanol), thereby obtaining the subject compound (306 mg) as a pale-yellow oily substance.

MS(FAB,Pos.):m/z=465[M+H]$^+$

Production Example 52-4

Synthesis of (4-dipropylamino-butyl)-(4-{[(1H-imidazol-2-ylmethyl)-(1-methyl-1H-imidazol-2-ylmethyl)-amino]-methyl}-benzyl)-cyanamide [Compound No. 52]

The compound (13.4 mg) obtained in Example 52-3 was dissolved in THF (0.26 ml) and added with triethylamine (10 µl) and bromocyan (3.65 mg) and the whole was stirred at room temperature for 2 hours under a nitrogen atmosphere. After completion of the reaction, the solution was added with a saturated aqueous sodium hydrogen carbonate solution to neutralize the solution and the solvent was distilled off. The residue was purified through silica gel column chromatography (chloroform/methanol) and treated with tartaric acid, thereby obtaining a tartrate (12.5 mg) of the subject compound as a white solid.

MS(FAB,Pos.):m/z=491[M+H]$^+$ $^1$H-NMR(500 MHz,CDCl$_3$):δ=0.86(6H,t,J=7.4 Hz),1.39-1.50(6H,m),1.67(2H,quint.,J=7.5 Hz),2.30-2.34(4H,m),2.39

(2H,t,J=7.3 Hz),2.96(2H,t,J=7.3 Hz),3.48(2H,s),3.58(3H,s), 3.60(2H,s),3.69(2H,s),4.17(2H,s),6.89(1H,d,J=1.2 Hz),7.00 (1H,d,J=1.2 Hz),7.08(1H,brs),7.13(1H,brs),7.31(2H,d,J=8.1 Hz),7.44(2H,d,J=8.1 Hz),12.37(1H,brs).

EXAMPLE 53

Production Example 53

Synthesis of (4-dipropylamino-butyl)-(4-{[(1H-imidazol-2-ylmethyl)-(1-methyl-1H-imidazol-2-ylmethyl)-amino]-methyl}-benzyl)-formamide [Compound No. 53]

EXAMPLE 53-1

Synthesis of (4-dipropylamino-butyl)-(4-{[(1H-imidazol-2-ylmethyl)-(1-methyl-1H-imidazol-2-ylmethyl)-amino]-methyl}-benzyl)-formamide [Compound No. 53]

The compound (82.9 mg) obtained in Example 52-3 was dissolved in ethanol (1.0 ml) and added with formic acid (50 µl) and formamide (50 µl). The whole was stirred at an outside temperature of 10° C. for 3 hours. The solution was added with additional formic acid (60 µl) and the whole was stirred for 15 hours. After completion of the reaction, the solvent was distilled off. The residue was dissolved in chloroform and added with a 1 mol/l sodium hydroxide aqueous solution to adjust the pH to 11. The aqueous layer was extracted with chloroform. The organic layer was washed with a saturated saline solution and dried with anhydrous sodium sulfate. The solvent was distilled off. The residue was purified through silica gel column chromatography (chloroform/methanol) and treated with hydrochloric acid, thereby obtaining a hydrochloride (27.0 mg) of the subject compound as a yellow solid.

MS(FAB,Pos.):m/z=494[M+H]$^+$
$^1$H-NMR(500 MHz,DMSO-d$_6$: δ=0.85(6H,t,J=7.2 Hz), 1.23-1.56(6H,m),2.29-2.37(6H,m),3.14(2H,t,J=7.0 Hz), 3.23(2H,t,J=7.3 Hz),3.46(2H,s),3.49(2H,s),3.57(2H,s),3.59 (2H,s),3.60(3H,s),3.67(2H,s),3.68(2H,s),4.38(2H,s),4.53 (2H,s),6.88(1H,d,J=1.2 Hz),6.89(1H,d,J=1.4 Hz),7.00(1H,d, J=1.2 Hz),7.01(2H,d,J=1.2 Hz),7.08(1H,s),7.13(1H,s),7.18 (1H,d,J=8.3 Hz),7.22(1H,d,J=8.0 Hz),7.37(1H,d,J=8.0 Hz), 7.43(1H,d,J=8.3 Hz),8.20(1H,s),8.28(1H,s),12.38(1H,brs).

EXAMPLE 54

Production Example 54

Synthesis of [(4-{[(1-carboxymethyl-1H-imidazol-2-ylmethyl)-(1-methyl-1H-imidazol-2-ylmethyl)-amino]-methyl}-benzyl)-(4-dipropylamino-butyl) amino]-acetic acid [Compound No. 54]

EXAMPLE 54-1

Synthesis of [(4-dipropylamino-butyl)-(4-{[(1-methoxycarbonylmethyl-1H-imidazol-2-ylmethyl)-(1-methyl-1H-imidazol-2-ylmethyl)-amino]-methyl}-benzyl)-amino]-acetic acid methyl ester The compound (81.9 mg) obtained in Example 52-3 was dissolved in THF (2.0 ml) and added with triethylamine (76.0 µl) and methyl bromoacetate (46.0 µl) and the whole was stirred at room temperature for 11 hours under a nitrogen atmosphere. After completion of the reaction, the solution was added with methanol and the solvent was distilled off under reduced pressure. The residue was purified through silica gel column chromatography (chloroform/methanol), thereby obtaining the subject compound (23.7 mg) as a yellow oily substance.

MS(FAB,Pos.):m/z=610[M+H]$^+$

EXAMPLE 54-2

Synthesis of [(4-{[(1-carboxymethyl-1H-imidazol-2-ylmethyl)-(1-methyl-1H-imidazol-2-ylmethyl)-amino]-methyl}-benzyl)-(4-dipropylamino-butyl) amino]-acetic acid [Compound No. 54]

The compound (23.7 mg) obtained in Example 54-1 was dissolved in 1,4-dioxane (1.0 ml) and added with concentrated hydrochloric acid (1.0 ml) and the whole was refluxed under heating for 4 hours. After completion of the reaction, the solvent was distilled off under reduced pressure, thereby obtaining a hydrochloride (17.2 mg) of the subject compound as a yellow solid.

MS(FAB,Pos.):m/z=582[M+H]$^+$
$^1$H-NMR(500 MHz,DMSO-d$_6$):δ=0.90(6H,t,J=7.3 Hz), 1.66-1.80(8H,m),2.94-3.17(8H,m),3.38-3.83(5H,m),3.90 (2H,brs),4.13(2H,brs),4.17(2H,brs),4.35(2H,brs),5.16(2H, brs),7.44(2H,d,J=8.3 Hz),7.47(2H,d,J=8.0 Hz),7.52(1H,s), 7.55(1H,s),7.65(1H,s),7.66(1H,s).

EXAMPLE 55

Production Example 55

Synthesis of [4-(1-benzyl-6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 55]

EXAMPLE 55-1

Synthesis of 3-benzyl-2-(4-t-butoxycarbonylamino-butyl)-3H-benzimidazol-5-carboxylic acid methyl ester The compound (965.3 mg) obtained in Example 2-1 was dissolved in DMF (20 ml). After having been cooled to 0° C., the reaction solution was added with 60% sodium hydride (221.8 mg) and the whole was stirred at room temperature for 1 hour. After that, benzylbromide (0.35 ml) was added to the solution and the whole was stirred at room temperature for 3 hours. The reaction solution was concentrated under reduced pressure. The resultant residue was added with distilled water and subjected to extraction with ethyl acetate. The organic layer was washed with a saturated saline solution and dried with anhydrous sodium sulfate. The drying agent was filtrated out and then the organic layer was concentrated under reduced pressure. The resultant residue was purified through silica gel column chromatography (chloroform/ethyl acetate), thereby obtaining the subject compound (0.469 g) as a white solid.

MS(FAB,Pos.):m/z=438[M+H]$^+$

EXAMPLE 55-2

Synthesis of 3-benzyl-2-(4-dipropylamino-butyl)-3H-benzimidazol-5-carboxylic acid methyl ester The compound (0.469 g) obtained in Example 55-1 was dissolved in methanol (5.0 ml) and added with a 4 mol/l hydrogen chloride/dioxane solution (3.0 ml) and the whole was stirred at room temperature for 2 hours. The reaction solution was concentrated under reduced pressure. The resultant residue was added with a 1 mol/l sodium hydroxide aqueous solution and the whole was subjected to extraction with chloroform. The organic layer was washed with a saturated saline solution and dried with anhydrous sodium sulfate. The drying agent was filtrated out and then the organic layer was concentrated under reduced pressure.

The resultant was dissolved in methanol (8.0 ml). The reaction solution was added with trimethyl orthoformate (0.25 ml) and the whole was cooled to 0° C. After that, a solution which propionaldehyde (134.4 mg) was dissolved in methanol (1.0 ml) was dropped thereto and the whole was stirred at room temperature for 25 minutes. Subsequently, the solution was added with sodium cyanoborohydride (214 mg) and the whole was stirred at room temperature for 16 hours. The reaction solution was concentrated under reduced pressure and the resultant residue was added with a 1 mol/l sodium hydroxide aqueous solution. The whole was subjected to extraction with chloroform. The organic layer was washed with a saturated saline solution and dried with anhydrous sodium sulfate. The drying agent was filtrated out and then the organic layer was concentrated under reduced pressure. The resultant residue was purified through silica gel column chromatography (hexane/ethyl acetate), thereby obtaining the subject compound (267 mg) as a yellow oily substance.

MS(FAB,Pos.):m/z=422[M+H]$^+$

EXAMPLE 55-3

Synthesis of 3-benzyl-2-(4-dipropylamino-butyl)-3H-benzimidazol-5-carbaldehyde

The compound (267 mg) obtained in Example 55-2 was dissolved in THF (5.0 ml). After having been cooled to 0° C., the reaction solution was added with Lithium aluminum hydride (38.5 mg) and the whole was stirred at room temperature for 40 minutes. After that, the solution was again cooled to 0° C. The reaction solution was added with acetone (1.0 ml) and ethyl acetate (2.0 ml) and the whole was stirred at room temperature for 20 minutes. Then, the reaction solution was added with a saturated aqueous sodium potassium tartrate solution and the whole was vigorously stirred at room temperature for 19 hours. The reaction solution was subjected to extraction with ethyl acetate. The organic layer was washed with a saturated saline solution and dried with an anhydrous sodium sulfate.

The drying agent was filtrated out and then the organic layer was concentrated under reduced pressure.

The resultant was dissolved in chloroform (5.0 ml). The reaction solution was added with manganese dioxide (1.14 g) and the whole was stirred at room temperature for 3 hours. The reaction solution was filtrated through Celite. The filtrate was concentrated under reduced pressure, thereby obtaining the subject compound (25.5 mg) as a yellow oily substance.

MS(FAB,Pos.):m/z=392[M+H]$^+$

EXAMPLE 55-4

Synthesis of [4-(1-benzyl-6-{[(1H-imidazol-2-ylmethyl)-(1-methyl-1H-imidazol-2-ylmethyl)-amino]-methyl}-1H-benzimidazol-2-yl)-butyl]-dipropyl-amine [Compound No. 55]

The compound (225 mg) obtained in Example 55-3 was dissolved in methanol (4.0 ml). The solution was added with the compound (64.5 mg) obtained in Example 14-7 and trimethyl orthoformate (0.13 ml) and the whole was stirred at room temperature for 1.5 hours. After having been cooled to 0° C., the reaction solution was added with sodium borohydride (20.8 mg) and the whole was stirred at room temperature for 20 minutes. After the reaction solution was concentrated under reduced pressure, the resultant residue was added with distilled water and the whole was subjected to extraction with chloroform. The organic layer was washed with a saturated saline solution and dried with an anhydrous sodium sulfate. The drying agent was filtrated out and then the organic layer was concentrated under reduced pressure.

The resultant was dissolved in methanol (6.0 ml). The reaction solution was added with 2-imidazole carboxaldehyde (83.3 mg) and sodium cyanoborohydride (77.3 mg). The whole was added with acetic acid to adjust the pH to 5 and stirred at room temperature for 18 hours. The reaction solution was concentrated under reduced pressure. The resultant residue was added with a 1 mol/l sodium hydroxide aqueous solution and the whole was subjected to extraction with chloroform. The organic layer was washed with a saturated saline solution and dried with anhydrous sodium sulfate. The drying agent was filtrated out and then the organic layer was concentrated under reduced pressure. The resultant residue was purified through silica gel column chromatography (hexane/ethyl acetate) and treated with hydrochloric acid, thereby obtaining a hydrochloride (174.3 mg) of the subject compound as a white solid.

MS(FAB,Pos.):m/z=567[M+H]$^+$ $^1$H-NMR(500 MHz,DMSO-d$_6$):δ=0.90(6H,t,J=7.3 Hz), 1.64-1.86(8H,m),2.95(4H,br),3.05(2H,br),3.28(2H,br),3.67 (3H,s),3.83(2H,s),4.10(2H,s),4.17(2H,s),5.94(2H,s),7.31-7.39(5H,m),7.49-7.54(3H,m),7.60(2H,s),7.72(1H,d,J=8.4 Hz),8.17(1H,s),10.43(1H,br),14.94(2H,br).

EXAMPLE 56

Production Example 56

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid ethyl ester [Compound No. 56]

EXAMPLE 56-1

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid ethyl ester [Compound No. 56]

The compound (135.4 mg) obtained in Example 51-1 was suspended in ethanol (13.5 ml) and the whole was refluxed under heating for 16 hours. After completion of the reaction, the solvent was distilled off. The resultant was added with saturated sodium hydrogen carbonate aqueous solution and the whole was subjected to extraction with chloroform. The resultant was dried with magnesium sulfate and the solvent was distilled off, thereby obtaining the subject compound (127.0 mg) as a colorless oily substance.

MS(FAB,Pos.):m/z=566[M+H]$^+$ $^1$H-NMR(500 MHz,CDCl$_3$):δ=0.85(6H,t,J=7.3 Hz),1.23 (3H,t,J=7.3 Hz),1.39-1.44(8H,m),2.18-2.37(6H,m),2.41-2.46(4H,m),2.78(2H,t,J=7.1 Hz),3.46(2H,s),3.55(5H,s),3.62 (2H,s),3.67(2H,s),4.10(2H,q,J=7.3 Hz),6.87(1H,d,J=1.2

Hz),6.99(1H,d,J=1.2 Hz),7.10(2H,d,J=21.0 Hz),7.26(2H,d,J=8.1 Hz),7.33(2H,d,J=8.1 Hz),12.34(1H,br).

EXAMPLE 57

Production Example 57

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid isopropyl ester [Compound No. 57]

EXAMPLE 57-1

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid isopropyl ester [Compound No. 57]

The hydrochloride (88.0 mg) of the compound obtained in Example 51-1 was added with 2-propanol (10 ml) and the whole was refluxed under heating for 2 hours. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate), thereby obtaining the subject compound (32.8 mg) as a colorless oily substance.

MS(FAB,Pos.):m/z=580[M+H]$^+$

EXAMPLE 58

Production Example 58

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-1-(cyclohexyloxycarbonyloxy)-ethyl ester [Compound No. 62]

EXAMPLE 58-1

Synthesis of 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid-1-(cyclohexyloxycarbonyloxy)-ethyl ester [Compound No. 62]

The compound (352.4 mg) obtained in Example 51-1, potassium carbonate (420.2 mg), and potassium iodide (41.5 mg) were suspended in anhydrous DMF (7.0 ml). The suspension was added with a DMF solution (3.5 ml) containing 1-chloro-ethyl ester cyclohexyl ester carboxylic acid (152.9 mg) and the whole was stirred at 60° C. for 15 hours. After completion of the reaction, the solvent was distilled off. The resultant was added with water and the whole was subjected to extraction with chloroform and dried with magnesium sulfate. The solvent was distilled off. The residue was purified through silica gel column chromatography (chloroform/ethyl acetate), thereby obtaining the subject compound (199.6 mg) as a colorless oily substance.

MS(FAB,Pos.):m/z=566[M+H]$^+$
$^1$H-NMR(500 MHz,CDCl$_3$):δ=0.85(6H,t,J=7.3 Hz),1.22-1.43(15H,m),1.48(3H,d,J=5.4 Hz),1.53-1.54(1H,m),1.73 (2H,m),1.91(2H,m),2.18-2.34(6H,m),2.42(2H,t,J=6.8 Hz), 2.48(2H,t,J=7.6 Hz),2.79(2H,t,J=7.8 Hz),3.46(2H,s),3.55 (5H,s),3.62(2H,s),3.67(2H,s),4.59-4.64(1H,m),6.75(1H,q, J=5.4 Hz),6.87(1H,d,J=1.2 Hz),6.99(1H,d,J=1.2 Hz),7.10 (2H,d,J=20.8 Hz),7.26(2H,d,J=8.1 Hz),7.33(2H,d,J=8.1 Hz), 12.34(1H,br).

EXAMPLE 59

Production Example 59

Synthesis of 2,2-dimethyl-propionic acid-3-[(4-dipropylamino-butyl)-4-{[1H-imidazol-2-ylmethyl)-(1-methyl-1H-imidazol-2-ylmethyl)-amino]-methyl}-benzyl]-amino]-propionyloxy methyl ester [Compound No. 65]

EXAMPLE 59-1

Synthesis of 2,2-dimethyl-propionic acid-3-[(4-dipropylamino-butyl)-4-{[(1H-imidazol-2-ylmethyl)-(1-methyl-1H-imidazol-2-ylmethyl)-amino]-methyl]-methyl}-amino]-propionyloxy methyl ester [Compound No. 65]

The compound (217.5 mg) obtained in Example 51-1, potassium carbonate (257.1 mg), and potassium iodide (24.9 mg) were suspended in anhydrous DMF (4.3 ml). The suspension was added with a DMF solution (0.7 ml) containing 2,2-dimethyl-propionic acid-1-chloro-ethyl ester (67.8 mg) and the whole was stirred at 60° C. for 15 hours. After completion of the reaction, the solvent was distilled off.

The resultant was added with water and the whole was subjected to extraction with chloroform and dried with magnesium sulfate. The solvent was distilled off. The residue was purified through silica gel column chromatography (chloroform/ethyl acetate), thereby obtaining the subject compound (13.8 mg) as a colorless oily substance.

MS(FAB,Pos.):m/z=652[M+H]$^+$

EXAMPLE 60

Production Example 60

Synthesis of 3-[(4-{[bis-(1H-imidazol-2-ylmethyl)-amino]-methyl}-benzyl)-(4-dipropylamino-butyl)-amino]-propionic acid [Compound No. 72]

EXAMPLE 60-1

Synthesis of 3-[(4-{[bis-(1H-imidazol-2-ylmethyl)-amino]-methyl}-benzyl)-(4-dipropylamino-butyl)-amino]-propionic acid [Compound No. 72]

The compound (550 mg) obtained in Example 34-1 was dissolved in anhydrous methanol (10 ml) and added with trimethyl orthoformate (239 μl) and 2-imidazole carboxaldehyde (154 mg) and the whole was stirred overnight at room temperature under a nitrogen atmosphere. Subsequently, the solution was added with sodium borohydride (55.2 mg) in an ice bath and the whole was stirred at room temperature for 3 hours. After completion of the reaction, the solution was added with distilled water and stirred for a while. The resultant was subjected to extraction with chloroform and washed with a saturated saline solution. The organic layer was dried with anhydrous sodium sulfate. The residue (738 mg) was dissolved in anhydrous methanol (15 ml) and added with sodium cyanoborohydride (152 mg), acetic acid (1.50 ml), and 2-imidazole carboxaldehyde (170 mg) and the whole was stirred overnight at room temperature under a nitrogen atmosphere. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate). The resultant compound (232 mg) was added with concentrated hydrochloric acid (20.0 ml) and the whole was refluxed under heating. After completion of the reaction, the solvent was distilled off, thereby obtaining a hydrochloride (262 mg) of the subject compound as a white solid.

MS(FAB,Pos.):m/z=524[M+H]$^+$ $^1$H-NMR(500 MHz,DMSO-d$_6$+D$_2$O):δ=0.92(6H,t,J=7.3 Hz),1.62-1.78(8H,m),2.85-2.86(2H,m),2.97-3.08(8H,m), 3.17(2H,t,J=7.6 Hz),3.73(2H,s),4.17(4H,s),4.27-4.30(2H, m),7.45(2H,t,J=8.4 Hz),7.50(2H,t,J=8.2 Hz),7.56(4H,s).

EXAMPLE 61

Production Example 61

Synthesis of (1H-imidazol-2-ylmethyl)-(1-methyl-1H-imidazol-2-ylmethyl)-[2-(4-piperidin-1-yl-butyl)-3-propyl-3H-benzimidazol-5-ylmethyl]-amine [Compound No. 80]

EXAMPLE 61-1

Synthesis of 5-piperidin-1-yl-pentanoic acid

5-Bromopentanoic acid methyl ester (1.22 g) was dissolved in acetonitrile (24.4 ml) and added with potassium carbonate (1.30 g), potassium iodide (0.104 g), and piperidine (0.928 ml) and the whole was stirred at 70° C. for 2.5 hours. The reaction solution was added with water and the whole was subjected to separation/extraction with chloroform. The organic layer was washed with a saturated saline solution and then dried with anhydrous sodium sulfate, followed by concentration under reduced pressure. The residue was again dissolved in 18% hydrochloric acid (20 ml) and the whole was refluxed under heating for 3 hours. The reaction solution was concentrated under reduced pressure. Recrystallization was performed with acetone/acetic acid, thereby obtaining a hydrochloride (1.15 g) of the subject compound as a colorless crystal.

MS(FAB,Pos.):m/z=186[M+H]$^+$

EXAMPLE 61-2

Synthesis of 5-piperidin-1-yl-pentanoic acid-(2-amino-5-cyano-phenyl)-amide

Commercially available 3,4-diaminobenzonitrile (0.461 g) was dissolved in DMF (18.4 ml) and added with WSCI hydrochloride (0.996 g), HOBt (0.702 g), and the compound (0.844 g) obtained in Example 60-1 and the whole was stirred at room temperature for 3 days. The reaction solution was concentrated under reduced pressure. The residue was added with water and subjected to separation/extraction with chloroform. The organic layer was washed with a saturated saline solution and then dried with anhydrous sodium sulfate, followed by concentration under reduced pressure. The residue was purified through silica gel column chromatography (chloroform/methanol), thereby obtaining the subject compound (1.04 g) as a yellow oily substance.

MS(FAB,Pos.):m/z=301[M+H]$^+$

EXAMPLE 61-3

Synthesis of 2-(4-piperidin-1-yl-butyl)-3-propyl-3H-benzimidazol-5-carbonitrile

The compound (1.04 g) obtained in Example 61-2 was dissolved in DMF (31.2 ml) and added with 60% sodium hydride (0.166 g) and 1-iodopropane (0.405 ml) while the whole was being stirred under ice-cooling. The solution was warmed to room temperature and stirred for 15 hours. The reaction solution was poured in ice-cold water and subjected to separation/extraction with chloroform. The organic layer was washed with a saturated saline solution and then dried with anhydrous sodium sulfate, followed by concentration under reduced pressure. The residue was again dissolved in a 4 mol/l hydrogen chloride/dioxane solution (10 ml) and the whole was stirred at room temperature for 1 hour. The reaction solution was concentrated under reduced pressure. The residue was dissolved in chloroform and washed with a 1 mol/l sodium hydroxide aqueous solution and a saturated saline solution. Then, the resultant was dried with anhydrous sodium sulfate and concentrated under reduced pressure. The residue was purified through silica gel column chromatography (chloroform), thereby obtaining the subject compound (451.8 mg) as a yellow oily substance.

MS(FAB,Pos.):m/z=325[M+H]$^+$

EXAMPLE 61-4

Synthesis of (1H-imidazol-2-ylmethyl)-[2-(4-piperidin-1-yl-butyl)-3-propyl-3H-benzimidazol-5-ylmethyl]-amine The compound (451.8 mg) obtained in Example 61-3 was dissolved in ethanol (18.1 ml) and added with a 1 mol/l sodium hydroxide aqueous solution (4.52 ml) and Raney nickel. The whole was stirred at room temperature for 20 hours under a hydrogen atmosphere. The reaction solution was filtrated through Celite and the filtrate was concentrated under reduced pressure. The residue was added with water and the whole was subjected to separation/extraction with chloroform. The organic layer was washed with a saturated saline solution and then dried with anhydrous sodium sulfate, followed by concentration under reduced pressure. The residue was again dissolved in methanol (22.1 ml) and added with 2-imidazole carboxaldehyde (194.0 mg) and trimethyl orthoformate (0.442 ml). The whole was stirred at room temperature for 1.5 hours. Subsequently, the solution was added with sodium borohydride (152.8 mg) under ice-cooling and the whole was stirred at room temperature for additional 30 minutes. The reaction solution was concentrated under reduced pressure. The residue was added with water and the whole was subjected to separation/extraction with chloroform. The organic layer washed with a saturated saline solution and dried with anhydrous sodium sulfate, followed by concentration under reduced pressure. The residue was purified through silica gel column chromatography (chloroform/methanol), thereby obtaining the subject compound (429.5 mg) as a yellow oily substance.

MS(FAB,Pos.):m/z=409[M+H]$^+$

EXAMPLE 61-5

Synthesis of (1H-imidazol-2-ylmethyl)-(1-methyl-1H-imidazol-2-ylmethyl)-[2-(4-piperidin-1-yl-butyl)-3-propyl-3H-benzimidazol-5-ylmethyl]-amine [Compound No. 80]

The compound (429.5 mg) obtained in Example 61-4 was dissolved in methanol (21.5 ml) and added with 1-methyl-2-imidazole carboxaldehyde (173.6 mg) and sodium cyanoborohydride (132.1 mg). After the solution was adjusted to pH 4 with acetic acid, the whole was stirred at room temperature for 4 days. The reaction solution was concentrated under reduced pressure. The residue was dissolved in chloroform and washed with a 1 mol/l sodium hydroxide aqueous solution and a saturated saline solution. Then, the resultant was dried with anhydrous sodium sulfate and concentrated under reduced pressure. The residue was purified through silica gel column chromatography (chloroform/methanol) and treated with hydrochloric acid, thereby obtaining a hydrochloride (559.2 mg) of the subject compound as a pale-yellow solid.

MS(FAB,Pos.):m/z=503[M+H]$^+$
$^1$H-NMR(500 MHz,DMSO-d$_6$+D$_2$O):δ=0.98(3H,t,J=7.3 Hz),1.69-1.92(12H,m),2.84-2.88(2H,m),3.08-3.11(2H,m), 3.23-3.26(2H,m),3.41-3.46(2H,m),3.72(3H,s),3.91(2H,s), 4.11(2H,s),4.20(2H,s),4.48(2H,t,J=7.5 Hz),7.50(2H,s),7.56 (1H,d,J=8.5 Hz),7.61(2H,s),7.71(1H,d,J=8.5 Hz),8.23(1H, s).

EXAMPLE 62

Production Example 62

Synthesis of 3-[(4-[[(1H-imidazol-2-ylmethyl)-(1-methyl-1H-imidazol-2-ylmethyl)-amino]-methyl]-benzyl)-(4-piperidin-1-yl-butyl)-amino]-propionic acid [Compound No. 81]

EXAMPLE 62-1

Synthesis of (4-[[(2-cyano-ethyl)-(4-piperidin-1-yl-butyl)-amino]-methyl]-benzyl)-carbamic acid t-butyl ester The compound (1.04 g) obtained in Example 23-3 was dissolved in anhydrous methanol (40 ml) and added with 4,4-diethoxy-butylamine (863 mg) and trimethyl orthoformate (1.44 ml). The whole was stirred at room temperature for 3 hours. The solution was added with sodium borohydride (499 mg) and the whole was stirred at room temperature for 30 minutes. After completion of the reaction, the solvent was distilled off. The resultant was added with water, subjected to extraction with chloroform, and then dried with magnesium sulfate. The solvent was distilled off. The residue was purified through silica gel column chromatography (hexane/ethyl acetate).

The resultant was dissolved in methanol (25 ml) and water (4.8 ml) and added with acrylonitrile (0.43 ml). The whole was stirred at room temperature for 16.5 hours. After completion of the reaction, the solvent was distilled off. The resultant was subjected to extraction with chloroform and dried with magnesium sulfate. The solvent was distilled off.

The resultant was dissolved in THF (12 ml), acetone (12 ml), and 1 mol/l hydrochloric acid (12 ml) and the whole was stirred at room temperature for 3 hours. After completion of the reaction, the solvent was distilled off. The resultant was added with a 1 mol/l sodium hydroxide aqueous solution and the whole was subjected to extraction with chloroform.

The resultant was dried with magnesium sulfate and the solvent was distilled off.

The resultant was dissolved in anhydrous methanol (26 ml) and added with piperidine (0.49 ml) and sodium cyanoborohydride (415 mg). After the solution was adjusted to pH 5 with acetic acid, the whole was stirred at room temperature for 3 days. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off. The residue was purified through silica gel column chromatography (hexane/ethyl acetate), thereby obtaining the subject compound (1.13 g) as a colorless oily substance.

MS(FAB,Pos.):m/z=429[M+H]$^+$
$^1$H-NMR(500 MHz,CDCl$_3$):δ=1.27-1.50(6H,m),1.47(9H, s),1.55-1.60(4H,m),2.25(2H,t,J=7.3 Hz),2.34(4H,br),2.40 (2H,t,J=7.0 Hz),2.49(2H,t,J=6.9 Hz),2.77(2H,t,J=7.0 Hz), 3.59(2H,s),4.31(2H,d,J=5.5 Hz),7.23(2H,d,J=7.9 Hz),7.29 (2H,d,J=8.2 Hz).

EXAMPLE 62-2

Synthesis of 3-[(4-[[(1H-imidazol-2-ylmethyl)-amino]-methyl]-benzyl)-(4-piperidin-1-yl-butyl)-amino]-propionic acid methyl ester The compound (1.12 g) obtained in Example 62-1 was dissolved in methanol (11.2 ml) and added with a 4 mol/l hydrogen chloride/dioxane solution (6.7 ml) and the whole was stirred at room temperature for 2 hours. Further, the solution was added with a 10% hydrogen chloride/methanol solution (18 ml) and the whole was stirred overnight at 60° C. After completion of the reaction, the solvent was distilled off. The resultant was adjusted to pH 8 with a 1 mol/l sodium hydroxide aqueous solution and saturated aqueous sodium hydrogen carbonate solution. The whole was subjected to extraction with chloroform and dried with magnesium sulfate. The solvent was distilled off.

The resultant was dissolved in anhydrous methanol (24.5 ml) and added with 2-imidazole carboxaldehyde (245 mg) and trimethyl orthoformate (0.56 ml). The whole was stirred at room temperature for 20 hours. Then, the solution was added with sodium borohydride (193 mg) and the whole was stirred at room temperature for 1 hour. The solvent was distilled off. The resultant was added with water and the whole was subjected to extraction with chloroform. The resultant was dried with magnesium sulfate. The solvent was distilled off. The residue was purified through silica gel column chromatography (chloroform/methanol), thereby obtaining the subject compound (403 mg) as a colorless oily substance.

MS(FAB,Pos.):m/z=442[M+H]$^+$

EXAMPLE 62-3

Synthesis of 3-[(4-[[(1H-imidazol-2-ylmethyl)-(1-methyl-1H-imidazol-2-ylmethyl)-amino]-methyl]-benzyl)-(4-piperidin-1-yl-butyl)-amino]-propionic acid methyl ester The compound (403 mg) obtained in Example 62-2 was dissolved in anhydrous methanol (16 ml) and added with 1-methyl-2-imidazole carboxaldehyde (151 mg) and sodium cyanoborohydride (172 mg). After the solution was adjusted to pH 5 with acetic acid, the whole was stirred at room temperature for 18 hours. After completion of the reaction, the solvent was distilled off. The resultant was added with a 1 mol/l sodium hydroxide aqueous solution and the whole was subjected to extraction with chloroform. The resultant was dried with magnesium sulfate and the solvent was distilled off. The resultant was purified through silica gel column chromatography (chloroform/ethyl acetate), thereby obtaining the subject compound (333 mg) as a colorless oily substance.

MS(FAB,Pos.):m/z=536[M+H]$^+$

EXAMPLE 62-4

Synthesis of 3-[(4-[[(1H-imidazol-2-ylmethyl)-(1-methyl-1H-imidazol-2-ylmethyl)-amino]-methyl]-benzyl)-(4-piperidin-1-yl-butyl)-amino]-propionic acid [Compound-No. 81]

The compound (333 mg) obtained in Example 62-3 was dissolved in water (0.5 ml) and concentrated hydrochloric acid (6.0 ml) and the whole was refluxed under heating for 2 hours. After completion of the reaction, the solvent was distilled off, thereby obtaining a hydrochloride (336 mg) of the subject compound as a white solid.

MS(FAB,Pos.):m/z=522[M+H]$^+$ $^1$H-NMR(500 MHz,DMSO-d$_6$):δ=1.71-1.80(10H,m), 2.80-2.99(8H,m),3.14(2H,m),3.37(2H,d,J=12.4 Hz),3.71 (3H,s),3.73(2H,s),4.11(2H,s),4.19(2H,s),4.26(2H,s),7.45 (2H,d,J=8.2 Hz),7.51-7.54(4H,m),7.63(2H,s).

EXAMPLE 63

Production Example 63

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetonitrile [Compound No. 82]

EXAMPLE 63-1

Synthesis of (4-[[cyanomethyl-(4-dipropylamino-butyl)-amino]-methyl]-benzyl)-carbamic acid t-butyl ester The compound (522 mg) obtained in Example 23-4 was dissolved in DMF (10 ml) and added with triethylamine (372 μl) and bromoacetonitrile (139 μl) and the whole was stirred overnight at room temperature. After completion of the reaction, the solvent was distilled off. The residue was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate and the solvent was distilled off. The residue was purified through silica gel column chromatography (hexane/ethyl acetate), thereby obtaining the subject compound (469 mg) as a colorless oily substance.

MS(FAB,Pos.):m/z=431[M+H]$^+$

EXAMPLE 63-2

Synthesis of [4-(aminomethyl-benzyl)-(4-dipropylamino-butyl)-amino]-acetonitrile The compound (147 mg) obtained in Example 63-1 was dissolved in anhydrous THF (1.5 ml) and added with a 4 mol/l hydrogen chloride/dioxane solution (3.00 ml) and the whole was stirred at room temperature for 1 hour. After completion of the reaction, the solvent was distilled off. The resultant was added with a saturated aqueous sodium hydrogen carbonate solution and the whole was subjected to extraction with chloroform and washed with a saturated saline solution. The organic layer was dried with anhydrous sodium sulfate. The solvent was distilled off, thereby obtaining the subject compound (103 mg) as a pale-yellow oily substance.

MS(FAB,Pos.):m/z=331[M+H]$^+$

EXAMPLE 63-3

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetonitrile [Compound No. 82]

The compound (103 mg) obtained in Example 63-2 was dissolved in anhydrous methanol (2.0 ml) and added with trimethyl orthoformate (51.1 μl) and 2-imidazole carboxaldehyde (32.9 mg). The whole was stirred overnight at room temperature under a nitrogen atmosphere. Subsequently, the solution was added with sodium borohydride (11.8 mg) in an ice bath and the whole was stirred at room temperature for 2 hours. After completion of the reaction, the resultant was added with distilled water and the whole was stirred for a while. The resultant was subjected to extraction with chloroform and washed with a saturated saline solution. The organic layer was dried with anhydrous sodium sulfate. The residue (127 mg) was dissolved in anhydrous methanol (3.0 ml) and added with sodium cyanoborohydride (29.2 mg), acetic acid (300 μl), and 1-methyl-2-imidazole carboxaldehyde (37.5 mg). The whole was stirred at room temperature for 3 days under a nitrogen atmosphere. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate) and treated with tartaric acid, thereby obtaining tartrate (191 mg) of the subject compound as a white solid.

MS(FAB,Pos.):m/z=505[M+H]$^+$ $^1$H-NMR(500 MHz,DMSO-d$_6$+D$_2$O):δ=0.89(6H,t,J=7.5 Hz),1.46-1.52(2H,m),1.56-1.64(6H,m),2.49-2.52(2H,m), 2.94-3.00(6H,m),3.51(3H,s),3.54(2H,s),3.58(2H,s),3.60 (2H,s),3.61(2H,s),3.62(2H,s),4.21(6H,s),6.85(1H,d,J=1.2 Hz),7.04(2H,s),7.10(1H,d,J=1.2 Hz),7.25(2H,d,J=7.9 Hz), 7.34(2H,d,J=8.2 Hz).

EXAMPLE 64

Production Example 64

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid methyl ester [Compound No. 83]

EXAMPLE 64-1

Synthesis of [(4-aminomethyl-benzyl)-(4-dipropylamino-butyl)-amino]-acetic acid methyl ester The compound (265 mg) obtained in Example 63-1 was dissolved in anhydrous methanol (2.5 ml) and added with a 4 mol/l hydrogen chloride/dioxane solution (5.00 ml) and the whole was stirred overnight at room temperature. After completion of the reaction, the solvent was distilled off. The resultant was added with a saturated aqueous sodium hydrogen carbonate solution. The whole was subjected to extraction with chloroform and washed with a saturated saline solution. The organic layer was dried with anhydrous sodium sulfate. The solvent was distilled off, thereby obtaining the subject compound (161 mg) as a pale-yellow oily substance.

MS(FAB,Pos.):m/z=364[M+H]$^+$

EXAMPLE 64-2

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid methyl ester [Compound No. 83]

The compound (161 mg) obtained in Example 64-1 was dissolved in anhydrous methanol (3.0 ml) and added with trimethyl orthoformate (72.5 μl) and 2-imidazole carboxaldehyde (46.7 mg). The whole was stirred overnight at room temperature under a nitrogen atmosphere. Subsequently, the solution was added with sodium borohydride (16.7 mg) in an ice bath and the whole was stirred at room temperature for 2 hours. After completion of the reaction, the resultant was added with distilled water and the whole was stirred for a while. The resultant was subjected to extraction with chloroform and washed with a saturated saline solution. The organic layer was dried with anhydrous sodium sulfate. The residue (167 mg) was dissolved in anhydrous methanol (3.0 ml) and added with sodium cyanoborohydride (35.4 mg), acetic acid (300 μl), and 1-methyl-2-imidazole carboxaldehyde (45.5 mg). The whole was stirred at room temperature for 3 days under a nitrogen atmosphere. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate) and treated with hydrochloric acid, thereby obtaining a hydrochloride (88.6 mg) of the subject compound as a white solid.

MS(FAB,Pos.):m/z=538[M+H]$^+$

EXAMPLE 65

Production Example 65

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid [Compound No. 84]

EXAMPLE 65-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid [Compound No. 84]

The hydrochloride (30.8 mg) of the compound obtained in Example 64-2 was added with concentrated hydrochloric acid (3.00 ml) and the whole was refluxed under heating. After completion of the reaction, the solvent was distilled off, thereby obtaining a hydrochloride (30.5 mg) of the subject compound as a white solid.

MS(FAB,Pos.):m/z=524[M+H]$^+$ $^1$H-NMR(500 MHz,DMSO-d$_6$+D$_2$O):δ=0.92(6H,t,J=7.3 Hz),1.62-1.70(6H,m),1.74-1.82(2H,m),2.97-3.01(4H,m), 3.06(2H,t,J=7.6 Hz),3.14(2H,t,J=7.6 Hz),3.72(3H,s),3.75 (2H,s),3.96(2H,s),4.09(2H,s),4.17(2H,s),4.35(2H,s),7.43-7.49(6H,m),7.60(2H,s).

EXAMPLE 66

Production Example 66

Synthesis of 3-[(4-dipropylamino-butyl)-(4-[[(1H-imidazol-2-ylmethyl)-(1-methyl-1H-imidazol-2-ylmethyl)-amino]-methyl]-benzyl)-amino]-propionic acid-1-isopropoxycarbonyloxy-ethyl ester [Compound No. 85]

EXAMPLE 66-1

Synthesis of 3-[(4-dipropylamino-butyl)-(4-[[(1H-imidazol-2-ylmethyl)-(1-methyl-1H-imidazol-2-ylmethyl)-amino]-methyl]-benzyl)-amino]-propionic acid-1-isopropoxycarbonyloxy-ethyl ester [Compound No. 85]

The compound (217.0 mg) obtained in Example 51-1, potassium carbonate (257.1 mg), and potassium iodide (24.9 mg) were suspended in anhydrous DMF (4.3 ml) The suspension was added with a DMF solution (0.7 ml) containing carboxylic acid-1-chloro-ethyl ester isopropyl ester (74.9 mg) and the whole was stirred at 60° C. for 15 hours. After completion of the reaction, the solvent was distilled off. The resultant was added with water and the whole was subjected to extraction with chloroform and dried with magnesium sulfate. The solvent was distilled off. The residue was purified through silica gel column chromatography (chloroform/ethyl acetate), thereby obtaining the subject compound (13.8 mg) as a colorless oily substance.

MS(FAB,Pos.):m/z=668[M+H]$^+$ $^1$H-NMR(500 MHz,CDCl$_3$):δ=0.85(6H,t,J=7.3 Hz),1.29 (6H,dd,J=2.9,6.1 Hz),1.40-1.44(8H,m),1.48(3H,d,J=5.4 Hz),2.32-2.35(6H,m),2.42(2H,t,J=6.8 Hz),2.48(2H,t,J=7.6 Hz),2.79(2H,t,J=7.1 Hz),3.46(2H,s),3.55(5H,s),3.62(2H,s), 3.67(2H,s),4.87(1H,quint.,J=6.3 Hz),6.74(1H,q,J=5.4 Hz), 6.87(1H,d,J=1.2 Hz),6.99(1H,d,J=1.2 Hz),7.10(2H,d,J=20.7 Hz),7.26(2H,d,J=8.1 Hz),7.33(2H,d,J=8.1 Hz),7.47(1H,br).

EXAMPLE 67

Production Example 67

Synthesis of 3-[(4-[[bis-(1H-imidazol-2-ylmethyl)-amino]-methyl]-benzyl)-(4-dipropylamino-butyl)-amino]-propionic acid methyl ester [Compound No. 86]

EXAMPLE 67-1

Synthesis of 3-[(4-[[bis-(1H-imidazol-2-ylmethyl)-amino]-methyl]-benzyl)-(4-dipropylamino-butyl)-amino]-propionic acid methyl ester [Compound No. 86]

The compound (550 mg) obtained in Example 34-1 was dissolved in anhydrous methanol (10 ml) and added with trimethyl orthoformate (239 μl) and 2-imidazole carboxaldehyde (154 mg). The whole was stirred overnight at room temperature under a nitrogen atmosphere. Subsequently, the solution was added with sodium borohydride (55.2 mg) in an ice bath and the whole was stirred at room temperature for 3 hours. After completion of the reaction, the resultant was added with distilled water and the whole was stirred for a while. The resultant was subjected to extraction with chloroform and washed with a saturated saline solution. The organic layer was dried with anhydrous sodium sulfate. The residue (738 mg) was dissolved in anhydrous methanol (15 ml) and added with sodium cyanoborohydride (152 mg),acetic acid (1.50 ml), and 2-imidazole carboxaldehyde (170 mg). The whole was stirred overnight at room temperature under a nitrogen atmosphere. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate) and treated with hydrochloric acid, thereby obtaining a hydrochloride (225 mg) of the subject compound as a white solid.

MS(FAB,Pos.):m/z=538[M+H]$^+$
$^1$H-NMR(500 MHz,DMSO-d$_6$+D$_2$O):δ=0.92(6H,t,J=7.2 Hz),1.64-1.79(8H,m),2.92-3.07(10H,m),3.21(2H,t,J=7.6 Hz),3.64(3H,s),3.72(2H,s),4.16(2H,s),4.27-4.31(2H,m), 7.45(2H,d,J=8.4 Hz),7.50(2H,d,J=8.2 Hz),7.57(4H,s).

EXAMPLE 68

Production Example 68

Synthesis of [(4-[[bis-(1H-imidazol-2-ylmethyl)-amino]-methyl]-benzyl)-(4-dipropylamino-butyl)-amino]-acetic acid methyl ester [Compound No. 87]

EXAMPLE 68-1

Synthesis of [(4-[[bis-(1H-imidazol-2-ylmethyl)-amino]-methyl]-benzyl)-(4-dipropylamino-butyl)-amino]-acetic acid methyl ester [Compound No. 87]

The compound (1.4928 g) obtained in Example 64-1 was dissolved in anhydrous methanol (59.6 ml) and added with 2-imidazole carboxaldehyde (1.1848 g) and sodium cyanoborohydride (1.0331 g). After the solution was adjusted to pH 5 with acetic acid, the whole was stirred at room temperature for 3 days. After completion of the reaction, the resultant was added with a 1 mol/l sodium hydroxide aqueous solution and the whole was subjected to extraction with chloroform. The resultant was dried with magnesium sulfate and the solvent was distilled off. The residue was purified through silica gel column chromatography (chloroform/ethyl acetate) and treated with hydrochloric acid, thereby obtaining a hydrochloride (705.7 mg) of the subject compound as a white solid.

MS(FAB,Pos.):m/z=524[M+H]$^+$
$^1$H-NMR(500 MHz,DMSO-d$_6$+D$_2$O):δ=0.92(6H,t,J=7.3 Hz),1.64-1.70(6H,m),1.77(2H,m),2.97-3.00(4H,m),3.03-3.06(2H,m),3.15(2H,t,J=7.9 Hz),3.67(3H,s),3.72(2H,s),4.06 (2H,s),4.15(4H,s),4.35(2H,s), 7.45-7.49(4H,m),7.58(4H,s).

EXAMPLE 69

Production Example 69

Synthesis of [(4-[[bis-(1H-imidazol-2-ylmethyl)-amino]-methyl]-benzyl)-(4-dipropylamino-butyl)-amino]-acetic acid [Compound No. 88]

EXAMPLE 69-1

Synthesis of [(4-[[bis-(1H-imidazol-2-ylmethyl)-amino]-methyl]-benzyl)-(4-dipropylamino-butyl)-amino]-acetic acid [Compound No. 88]

The compound (533.4 mg) obtained in Example 68-1 was dissolved in water (0.5 ml) and added with concentrated hydrochloric acid (2.5 ml). The whole was refluxed under heating for 30 minutes. After completion of the reaction, the solvent was distilled off, thereby obtaining a hydrochloride (384.1 mg) of the subject compound as a white solid.

MS(FAB,Pos.):m/z=510[M+H]$^+$
$^1$H-NMR(500 MHz,DMSO-d$_6$+D$_2$O):δ=0.92(6H,t,J=7.3 Hz),1.62-1.68(6H,m),1.77(2H,m),2.97-3.00(4H,m),3.05 (2H,t,J=7.9 Hz),3.12(2H,t,J=7.5 Hz),3.72(2H,s),3.96(2H,s), 4.14(4H,s),4.34(2H,s),7.44-7.49(4H,m),7.56(4H,s).

EXAMPLE 70

Production Example 70

Synthesis of [(4-dipropylamino-butyl)-([[(1H-imidazol-2-ylmethyl)-(1-methyl-1H-imidazol-2-ylmethyl)-amino]-methyl]-benzyl)-amino]-acetic acid benzyl ester [Compound No. 89]

EXAMPLE 70-1

Synthesis of [(4-dipropylamino-butyl)-([[(1H-imidazol-2-ylmethyl)-(1-methyl-1H-imidazol-2-ylmethyl)-amino]-methyl]-benzyl)-amino]-acetic acid benzyl ester [Compound No. 89]

The compound (145.0 mg) obtained in Example 65-1 was dissolved in benzyl alcohol (3.0 ml) and added with WSCI hydrochloride (58.9 mg) and HOBt (41.5 mg) and the whole was stirred at room temperature for 18 hours. After completion of the reaction, the resultant was added with 1 mol/l hydrochloric acid and excess benzyl alcohol was removed with chloroform. The resultant was added with a 1 mol/l sodium hydroxide aqueous solution to make the resultant alkaline. The whole was subjected to extraction with chloroform, washed with a saturated saline solution, and then dried with anhydrous sodium sulfate. After filtration, the solvent was distilled off under reduced pressure. The residue was purified through silica gel column chromatography (chloroform/ethyl acetate) and treated to make hydrochloric acid, thereby obtaining a hydrochloride (33.0 mg) of the subject compound as a white solid.

MS(FAB,Pos.):m/z=614[M+H]$^+$ $^1$H-NMR(500 MHz,DMSO-d$_6$):δ=0.89(6H,t,J=7.3 Hz), 1.60-1.70(8H,m),2.80-3.00(4H,m),2.98-3.04(8H,m),3.20-3.50(5H,m),3.68(4H,s),4.07(2H,s),4.14(2H,s),5.17(2H,br), 7.30-7.31(3H,m),7.32-7.46(6H,m),7.50-7.51(2H,m),7.62 (2H,s).

EXAMPLE 71

Production Example 71

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-morpholin-4-yl-ethyl ester [Compound No. 90]

EXAMPLE 71-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-morpholin-4-yl-ethyl ester [Compound No. 90]

The compound (185.8 mg) obtained in Example 65-1 was dissolved in a small amount of water. The solution was added with chloroform and a 1 mol/l sodium hydroxide aqueous solution, and the organic layer and an oily substance were collected, followed by drying with anhydrous magnesium sulfate. After filtration, the solvent was distilled off. An anhydrous DMF solution (2 ml) containing the resultant sodium salt (143.6 mg) and N-(2-hydroxyethyl)morpholine (38 mg) was added with HOBt (37 mg) and WSCI hydrochloride (63 mg) and the whole was stirred overnight. After the solvent was distilled off, the resultant was dissolved in chloroform and washed with a saturated aqueous sodium hydrogen carbonate solution. The aqueous layer was extracted with chloroform and dried with anhydrous magnesium sulfate. The reaction mixture obtained by distillating the solvent off was purified through silica gel column chromatography (chloroform). The resultant was dissolved in dioxane and a salt was allowed to precipitate with a 4 mol/l hydrogen chloride/dioxane solution. After the solvent was distilled off, the solid substance was pulverized and dried under reduced pressure, thereby obtaining a hydrochloride (143,4 mg) of the subject compound as a white solid.

MS(FAB,Pos.):m/z=637[M+H]$^+$ $^1$H-NMR(500 MHz,CDCl$_3$):δ=0.86(6H,t,J=7.3 Hz),1.38-1.56(8H,m),2.28-2.38(6H,m),2.46-2.58(6H,m),2.60-2.65 (2H,m),3.31(2H,s),3.47(2H,s),3.57(3H,s),3.61(2H,s),3.67-3.69(4H,m),3.73(2H,t,J=4.9 Hz),3.76(2H,s),4.23(2H,t,J=5.6 Hz),6.88(1H,d,J=1.2 Hz),7.00(1H,d,J=1.2 Hz),7.08(1H,bs), 7.12(1H,bs),7.31(2H,d,J=8.1 Hz),7.35(2H,d,J=7.8 Hz), 12.32(1H,bs).

EXAMPLE 72

Production Example 72

Synthesis of [[4-(dipropyl-amino)-butyl]-(4-[[1H-imidazol-2-ylmethyl)-(1-methyl-1H-imidazol-2-ylmethyl)-amino]-methyl]-benzyl)-amino]-acetic acid ethyl ester [Compound No. 91]

EXAMPLE 72-1

Synthesis of [[4-(t-butoxycarbonylamino-methyl)-benzyl]-(4-dipropylamino-butyl)-amino]-acetic acid ethyl ester The compound (28.58 g) obtained in Example 23-4 was dissolved in anhydrous DMF (560 ml) and added with triethylamine (20.35 ml) and ethyl bromoacetate (12.14 ml) and the whole was stirred at room temperature for 2 hours. After completion of the reaction, the solvent was distilled off. The resultant was dissolved in ethyl acetate and washed with water, followed by drying with magnesium sulfate. The solvent was distilled off. The residue was purified through silica gel column chromatography (hexane/ethyl acetate), thereby obtaining the subject compound (21.265 g) as a colorless oily substance.

MS(FAB,Pos.):m/z=478[M+H]$^+$ $^1$H-NMR(500 MHz,CDCl$_3$):δ=0.86(6H,t,J=7.3 Hz),1.26 (3H,t,J=7.1 Hz),1.40-1.50(8H,m),1.46(9H,s),2.32-2.39(6H, m),2.62(2H,t,J=7.6 Hz),3.28(2H,s),3.75(2H,s),4.12-4.17 (2H,m),4.82(1H,br),7.22(2H, d,J=8.1 Hz),7.30(2H,d,J=8.1 Hz).

EXAMPLE 72-2

Synthesis of [(4-aminomethyl-benzyl)-(4-dipropylamino-butyl)-amino]-acetic acid ethyl ester The compound (21.265 g) obtained in Example 72-1 was dissolved in ethanol (100 ml) and added with a 4 mol/l hydrogen chloride/dioxane solution (140 ml) and the whole was stirred at room temperature for 1 hour. Subsequently, the solution was stirred at 40° C. for 1 hour. After completion of the reaction, the solvent was distilled off. The resultant was added with a 1 mol/l sodium hydroxide aqueous solution to make the pH thereof to 12. The solution was subjected to extraction with chloroform and dried with magnesium sulfate. The solvent was distilled off, thereby obtaining the subject compound (16.46 g) as a colorless oily substance.

MS(FAB,Pos.):m/z=378[M+H]$^+$ $^1$H-NMR(500 MHz,CDCl$_3$):δ=0.86(6H,t,J=7.3 Hz),1.26 (3H,t,J=7.1 Hz),1.41-1.52(8H,m),2.33-2.40(6H,m),2.63(2H, t,J=7.3 Hz),3.29(2H,s),3.76(2H,s),3.85(2H,s),4.15(2H,t, J=7.2 Hz),7.25(2H,d,J=8.2 Hz),7.31(2H,d,J=8.1 Hz).

EXAMPLE 72-3

Synthesis of [[4-(dipropyl-amino)-butyl]-(4-[[1H-imidazol-2-ylmethyl)-(1-methyl-1H-imidazol-2-ylmethyl)-amino]-methyl]-benzyl)-amino]-acetic acid ethyl ester [Compound No. 91]

The compound (16.46 g) obtained in Example 72-2 was dissolved in anhydrous ethanol (320 ml) and added with 2-imidazole carboxaldehyde (6.285 g) and triethyl orthoformate (21.76 ml). The whole was stirred at room temperature for 3 hours. After having been cooled with ice, the solution was added with sodium borohydride (4.948 g) and the whole was stirred at room temperature for 30 minutes. After completion of the reaction, the solvent was distilled off. The resultant was added with water and the whole was subjected to extraction with chloroform and dried with magnesium sulfate, followed by distillating off the solvent.

The resultant was dissolved in anhydrous ethanol (400 ml) and added with 1-methyl-2-imidazole carboxaldehyde (7.202 g) and sodium triacetoxyborohydride (18.48 g). The whole was stirred at room temperature for 5 hours. Saturated sodium hydrogen carbonate water was added thereto. The solvent was distilled off and the resultant was subjected to extraction with chloroform and dried with magnesium sulfate. The solvent was distilled off. The residue was purified through silica gel column chromatography (chloroform/ethyl acetate).

L-tartaric acid (16.165 g; 107.7 mmol) was dissolved in ethanol (162 ml) and then an ethanol solution (99 ml) containing the above-mentioned compound (19.782 g) was dropped thereto. The whole was stirred at room temperature for 15 minutes. The supernatant was decanted and washed with ethanol (40 ml). The resultant was dried, thereby obtaining tartrate (30.8 g) of the subject compound as a white solid.

MS(FAB,Pos.):m/z=552[M+H]$^+$ $^1$H-NMR(500 MHz,DMSO-d$_6$+D$_2$O):δ=1.07(6H,t,J=7.0 Hz),1.18(3H,t,J=7.1 Hz),1.46-1.48(2H,m),1.57-1.62(6H,m), 2.56(2H,t,J=7.2 Hz),2.93-3.00(6H,m),3.26(2H,s),3.50(3H, s),3.52(2H,s),3.58(2H,s),3.59(2H,s),3.66(2H,s),4.07(2H,q, J=7.2 Hz),4.20(6H,s),7.03(1H,s),7.09(2H,s),7.09(1H,s),7.24 (2H,d,J=7.9 Hz),7.30(2H,d,J=8.1 Hz).

EXAMPLE 73

Production Example 73

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-methoxy-ethyl ester [Compound No. 92]

EXAMPLE 73-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-methoxy-ethyl ester [Compound No. 92]

The compound (190.7 mg) obtained in Example 65-1 was dissolved in 2-methoxyethanol (4.0 ml) and the whole was stirred at 80° C. for 21 hours. After completion of the reaction, the solvent was distilled off. The resultant was added with a saturated aqueous sodium hydrogen carbonate solution and the whole was subjected to extraction with chloroform and dried with magnesium sulfate. The solvent was distilled off. The residue was purified through silica gel column chromatography (chloroform/ethyl acetate) and treated with hydrochloric acid, thereby obtaining a hydrochloride (37.9 mg) of the subject compound as a white solid.

MS(FAB,Pos.):m/z=582[M+H]$^+$ $^1$H-NMR(500 MHz,DMSO-d$_6$+D$_2$O):δ=0.92(6H,t,J=7.3 Hz),1.63-1.67(6H,m),1.70-1.80(2H,m),2.97-3.01(4H,m), 3.05-3.06(4H,m),3.54-3.56(2H,m),3.69(3H,s),3.71(3H,s), 3.73(2H,s),3.90-4.00(2H,m),4.07(2H,s),4.15(2H,s),4.24-4.25(4H,m),7.41(4H,s),7.48(2H,s),7.60(2H,s).

EXAMPLE 74

Production Example 74

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid cinnamyl ester [Compound No. 93]

EXAMPLE 74-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid cinnamyl ester [Compound No. 93]

The hydrochloride (203 mg) of the compound obtained in Example 65-1 was dissolved in DMF (3.0 ml) and added with cinnamyl alcohol (73.9 μl) and the whole was refluxed overnight under heating. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/ethyl acetate) and treated with hydrochloric acid, thereby obtaining a hydrochloride (19.1 mg) of the subject compound as a brownish-red solid.

MS(FAB,Pos.):m/z=640[M+H]$^+$ $^1$H-NMR(500 MHz,DMSO-d$_6$+D$_2$O):δ=0.91(6H,t,J=7.2 Hz),1.61-1.73(8H,m),2.96-3.06(8H,m),3.66(2H,s),3.69(3H, s),3.75(4H,s),4.05(2H,s),4.13(2H,s),4.80(2H,d,J=6.3 Hz), 6.36(1H,td,J=6.3,15.7 Hz),6.73(1H,d,J=15.7 Hz),7.20-7.51 (11H,m),7.59(2H,s).

EXAMPLE 75

Production Example 75

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-(2-hydroxy-ethoxy)-ethyl ester [Compound No. 94]

EXAMPLE 75-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-2-(2-hydroxy-ethoxy)-ethyl ester [Compound No. 94]

The compound (424.0 mg) obtained in Example 65-1 was dissolved in diethylene glycol (8.0 ml) and the whole was stirred at 80° C. for 3 days. After completion of the reaction, the resultant was added with chloroform and washed with water, followed by drying with magnesium sulfate. The solvent was distilled off. The residue was purified through silica gel column chromatography (chloroform/methanol) and treated with hydrochloric acid, thereby obtaining a hydrochloride (280.2 mg) of the subject compound as a white solid.

MS(FAB,Pos.):m/z=612[M+H]$^+$ $^1$H-NMR(500 MHz,DMSO-d$_6$+D$_2$O):δ=0.92(6H,t,J=7.2 Hz),1.63-1.69(6H,m),1.80(2H,m),2.98-3.01(4H,m),3.06 (2H,t,J=8.2 Hz),3.17(2H,t,J=7.9 Hz),3.43-3.51(4H,m),3.65

(2H,t,J=3.8 Hz),3.73(3H,s),3.78(2H,s),4.06(2H,s),4.12(2H,s),4.20(2H,s),4.27(2H,t,J=4.0 Hz),4.37(2H,s),7.43-7.49(6H,m),7.60(2H,s).

EXAMPLE 76

Production Example 76

Synthesis of (4-dipropylamino-butyl)-(4-[[(1H-imidazol-2-ylmethyl)-(1-methyl-1H-imidazol-2-ylmethyl)-amino]-methyl]-benzyl)-carbamic acid t-butyl ester [Compound No. 95]

EXAMPLE 76-1

Synthesis of 2-[4-[(4-dipropylaminobutylamino)methyl]benzyl]isoindol-1,3-dione

The compound (103 mg) obtained in Example 1-1 was dissolved in anhydrous methanol (10 ml) and added with the hydrochloride (114 mg) of the compound obtained in Example 1-2. The solution was added with triethylamine (0.108 ml) and anhydrous magnesium sulfate (3 g) and the whole was stirred at room temperature for 1 hour. The solution was subjected to filtration through Celite to remove anhydrous magnesium sulfate and methanol was distilled off, followed by drying with a vacuum pump. The resultant was dissolved in anhydrous methanol (10 ml) and sodium borohydride (22.0 mg) was gradually added thereto under ice-cooling. The solution was warmed back to room temperature and stirred for 1 hour. After completion of the reaction, methanol was distilled off. The resultant was added with water and chloroform and the organic layer was extracted. The resultant was dried with anhydrous sodium sulfate and the solvent was distilled off. The residue was purified through silica gel column chromatography (chloroform/methanol/water), thereby obtaining the subject compound (60.3 mg) as a pale-yellow viscous liquid.

MS(FAB,Pos.):m/z=420[M+H]$^+$

EXAMPLE 76-2

Synthesis of [4-(1,3-dioxo-1,3-dihydro-isoindol-2-ylmethyl)-benzyl]-(4-dipropylamino-butyl)-carbamic acid t-butyl ester The compound (60.3 mg) obtained in Example 76-1 was dissolved in chloroform and added with di-t-butoxy dicarbonate (47.0 mg). The whole was stirred at room temperature for 30 minutes and then concentrated. The resultant was purified through silica gel column chromatography (chloroform/methanol), thereby obtaining the subject compound (70.0 mg) as a colorless viscous liquid.

MS(FAB,Pos.):m/z=522[M+H]$^+$

EXAMPLE 76-3

Synthesis of (4-aminomethyl-benzyl)-(4-dipropylamino-butyl)-carbamic acid t-butyl ester The compound (70.0 mg) obtained in Example 76-2 was added with a 40% methylamine/methanol solution (3.0 ml) and the whole was stirred at room temperature for 14 hours. After completion of the reaction, the solvent was distilled off. The resultant was added with a 1 mol/l sodium hydroxide aqueous solution and chloroform to extract the aqueous layer with chloroform. The resultant was dried with anhydrous sodium sulfate and the solvent was distilled off, thereby obtaining the subject compound (65.5 mg) as a colorless viscous liquid.

EXAMPLE 76-4

Synthesis of (4-dipropylamino-butyl)-(4-[[(1H-imidazol-2-ylmethyl)-amino]-methyl]-benzyl)-carbamic acid t-butyl ester The compound (0.78 g) obtained in Example 76-3 was dissolved in methanol (20 ml) and added with 2-imidazole carboxaldehyde (214.6 mg). The whole was stirred at room temperature for 17 hours. After the solvent was distilled off, the resultant was dried under vacuum, dissolved in methanol (15 ml), and added with sodium borohydride (217.8 mg) and the whole was stirred at room temperature for 45 minutes. The reaction solution was added with a saturated aqueous ammonium chloride solution (10 ml) and the whole was stirred at room temperature for 15 minutes. The reaction solution was added with a saturated saline solution and subjected to extraction with chloroform, followed by drying with anhydrous sodium sulfate. The solvent was distilled off. Then, the resultant residue was purified through silica gel column chromatography (chloroform/ethyl acetate), thereby obtaining the subject compound (1.01 g) as a yellow solid.

MS(FAB,Pos.):m/z=472[M+H]$^+$ $^1$H-NMR(500 MHz,CDCl$_3$):δ=0.86(6H,t,J=7.3 Hz),1.26-1.49(17H,m),2.32-2.35(6H,m),3.12(1H,brs),3.21(1H,brs),3.79(2H,brs),3.92(2H,brs),4.12(1H,brs),4.13(1H,brs),6.99(2H,s),7.20(2H,brs),7.25(2H,d,J=7.5 Hz).

EXAMPLE 76-5

Synthesis of (4-dipropylamino-butyl)-(4-[[(1H-imidazol-2-ylmethyl)-(1-methyl-1H-imidazol-2-ylmethyl)-amino]-methyl]-benzyl)-carbamic acid t-butyl ester [Compound No. 95]

The compound (231 mg) obtained in Example 76-4 was dissolved in anhydrous methanol (5.0 ml) and added with sodium cyanoborohydride (61.6 mg), acetic acid (2.00 ml), and 1-methyl-2-imidazole carboxaldehyde (80.9 mg). The whole was stirred at room temperature for 6 days under a nitrogen atmosphere. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated aqueous sodium hydrogen carbonate solution and a saturated saline solution. The organic layer was dried with anhydrous sodium sulfate. The solvent was distilled off. The residue was purified through silica gel column chromatography (chloroform/methanol/water), thereby obtaining the subject compound (197 mg) as a colorless oily substance.

MS(FAB,Pos.):m/z=566[M+H]$^+$

EXAMPLE 77

Production Example 77

Synthesis of N-(2-chloro-4-[[(1H-imidazol-2-ylm-ethyl)-(1-methyl-1H-imidazol-2-ylmethyl)-amino]-methyl]-benzyl)-N-methyl-N',N'-dipropyl-butane-1,4-diamine [Compound No. 96]

EXAMPLE 77-1

Synthesis of N-methyl-N',N'-dipropyl-butane-1,4-diamine

Acetic anhydride (0.60 ml) was added with formic acid (0.29 ml) and the whole was refluxed under heating for 1.5 hours. After completion of the reaction, the solution was cooled back to room temperature and added with THF (2.0 ml) and a THF solution (8.0 ml) containing the compound (400 mg) obtained in Example 1-2 and the whole was stirred at room temperature for about 4 hours. After completion of the reaction, the solvent was distilled off.

Lithium aluminum hydride (429 mg) was suspended in anhydrous THF (10 ml). The anhydrous THF solution (8.0 ml) containing the compound obtained in the above procedure was dropped thereto. The whole was stirred at room temperature for 4 hours. The solution was added with sodium sulfate decahydrate and a 20% sodium hydroxide aqueous solution. The suspension was filtrated through Celite and the solvent was distilled off. The residue was purified through silica gel column chromatography (chloroform/ethyl acetate), thereby obtaining the subject compound (61.8 mg) as a colorless oily substance.

MS(FAB,Pos.):m/z=187[M+H]$^+$
$^1$H-NMR(500 MHz,CDCl$_3$):δ=0.87(6H,t,J=7.3 Hz),1.41-1.50(8H,m),2.35-2.42(6H,m),2.43(3H,s),2.58(2H,t,J=6.8 Hz).

EXAMPLE 77-2

Synthesis of 3-chloro-4-methyl-benzoic acid methyl ester

3-Chloro-4-methyl-benzonitrile (1.09 g) was dissolved in methanol (12 ml). The reaction solution was added with a 1 mol/l sodium hydroxide aqueous solution (10 ml) and the whole was refluxed under heating for 1 hour. The reaction solution was cooled to room temperature. After having been added with 1 mol/l hydrochloric acid to make the pH to 3, the reaction solution was subjected to extraction with chloroform. The organic layer was washed with a saturated saline solution and then dried with anhydrous sodium sulfate. After the drying agent was filtrated out, the resultant was concentrated under reduced pressure and the resultant residue was dissolved in methanol (15 ml). The reaction solution was added with concentrated sulfuric acid (1 ml) and the whole was refluxed under heating for 6 hours. After having been cooled to room temperature, the reaction solution was added with a saturated aqueous sodium hydrogen carbonate solution to adjust the pH to 9 and then subjected to extraction with ethyl acetate. The organic layer was washed with a saturated saline solution and then dried with anhydrous sodium sulfate. After the drying agent was filtrated out, the solution was concentrated under reduced pressure, thereby obtaining the subject compound (1.125 g) as a white solid.

MS(FAB,Pos.):m/z=185[M+H]$^+$
$^1$H-NMR(500 MHz,CDCl$_3$):δ=2.43(3H,s),3.91(3H,s),7.29(1H,d,J=8.1 Hz),7.82(2H,d,J=8.1 Hz),8.01(1H,s).

EXAMPLE 77-3

Synthesis of 3-chloro-4-[[(4-dipropylamino-butyl)-methyl-amino]-methyl]-benzoic acid methyl ester The compound (0.98 g) obtained in Example 77-2 was dissolved in carbon tetrachloride (21.4 ml). The reaction solution was added with NBS (1.033 g) and AIBN (68.0 mg) and the whole was refluxed under heating for 30 minutes. After the reaction solution was cooled to room temperature, the precipitated solid was filtrated out through Celite. The filtrate was concentrated under reduced pressure and the resultant residue was dissolved in DMF (27 ml). The reaction solution was added with the compound (1.0929 g) obtained in Example 77-1 and potassium carbonate (1.323 g) and the whole was stirred at room temperature for 2 hours. The reaction solution was added with distilled water and subjected to extraction with t-butyl methyl ether. The organic layer was washed with a saturated saline solution and then dried with anhydrous sodium sulfate. After the drying agent was filtrated out, the resultant was concentrated under reduced pressure. The resultant residue was purified through silica gel column chromatography (chloroform/ethyl acetate to chloroform/methanol), thereby obtaining the subject compound (526.4 mg) as a yellow oily substance.

MS(FAB,Pos.):m/z=369[M+H]$^+$

EXAMPLE 77-4

Synthesis of (3-chloro-4-[[(4-dipropylamino-butyl)-methyl-amino]-methyl]-phenyl)-methanol The compound (526.4 mg) obtained in Example 77-3 was dissolved in THF (10 ml) and the whole was cooled to 0° C. Under a nitrogen atmosphere, a 0.94 mol/l DIBAL n-hexane solution (3 ml) was dropped to the reaction solution and the whole was stirred at room temperature for 1 hour. After having been cooled to 0° C., the reaction solution was added with ethyl acetate (10 ml) and acetone (10 ml) and the whole was stirred at room temperature for 1 hour. The reaction solution was added with a saturated aqueous sodium potassium tartrate solution (30 ml) and the whole was vigorously stirred at room temperature for 2 hours and then subjected to extraction with ethyl acetate. The organic layer was washed with a saturated saline solution and then dried with anhydrous sodium sulfate. After the drying agent was filtrated out, the resultant was concentrated under reduced pressure. The resultant residue was purified through silica gel column chromatography (n-hexane/ethyl acetate), thereby obtaining the subject compound (290.8 mg) as a yellow oily substance.

MS(FAB,Pos.):m/z=341[M+H]$^+$

EXAMPLE 77-5

Synthesis of 3-chloro-4-[[(4-dipropylamino-butyl)-methyl-amino]-methyl]-benzaldehyde The compound (290.8 mg) obtained in Example 77-4 was dissolved in chloroform (6 ml). The reaction solution was added with manganese dioxide (1.4331 g) and the whole was stirred at room temperature for 22 hours. The catalyst was filtrated out through Celite. The filtrate was concentrated under reduced pressure, thereby obtaining the subject compound (256.4 mg) as a colorless oily substance.

MS(FAB,Pos.):m/z=339[M+H]$^+$
$^1$H-NMR(500 MHz,CDCl$_3$):δ=0.89(6H,t,J=7.3 Hz),1.53-1.73(10H,m),2.24(3H,s),2.48(6H,br),3.64(2H,s),7.71(1H,d,J=8.5 Hz),7.75(1H,d,J=8.5 Hz),7.86(1H,s),9.96(1H,s).

EXAMPLE 77-6

Synthesis of N-(2-chloro-4-[[(1H-imidazol-2-ylmethyl)-(1-methyl-1H-imidazol-2-ylmethyl)-amino]-methyl]-benzyl)-N-methyl-N',N'-dipropyl-butane-1,4-diamine [Compound No. 96]

The compound (124.0 mg) obtained in Example 77-5 was dissolved in methanol (1.5 ml). The reaction solution was added with the compound (45.2 mg) obtained in Example 14-7 and trimethyl orthoformate (0.2 ml) and the whole was stirred at room temperature for 2 hours. The reaction solution was cooled to 0° C. and added with sodium borohydride (27.8 mg) and the whole was stirred at room temperature for 10 minutes. The reaction solution was added with a saturated aqueous ammonium chloride solution and the whole was stirred at room temperature for 20 minutes. The reaction solution was added with distilled water and subjected to extraction with chloroform. The organic layer was washed with a saturated saline solution and dried with anhydrous sodium sulfate. After the drying agent was filtrated out, the resultant was concentrated under reduced pressure and the resultant residue was dissolved in methanol (2 ml). The reaction solution was added with 2-imidazole carboxaldehyde (53.9 mg) and sodium cyanoborohydride (59.3 mg) and solution was adjusted to pH 5 with acetic acid. The whole was stirred at room temperature for 15 hours. The reaction solution was added with a 1 mol/l sodium hydroxide aqueous solution and the whole was subjected to extraction with chloroform. The organic layer was washed with a saturated saline solution and dried with anhydrous sodium sulfate. After the drying agent was filtrated out, the resultant was concentrated under reduced pressure. The resultant residue was purified through silica gel column chromatography (chloroform/ethyl acetate) and treated with hydrochloric acid, thereby obtaining a hydrochloride (42.3 mg) of the subject compound as a pale-pink solid.

MS(FAB,Pos.):m/z=514[M+H]$^+$
$^1$H-NMR(500 MHz,DMSO-d$_6$):δ=0.91(6H,t,J=7.3 Hz),1.64-1.73(8H,m),2.64(3H,s),2.95-3.16(8H,m),3.73(3H,s),3.77(2H,s),4.12(2H,s),4.20(2H,s),4.27(1H,br),4.44(1H,br),7.47(1H,d,J=7.9 Hz),7.54(1H,d,J=1.9 Hz),7.55(1H,d,J=1.9 Hz),7.60(1H,s),7.65(2H,s),7.77(1H,d,J=7.9 Hz),10.33(1H,br),10.84(1H,br).

EXAMPLE 78

Production Example 78

Synthesis of [(4-[[bis-(1H-imidazol-2-ylmethyl)-amino]-methyl]-benzyl)-(4-dipropylamino-butyl)-amino]-acetic acid ethyl ester [Compound No. 97]

EXAMPLE 78-1

Synthesis of [(4-[[bis-(1H-imidazol-2-ylmethyl)-amino]-methyl]-benzyl)-(4-dipropylamino-butyl)-amino]-acetic acid ethyl ester [Compound No. 97]

The compound (275.6 mg) obtained in Example 69-1 was dissolved in ethanol (11 ml) and the whole was refluxed under heating for 21 hours.

After completion of the reaction, the solvent was distilled off. The resultant was added with a 1 mol/l sodium hydroxide aqueous solution and the whole was subjected to extraction with chloroform. The resultant was dried with magnesium sulfate, distilled the solvent off and treated with hydrochloric acid, thereby obtaining a hydrochloride (181.4 mg) of the subject compound as a white solid.

MS(FAB,Pos.):m/z=538[M+H]$^+$
$^1$H-NMR(500 MHz,DMSO-d$_6$+D$_2$O):δ=0.92(6H,t,J=7.3 Hz),1.18(3H,t,J=7.2 Hz),1.63-1.68(6H,m),1.76(2H,br),2.97-3.00(4H,m),3.05(2H,t,J=7.8 Hz),3.13(2H,br),3.71(2H,s),4.03(2H,s),4.10-4.15(6H,m),4.32(2H,s),7.46(4H,dd,J=8.4,15.4 Hz),7.58(4H,d,J=4.4 Hz).

EXAMPLE 79

Production Example 79

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid 3,7,11-trimethyl-dodeca-2,6,10-trienyl ester [Compound No. 98]

EXAMPLE 79-1

Synthesis of [(4-dipropylamino-butyl)-(4-[[(1H-imidazol-2-ylmethyl)-(1-methyl-1H-imidazol-2-ylmethyl)-amino]-methyl]-benzyl)-amino]-acetic acid-3,7,11-trimethyl-dodeca-2,6,10-trienyl ester [Compound No. 98]

The compound (182 mg) obtained in Example 65-1 was suspended in chloroform and added with a 1 mol/l sodium hydroxide aqueous solution and the aqueous layer was extracted with chloroform. The organic layer was washed with a saturated saline solution and dried with anhydrous sodium sulfate. After filtration, the solution was concentrated and evaporated to dryness under reduced pressure, thereby obtaining a sodium salt thereof (122 mg) as a pale-yellow solid. The sodium salt was dissolved in chloroform and added with WSCI hydrochloride (58.2 mg), HOBt (34.7 mg), farnesol (290 μl), and N-methyl morpholine (33.4 μl) at room temperature under a nitrogen atmosphere and the whole was stirred for 3.5 hours. The reaction solution was concentrated under reduced pressure and the residue was left standing at room temperature for 14 hours. After completion of the reaction, the resultant was diluted with chloroform and added with a saturated aqueous sodium hydrogen carbonate solution and the aqueous layer was extracted with chloroform. The organic layer was washed with a saturated saline solution and then dried with anhydrous sodium sulfate. After filtration, the resultant was concentrated and evaporated to dryness under reduced pressure. The residue was purified through silica gel column chromatography (chloroform/ethyl acetate) and treated with hydrochloric acid, thereby obtaining a hydrochloride (191 mg) of the subject compound as a pale-yellow solid.

MS(FAB,Pos.):m/z=728[M+H]$^+$
$^1$H-NMR(500 MHz,CDCl$_3$):δ=0.85(6H,t,J=7.3 Hz),1.24-1.60(8H,m),1.68(9H,d,J=1.2 Hz),2.32-2.39(6H,m),2.63(2H,t,J=7.0 Hz),3.30(2H,s), 3.45(2H,s),3.53(3H,s),3.63(2H,s),3.67(2H,s),3.76(2H,s),4.16(2H,d,J=7.0 Hz),5.08-5.12(2H,m),5.42-5.44(1H,m),6.86(1H,d,J=1.2 Hz),6.99(1H,d,J=1.2 Hz),7.07(1H,s),7.11(1H,s),7.30(2H,d,J=8.1 Hz),7.33(2H,d,J=8.1 Hz).

EXAMPLE 80

Production Example 80

Synthesis of 2-[(4-dipropylamino-butyl)-(4-[[(1H-imidazol-2-ylmethyl)-(1-methyl-1H-imidazol-2-ylmethyl)-amino]-methyl]-benzyl)-amino]-N,N-dimethyl-acetamide [Compound No. 99]

EXAMPLE 80-1

Synthesis of 2-[(4-dipropylamino-butyl)-(4-[[(1H-imidazol-2-ylmethyl)-(1-methyl-1H-imidazol-2-ylmethyl)-amino]-methyl]-benzyl)-amino]-N,N-dimethyl-acetamide [Compound No. 99]

The hydrochloride (190 mg) of the compound obtained in Example 65-1 was dissolved in DMF (5.0 ml) and added with N-(2-hydroxyethyl)-succinimide (57.8 mg) and the whole was refluxed under heating for 4 hours. After completion of the reaction, the solvent was distilled off. The resultant was dissolved in chloroform and added with a saturated aqueous sodium hydrogen carbonate solution and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (chloroform/methanol) and treated with hydrochloric acid, thereby obtaining a hydrochloride (82.5 mg) of the subject compound as a pale-yellow solid.

MS(FAB,Pos.):m/z=551[M+H]$^+$
$^1$H-NMR(500 MHz,DMSO-d$_6$+D$_2$O):δ=0.92(6H,t,J=7.3 Hz),1.64-1.68(8H, m),2.84(3H,s),2.90(3H,s),2.97-3.01(4H,m),3.06(4H,t,J=7.2 Hz), 3.72(3H,s),4.08(2H,s),4.16(2H,s), 4.15-4.39(4H,m),7.43(2H,d,J=8.2 Hz),7.47-7.49(4H,m), 7.60(2H,s).

EXAMPLE 81

Production Example 81

Synthesis of [(4-[[bis-(1-methyl-1H-imidazol-2-ylmethyl)-amino]-methyl]-benzyl)-(4-dipropylamino-butyl)-amino]-acetic acid [Compound No. 100]

EXAMPLE 81-1

Synthesis of [(4-[[bis-(1-methyl-1H-imidazol-2-ylmethyl)-amino]-methyl]-benzyl)-(4-dipropylamino-butyl)-amino]-acetic acid methyl ester The compound (1.78 g) obtained in Example 64-1 was dissolved in methanol (30 ml) and added with trimethyl orthoformate (1.8 ml), acetic acid (1.0 ml), and sodium cyanoborohydride (0.324 g). The mixture was gradually added with a methanol solution (5.0 ml) containing 1-methyl-2-imidazole carboxaldehyde (0.550 g) and the whole was stirred at room temperature for 1 hour. Further, sodium cyanoborohydride (0.486 g) and a methanol solution (6.0 ml) containing 1-methyl-2-imidazole carboxaldehyde (0.660 g) were added thereto and the whole was stirred at room temperature for 63 hours. After completion of the reaction, the solvent was distilled off under reduced pressure. The residue was dissolved in chloroform and washed with a saturated aqueous sodium hydrogen carbonate solution and then the whole was subjected to extraction with chloroform. The organic layer was a saturated saline solution and dried with anhydrous sodium sulfate. After filtration, the solvent was distilled off under reduced pressure. The residue was purified through silica gel column chromatography (chloroform/ethyl acetate), thereby obtaining the subject compound (1.18 g) as a colorless oily substance.

MS(FAB,Pos.):m/z=552[M+H]$^+$

EXAMPLE 81-2

Synthesis of [(4-[[bis-(1-methyl-1H-imidazol-2-ylmethyl)-amino]-methyl]-benzyl)-(4-dipropylamino-butyl)-amino]-acetic acid [Compound No. 100]

The compound (36.8 mg) obtained in Example 81-1 was dissolved in concentrated hydrochloric acid (1.0 ml) and the whole was stirred at 100° C. for 1 hour. After completion of the reaction, the solution was concentrated and dried under vacuum, thereby obtaining a hydrochloride (46.8 mg) of the subject compound as a white solid.

MS(FAB,Pos.):m/z=538[M+H]$^+$
$^1$H-NMR(500 MHz,DMSO-d$_6$):δ=0.90(6H,t,J=7.3 Hz), 1.65-1.73(6H,m),1.82(2H,br),2.93-2.98(4H,m),3.00-3.04 (2H,m),3.13(2H,br),3.76(6H,s),3.79(2H,s),3.84-4.35(6H, m),4.37(2H,s),7.44(2H,d,J=8.2 Hz), 7.49(2H,d,J=8.2 Hz), 7.53(2H,s),7.59(2H,s),10.83(1H,br).

EXAMPLE 82

Production Example 82

Synthesis of [(4-[[bis-(1-methyl-1H-imidazol-2-ylmethyl)-amino]-methyl]-benzyl)-(4-dipropylamino-butyl)-amino]-acetic acid ethyl ester [Compound No. 101]

EXAMPLE 82-1

Synthesis of [(4-[[bis-(1-methyl-1H-imidazol-2-ylmethyl)-amino]-methyl]-benzyl)-(4-dipropylamino-butyl)-amino]-acetic acid ethyl ester [Compound No. 101]

The compound (1.02 g) obtained in Example 81-2 was dissolved in ethanol (15 ml) and added with concentrated hydrochloric acid (1.0 ml) and Molecular Sieves 3A (3.2 g) and the whole was refluxed for 2 hours. After completion of the reaction, filtration was performed and the filtrate was concentrated. The residue was dissolved in chloroform and washed with a 1 mol/l sodium hydroxide aqueous solution, followed by extraction with chloroform. The organic layer was dried with anhydrous sodium sulfate. After filtration, the solvent was distilled off under reduced pressure. The residue was purified through silica gel column chromatography (chloroform/ethyl acetate), thereby obtaining the subject compound (121.8 mg) as a colorless oily substance. 50.5 mg of the colorless oily substance was treated to make a hydrochloride thereof, thereby obtaining a hydrochloride (61.9 mg) of the subject compound as a white solid.

MS(FAB,Pos.):m/z=566[M+H]$^+$
$^1$H-NMR(500 MHz,DMSO-d$_6$):δ=0.79(6H,t,J=7.3 Hz), 1.18(3H,t,J=7.1 Hz), 1.32(4H,sext.,J=7.3 Hz),1.28-1.41(4H, m),2.22-2.27(6H,m),3.24(2H,s),3.30(6H,s),3.31-3.40(2H, br),3.52(2H,s),3.56(4H,s),3.66(2H,s),4.06(2H,q,J=7.1 Hz), 6.78(2H,s),7.05(2H,s),7.18(2H,d, J=8.1 Hz),7.23(2H,d, J=8.1 Hz).

EXAMPLE 83

Production Example 83

Synthesis of [(4-dipropylamino-butyl)-([[(1H-imidazol-2-ylmethyl)-(1-methyl-1H-imidazol-2-ylmethyl)-amino]-methyl]-benzyl)-amino]-acetic acid-(R)-(−)-tetrahydrofuran-2-ylmethyl ester [Compound No. 102]

EXAMPLE 83-1

Synthesis of [(4-dipropylamino-butyl)-([[(1H-imidazol-2-ylmethyl)-(1-methyl-1H-imidazol-2-ylmethyl)-amino]-methyl]-benzyl)-amino]-acetic acid-(R)-(−)-tetrahydrofuran-2-ylmethyl ester [Compound No. 102]

The compound (145.0 mg) obtained in Example 65-1 was dissolved in chloroform (2.0 ml) and added with WSCI hydrochloride (74.5 mg), HOBt (53.0 mg), and N-methyl morpholine (142 μl) and the whole was stirred at room temperature for 30 minutes. The solution was added with (R)-(−)-tetrahydrofurufuryl alcohol (270 mg) and the whole was stirred at room temperature for 4 hours. After completion of the reaction, the solvent was distilled off under reduced pressure. The residue was purified through silica gel column chromatography (chloroform/ethyl acetate) and treated with hydrochloric acid, thereby obtaining a hydrochloride (62.5 mg) of the subject compound as a white solid.

MS(FAB,Pos.):m/z=608[M+H]$^+$ $^1$H-NMR(500 MHz,DMSO-d$_6$):δ=0.90(6H,t,J=7.3 Hz), 1.53-1.59(2H,m),1.64-1.73(6H,m),1.73-1.86(6H,m),1.92-1.95(1H,m),2.91-2.98(4H, m),2.98-3.04(2H,m),3.12(2H,br),3.29-3.36(2H,m),3.60(4H,s),4.12(2H,s),4.20(2H,s),4.36(2H,br),7.48(4H,br),7.53(2H,d,J=7.9 Hz), 7.63(2H,s).

EXAMPLE 84

Production Example 84

Synthesis of ([4-[(4-[[(1H-imidazol-2-ylmethyl)-(1-methyl-1H-imidazol-2-ylmethyl)-amino]-methyl]-benzyl)-methyl-amino]-butyl]-propyl-amino)-acetic acid [Compound No. 103]

EXAMPLE 84-1

Synthesis of (4-propylamino-butyl)-carbamic acid t-butyl ester

In methanol (6.0 ml), (4-amino-butyl)-carbamic acid t-butyl ester (400.0 mg) was dissolved. After acetic acid (0.12 ml) and sodium cyanoborohydride (172.5 mg) were added to the solution, propionaldehyde (0.155 ml) was dropped thereto and the whole was stirred at room temperature for 2 hours. After completion of the reaction, the solvent was distilled off and the residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (hexane/ethyl acetate), thereby obtaining the subject compound (339.6 mg) as a colorless oily substance.

MS(FAB,Pos.):m/z=231[M+H]$^+$

EXAMPLE 84-2

Synthesis of [(4-t-butoxycarbonylamino-butyl)-propyl-amino]-acetic acid ethyl ester The compound (339.0 mg) obtained in Example 84-1 was dissolved in chloroform (5.1 ml) and added with triethylamine (0.41 ml). Ethyl bromoacetate (0.20 ml) was dropped to the solution and the whole was stirred at room temperature for 2 days. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (hexane/ethyl acetate), thereby obtaining the subject compound (273.9 mg) as a colorless oily substance.

MS(FAB,Pos.):m/z=317[M+H]$^+$

EXAMPLE 84-3

Synthesis of 4-[[(1H-imidazol-2-ylmethyl)-(1-methyl-1H-imidazol-2-ylmethyl)-amino]-methyl]-benzoic acid methyl ester Commercially available methyl 4-aminomethyl-benzoate hydrochloride was subjected to desalting, thereby obtaining a free compound. The resultant free compound (1.04 g) was dissolved in methanol (15.0 ml) and added with 2-imidazole carboxaldehyde (0.529 g), and the whole was stirred at room temperature for 14 hours. After having been cooled to 0° C., the solution was added with sodium borohydride (0.249 g) and the whole was stirred at 0° C. for 30 minutes and then at room temperature for 30 minutes. After completion of the reaction, the solvent was distilled off. The residue was dissolved in chloroform and washed with a 1 mol/l sodium hydroxide aqueous solution, followed by extraction with chloroform. The extract was washed with a saturated saline solution and dried with anhydrous sodium sulfate. After filtration, the solvent was distilled off, thereby obtaining a crude product (1.47 g) of 4-[[(1H-imidazol-2-ylmethyl)-amino]-methyl]-benzoic acid methyl ester. The resultant crude product (1.47 g) was dissolved in methanol (15.0 ml) and added with 1-methyl-2-imidazole carboxaldehyde (0.844 g) and the whole was stirred at room temperature for 1 hour. After having been cooled to 0° C., the solution was added with sodium triacetoxyborohydride (2.18 g) and then the whole was stirred at room temperature for 22 hours. After completion of the reaction, the solvent was distilled off. The residue was dissolved in chloroform and washed with a 1 mol/l sodium hydroxide aqueous solution. After extraction with chloroform, the organic layer was washed with a saturated saline solution and dried with anhydrous sodium sulfate. After filtration, the solvent was distilled off. The residue was purified through silica gel column chromatography (chloroform/ethyl acetate), thereby obtaining the subject compound (1.44 g) as white foam.

MS(FAB,Pos.):m/z=340[M+H]$^+$
$^1$H-NMR(500 MHz,CDCl$_3$):δ=3.46(2H,s),3.57(3H,s), 3.61(2H,s),3.74(2H,s),3.92(3H,s),6.89(1H,s),7.01(1H,s), 7.08-7.13(2H,br),7.50(2H,d,J=8.5 Hz),8.02(2H,d,J=8.5 Hz).

EXAMPLE 84-4

Synthesis of 4-[[(1H-imidazol-2-ylmethyl)-(1-methyl-1H-imidazol-2-ylmethyl)-amino]-methyl]-phenyl)-methanol The compound (1.43 g) obtained in Example 84-3 was dissolved in THF (32.0 ml) and the whole was cooled to −20° C. The solution was gradually added with a 65% sodium bis(2-methoxyethoxy)aluminum hydride/toluene solution (2.0 ml) and the whole was stirred for 2 days. After completion of the reaction, the solution was added with methanol (2.0 ml) and a 10% aqueous sodium potassium tartrate solution and the whole was stirred for a while. After THF was distilled off under reduced pressure, the solution was subjected to extraction with chloroform, washed with a saturated saline solution, and dried with anhydrous sodium sulfate. After filtration, the solvent was distilled off. The residue was purified through silica gel column chromatography (chloroform/methanol), thereby obtaining the subject compound (1.10 g) as pale-yellow foam.
MS(FAB,Pos.):m/z=312[M+H]$^+$
$^1$H-NMR(500 MHz,CDCl$_3$):δ=3.50(4H,s),3.52(3H,s), 3.56(2H,s),4.48(2H,d,J=4.9 Hz),5.18(1H,t,J=5.5 Hz),6.81 (1H,s),6.87(1H,s),7.10(2H,d,J=10.0 Hz),7.27(2H,d,J=8.1 Hz),7.33(2H,d,J=8.1 Hz).

EXAMPLE 84-5

Synthesis of (4-[[(1H-imidazol-2-ylmethyl)-(1-methyl-1H-imidazol-2-ylmethyl)-amino]-methyl]-benzaldehyde The compound (1.10 g) obtained in Example 84-4 was dissolved in dichloromethane (20.0 ml) and added with manganese dioxide (chemically processed product) (3.07 g) and the whole was stirred at room temperature for 16 hours. After completion of the reaction, the filtration through Celite was performed and the filtrate was concentrated. The residue was purified through silica gel column chromatography (chloroform/methanol), thereby obtaining the subject compound (0.79 g) as a pale-yellow oily substance.
MS(FAB,Pos.):m/z=310[M+H]$^+$
$^1$H-NMR(500 MHz,CDCl$_3$):δ=3.50(2H,s),3.60(5H,s), 3.76(2H,s),6.90(1H,s),7.02(1H,s),7.04-7.15(2H,br),7.61 (2H,d,J=8.1 Hz),7.87(2H, d,J=8.1 Hz),10.01(1H,s).

EXAMPLE 84-6

Synthesis of [[4-(4-[[(1H-imidazol-2-ylmethyl)-(1-methyl-1H-imidazol-2-ylmethyl)-amino]-methyl]-benzylamino)-butyl]-propyl-amino]-acetic acid ethyl ester The compound (273.0 mg) obtained in Example 84-2 was dissolved in ethanol (2.7 ml) and added with a 4 mol/l hydrogen chloride/dioxane solution (2.7 ml) and the whole was stirred at room temperature for 1 hour. Further, the solution was added with a 4 mol/l hydrogen chloride/dioxane solution (1.0 ml) and the whole was stirred at room temperature for 30 minutes. After completion of the reaction, the solvent was distilled off, thereby obtaining a crude product (350.0 mg) of [(4-amino-butyl)-propyl-amino]-acetic acid ethyl ester as a colorless oily substance. The resultant crude product (350.0 mg) was dissolved in ethanol (4.5 ml) and added with an ethanol solution (2.6 ml) containing the compound (258 mg) obtained in Example 84-5, acetic acid (0.10 ml), and sodium triacetoxyborohydride (267.0 mg) and the whole was stirred at room temperature for 2 hours. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (chloroform/methanol), thereby obtaining the subject compound (238.0 mg) as a pale-yellow oily substance.
MS(FAB,Pos.):m/z=510[M+H]$^+$

EXAMPLE 84-7

Synthesis of ([4-[4-[[(1H-imidazol-2-ylmethyl)-(1-methyl-1H-imidazol-2-ylmethyl)-amino]-methyl]-benzyl)-methyl-amino]-butyl]-propyl-amino)-acetic acid ethyl ester The compound (169.0 mg) obtained in Example 84-6 was dissolved in ethanol (5.1 ml) and added with a 36% formaldehyde aqueous solution (0.08 ml) and formic acid (0.08 ml) and the whole was refluxed for 1 hour. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (chloroform/methanol), thereby obtaining the subject compound (71.0 mg) as a colorless oily substance.
MS(FAB,Pos.):m/z=524[M+H]$^+$

EXAMPLE 84-8

Synthesis of ([4-[(4-[[(1H-imidazol-2-ylmethyl)-(1-methyl-1H-imidazol-2-ylmethyl)-amino]-methyl]-benzyl)-methyl-amino]-butyl]-propyl-amino)-acetic acid [Compound No. 103]

The compound (71.0 mg) obtained in Example 84-7 was dissolved in concentrated hydrochloric acid and the whole was refluxed for 2 hours. After completion of the reaction, the solvent was distilled off and the residue was dried under vacuum, thereby obtaining a hydrochloride (87.9 mg) of the subject compound as a white solid.
MS(FAB,Pos.):m/z=496[M+H]$^+$
$^1$H-NMR(500 MHz,DMSO-d$_6$+H$_2$O):δ=0.91(3H,t,J=7.3 Hz),1.63-1.83(6H, m),2.58(3H,s),2.81-3.14(4H,m),3.18(2H, t,J=7.8 Hz),3.66-3.89(2H,m),3.72(3H,s),4.10(2H,s),4.12 (3H,s),4.18(2H,s),4.29-4.37(1H,m),7.40(2H,d,J=8.3 Hz), 7.43-7.49(4H,m),7.59(2H,s).

EXAMPLE 85

Production Example 85

Synthesis of ([4-[carboxymethyl-(4-[[(1H-imidazol-2-ylmethyl)-(1-methyl-1H-imidazol-2-ylmethyl)-amino]-methyl]-benzyl)-amino]-butyl]-propyl-amino)-acetic acid [Compound No. 104]

EXAMPLE 85-1

Synthesis of ([4-[ethoxycarbonylmethyl-(4-[[1H-imidazol-2-ylmethyl]-(1-methyl-1H-imidazol-2-ylmethyl)-amino]-methyl]-benzyl]-amino]-butyl]-propyl-amino)-acetic acid ethyl ester The compound (169.0 mg) obtained in Example 84-6 was dissolved in chloroform (2.5 ml) and added with triethylamine (0.055 ml). Then, ethyl bromoacetate (0.045 ml) was dropped to the solution and the whole was stirred at room temperature for 16 hours. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (chloroform/ethyl acetate), thereby obtaining the subject compound (31.5 mg) as a colorless oily substance.

MS(FAB,Pos.):m/z=596[M+H]$^+$

EXAMPLE 85-2

Synthesis of ([4-[carboxymethyl-(4-[[(1H-imidazol-2-ylmethyl)-(1-methyl-1H-imidazol-2-ylmethyl)-amino]-methyl]-benzyl)-amino]-butyl]-propyl-amino)-acetic acid [Compound No. 104]

The compound (10.1 mg) obtained in Example 85-1 was dissolved in concentrated hydrochloric acid and the whole was refluxed for 1 hour. After completion of the reaction, the solvent was distilled off and the residue was dried under vacuum, thereby obtaining a hydrochloride (13.8 mg) of the subject compound as a white solid.

MS(FAB,Pos.):m/z=540[M+H]$^+$
$^1$H-NMR(500 MHz,DMSO-d$_6$+D$_2$O):δ=0.90(3H,t,J=7.3 Hz),1.63-1.80(6H, m),3.06-3.20(6H,m),3.71(3H,s),3.95(2H, s),4.09(2H,s),4.13(2H, s),4.17(2H,s),4.35(2H,s),7.43-7.49 (6H,m),7.59(2H,s).

EXAMPLE 86

Production Example 86

Synthesis of (2-[[(1-carboxymethyl-1H-imidazol-2-ylmethyl)-(4-[[(4-dipropylamino-butyl)-methyl-amino]-methyl]-benzyl)-amino]-methyl]-imidazol-1-yl)-acetic acid [Compound No. 105]

EXAMPLE 86-1

Synthesis of (2-[[(4-[[(4-dipropylamino-butyl)-methyl-amino]-methyl]-benzyl)-(1-ethoxycarbonylmethyl-1H-imidazol-2-ylmethyl)-amino]-methyl]-imidazol-1-yl)-acetic acid ethyl ester In THF (10 ml), N-(4-[[bis-(1H-imidazol-2-ylmethyl)-amino]-methyl]-benzyl)-N-methyl-N',N'-dipropyl-butane-1,4-diamine (533 mg) obtained by a known technique was dissolved. The solution was added with sodium t-butoxide (290 mg) under a nitrogen atmosphere under ice-cooling and the whole was warmed back to room temperature and then stirred for 1.5 hours. Under ice-cooling, the solution was gradually added with ethyl bromoacetate (280 μl) and the whole was stirred at 1.5 hours while being cooled with ice. After completion of the reaction, the solution was neutralized by addition of acetic acid (30 μl) under ice-cooling. The solvent was distilled off under reduced pressure and the residue was diluted with chloroform and added with a saturated aqueous sodium hydrogen carbonate solution to make the pH of the aqueous layer to 8. The aqueous layer was subjected to extraction with chloroform. The combined organic layer was washed with a saturated saline solution and dried with anhydrous sodium sulfate. After filtration, the filtrate was concentrated and evaporated to dryness under reduced pressure and the residue was purified through silica gel column chromatography (chloroform/ethanol), thereby obtaining the subject compound (280 mg) as a yellow oily substance.

MS(FAB,Pos.):m/z=638[M+H]$^+$
$^1$H-NMR(500 MHz,CDCl$_3$):δ=0.86(6H,t,J=7.3 Hz),1.23 (3H,t,J=7.1 Hz), 1.41-1.47(8H,m),2.14(3H,s),2.14-2.41(8H, m),3.44(2H,s),3.61(2H,s),3.64(2H,s),3.66(2H,s),4.10(2H,q, J=7.1 Hz),4.51(4H,s),6.84(2H,d,J=1.2 Hz),6.97(2H,d,J=1.5 Hz),7.16(2H,d,J=8.3 Hz),7.24(2H,d,J=8.3 Hz).

EXAMPLE 86-2

Synthesis of (2-[[(1-carboxymethyl-1H-imidazol-2-ylmethyl)-(4-[[(4-dipropylamino-butyl)-methyl-amino]-methyl]-benzyl)-amino]-methyl]-imidazol-1-yl)-acetic acid [Compound No. 105]

The compound (34.1 mg) obtained in Example 86-1 was dissolved in dioxane (1.0 ml) and added with concentrated hydrochloric acid (500 μl) at room temperature and the whole was stirred at an outside temperature of 100° C. for 4 hours. After completion of the reaction, the resultant was concentrated and evaporated to dryness under reduced pressure, thereby obtaining a hydrochloride (43.4 mg) of the subject compound as a white solid.

MS(FAB,Pos.):m/z=583[M+H]$^+$
$^1$H-NMR(500 MHz,DMSO-d$_6$):δ=0.90(6H,t,J=7.3 Hz), 1.63-1.91(8H,m),2.57(3H,s),3.16-3.50(8H,m),3.63-3.90 (8H,m),5.10(4H,brs),7.44(2H,d,J=8.1 Hz),7.49(2H,d,J=8.1 Hz),10.49(2H,brs).

EXAMPLE 87

Production Example 87

Synthesis of (2-[[(4-[[(4-dipropylamino-butyl)-methyl-amino]-methyl]-benzyl)-(1-methyl-1H-imidazol-2-ylmethyl)-amino]-methyl]-imidazol-1-yl)-acetic acid [Compound No. 106]

EXAMPLE 87-1

Synthesis of (2-[[(4-[[(4-dipropylamino-butyl)-methyl-amino]-methyl]-benzyl)-(1-methyl-1H-imidazol-2-ylmethyl)-amino]-methyl]-imidazol-1-yl)-acetic acid ethyl ester In THF (10 ml), N-(4-[[(1H-imidazol-2-ylmethyl)-(1-methyl-1H-imidazol-2-ylmethyl)-amino]-methyl]-benzyl)-N-methyl-N',N'-dipropyl-butane-1,4-diamine (835 mg)

obtained by a known technique was dissolved. The solution was added with sodium t-butoxide (200 mg) under a nitrogen atmosphere under ice-cooling and the whole was warmed back to room temperature and then stirred for 1.5 hours. Under ice-cooling, the solution was gradually added with ethyl bromoacetate (230 µl) and the whole was stirred at 1.5 hours while being cooled with ice. After completion of the reaction, the solution was neutralized by addition of acetic acid (30 µl) under ice-cooling. The solvent was distilled off under reduced pressure and the residue was diluted with chloroform and added with a saturated aqueous sodium hydrogen carbonate solution to make the pH of the aqueous layer to 8. The aqueous layer was subjected to extraction with chloroform. The combined organic layer was washed with a saturated saline solution and dried with anhydrous sodium sulfate. After filtration, the resultant was concentrated and evaporated to dryness under reduced pressure and the residue was purified through silica gel column chromatography (chloroform/ethanol), thereby obtaining the subject compound (522 mg) as a yellow oily substance.

MS(FAB,Pos.):m/z=566[M+H]$^+$ $^1$H-NMR(500 MHz,CDCl$_3$):δ=0.86(6H,t,J=7.6 Hz),1.23 (3H,t,J=8.1 Hz), 1.41-1.51(8H,m),2.14(3H,s),2.33-2.41(8H,m),3.28(3H,s),3.44(2H,s),3.61(2H,s),3.62(2H,s),3.71(2H,s), 4.11(2H,q,J=7.1 Hz),4.56(2H,s),6.78(1H,d,J=1.2 Hz),6.85 (1H,d,J=1.5 Hz),6.92(1H,d,J=1.5 Hz),6.97(1H,d,J=1.5 Hz), 7.16(2H,d,J=8.1 Hz),7.23(2H,d,J=8.1 Hz).

EXAMPLE 87-2

Synthesis of (2-[[(4-[[(4-dipropylamino-butyl)-methyl-amino]-methyl]-benzyl)-(1-methyl-1H-imidazol-2-ylmethyl)-amino]-methyl]-imidazol-1-yl)-acetic acid [Compound No. 106]

The compound (41.6 mg) obtained in Example 87-1 was dissolved in dioxane (0.80 ml) and added with concentrated hydrochloric acid (800 µl) at room temperature and the whole was stirred at an outside temperature of 100° C. for 5 hours. After completion of the reaction, the resultant was concentrated and evaporated to dryness under reduced pressure, thereby obtaining a hydrochloride (78.7 mg) of the subject compound as a white solid.

MS(FAB,Pos.):m/z=538[M+H]$^+$ $^1$H-NMR(500 MHz,DMSO-d$_6$):δ=0.90(6H,t,J=7.3 Hz), 1.64-1.91(8H,m),2.52(3H,s),3.44-3.54(8H,m),3.66-3.91 (9H,m),4.11(2H,s),5.12(2H, s),7.41(2H,d,J=7.6 Hz),7.49 (2H,d,J=8.0 Hz),7.51(1H,s),7.53(1H, s),7.62(1H,s),7.63(1H, s),10.37(1H,brs),11.05(1H,brs).

EXAMPLE 88

Production Example 88

Synthesis of 4-[[(4-dipropylamino-butyl)-methyl-amino]-methyl]-N-(1H-imidazol-2-ylmethyl)-N-(1-methyl-1H-imidazol-2-ylmethyl)-benzamide [Compound No. 107]

EXAMPLE 88-1

Synthesis of 4-[(4-dipropylamino-butylamino)-methyl]-benzoic acid methyl ester

Commercially available methyl 4-aminomethyl-benzoate (153 mg) was dissolved in methanol (4.0 ml) and added with the compound (209 mg) obtained in Example 17-5 and trimethyl orthoformate (200 µl) and the whole was stirred at room temperature for 2 hours. After having been cooled to 0° C., the solution was added with sodium borohydride (100 mg) and the whole was stirred at 0° C. for 1 hour. After completion of the reaction, the solvent was distilled off under reduced pressure. The residue was dissolved in chloroform and washed with water, followed by extraction with chloroform. The organic layer was washed with a saturated saline solution and dried with anhydrous sodium sulfate. After filtration, the solvent was distilled off under reduced pressure. The residue was purified through silica gel column chromatography (chloroform/ethyl acetate), thereby obtaining the subject compound (310 mg) as a colorless oily substance.

MS(FAB,Pos.):m/z=321[M+H]$^+$

EXAMPLE 88-2

Synthesis of 4-[[(4-dipropylamino-butyl)-methyl-amino]-methyl]-benzoic acid methyl ester The compound (310 mg) obtained in Example 88-1 was dissolved in ethanol (4.5 ml) and added with a 36% formaldehyde aqueous solution (150 µl) and formic acid (175 µl) and the whole was refluxed for 2 hours. After completion of the reaction, the solvent was distilled off under reduced pressure. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off under reduced pressure. The residue was purified through silica gel column chromatography (hexane/ethyl acetate), thereby obtaining the subject compound (234 mg) as a colorless oily substance.

MS(FAB,Pos.):m/z=335[M+H]$^+$

EXAMPLE 88-3

Synthesis of 4-[[(4-dipropylamino-butyl)-methyl-amino]-methyl]-benzoic acid

The compound (234 mg) obtained in Example 88-2 was dissolved in methanol (2.5 ml) and added with 1 mol/l sodium hydroxide aqueous solution (2.5 ml) and the whole was stirred at room temperature for 16 hours. After completion of the reaction, the solution was neutralized with a 1 mol/l hydrochloric acid and the solvent was distilled off under reduced pressure. The residue was suspended in ethanol and then a white precipitate was filtrated out. The organic layer was distilled off under reduced pressure and the residue was dried under vacuum, thereby obtaining the subject compound (204 mg) as a pale-yellow oily substance.

MS(FAB,Pos.):m/z=321[M+H]$^+$

EXAMPLE 88-4

Synthesis of (1H-imidazol-2-ylmethyl)-(1-methyl-1H-imidazol-2-ylmethyl)-amine

The compound (201 mg) obtained in Example 14-7 was dissolved in methanol (4.0 ml) and added with trimethyl orthoformate (200 µl) and 2-imidazole carboxaldehyde (115 mg) and the whole was stirred at room temperature for 30 minutes. After having been cooled to 0° C., the solution was added with sodium borohydride (89.6 mg) and then the whole was stirred at room temperature for 1 hour. After completion of the reaction, the solvent was distilled off under reduced pressure. The residue was dissolved in chloroform and washed with water, followed by extraction with chloroform. The organic layer was washed with a saturated saline solution and dried with anhydrous sodium sulfate. After filtration, the solvent was distilled off under reduced pressure. The residue was purified through silica gel column chromatography (chloroform/methanol), thereby obtaining the subject compound (137 mg) as a pale-yellow oily substance.

MS(FAB,Pos.):m/z=192[M+H]$^+$

EXAMPLE 88-5

Synthesis of 4-[[(4-dipropylamino-butyl)-methyl-amino]-methyl]-N-(1H-imidazol-2-ylmethyl)-N-(1-methyl-1H-imidazol-2-ylmethyl)-benzamide [Compound No. 107]

The compound (204 mg) obtained in Example 88-3, WSCI hydrochloride (184 mg), and HOBt (129 mg) were dissolved in chloroform (4.0 ml), and the whole was stirred at room temperature for 30 minutes. Then, the solution was dropped into a chloroform solution (2.0 ml) containing the compound (137 mg) obtained in Example 88-4 and the whole was stirred at room temperature for 15 hours. After completion of the reaction, the solvent was distilled off under reduced pressure. Then, the residue was dissolved in chloroform and washed with a saturated saline solution, followed by extraction with chloroform. The organic layer was washed with a saturated saline solution and dried with anhydrous sodium sulfate. After filtration, the solvent was distilled off under reduced pressure. The residue was purified through silica gel column chromatography (hexane/ethyl acetate), thereby obtaining the subject compound (31.5 mg) as a pale-yellow oily substance. The pale-yellow oily substance was treated with hydrochloric acid, thereby obtaining a hydrochloride (43.5 mg) of the subject compound as a pale-yellow solid.

MS(FAB,Pos.):m/z=494[M+H]$^+$ $^1$H-NMR(500 MHz,DMSO-d$_6$):δ=0.90(6H,t,J=7.3 Hz), 1.60-1.84(8H,m),2.62(3H,s),2.88-3.12(8H,m),3.28-3.60 (3H,m),3.84-3.96(2H,m),4.20-4.28(1H,m),4.32-4.40(1H, m),4.92-5.16(2H,m),7.56-7.72(8H,m).

EXAMPLE 89

Production Example 89

Synthesis of 2-[(4-dipropylamino-butyl)-(4-[[(1H-imidazol-2-ylmethyl)-(1-methyl-1H-imidazol-2-ylmethyl)-amino]-methyl]-benzyl)-amino]-malonic acid diethyl ester [Compound No. 108]

EXAMPLE 89-1

Synthesis of 2-[[4-(t-butoxycarbonylamino-methyl)-benzyl]-(4-dipropylamino-butyl)-amino]-malonic acid diethyl ester The compound (520 mg) obtained in Example 23-4 was dissolved in anhydrous DMF (10 ml) and added with diisopropylethylamine (463 μl) and diethyl bromomalonate (340 μl) and the whole was stirred at room temperature for 2 hours. After completion of the reaction, a saturated aqueous sodium hydrogen carbonate solution was added thereto and the whole was stirred for a while. The solution was subjected to extraction with chloroform and washed with a saturated saline solution. The organic layer was dried with anhydrous sodium sulfate. The solvent was distilled off. The residue was purified through silica gel column chromatography (hexane/ethyl acetate), thereby obtaining the subject compound (421 mg) as a colorless oily substance.

MS(FAB,Pos.):m/z=550[M+H]$^+$ $^1$H-NMR(500 MHz,CDCl$_3$):δ=0.85(6H,t,J=7.3 Hz),1.29 (6H,t,J=7.1 Hz), 1.37-1.44(8H,m),1.46(9H,s),2.30-2.35(6H, m),2.68(2H,t,J=6.8 Hz), 3.84(2H,s),4.21(1H,s),4.23(4H,q, J=7.1 Hz),4.30(2H,d,J=5.8 Hz), 4.81(1H,br),7.21(2H,d, J=8.1 Hz),7.35(2H,d,J=8.1 Hz).

EXAMPLE 89-2

Synthesis of 2-[(4-aminomethyl-benzyl)-(4-dipropylamino-butyl)-amino]-malonic acid diethyl ester The compound (421 mg) obtained in Example 89-1 was dissolved in anhydrous ethanol (4.0 ml) and added with a 4 mol/l hydrogen chloride/dioxane solution (4.00 ml) and the whole was stirred at room temperature for 3 hours. After completion of the reaction, the solvent was distilled off. The resultant was added with a 1 mol/l sodium hydroxide aqueous solution and the whole was subjected to extraction with chloroform and washed with a saturated saline solution. The organic layer was dried with anhydrous sodium sulfate. The solvent was distilled off, thereby obtaining the subject compound (338 mg) as a pale-yellow oily substance.

MS(FAB,Pos.):m/z=450[M+H]$^+$

EXAMPLE 89-3

Synthesis of 2-[(4-dipropylamino-butyl)-(4-[[(1H-imidazol-2-ylmethyl)-(1-methyl-1H-imidazol-2-ylmethyl)-amino]-methyl]-benzyl)-amino]-malonic acid diethyl ester [Compound No. 108]

The compound (338 mg) obtained in Example 89-2 was dissolved in anhydrous ethanol (6 ml) and added with triethyl orthoformate (375 μl) and 2-imidazole carboxaldehyde (86.7 mg) and the whole was stirred overnight at room temperature under a nitrogen atmosphere. Subsequently, sodium borohydride (56.9 mg) was added thereto in an ice bath and the whole was stirred at room temperature for 2 hours. After completion of the reaction, distilled water was added thereto and the whole was stirred for a while. The solution was subjected to extraction with chloroform and washed with a saturated saline solution. The organic layer was dried with anhydrous sodium sulfate. The residue (463 mg) was dissolved in anhydrous ethanol (10 ml) and added with sodium triacetoxyborohydride (556 mg) and 1-methyl-2-imidazole carboxaldehyde (116 mg) and the whole was stirred at room temperature for 3 days under a nitrogen atmosphere. After completion of the reaction, the solvent was distilled off and the resultant was dissolved in chloroform and added with a saturated aqueous sodium hydrogen carbonate solution. The whole was stirred for a while. The solution was subjected to extraction with chloroform and washed with a saturated saline solution. The organic layer was dried with anhydrous sodium sulfate. The solvent was distilled off and the residue was purified through silica gel column chromatography (chloroform/ethyl acetate) and treated with hydrochloric acid, thereby obtaining a hydrochloride (262 mg) of the subject compound as a white solid.

MS(FAB,Pos.):m/z=624[M+H]$^+$ $^1$H-NMR(500 MHz,DMSO-d$_6$+D$_2$O):δ=0.90(6H,t,J=7.3 Hz),1.21(6H,t,J=7.2 Hz),1.43-1.46(2H,m),1.55-1.66(6H,m), 2.63(2H,t,J=6.9 Hz),2.92-2.98.(6H,m),3.69(2H,s),3.70(3H, s),3.72(2H,s),4.10(2H,s),4.15-4.21(7H,m),7.23(2H,d,J=8.1 Hz),7.31(2H,d,J=8.2 Hz),7.46(1H,d,J=2.0 Hz),7.47(1H,d,J=2.0 Hz),7.58(2H,s).

EXAMPLE 90

Production Example 90

Synthesis of (2-{2-[(4-{[(1H-imidazol-2-ylmethyl)-(1-methyl-1H-imidazol-2-ylmethyl)-amino]-methyl}-benzyl)-methyl-amino]-ethoxy}-ethyl)-dipropyl-amine [Compound No. 109]

EXAMPLE 90-1

Synthesis of [2-(2-amino-ethoxy)-ethyl]-carbamic acid t-butyl ester

In anhydrous DMF (90 ml), 2,2'-oxybisethylamine (459 mg) was dissolved. The solution was added with triethylamine (1.16 ml) and di-t-butoxy dicarbonate (339 mg) and the whole was stirred overnight at room temperature. After completion of the reaction, the solvent was distilled off. The resultant was dissolved in chloroform and added with distilled water and the whole was stirred for a while. The solution was subjected to extraction with chloroform and washed with a saturated saline solution. The organic layer was dried with anhydrous sodium sulfate. The solvent was distilled off, thereby obtaining the subject compound (450 mg) as a colorless oily substance.
MS(FAB,Pos.):m/z=205[M+H]$^+$

EXAMPLE 90-2

Synthesis of [2-(2-dipropylamino-ethoxy)-ethyl]-carbamic acid t-butyl ester

The compound (279 mg) obtained in Example 90-1 was dissolved in anhydrous methanol (5.5 ml) and added with trimethyl orthoformate (374 µl) and sodium cyanoborohydride (257 mg). The solution was added with propionaldehyde (246 µl) in an ice bath and the whole was stirred overnight at room temperature. After completion of the reaction, the solvent was distilled off. The resultant was dissolved in chloroform and added with distilled water and the whole was stirred for a while. The resultant was subjected to extraction with chloroform and washed with a saturated saline solution. The organic layer was dried with anhydrous sodium sulfate. The solvent was distilled off and the residue was purified through silica gel column chromatography (hexane/ethyl acetate), thereby obtaining the subject compound (130 mg) as a colorless oily substance.
MS(FAB,Pos.):m/z=289[M+H]$^+$

EXAMPLE 90-3

Synthesis of [2-(2-amino-ethoxy)-ethyl]-dipropyl-amine

The compound (128 mg) obtained in Example 90-2 was dissolved in anhydrous methanol (2.0 ml) and added with a 4 mol/l hydrogen chloride/dioxane solution (2.00 ml) and the whole was stirred at room temperature for 2 hours. After completion of the reaction, the solvent was distilled off. The resultant was added with a 1 mol/l sodium hydroxide aqueous solution and the whole was subjected to extraction with chloroform and washed with a saturated saline solution. The organic layer was dried with anhydrous sodium sulfate. The solvent was distilled off, thereby obtaining the subject compound (81.0 mg) as a colorless oily substance.
MS(FAB,Pos.):m/z=189[M+H]$^+$

EXAMPLE 90-4

Synthesis of (4-{[2-(2-dipropylamino-ethoxy)-ethylamino]-methyl}-benzyl)-carbamic acid t-butyl ester The compound (81.0 mg) obtained in Example 90-3 was dissolved in anhydrous methanol (2.0 ml) and added with trimethyl orthoformate (94.1 µl) and the compound (101 mg) obtained in Example 23-3 and the whole was stirred overnight at room temperature under a nitrogen atmosphere. Subsequently, sodium borohydride (32.6 mg) was added thereto in an ice bath and the whole was stirred at room temperature for 1 hour. After completion of the reaction, the solvent was distilled off. The resultant was dissolved in chloroform and added with distilled water and the whole was stirred for a while. The resultant was subjected to extraction with chloroform and washed with a saturated saline solution. The organic layer was dried with anhydrous sodium sulfate. The solvent was distilled off, thereby obtaining the subject compound (158 mg) as a colorless oily substance.
MS(FAB,Pos.):m/z=408[M+H]$^+$

EXAMPLE 90-5

Synthesis of (4-{[(4-dipropylaminomethyl-benzyl)-methyl-amino]-methyl}-benzyl)-carbamic acid t-butyl ester The compound (67.2 mg) obtained in Example 90-4 was dissolved in methanol (1.5 ml) and added with sodium cyanoborohydride (31.1 mg), acetic acid (150 µl), and a 36% formaldehyde aqueous solution (18.6 µl). The whole was stirred overnight at room temperature under a nitrogen atmosphere. After completion of the reaction, the solvent was distilled off. The resultant was dissolved in chloroform and added with a saturated aqueous sodium hydrogen carbonate solution, followed by stirring for a while. The resultant was subjected to extraction with chloroform and washed with a saturated saline solution. The organic layer was dried with anhydrous sodium sulfate. The solvent was distilled off and the residue was purified through silica gel column chromatography (hexane/ethyl acetate), thereby obtaining the subject compound (102 mg) as a colorless oily substance.
MS(FAB,Pos.):m/z=422[M+H]$^+$
$^1$H-NMR(500 MHz,CDCl$_3$):δ=0.86(6H,t,J=7.3 Hz),1.41-1.49(4H,m),1.46(9H,s),2.25(3H,s),2.41(4H,t,J=7.3 Hz),2.59 (2H,t,J=6.1 Hz),2.64(2H,t,J=6.3 Hz),3.49(2H,t,J=6.3 Hz), 3.53(3H,s),3.57(2H,t,J=6.1 Hz),4.30(2H,d,J=6.6 Hz), 7.22 (2H,d,J=8.3 Hz),7.28(2H,d,J=8.1 Hz).

EXAMPLE 90-6

Synthesis of (2-{2-[(4-aminomethyl-benzyl)-methyl-amino]-ethoxy}-ethyl)-dipropyl-amine The compound (102 mg) obtained in Example 90-5 was dissolved in anhydrous methanol (1.0 ml) and added with a 4 mol/l hydrogen chloride/dioxane solution (1.00 ml) and the whole was stirred at room temperature for 2 hours. After completion of the reaction, the solvent was distilled off. The resultant was added with a 1 mol/l sodium hydroxide aqueous solution and the whole was subjected to extraction with chloroform and washed with a saturated saline solution. The organic layer was dried with anhydrous sodium sulfate. The solvent was distilled off, thereby obtaining the subject compound (78.5 mg) as a colorless oily substance.

MS(FAB,Pos.):m/z=322[M+H]$^+$

EXAMPLE 90-7

Synthesis of (2-{2-[(4-{[(1H-imidazol-2-ylmethyl)-(1-methyl-1H-imidazol-2-ylmethyl)-amino]-methyl}-benzyl)-methyl-amino]-ethoxy}-ethyl)-dipropyl-amine [Compound No. 109]

The compound (78.5 mg) obtained in Example 90-6 was dissolved in anhydrous methanol (1.6 ml) and added with trimethyl orthoformate (40.1 µl) and 2-imidazole carboxaldehyde (25.8 mg) and the whole was stirred overnight at room temperature under a nitrogen atmosphere. Subsequently, sodium borohydride (18.5 mg) was added thereto in an ice bath and the whole was stirred at room temperature for 1 hour. After completion of the reaction, the solvent was distilled off and the resultant was dissolved in chloroform and added with distilled water. The whole was stirred for a while. The solution was subjected to extraction with chloroform and washed with a saturated saline solution. The organic layer was dried with anhydrous sodium sulfate. The residue (97.0 mg) was dissolved in ethanol (2.0 ml) and added with sodium triacetoxyborohydride (154 mg) and 1-methyl-2-imidazole carboxaldehyde (29.3 mg) and the whole was stirred overnight at room temperature under a nitrogen atmosphere. After completion of the reaction, the solvent was distilled off and the resultant was dissolved in chloroform and added with a saturated aqueous sodium hydrogen carbonate solution. The whole was stirred for a while. The solution was subjected to extraction with chloroform and washed with a saturated saline solution. The organic layer was dried with anhydrous sodium sulfate. The solvent was distilled off and the residue was purified through silica gel column chromatography (chloroform/ethyl acetate) and treated with hydrochloric acid, thereby obtaining a hydrochloride (106 mg) of the subject compound as a white solid.

MS(FAB,Pos.):m/z=496[M+H]$^+$
$^1$H-NMR(500 MHz,DMSO-d$_6$+D$_2$O):δ=0.91(6H,t,J=7.3 Hz),1.68-1.73(4H, m),2.68(3H,s),3.02-3.07(4H,m),3.17-3.19(2H,m),3.20-3.31(2H,m),3.71(3H,s),3.74(2H,s),3.75-3.78(2H,m),3.80-3.83(2H,m),4.10(2H,s),4.18(2H,s),4.28(2H,dd,J=31.4,12.8 Hz),7.39(2H,d,J=8.1 Hz), 7.47(1H,d,J=2.0 Hz),7.48(1H,d,J=2.0 Hz),7.50(2H,d,J=8.2 Hz), 7.60(2H,s).

EXAMPLE 91

Production Example 91

Synthesis of N-(4-{[(1H-imidazol-2-ylmethyl)-(1-methyl-1H-imidazol-2-ylmethyl)-amino]-methyl}-benzyl)-N',N'-dipropyl-N-(1H-tetrazol-5-ylmethyl)-butane-1,4-diamine [Compound No. 110]

EXAMPLE 91-1

Synthesis of 4-{[(1-methyl-1H-imidazol-2-ylmethyl)-(1-trityl-1H-imidazol-2-ylmethyl)-amino]-methyl}-benzaldehyde The compound (281 mg) obtained in Example 84-5 was dissolved in dichloromethane (6.0 ml) and added with diisopropylethylamine (310 µl) at room temperature under a nitrogen atmosphere. The solution was added with tritylchloride (310 mg) under ice-cooling and the whole was stirred at room temperature for 4 hours. After completion of the reaction, methanol was added thereto. The solvent was distilled off under reduced pressure and the residue was diluted with chloroform and added with water. The aqueous layer was subjected to extraction with chloroform. The combined organic layer was washed with a saturated saline solution and dried with anhydrous sodium sulfate. After filtration, the solution was concentrated and evaporated to dryness under reduced pressure and the residue was purified through silica gel column chromatography (chloroform/methanol), thereby obtaining the subject compound (217 mg) as a yellow oily substance.

MS(FAB,Pos.):m/z=552[M+H]$^+$
$^1$H-NMR(500 MHz,CDCl$_3$):δ=2.84(2H,s),3.33(2H,s),3.47(2H,s),3.77 (3H,s),6.73(1H,d,J=1.2 Hz),6.78(1H,d,J=1.5 Hz),6.83(1H,d,J=1.2 Hz), 7.03(1H,d,J=1.5 Hz),7.05-7.28(17H,m),7.67(2H,d,J=8.3 Hz),9.95(1H,s).

EXAMPLE 91-2

Synthesis of N-(4-{[(1-methyl-1H-imidazol-2-ylmethyl)-(1-trityl-1H-imidazol-2-ylmethyl)-amino]-methyl}-benzyl)-N',N'-dipropyl-butane-1,4-diamine The compound (47.2 mg) obtained in Example 91-1 was dissolved in methanol (1.0 ml) and trimethyl orthoformate (28.0 µl) and a methanol solution containing the compound (14.7 mg) obtained in Example 1-2 were dropped thereto at room temperature under a nitrogen atmosphere. The whole was stirred for 12 hours. Sodium borohydride (10.0 mg) was added thereto under ice-cooling and the whole was warmed back to room temperature and stirred for 2 hours. After completion of the reaction, water was added thereto. The solvent was distilled off under reduced pressure. The resultant was diluted with chloroform and added with water, and the aqueous layer was subjected to extraction with chloroform. The combined organic layer was washed with a saturated saline solution and dried with anhydrous sodium sulfate. After filtration, the solution was concentrated and evaporated to dryness under reduced pressure and the residue was purified through silica gel column chromatography (chloroform/methanol), thereby obtaining the subject compound (51.6 mg) as a pale-yellow solid.

MS(FAB,Pos.):m/z=708[M+H]$^+$
$^1$H-NMR(500 MHz,CDCl$_3$):δ=0.86(6H,t,J=7.3 Hz),1.25-1.64(8H,m),2.33-2.37(4H,m),2.41(2H,t,J=6.7 Hz),2.61(2H,t,J=6.7 Hz),2.83(2H,s), 3.19(2H,s),3.39(2H,s),3.72(2H,s),3.77(3H,s),6.74(1H,d,J=1.2 Hz),6.77(1H,d,J=1.5 Hz),6.83(1H,d,J=1.2 Hz), 7.02(1H,d,J=1.5 Hz), 7.02-7.29(19H,m).

EXAMPLE 91-3

Synthesis of 5-chloromethyl-1-(tetrahydro-pyran-2-yl)-1H-tetrazole

5-Chloromethyl-1(2)H-tetrazole (52.8 mg) was dissolved in anhydrous dichloromethane (3.0 ml) and anhydrous DMF (0.50 ml) and added with 2,4-dihydro-2H-pyran (50.0 µl) at room temperature under a nitrogen atmosphere. The solution was added with pyridinium-p-toluenesulfonate (11.9 mg) under ice-cooling and warmed back to room temperature and the whole was stirred for 2 hours. Further, 2,4-dihydro-2H-pyran (75.0 µl) was added thereto and pyridinium-p-toluenesulfonate (22.0 mg) was added thereto under ice-cooling. The solution was warmed back to room temperature and stirred for 22 hours. After completion of the reaction, the reaction solution was poured into a saturated aqueous sodium hydrogen carbonate solution (10 ml) under ice-cooling to make the pH of the aqueous layer to 8. The aqueous layer was subjected to extraction with chloroform. The combined organic layer was washed with a saturated saline solution and dried with anhydrous sodium sulfate. After filtration, the solution was concentrated and evaporated to dryness under reduced pressure and the residue was purified through silica gel column chromatography (toluene/acetone), thereby obtaining the subject compound (4.6 mg) as a colorless oily substance.
$^1$H-NMR(500 MHz,CDCl$_3$):δ=1.64-1.82(3H,m),2.14-2.48(3H,m),3.74-3.90(2H,m),4.88(1H,d,J=12.7 Hz),4.97(1H,d,J=12.7 Hz),5.86(1H,dd, J=3.4 Hz,7.5 Hz).

EXAMPLE 91-4

Synthesis of N-(4-{[(1-methyl-1H-imidazol-2-ylmethyl)-(1-trityl-1H-imidazol-2-ylmethyl)-amino]-methyl}-benzyl)-N',N'-dipropyl-N-[1-(tetrahydro-pyran-2-yl)-1H-tetrazol-5-ylmethyl]-butane-1,4-diamine The compound (57.7 mg) obtained in Example 91-2 was dissolved in anhydrous DMF (1.2 ml) and added with diisopropylethylamine (34.0 μl), potassium iodide (15.2 mg), and the compound (chloro derivative) (28.0 mg) obtained in Example 91-3 at room temperature under a nitrogen atmosphere. The whole was stirred overnight at room temperature. After completion of the reaction, methanol was added thereto. The solution was concentrated and evaporated to dryness under reduced pressure and the residue was purified through silica gel column chromatography (chloroform/ethyl acetate), thereby obtaining the subject compound (35.6 mg) as a pale-yellow oily substance.
MS(FAB,Pos.):m/z=874[M+H]$^+$
$^1$H-NMR(500 MHz,CDCl$_3$):δ=0.85(6H,t,J=7.3 Hz),1.30-1.62(11H,m),2.28-2.53(1H,m),2.84(2H,s),3.20(2H,s)3.40 (2H,s),3.41(1H,d,J=13.2 Hz),3.64(1H,d,J=13.4 Hz),3.76 (3H,s) 3.81(1H,d,J=14.1 Hz),3.93(1H,d,J=13.9 Hz),5.64 (1H,dd,J=3.2,8.5 Hz),6.74(1H,d,J=1.2 Hz), 6.77(1H,d,J=1.5 Hz),6.83(1H,d,J=1.2 Hz),7.01(1H,d,J=1.2 Hz),7.06-7.30 (19H,m).

EXAMPLE 91-5

Synthesis of N-(4-{[(1H-imidazol-2-ylmethyl)-(1-methyl-1H-imidazol-2-ylmethyl)-amino]-methyl}-benzyl)-N',N'-dipropyl-N-(1H-tetrazol-5-ylmethyl)-butane-1,4-diamine [Compound No. 110]

The compound (35.6 mg) obtained in Example 91-4 was dissolved in methanol (0.80 ml) and added with a 10% hydrogen chloride/methanol solution (0.80 ml) and the whole was stirred overnight at room temperature. After completion of the reaction, the solvent was distilled off under reduced pressure. The residue was added with ethyl acetate and water, and the aqueous layer was washed with ethylacetate. The aqueous layer was concentrated and evaporated to dryness under reduced pressure, thereby obtaining a hydrochloride (23.9 mg) of the subject compound as a white solid.
MS(FAB,Pos.):m/z=548[M+H]$^+$
$^1$H-NMR(500 MHz,DMSO-d$_6$):δ=0.90(6H,t,J=7.3 Hz), 1.64-2.00(8H,m),2.93-3.17(8H,m),3.72(4H,s),3.74(2H,s), 4.13(3H,s),4.22(2H,s),4.34(2H,s),7.44(1H,s),7.46(1H,s), 7.53(1H,s),7.54(1H,s),7.54(2H,d,J=8.7 Hz),7.58(2H,d,J=8.1 Hz),10.6(1H,brs),15.0(1H,brs).

EXAMPLE 92

Production Example 92

Synthesis of 5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 111]

EXAMPLE 92-1

Synthesis of 5-t-butoxycarbonylamino-(2S)-(9H-fluoren-9-ylmethoxycarbonylamino)-pentanoic acid ethyl ester In DMF (50.0 ml), 5-t-butoxycarbonylamino-(2S)-(9H-fluoren-9-ylmethoxycarbonylamino)-pentanoic acid (2.50 g) was dissolved. The solution was added with WSCI hydrochloride (1.21 g) and HOBt (0.84 g) and the whole was stirred at room temperature for 1.5 hours. The solution was added with ethanol (1.0 ml) and the whole was stirred at room temperature for additional 17 hours. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The residue was purified through silica gel column chromatography (hexane/ethyl acetate), thereby obtaining the subject compound (1.22 g) as a white solid.
MS(FAB,Pos.):m/z=483[M+H]$^+$
$^1$H-NMR(500 MHz,CDCl$_3$):δ=1.29(3H,t,J=7.1 Hz),1.45 (9H,s),1.49-1.57(2H,m),1.64-1.71(1H,m),1.84-1.94(1H,m), 3.11-3.20(2H,br),4.19-4.26(3H,m),4.33-4.40(1H,m),4.41 (2H,d,J=7.1 Hz),4.54-4.60(1H,br),5.40-5.47(1H,br),7.32 (2H,t,J=7.6 Hz),7.40(2H,t,J=7.6 Hz),7.57-7.63(2H,m),7.77 (2H,d,J=7.6 Hz).

EXAMPLE 92-2

Synthesis of 5-maino-(2S)-(9H-fluoren-9-ylmethoxycarbonylamino)-pentanoic acid ethyl ester The compound (874.0 mg) obtained in Example 92-1 was dissolved in ethanol (8.7 ml) and added with a 4 mol/l hydrogen chloride/dioxane solution (8.7 ml) and the whole was stirred at room temperature for 1.5 hours. After completion of the reaction, the solvent was distilled off and the residue was dried under vacuum, thereby obtaining a crude product (817.9 mg) of (2S)-amino-5-dipropylamino-pentanoic acid ethyl ester as hydrochloride.
MS(FAB,Pos.):m/z=483[M+H]+

EXAMPLE 92-3

Synthesis of (2S)-amino-5-dipropylamino-pentanoic acid ethyl ester 300.0 mg of the crude product obtained in Example 92-2 were dissolved in ethanol (6.0 ml) and added with a 1 mol/l sodium hydroxide aqueous solution (0.72 ml) and the whole was adjusted to about pH 5 by addition of acetic acid. The solution was added with sodium cyanoborohydride (144.5 mg) and propionaldehyde (0.155 ml) was dropped thereto. The whole was stirred at room temperature for 1 hour. After completion of the reaction, the solvent was distilled off and the residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off. The resultant crude product was dissolved in DMF (6.4 ml) and added with diethylamine (0.32 ml) and the whole was stirred at room temperature for 2 hours. After completion of the reaction, the solvent was distilled off and the residue was purified through silica gel column chromatography (chloroform), thereby obtaining the subject compound (54.2 mg) as a colorless oily substance.

MS(FAB,Pos.):m/z=245[M+H]$^+$

EXAMPLE 92-4

Synthesis of 5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 111]

The compound (54.2 mg) obtained in Example 92-3 and the compound (76.8 mg) obtained in Example 84-5 were dissolved in ethanol (4.3 ml) and added with acetic acid (80 μl). The solution was added with sodium cyanoborohydride (49.6 mg) and the whole was stirred at room temperature for 1.5 hours. The solution was added with a 36% formaldehyde aqueous solution (0.10 ml) and the whole was stirred at room temperature for 1 hour. After completion of the reaction, the solvent was distilled off and the residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off and the residue was purified through silica gel column chromatography (chloroform), thereby obtaining the subject compound (94.9 mg) as a colorless oily substance.

MS(FAB,Pos.):m/z=552[M+H]$^+$ $^1$H-NMR(500 MHz,CDCl$_3$):δ=0.86(6H,t,J=7.3 Hz),1.31 (3H,t,J=7.1 Hz),1.39-1.48(5H,m),1.53-1.63(1H,m),1.67-1.73(2H,m),2.25(3H,s),2.33-2.37(4H,m),2.41(2H,t,J=7.3 Hz),3.30(1H,t,J=7.6 Hz),3.47(2H,s),3.56(3H,s),3.59-3.62 (3H,m),3.68(2H,s),3.76-3.79(1H,m),4.16-4.24(2H,m),6.87 (1H,s), 7.00(1H,s),7.10(2H,d,J=21.7 Hz),7.29(2H,d,J=8.3 Hz), 7.34(2H,d,J=8.3 Hz).

EXAMPLE 93

Production Example 93

Synthesis of 5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid [Compound No. 112]

EXAMPLE 93-1

Synthesis of 5-dipropylamino-(2S)-[(4-{[(1H-imidazol-2-ylmethyl)-(1-methyl-1H-imidazol-2-ylmethyl)-amino]-methyl}-benzyl)-methyl-amino]-pentanoic acid [Compound No. 112]

The compound (42.9 mg) obtained in Example 92-4 was dissolved in concentrated hydrochloric acid (1.0 ml) and the whole was stirred at 100° C. for 5 hours. After completion of the reaction, the solvent was distilled off under reduced pressure and the residue was dried under vacuum, thereby obtaining a hydrochloride (52.3 mg) of the subject compound as a white solid.

MS(FAB,Pos.):m/z=524[M+H]$^+$ $^1$H-NMR(500 MHz,DMSO-d$_6$):δ=0.91(6H,t,J=7.3 Hz), 1.64-1.72(4H,m),1.76-1.92(2H,br),1.93-2.04(1H,br),2.12-2.24(1H,br),2.60-2.72(3H,br),2.92-3.04(4H,m),3.06-3.14 (2H,m),3.40-3.80(7H,m),3.84-3.94(1H,br),4.12(2H,s),4.19 (2H,s),7.48(4H,s),7.52-7.54(2H,m), 7.61-7.63(2H,m), 10.48-10.60(1H,br).

EXAMPLE 94-1

Synthesis of (S)-2-(9H- fluorine-9-ylmethoxycarbonylamimo)-5-[(4-{[1H-imidazol-2ylmethyl)-(1methyl -1H-imidazol-2-ylmethyl)-amino]-methyl}-benzyl)-methyl-amino]-pentanoic acid ethyl ester 268.0 mg of the crude product obtained in Example 92-2 and 180.0 mg of the compound obtained in Example 84-5 were dissolved in ethanol (7.0 ml) and added with acetic acid (180 μl). The solution was added with sodium cyanoborohydride (98.0 mg) and the whole was stirred at room temperature for 1.5 hours. Then, the solution was added with a 36% formaldehyde aqueous solution (0.242 ml) and the whole was stirred at room temperature for 15 hours. Further, the solution was added with sodium cyanoborohydride (39.0 mg) and the whole was stirred at room temperature for 6 hours. After completion of the reaction, the solvent was distilled off and the residue was dried under vacuum, thereby obtaining the subject compound (382.4 mg) as a pale-yellow solid.

MS(FAB,Pos.):m/z=690[M+H]$^+$

EXAMPLE 94-2

Synthesis of (2S)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 113]

The compound (382.0 mg) obtained in Example 94-1 was dissolved in DMF (7.6 ml) and added with diethylamine (0.40 ml) and the whole was stirred at room temperature for 3 hours. After completion of the reaction, the solvent was distilled off under reduced pressure and the residue was dried under vacuum, thereby obtaining a crude product of (2S)-amino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester. The resultant crude product was dissolved in ethanol (7.0 ml) and added with an acetic acid (0.20 ml) and sodium cyanoborohydride (117.0 mg). Propionaldehyde (0.127 ml) was dropped thereto and the whole was stirred at room temperature for 1.5 hours. After completion of the reaction, the solvent was distilled off. The residue was dissolved in chloroform and washed with a 1 mol/l sodium hydroxide aqueous solution, followed by extraction with chloroform. The organic layer was washed with a saturated saline solution and dried with anhydrous sodium sulfate. After filtration, the solvent was distilled off and the residue was purified through silica gel column chromatography (chloroform), thereby obtaining the subject compound (109.1 mg) as a colorless oily substance.

MS(FAB,Pos.):m/z=552[M+H]$^+$ $^1$H-NMR(500 MHz,CDCl$_3$):δ=0.85(6H,t,J=7.3 Hz),1.26 (3H,t,J=7.1 Hz), 1.34-1.53(5H,m),1.57-1.75(3H,m),2.17

(3H,s),2.36-2.43(4H,m),2.51-2.57(2H,m),3.28(1H,t,J=7.2 Hz),3.46(4H,s),3.55(3H,s),3.62(2H,s),3.68(2H,s),4.10-4.18 (2H,m),6.87(1H,s),7.00(1H,s),7.07-7.15(2H,br),7.27(2H,d, J=8.1 Hz),7.34(2H,d,J=8.1 Hz).

EXAMPLE 95

Production Example 95

Synthesis of (2S)-dipropylamino-5-[(4-{[(1H-imida-zol-2-ylmethyl)-(1-methyl-1H-imidazol-2-ylmethyl)-amino]-methyl}-benzyl)-methyl-amino]-pentanoic acid [Compound No. 114]

EXAMPLE 95-1

Synthesis of (2S)-dipropylamino-5-[(4-{[(1H-imida-zol-2-ylmethyl)-(1-methyl-1H-imidazol-2-ylmethyl)-amino]-methyl}-benzyl)-methyl-amino]-pentanoic acid [Compound No. 114]

The compound (33.0 mg) obtained in Example 94-2 was dissolved in concentrated hydrochloric acid (1.0 ml) and the whole was stirred at 100° C. for 5 hours. After completion of the reaction, the solvent was distilled off under reduced pressure and the residue was dried under vacuum, thereby obtaining a hydrochloride (32.8 mg) of the subject compound as a white solid.

MS(FAB,Pos.):m/z=524[M+H]$^+$
$^1$H-NMR(500 MHz,DMSO-d$_6$):δ=0.90(6H,t,J=7.3 Hz), 1.68-1.80(4H,br), 1.84-2.16(4H,m),1.56-2.64(3H,m),2.90-3.16(6H,m),3.70-3.76(4H,m),4.00-4.50(7H,m),7.44-7.56 (6H,m),7.64-7.68(2H,m),10.43-10.52(1H,m),11.10-11.24 (1H,br).

EXAMPLE 96

Production Example 96

Synthesis of 5-dipropylamino-(2R)-[(4-{[(1H-imida-zol-2-ylmethyl)-(1-methyl-1H-imidazol-2-ylmethyl)-amino]-methyl}-benzyl)-methyl-amino]-pentanoic acid ethyl ester [Compound No. 115]

EXAMPLE 96-1

Synthesis of 5-t-butoxycarbonylamino-(2R)-(9H-fluoren-9-ylmethoxycarbonylamino)-pentanoic acid ethyl ester In ethanol (60 ml), 5-t-butoxycarbonylamino-(2R)-(9H-fluoren-9-ylmethoxycarbonylamino)-pentanoic acid (1.9914 g) was dissolved. The solution was added with HOBt (770.2 mg) and WSCI hydrochloride (1.0927 g) and the whole was stirred at room temperature for 2 hours. After completion of the reaction, the solvent was distilled off. The residue was dissolved in chloroform and washed with 1 mol/l hydrochloric acid, a 1 mol/l sodium hydroxide aqueous solution, and a saturated saline solution, followed by drying with magnesium sulfate. The residue was purified through silica gel column chromatography (hexane/ethyl acetate), thereby obtaining the subject compound (1.9846 g) as a white solid.

MS(FAB,Pos.):m/z=483[M+H]$^+$
$^1$H-NMR(500 MHz,CDCl$_3$):δ=1.29(3H,t,J=7.1 Hz),1.45 (9H,s),1.48-1.57(2H,m),1.65-1.69(1H,m),1.85-1.91(1H,m), 3.15(2H,br),4.12-4.24(3H,m),4.34-4.38(1H,m),4.41(2H,d, J=6.8 Hz),4.58(1H,br),5.45(1H,d,J=7.8 Hz),7.31-7.34(2H, m),7.39-7.42(2H,m),7.60-7.62(2H,m), 7.77(2H,d,J=7.6 Hz).

EXAMPLE 96-2

Synthesis of (2R)-amino-5-t-butoxycarbonylamino-pentanoic acid ethyl ester

The compound (1.9846 g) obtained in Example 96-1 was dissolved in DMF (19 ml) and added with diethylamine (14 ml) and the whole was stirred at room temperature for 30 minutes. After completion of the reaction, the solvent was distilled off. The residue was purified through silica gel column chromatography (chloroform/methanol), thereby obtaining the subject compound (1.2212 g) as a colorless oily substance.

MS(FAB,Pos.):m/z=261[M+H]$^+$

EXAMPLE 96-3

Synthesis of 5-t-butoxycarbonylamino-(2R)-[(4-{ [(1H-imidazol-2-ylmethyl)-(1-methyl-1H-imidazol-2-ylmethyl)-amino]-methyl}-benzyl)-methyl-amino]-pentanoic acid ethyl ester The compound (694.2 mg) obtained in Example 96-2 was dissolved in anhydrous methanol (20.8 ml) and added with the compound (909.5 mg) obtained in Example 84-5 and trimethyl orthoformate (0.876 ml) and the whole was stirred at room temperature for 17 hours. After having been cooled with ice, the solution was added with sodium borohydride (303 mg) and the whole was stirred at room temperature for 1 hour. After completion of the reaction, the solvent was distilled off. The resultant was added with water and subjected to extraction with chloroform. The resultant was washed with a saturated saline solution and dried with magnesium sulfate, followed by distillating off the solvent.

The resultant was dissolved in anhydrous methanol (44 ml) and added with a 36% formaldehyde aqueous solution (0.31 ml) and sodium cyanoborohydride (503.3 mg) and the whole was adjusted to pH 5 with acetic acid, followed by stirring at room temperature for 17 hours. After completion of the reaction, the solvent was distilled off. The resultant was added with a saturated aqueous sodium hydrogen carbonate solution and subjected to extraction with chloroform, followed by drying with magnesium sulfate. The solvent was distilled off and the residue was purified through silica gel column chromatography (chloroform/ethyl acetate), thereby obtaining the subject compound (805.8 mg) as a colorless oily substance.

MS(FAB,Pos.):m/z=568[M+H]$^+$

EXAMPLE 96-4

Synthesis of 5-dipropylamino-(2R)-[(4-{[(1H-imida-zol-2-ylmethyl)-(1-methyl-1H-imidazol-2-ylmethyl)-amino]-methyl}-benzyl)-methyl-amino]-pentanoic acid ethyl ester [Compound No. 115]

The compound (805.8 mg) obtained in Example 96-3 was dissolved in ethanol (8.0 ml) and added with a 4 mol/l hydrogen chloride/dioxane solution (8.0 ml) and the whole was stirred at room temperature for 2 hours. After completion of the reaction, the solvent was distilled off. The resultant was added with a 1 mol/l sodium hydroxide aqueous solution and subjected to extraction with chloroform, followed by drying with magnesium sulfate. The solvent was distilled off.

The resultant was dissolved in ethanol (26.5 ml) and added with propionaldehyde (0.246 ml), triethyl orthoformate (0.709 ml), and sodium cyanoborohydride (267.7 mg). The whole was stirred at room temperature for 21 hours. After completion of the reaction, the solvent was distilled off. The residue was added with water, subjected to extraction with chloroform, and dried with magnesium sulfate. The solvent was distilled off. The residue was purified through silica gel column chromatography (chloroform/ethyl acetate), thereby obtaining the subject compound (205.2 mg) as a yellow oily substance.

MS(FAB,Pos.):m/z=552[M+H]$^+$ $^1$H-NMR(500 MHz,CDCl$_3$):δ=0.86(6H,t,J=7.3 Hz),1.31 (3H,t,J=7.1 Hz), 1.39-1.50(4H,m),1.66-1.75(4H,m),2.26 (3H,s),2.32-2.36(4H,m),2.39-2.42(2H,m),3.27-3.31(1H,m), 3.46(2H,s),3.56(3H,s),3.62(2H, s),3.68(2H,s),4.16-4.25(2H, m),6.88(1H,s),7.00(1H,s),7.08(1H, s),7.13(1H,s),7.28(2H,d, J=8.1 Hz),7.34(2H,d,J=8.1 Hz),12.35(1H,br).

EXAMPLE 97

Production Example 97

Synthesis of 5-dipropylamino-(2R)-[(4-{[(1H-imidazol-2-ylmethyl)-(1-methyl-1H-imidazol-2-ylmethyl)-amino]-methyl}-benzyl)-methyl-amino]-pentanoic acid [Compound No. 116]

EXAMPLE 97-1

Synthesis of 5-dipropylamino-(2R)-[(4-{[(1H-imidazol-2-ylmethyl)-(1-methyl-1H-imidazol-2-ylmethyl)-amino]-methyl}-benzyl)-methyl-amino]-pentanoic acid [Compound No. 116]

The hydrochloride (200 mg) of the compound obtained in EXAMPLE 96-4 was dissolved in concentrated hydrochloric acid (3 ml) and water (0.2 ml), and the whole was refluxed under heating for 4 hours. After completion of the reaction, the solvent was distilled off, thereby obtaining a hydrochloride (175.1 mg) of the subject compound as a white solid.

MS(FAB,Pos.):m/z=524[M+H]$^+$ $^1$H-NMR(500 MHz,DMSO-d$_6$+D$_2$O):δ=0.92(6H,t,J=7.2 Hz),1.62-1.70(4H, m),1.71-1.93(2H,m),1.99-2.01(1H,m), 2.15(1H,m),2.67(3H,s),2.99-3.02(4H,m),3.11-3.15(2H,m), 3.72(3H,s),3.75(2H,s),3.96-4.00(1H,m),4.10(2H,s),4.19 (2H,s),4.27(1H,m),4.33(1H,m),7.44(4H,d, J=4.3 Hz),7.48 (2H,d,J=1.5 Hz),7.61(2H,s).

EXAMPLE 98

Production Example 98

Synthesis of (2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 117]

EXAMPLE 98-1

Synthesis of 5-t-butoxycarbonylamino-(2R)-dipropylamino-pentanoic acid ethyl ester The compound (333.2 mg) obtained in Example 96-2 was dissolved in anhydrous methanol (13.2 ml) and added with propionaldehyde (0.221 ml), trimethyl orthoformate (0.42 ml), and sodium cyanoborohydride (241.3 mg). The whole was stirred at room temperature for 3 days. After completion of the reaction, the solvent was distilled off. The resultant was added with water, subjected to extraction with chloroform, and dried with magnesium sulfate. The solvent was distilled off. The residue was purified through silica gel column chromatography (chloroform/ethyl acetate), thereby obtaining the subject compound (156.5 mg) as a colorless oily substance.

MS(FAB,Pos.):m/z=345[M+H]$^+$

EXAMPLE 98-2

Synthesis of (2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid ethyl ester [Compound No. 117]

The compound (156.5 mg) obtained in Example 98-1 was dissolved in methanol (1.5 ml) and added with a 4 mol/l hydrogen chloride/dioxane solution (1.5 ml) and the whole was stirred at room temperature for 4 hours. After completion of the reaction, the solvent was distilled off. The resultant was added with a 1 mol/l sodium hydroxide aqueous solution and subjected to extraction with chloroform, followed by drying with magnesium sulfate. The solvent was distilled off.

The resultant was dissolved in anhydrous methanol (6 ml) and added with the compound (167.1 mg) obtained in Example 84-5 and trimethyl orthoformate (0.148 ml). The whole was stirred at room temperature for 16 hours. The solution was added with sodium borohydride (51.1 mg) and the whole was stirred at room temperature for 1 hour. After completion of the reaction, water was added thereto. The solvent was distilled off and the resultant was subjected to extraction with chloroform and dried with magnesium sulfate. The solvent was distilled off.

The resultant was dissolved in anhydrous methanol (9.7 ml) and added with a 36% formaldehyde aqueous solution (0.053 ml) and sodium cyanoborohydride (84.4 mg). The whole was adjusted to pH5 with acetic acid. The whole was stirred at room temperature for 18 hours. After completion of the reaction, the solvent was distilled off. The resultant was added with a 1 mol/l sodium hydroxide aqueous solution, subjected to extraction with chloroform, and dried with magnesium sulfate. The solvent was distilled off. The residue was purified through silica gel column chromatography (chloroform/ethyl acetate) and treated with hydrochloric acid, thereby obtaining a hydrochloride (120 mg) of the subject compound as a brown solid.

MS(FAB,Pos.):m/z=552[M+H]$^+$ $^1$H-NMR(500 MHz,DMSO-d$_6$:d=0.79(6H,t,J=7.1 Hz), 1.18(3H,t,J=7.1 Hz),1.24-1.40(6H,m),1.47-1.62(2H,m), 2.31-2.37(4H,m),2.43-2.49(2H,m),2.51(3H,s), 3.22(1H,t, J=8.1 Hz),3.34-3.42(2H,br),3.49-3.52(4H,m),3.50(3H,s), 3.56(2H,s),4.00-4.10(2H,m),6.80(1H,d,J=1.22 Hz),6.98-7.06(2H,br),7.07(1H,d,J=1.2 Hz), 7.22(2H,d,J=8.1 Hz),7.33 (2H,d,J=8.1 Hz).

EXAMPLE 99

Production Example 99

Synthesis of (2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid [Compound No. 118]

EXAMPLE 99-1

Synthesis of (2R)-dipropylamino-5-[(4-{[(1H-imidazol-2-ylmethyl)-(1-methyl-1H-imidazol-2-ylmethyl)-amino]-methyl}-benzyl)-methyl-amino]-pentanoic acid [Compound No. 118]

The compound (93.1 mg) obtained in Example 98-2 was dissolved in concentrated hydrochloric acid (2 ml) and water (0.1 ml), and the whole was refluxed under heating for 4 hours. After completion of the reaction, the solvent was distilled off, thereby obtaining a hydrochloride (90.3 mg) of the subject compound as a brown solid.
MS(FAB,Pos.):m/z=524[M+H]$^+$
$^1$H-NMR(500 MHz,DMSO-$d_6$+$D_2O$):δ=0.91(6H,t,J=7.1 Hz),1.67-1.73(4H, m),1.92(4H,m),2.59(3H,s),3.06-3.17(6H, m),3.72(3H,s),3.80(2H, s),4.11-4.13(1H,m),4.11(2H,s),4.19 (2H,s),4.31-4.34(2H,m),7.41(2H,d,J=7.9 Hz),7.45-7.47(2H, m),7.48(2H,s),7.60(2H,s).

EXAMPLE 100

Production Example 100

Synthesis of [(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid ethyl ester [Compound No. 119]

EXAMPLE 100-1

Synthesis of N-(4-{[(1H-imidazol-2-ylmethyl)-(1-methyl-1H-imidazol-2-ylmethyl)-amino]-methyl}-benzylidene)-N',N'-dipropyl-butane-1,4-diamine The compound (210 mg) obtained in Example 84-5 was dissolved in anhydrous methanol (6.3 ml) and added with the compound (117 mg) obtained in Example 1-2. The solution was added with trimethyl orthoformate (297 μl) and the whole was stirred at room temperature for 6.5 hours. After completion of the reaction, the solvent was distilled off, thereby obtaining the subject compound (325 mg) as a brown oily substance.
MS(FAB,Pos.):m/z=464[M+H]$^+$
$^1$H-NMR(500 MHz,CDCl$_3$):δ=0.87(6H,t,J=7.3 Hz),1.40-1.82(8H,m),2.34-2.46(6H,m),2.55-2.70(2H,m),3.45(2H,s), 3.55(3H,s),3.63(2H,s), 3.72(2H,s),6.88(1H,d,J=1.2 Hz),6.99 (1H,d,J=1.2 Hz),7.05-7.13(2H,m),7.46(2H,d,J=8.3 Hz),7.69 (2H,d,J=8.3 Hz),8.27(1H,s),12.39(1H,br).

EXAMPLE 100-2

Synthesis of [(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid ethyl ester [Compound No. 119]

The compound (147 mg) obtained in Example 100-1 was dissolved in anhydrous methylene chloride (4.41 ml) and added with ytterbium trifluoromethanesulfonate (59.2 mg). After having been cooled to 0° C., the solution was added with trimethylsilyl cyanide (130 μl) and warmed back to room temperature, followed by stirring for 24 hours. After that, the solution was again cooled to 0° C. and added with trimethylsilyl cyanide (130 μl) and warmed back to room temperature, followed by stirring for additional 30 hours. After completion of the reaction, the solvent was distilled off. The resultant was added with a saturated aqueous sodium hydrogen carbonate solution and subjected to extraction with chloroform. The organic layer was washed with a saturated saline solution and dried with anhydrous sodium sulfate. After that, the solvent was distilled off, thereby obtaining the subject compound (156 mg) as a pale-yellow oily substance.

The pale-yellow oily substance was dissolved in ethanol (4.7 ml) and added with concentrated hydrochloric acid (780 μl) and the whole was refluxed at 95° C. for 16 hours. The solution was cooled to room temperature and then the solvent was distilled off. The resultant was added with a saturated aqueous sodium hydrogen carbonate solution and subjected to extraction with chloroform. The organic layer was washed with a saturated saline solution and dried with anhydrous sodium sulfate. After that, the solvent was distilled off.

The resultant was dissolved in anhydrous ethanol (2.7 ml) and added with a 36% formaldehyde aqueous solution (71 μl) and sodium cyanoborohydride (27.9 mg). The whole was adjusted to pH 5 with acetic acid and stirred at room temperature for 1 hour. After completion of the reaction, the solvent was distilled off. The resultant was added with a saturated aqueous sodium hydrogen carbonate solution and subjected to extraction with chloroform. The organic layer was washed with a saturated saline solution and dried with anhydrous sodium sulfate, followed by distillating off the solvent. The residue was purified through silica gel column chromatography (chloroform/ethyl acetate), thereby obtaining the subject compound (13.2 mg) as a colorless oily substance.
MS(FAB,Pos.):m/z=552[M+H]$^+$
$^1$H-NMR(500 MHz,CDCl$_3$):δ=0.87(6H,t,J=7.3 Hz),1.27 (3H,t,J=7.1 Hz), 1.34-1.51(8H,m),2.27-2.40(6H,m),2.62-2.65(2H,m),3.29(3H,s),3.46(2H,s),3.57(3H,s),3.61(2H,s), 3.69(2H,s),3.85(1H,s),6.88(1H,d,J=1.2 Hz),7.00(1H,d,J=1.2 Hz),7.05-7.11(2H,m),7.30-7.36(4H, m),8.27(1H,s),12.35 (1H,br).

EXAMPLE 101

Production Example 101

Synthesis of [(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid [Compound No. 120]

EXAMPLE 101-1

Synthesis of [(4-dipropylamino-butyl)-methyl-amino]-(4-{[(1H-imidazol-2-ylmethyl)-(1-methyl-1H-imidazol-2-ylmethyl)-amino]-methyl}-phenyl)-acetic acid [Compound No. 120]

The compound (5.1 mg) obtained in Example 100-2 was dissolved in concentrated hydrochloric acid (204 μl) and the whole was refluxed at 100° C. for 20 hours. After completion of the reaction, the solvent was distilled off, thereby obtaining the subject compound (6.0 mg) as a white solid.

MS(FAB,Pos.):m/z=524[M+H]$^+$
$^1$H-NMR(500 MHz,DMSO-d$_6$):δ=0.91(6H,t,J=7.3 Hz), 1.63-1.69(8H,m), 2.95-2.98(6H,m),3.00-3.11(2H,m),3.24-3.51(5H,m),3.70(3H,s),3.72(2H,s),4.08(2H,s),4.14(1H,s), 7.45-7.55(6H,m),7.63-7.66(2H, m).

EXAMPLE 102

Production Example 102

Synthesis of 2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid ethyl ester [Compound No. 121]

EXAMPLE 102-1

Synthesis of 2,5-dimethyl benzoic acid methyl ester

In methanol (30 ml), 2,5-dimethylbenzoic acid (1.772 g) was dissolved. The reaction solution was added with concentrated sulfuric acid (0.7 ml) and the whole was refluxed under heating for 17 hours. After having been cooled to room temperature, the reaction solution was concentrated under reduced pressure. The resultant residue was added with a saturated aqueous sodium hydrogen carbonate solution to make the pH thereof to 9, followed by extraction with chloroform. The organic layer was washed with a saturated saline solution and dried with anhydrous sodium sulfate. After a drying agent was filtrated out, the filtrate was concentrated under reduced pressure. The resultant residue was purified through silica gel column chromatography (hexane/ethyl acetate), thereby obtaining the subject compound (1.9353 g) as a pale-yellow oily substance.
MS(FAB,Pos.):m/z=165[M+H]$^+$
1H-NMR(500 MHz,CDCl3):δ=2.34(3H,s),2.55(3H,s), 3.89(3H,s),7.13(1H,d,J=7.6 Hz),7.20(1H,d,J=7.6 Hz),7.72 (1H,s).

EXAMPLE 102-2

Synthesis of 6-hydroxymethyl-3H-isobenzofuran-1-one

The compound (1.1274 g) obtained in Example 102-1 was dissolved in carbon tetrachloride (19.2 ml). The reaction solution was added with N-bromosuccinimide (2.417 g) and benzoyl peroxide (147.2 mg), and the whole was refluxed under heating for 6.5 hours. After having been cooled to room temperature, the reaction solution was concentrated under reduced pressure. The resultant residue was purified through silica gel column chromatography (hexane/ethyl acetate), thereby obtaining a mixture (2.4003 g) containing 2,5-bis-bromomethyl-benzoic acid methyl ester. The resultant mixture was dissolved in a 50% 1,4-dioxane aqueous solution (48 ml). The reaction solution was added with calcium carbonate (3.4823 g) and the whole was stirred at 100° C. for 16.5 hours. After having been cooled to room temperature, the reaction solution was cooled to 0° C. and concentrated hydrochloric acid was gradually added thereto to make the pH of the solution to 2. After that, the whole was stirred at room temperature for 20 minutes. The reaction solution was subjected to extraction with ethyl acetate. The organic layer was washed with a saturated aqueous sodium hydrogen carbonate solution and a saturated saline solution and then dried with anhydrous sodium sulfate. After the drying agent was filtrated out, the filtrate was concentrated under reduced pressure. The resultant residue was purified through silica gel column chromatography (chloroform/ethyl acetate), thereby obtaining the subject compound (372.0 mg) as a white crystal.
MS(FAB,Pos.):m/z=165[M+H]$^+$
1H-NMR(500 MHz,CDCl$_3$):δ=1.91(1H,t,J=5.9 Hz),4.83 (2H,d,J=5.9 Hz), 5.33(2H,s),7.50(1H,d,J=7.8 Hz),7.72(1H, d,J=7.8 Hz),7.93(1H,s).

EXAMPLE 102-3

Synthesis of 2-{[(4-dipropylamino-butyl)-methyl-amino]-methyl}-5-(2-methoxy-methyoxyethoxym-ethyl)-benzoic acid The compound (160.7 mg) obtained in Example 102-2 was dissolved in chloroform (5 ml). The reaction solution was added with 2-methoxyethoxymethylchloride (485.2 mg) and diisopropylethylamine (540.2 mg) and the whole was stirred at room temperature for 16.5 hours. The reaction solution was added with 1 mol/l hydrochloric acid and subjected to extraction with chloroform. The organic layer was washed with a saturated saline solution and dried with anhydrous sodium sulfate. After the drying agent was filtrated out, the filtrate was concentrated under reduced pressure. The resultant residue was dissolved in methanol (3 ml). The reaction solution was added with a 1 mol/l sodium hydroxide aqueous solution (3 ml) and the whole was refluxed under heating for 1 hour. After having been cooled to room temperature, the reaction solution was concentrated under reduced pressure and subjected to extraction with chloroform. The aqueous layer was added with 1 mol/l hydrochloric acid to thereby adjust to pH 3, followed by extraction with chloroform. The organic layer was washed with a saturated saline solution and dried with anhydrous sodium sulfate. After the drying agent was filtrated out, the filtrate was concentrated under reduced pressure. The resultant residue was dissolved in chloroform (4 ml). The reaction solution was added with manganese dioxide (421.3 mg) and the whole was stirred at room temperature for 5.5 hours. The catalyst was filtrated out through Celite, and then the filtrate was concentrated under reduced pressure. The resultant residue was dissolved in methanol (3 ml). The reaction solution was added with N'-methyl-N,N-dipropyl-butane-1,4-diamine (187.7 mg) obtained by the method described in a Patent Document (WO 2004/024697) and sodium cyanoborohydride (178.7 mg). The solution was adjusted to pH 5 with acetic acid and stirred at room temperature for 15.5 hours. The reaction solution was concentrated under reduced pressure and added with a 1 mol/l sodium hydroxide aqueous solution, followed by extraction with chloroform. The organic layer was washed with a saturated saline solution and dried with anhydrous sodium sulfate. After the drying agent was filtrated out, the filtrate was concentrated under reduced pressure, thereby obtaining a crude product (263.3 mg) of the subject compound as a yellow oily substance.
MS(FAB,Pos.):m/z=439[M+H]$^+$

EXAMPLE 102-4

Synthesis of 2-{[(4-dipropylamino-butyl)-methyl-amino]-methyl}-5-hydroxymethyl-benzoic acid methyl ester The compound (263.3 mg) obtained in Example 102-3 was dissolved in ethanol (6 ml). The reaction solution was added with WSCI hydrochloride (147.5 mg) and HOBt (104.9 mg) and the whole was stirred at room temperature for 4 hours.

The reaction solution was concentrated under reduced pressure and added with a 1 mol/l sodium hydroxide aqueous solution, followed by extraction with chloroform. The organic layer was washed with a saturated saline solution and dried with anhydrous sodium sulfate. After the drying agent was filtrated out, the filtrate was concentrated under reduced pressure. The resultant residue was dissolved in 2-methyl-2-propanol (6 ml). The reaction solution was added with pyridinium p-toluenesulfonate (35.2 mg) and the whole was refluxed under heating for 2 days. After that, the solution was added with 1 mol/l hydrochloric acid (4 ml) and stirred at 90° C. for 30 minutes. After having been cooled to room temperature, the reaction solution was subjected to extraction with chloroform. The aqueous layer was added with a 1 mol/l sodium hydroxide aqueous solution to thereby adjust to pH 13, followed by extraction with chloroform. The organic layer was washed with a saturated saline solution and dried with anhydrous sodium sulfate. After the drying agent was filtrated out, the filtrate was concentrated under reduced pressure. The resultant residue was purified through silica gel column chromatography (hexane/ethyl acetate) thereby obtaining the subject compound (83.5 mg) as a colorless oily substance.

MS(FAB,Pos.):m/z=379[M+H]$^+$
1H-NMR(500 MHz,CDCl3):δ=0.86(6H,t,J=7.4 Hz),1.37-1.64(13H,m),2.15(3H,s),2.32-2.38(6H,m),3.78(2H,s),4.34 (2H,q,J=7.1 Hz),4.71(2H,s),7.43(1H,d,J=7.8 Hz),7.51(1H,d, J=7.8 Hz),7.74(1H,s).

EXAMPLE 102-5

Synthesis of 2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid ethyl ester [Compound No. 121]

The compound (83.5 mg) obtained in Example 102-4 was dissolved in chloroform (3 ml). The reaction solution was added with manganese dioxide (423.5 mg) and the whole was stirred at room temperature for 2 hours. The catalyst was filtrated out through Celite, and then the filtrate was concentrated under reduced pressure. The resultant residue was dissolved in methanol (1.5 ml). The reaction solution was added with the compound (45.2 mg) obtained in Example 88-4 and sodium cyanoborohydride (21.1 mg). The solution was adjusted to pH 5 with acetic acid and stirred at room temperature for 18 hours. The reaction solution was concentrated under reduced pressure and added with a 1 mol/l sodium hydroxide aqueous solution, followed by extraction with chloroform. The organic layer was washed with a saturated saline solution and dried with anhydrous sodium sulfate. After the drying agent was filtrated out, the filtrate was concentrated under reduced pressure. The resultant residue was purified through silica gel column chromatography (chloroform/ethyl acetate), thereby obtaining the subject compound (5.7 mg) as a colorless oily substance.

MS(FAB,Pos.):m/z=552[M+H]$^+$
1H-NMR(500 MHz,CDCl3):δ=0.86(6H,t,J=7.6 Hz),1.37-1.43(9H,m),1.69(4H,br),2.15(3H,s),2.35-2.37(6H,m),3.44 (2H,s),3.57(3H,s),3.64(2H,s),3.71(2H,s),3.75(2H,s),4.34 (2H,q,J=7.1 Hz),6.88(1H,d, J=1.5 Hz),7.00(1H,d,J=1.5 Hz), 7.08(1H,br),7.13(1H,br),7.45-7.50(2H,m),7.80(1H,s),12.34 (1H,br).

EXAMPLE 103

Production Example 103

Synthesis of 2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid [Compound. No. 122]

EXAMPLE 103-1

Synthesis of 2-{[(4-dipropylamino-butyl)-methyl-amino]-methyl}-5-{[(1H-imidazol-2-ylmethyl)-(1-methyl-1H-imidazol-2-ylmethyl)-amino]-methyl}-benzoic acid [Compound No. 122]

The compound (5.7 mg) obtained in Example 102-5 was suspended in distilled water (30 μl). The reaction solution was added with concentrated hydrochloric acid (100 μl) and the whole was stirred at 80° C. for 19 hours. After having been cooled to room temperature, the reaction solution was concentrated under reduced pressure, thereby obtaining the subject compound (6.9 mg) as a white solid.

MS(FAB,Pos.):m/z=524[M+H]$^+$
1H-NMR(500 MHz,DMSO-d$_6$):δ=0.92(6H,t,J=7.3 Hz), 1.66-1.82(8H,m), 2.61(3H,s),2.98(4H,br),3.05(2H,br),3.17 (2H,br),3.71(3H,s),3.83(2H,s),4.12(2H,s),4.21(2H,s),4.35 (1H,br),4.60(1H,br),7.49(1H,d,J=2.0 Hz),7.51(1H,d,J=2.0 Hz),7.59(1H,d,J=7.8 Hz),7.63(2H, s),7.74(1H,dd,J=7.8,1.7 Hz),7.93(1H,d,J=1.7 Hz),9.37(1H,br),10.35 (1H,br).

Next, the structural formulae of the compounds of the present invention including the compounds or the like produced in Production Examples described above are shown in Table 1.

TABLE 1

| No. | Structural Formula |
|---|---|
| 1 | 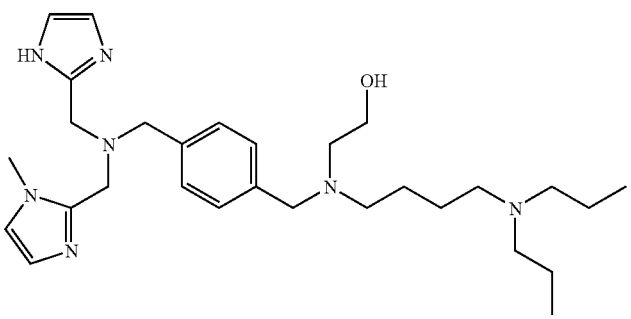 |

TABLE 1-continued

| No. | Structural Formula |
|---|---|
| 2 | |
| 3 | |
| 4 | |
| 5 | |
| 6 | |

TABLE 1-continued

| No. | Structural Formula |
|---|---|
| 7 | |
| 8 | |
| 9 | |
| 10 | |
| 11 | |

TABLE 1-continued
| No. | Structural Formula |
|---|---|
| 12 | 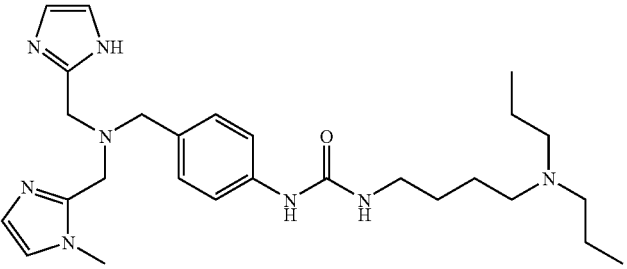 |
| 13 | 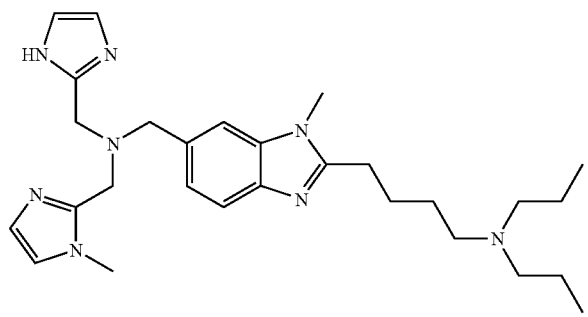 |
| 14 | 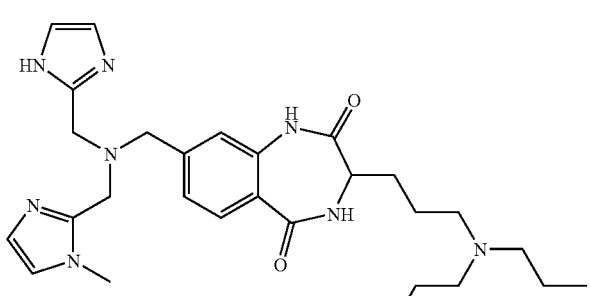 |
| 15 | 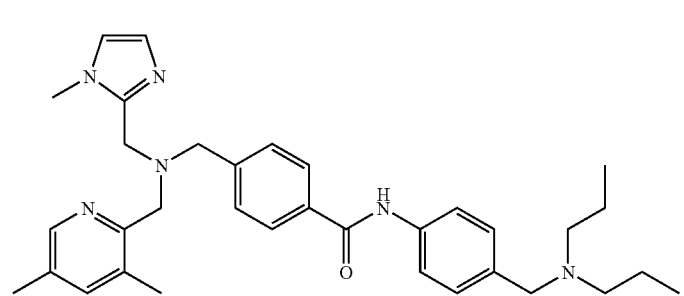 |
| 16 | 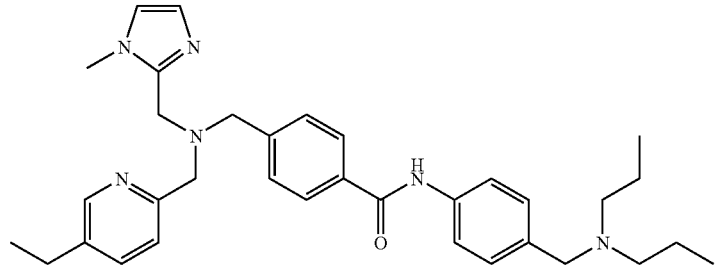 |

TABLE 1-continued
| No. | Structural Formula |
| --- | --- |
| 17 | 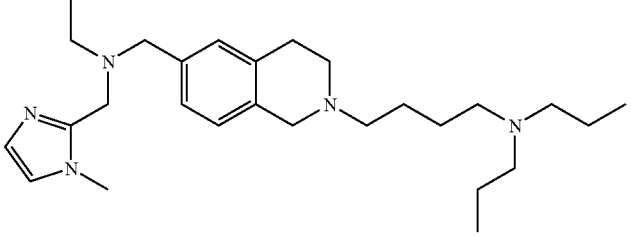 |
| 18 | 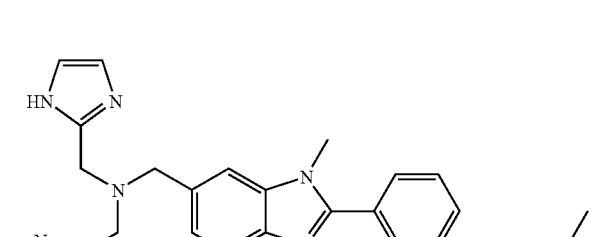 |
| 19 | 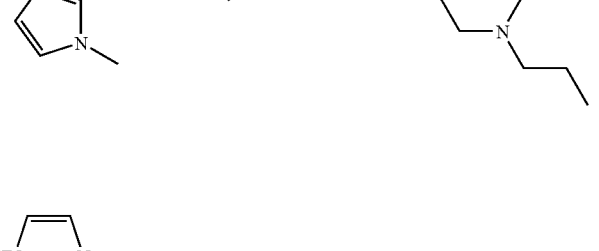 |
| 20 | 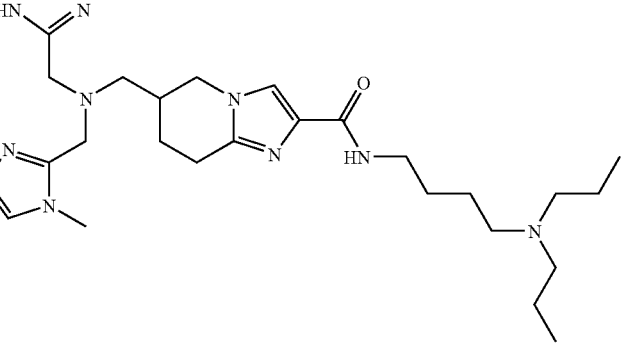 |

TABLE 1-continued
| No. | Structural Formula |
|---|---|
| 21 | 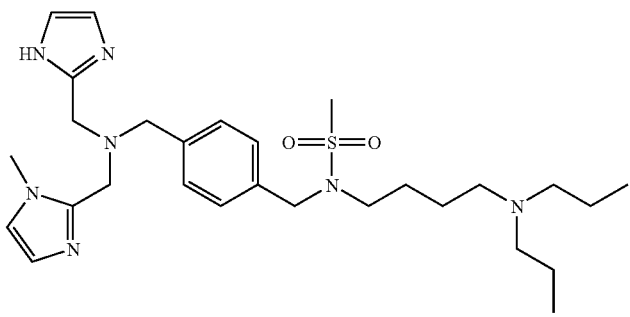 |
| 22 | 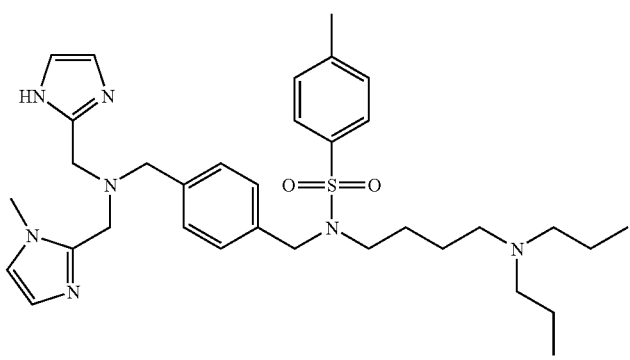 |
| 23 | 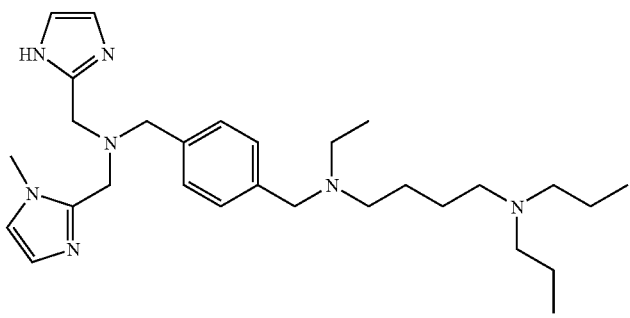 |
| 24 | 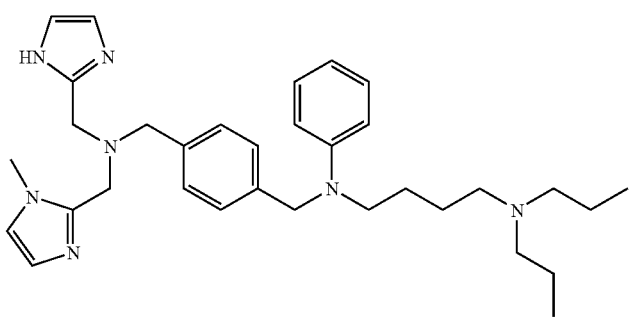 |

TABLE 1-continued
| No. | Structural Formula |
|---|---|
| 25 | 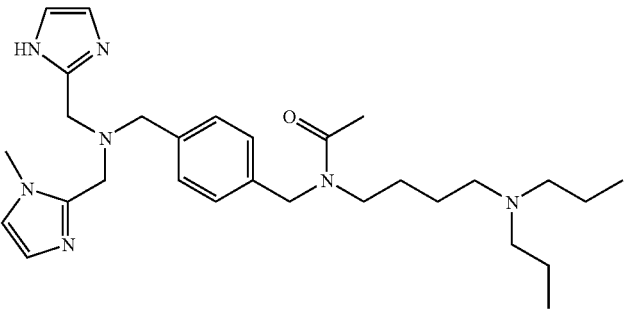 |
| 26 | 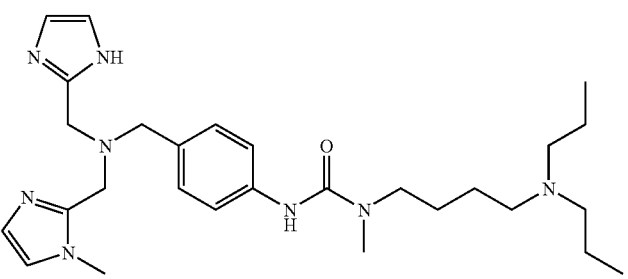 |
| 27 | 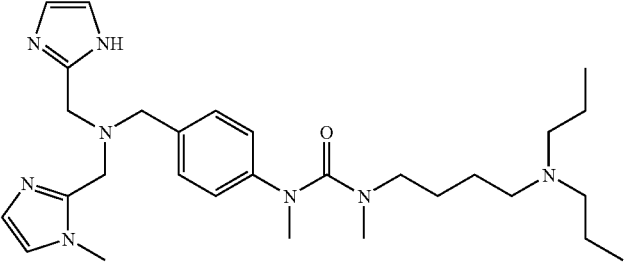 |
| 28 | 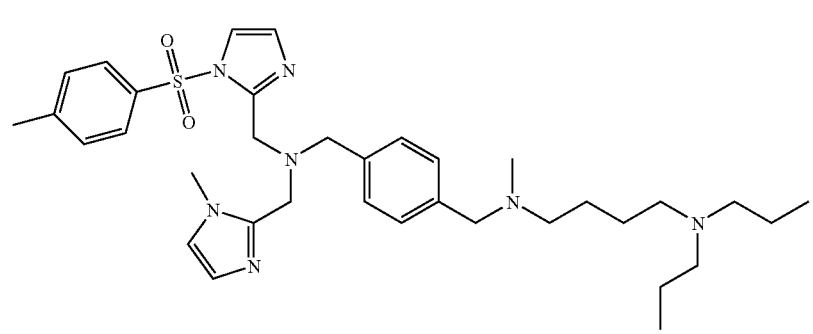 |
| 29 | 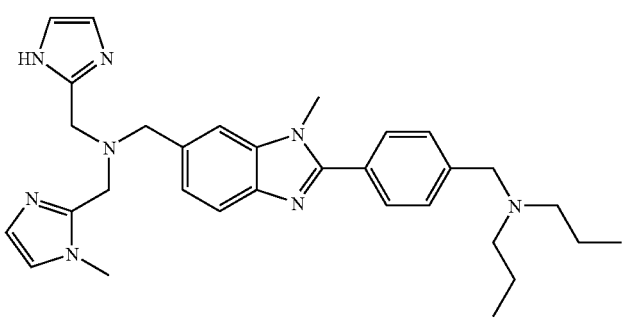 |

TABLE 1-continued

| No. | Structural Formula |
|---|---|
| 30 | |
| 31 | |
| 32 | |
| 33 | |

TABLE 1-continued
| No. | Structural Formula |
|---|---|
| 34 | 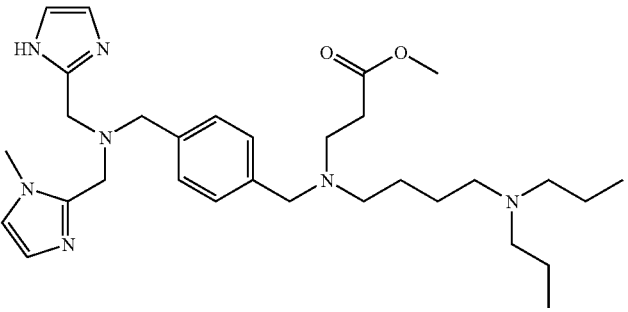 |
| 35 | 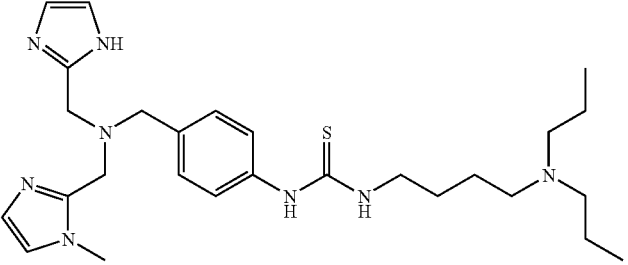 |
| 36 | 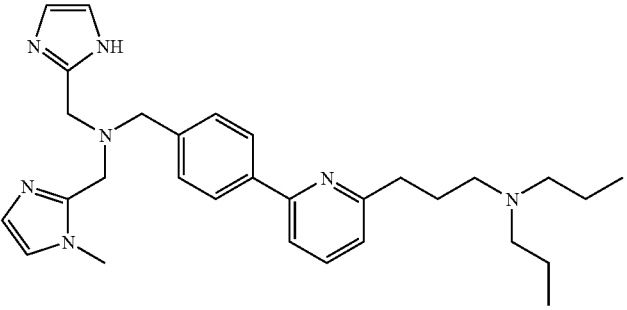 |
| 37 | 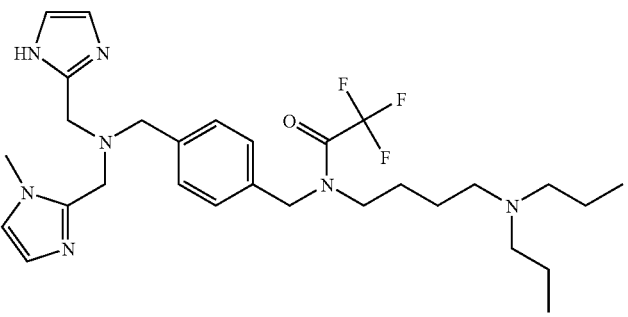 |
| 38 | 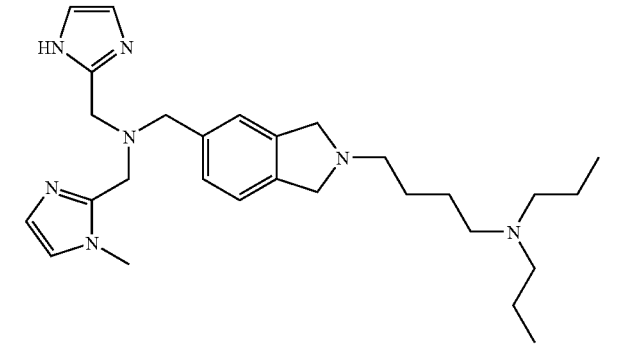 |

TABLE 1-continued
| No. | Structural Formula |
|---|---|
| 39 | 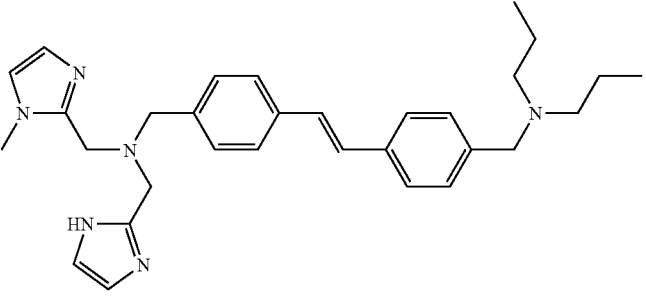 |
| 40 | 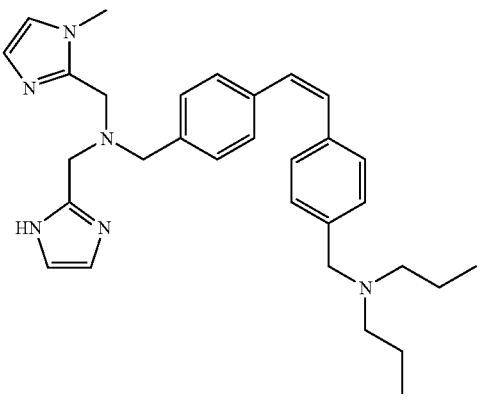 |
| 41 | 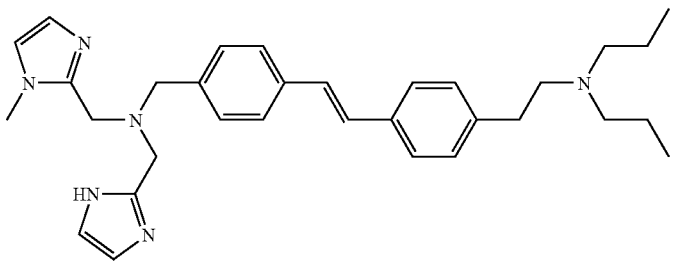 |
| 42 | 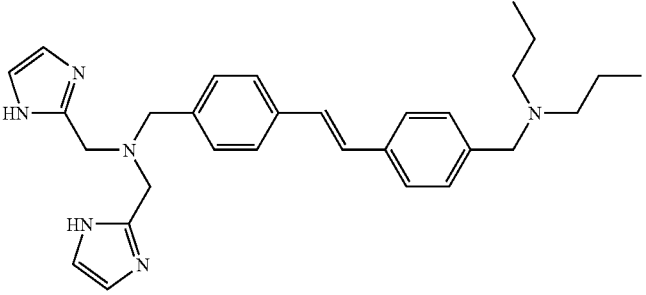 |
| 43 | 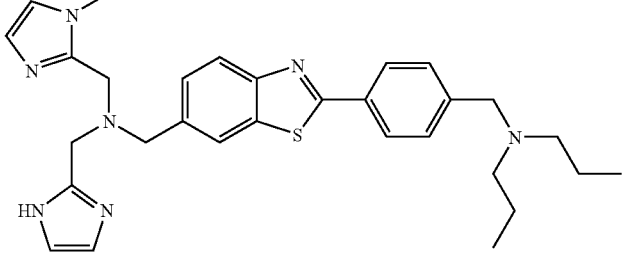 |

TABLE 1-continued
| No. | Structural Formula |
|---|---|
| 44 | 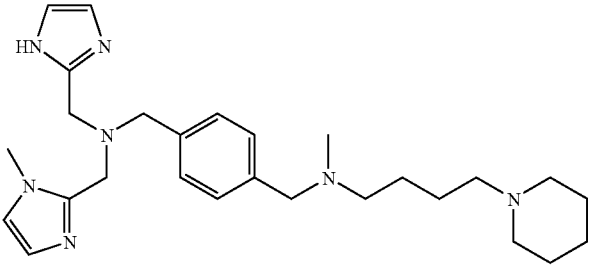 |
| 45 | 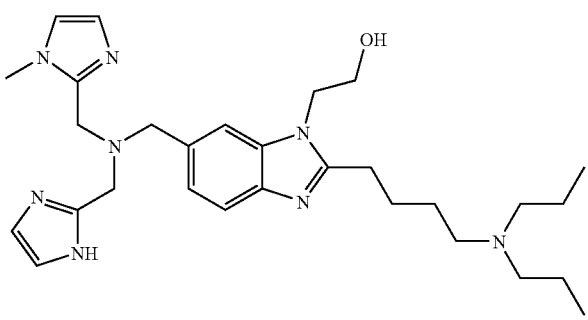 |
| 46 | 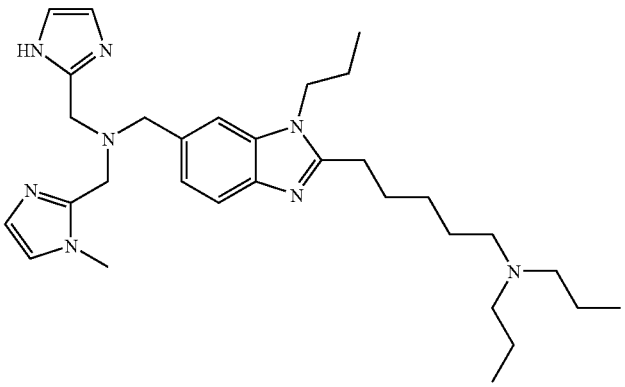 |
| 47 | 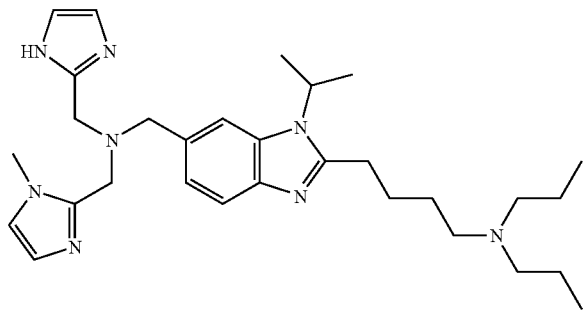 |

TABLE 1-continued
| No. | Structural Formula |
|---|---|
| 48 | 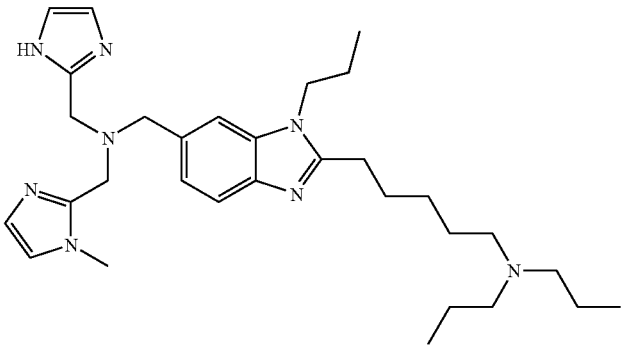 |
| 49 | 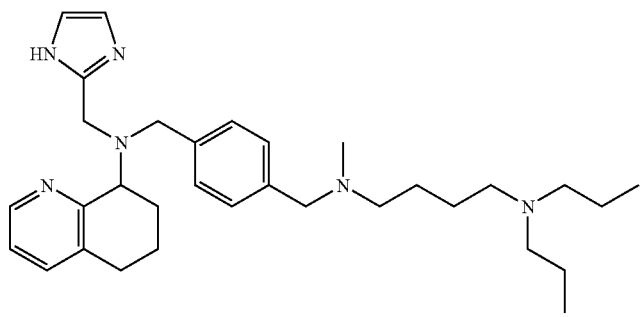 |
| 50 | 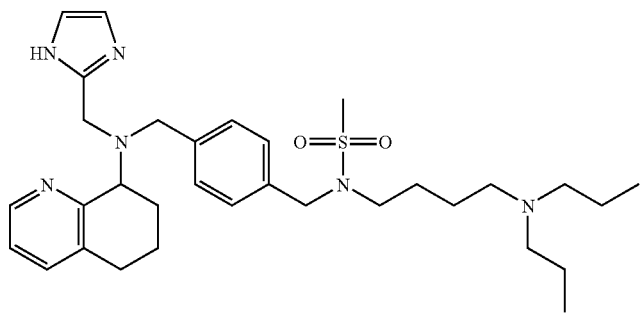 |
| 51 | 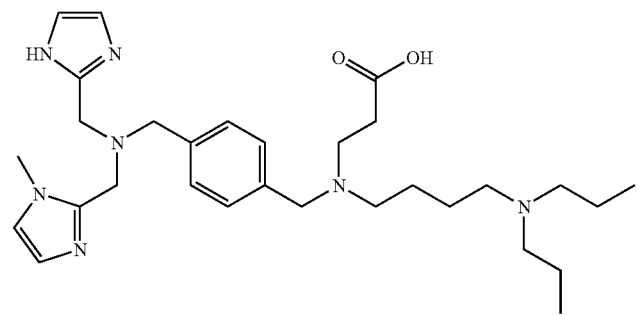 |

TABLE 1-continued
| No. | Structural Formula |
|---|---|
| 52 | 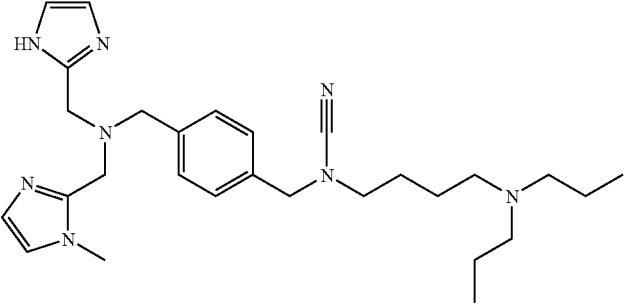 |
| 53 | 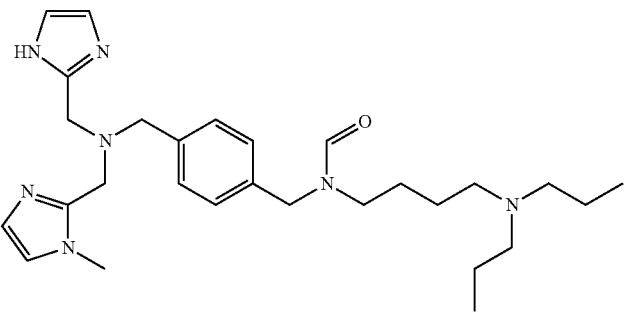 |
| 54 | 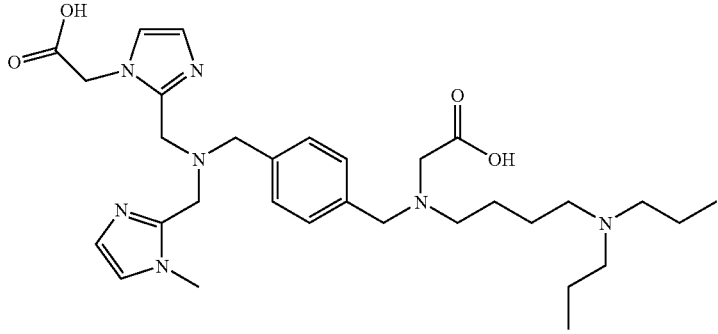 |
| 55 | 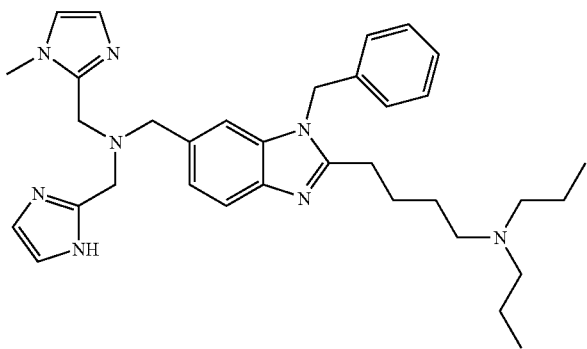 |

TABLE 1-continued
| No. | Structural Formula |
|---|---|
| 56 | 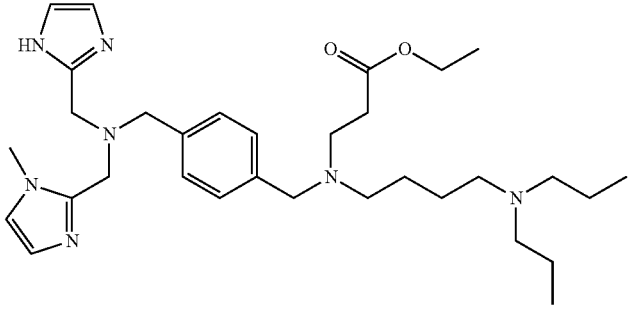 |
| 57 | 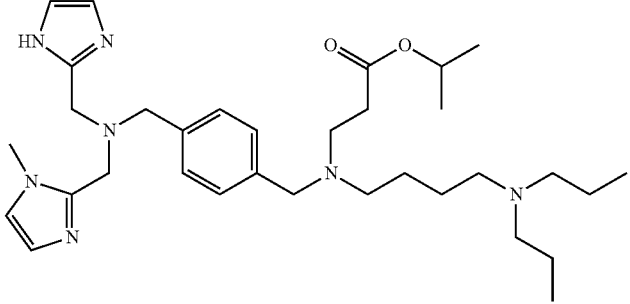 |
| 58 | 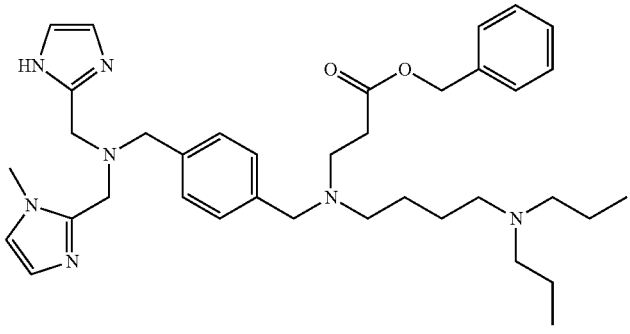 |
| 59 | 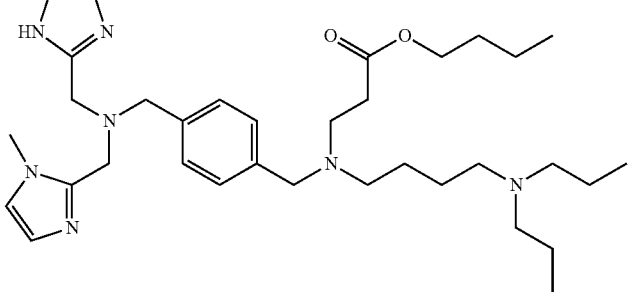 |

TABLE 1-continued

| No. | Structural Formula |
|---|---|
| 60 | |
| 61 | |
| 62 | |
| 63 | |
| 64 | |

TABLE 1-continued
| No. | Structural Formula |
| --- | --- |
| 65 | 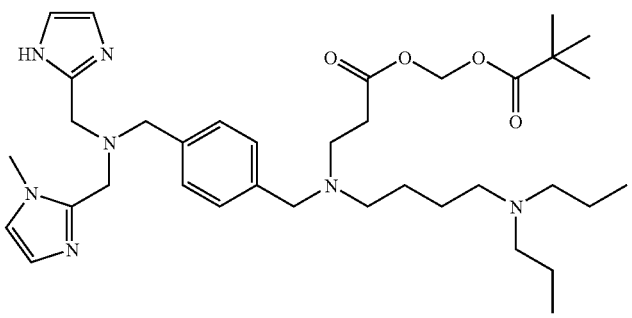 |
| 66 | 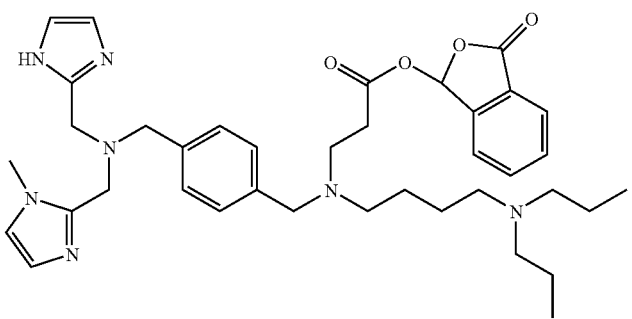 |
| 67 | 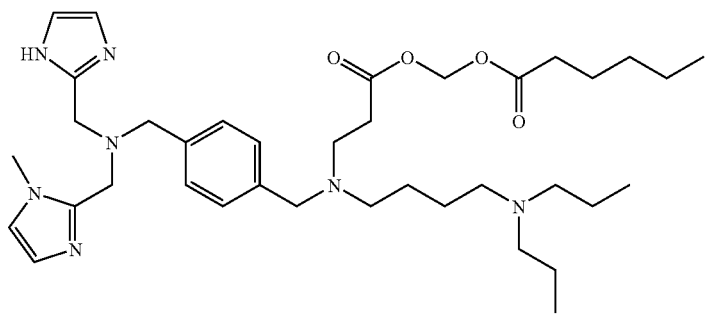 |
| 68 | 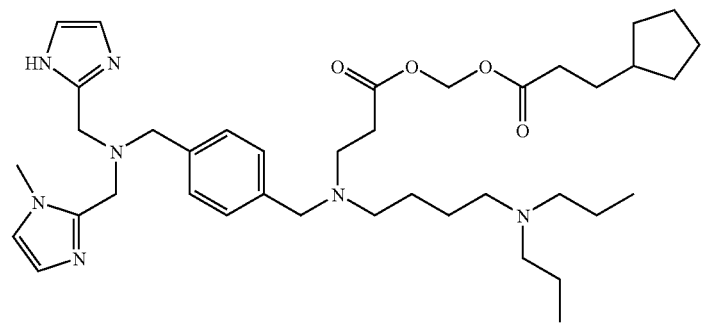 |

TABLE 1-continued

| No. | Structural Formula |
|---|---|
| 69 | |
| 70 | |
| 71 | |
| 72 | |
| 73 | |

TABLE 1-continued

| No. | Structural Formula |
|---|---|
| 74 | |
| 75 | |
| 76 | |
| 77 | |

TABLE 1-continued

| No. | Structural Formula |
|-----|---|
| 78 | |
| 79 | |
| 80 | |
| 81 | |
| 82 | |

TABLE 1-continued
| No. | Structural Formula |
|---|---|
| 83 | 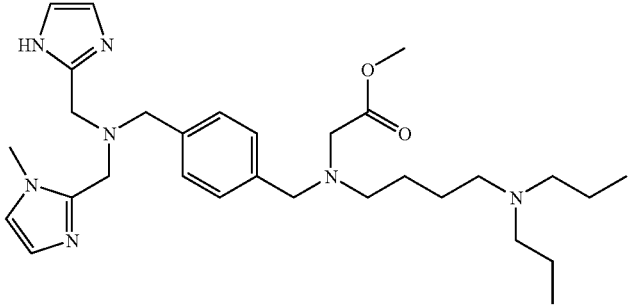 |
| 84 | 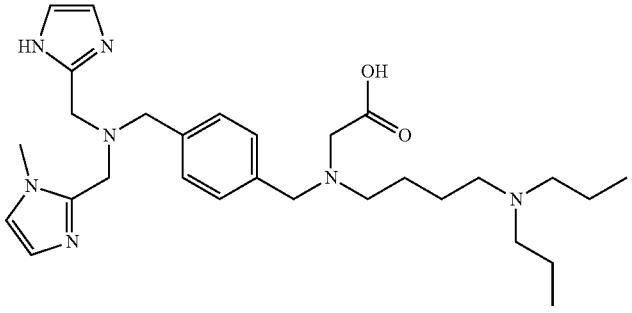 |
| 85 | 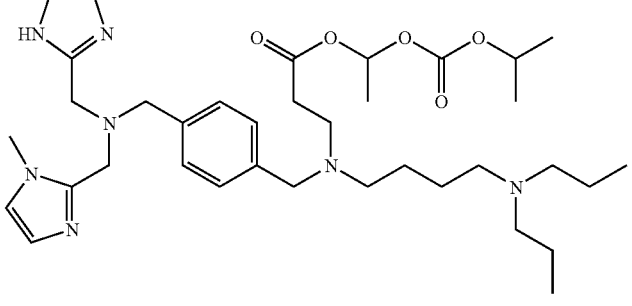 |
| 86 | 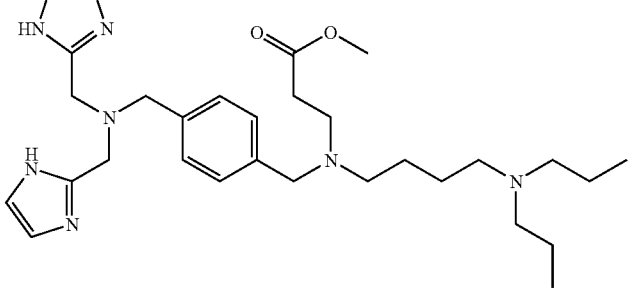 |
| 87 | 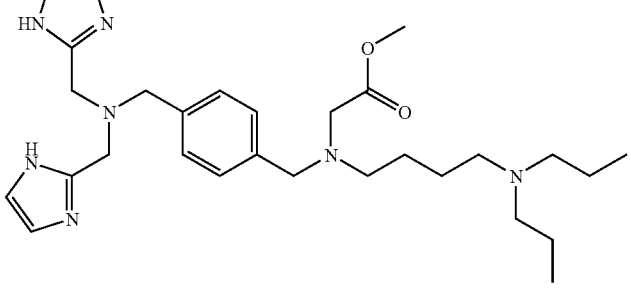 |

TABLE 1-continued
| No. | Structural Formula |
|---|---|
| 88 | 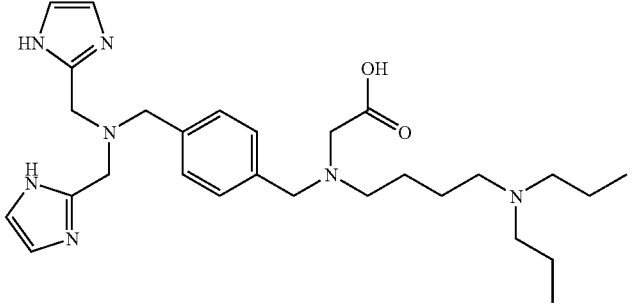 |
| 89 | 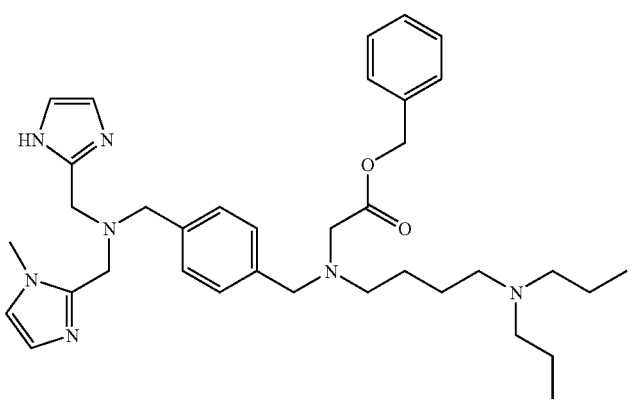 |
| 90 | 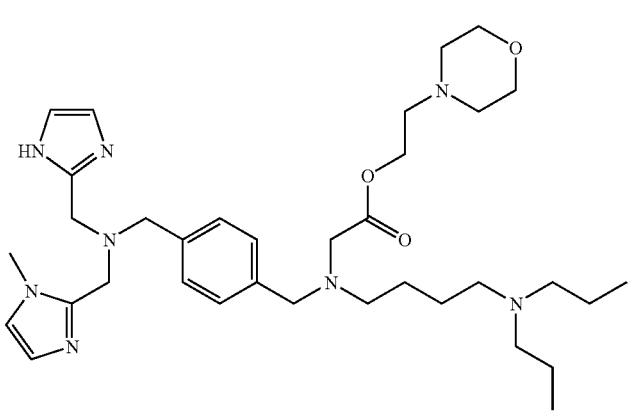 |
| 91 | 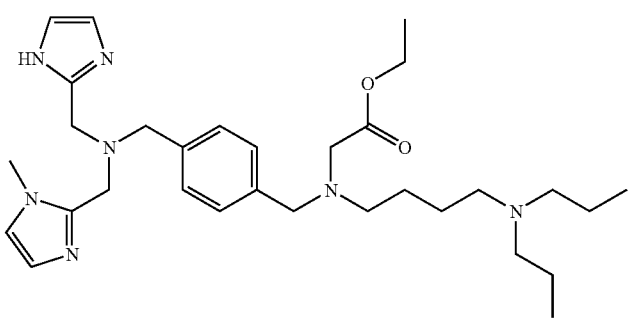 |

TABLE 1-continued
| No. | Structural Formula |
|---|---|
| 92 | 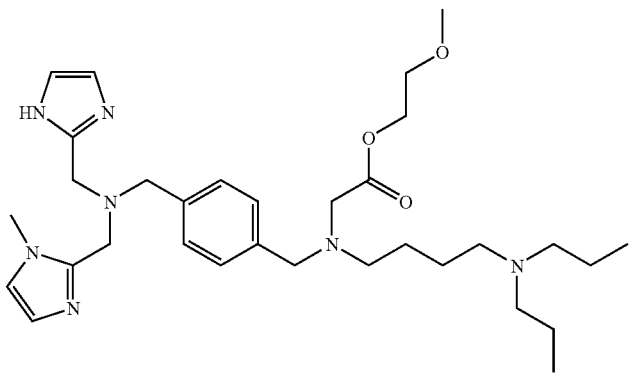 |
| 93 | 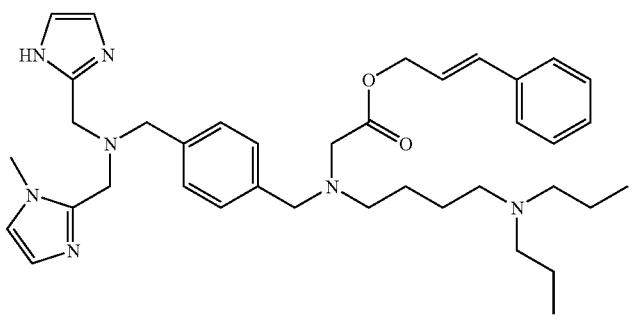 |
| 94 | 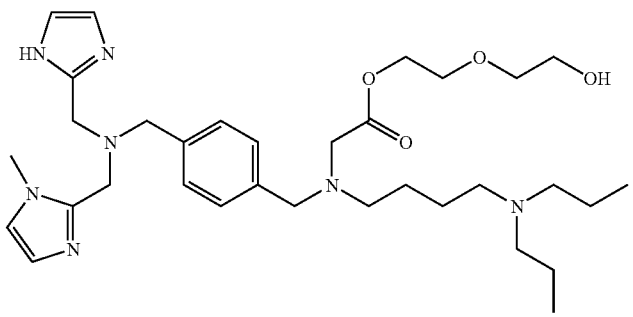 |
| 95 | 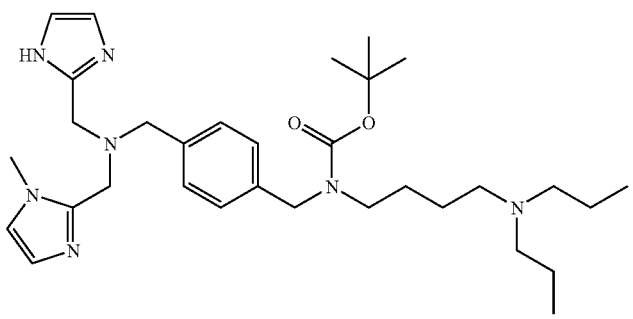 |

TABLE 1-continued

| No. | Structural Formula |
|---|---|
| 96 | |
| 97 | |
| 98 | |
| 99 | |
| 100 | |

TABLE 1-continued
| No. | Structural Formula |
|---|---|
| 101 | 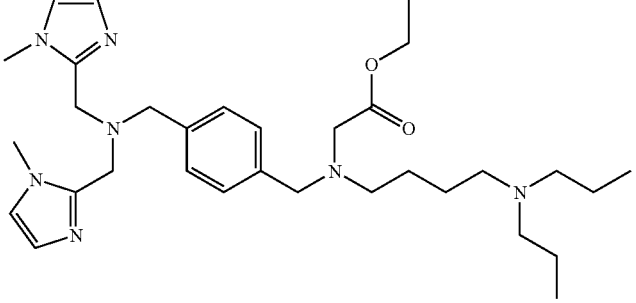 |
| 102 | 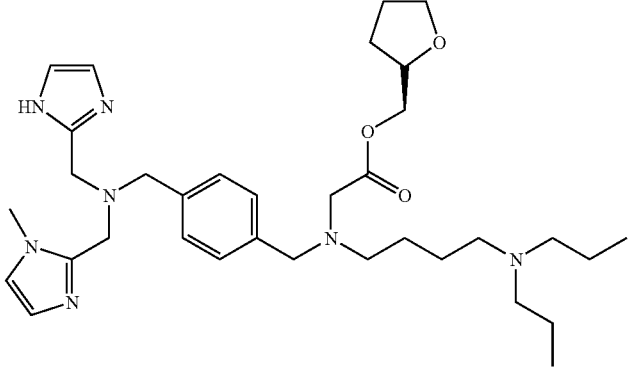 |
| 103 | 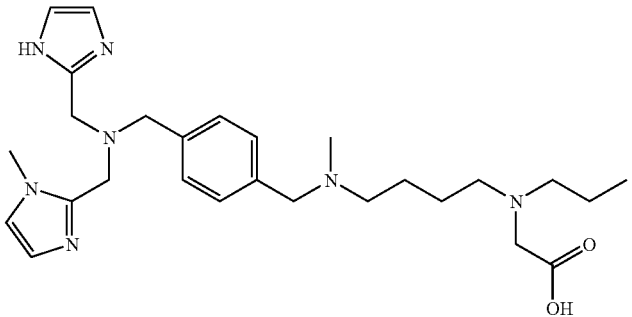 |
| 104 | 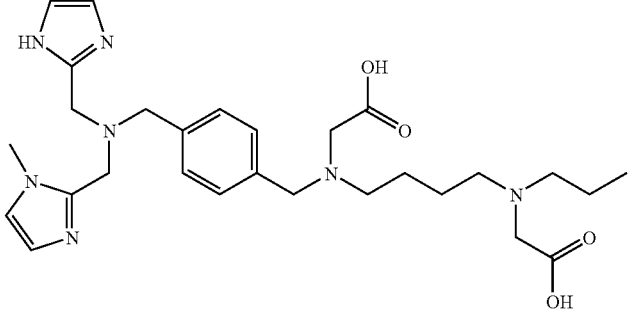 |

TABLE 1-continued

| No. | Structural Formula |
|---|---|
| 105 | |
| 106 | |
| 107 | |
| 108 | |
| 109 | |

TABLE 1-continued
| No. | Structural Formula |
|---|---|
| 110 | 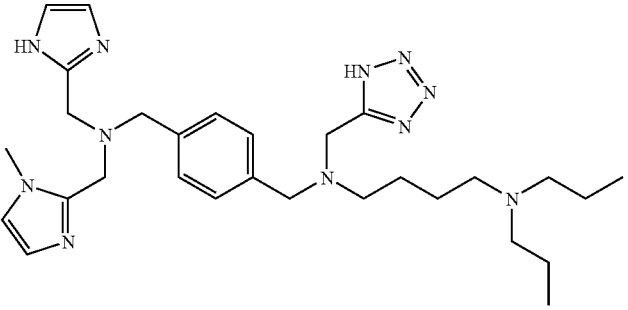 |
| 111 | 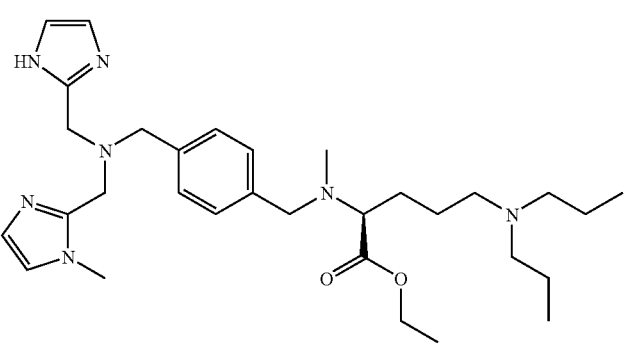 |
| 112 | 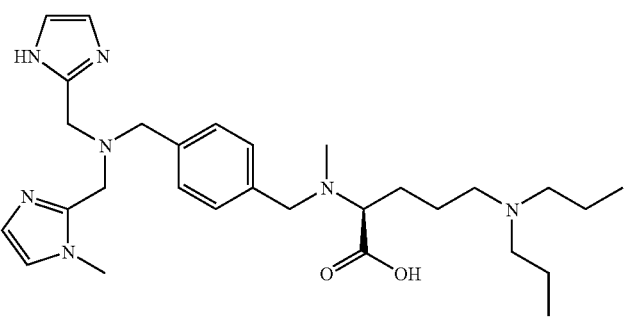 |
| 113 | 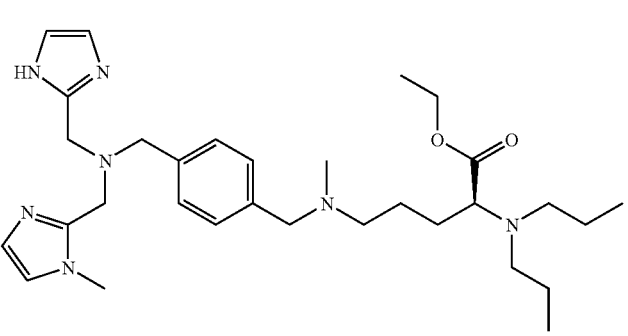 |
| 114 | 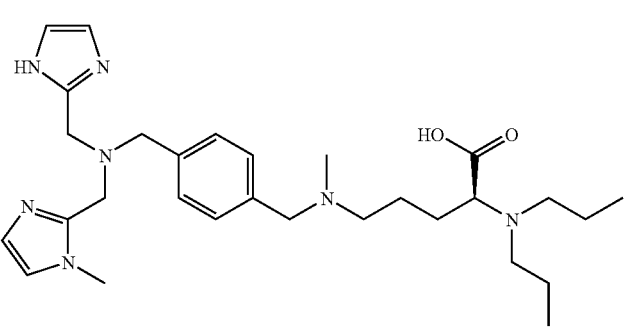 |

TABLE 1-continued
| No. | Structural Formula |
|---|---|
| 115 | 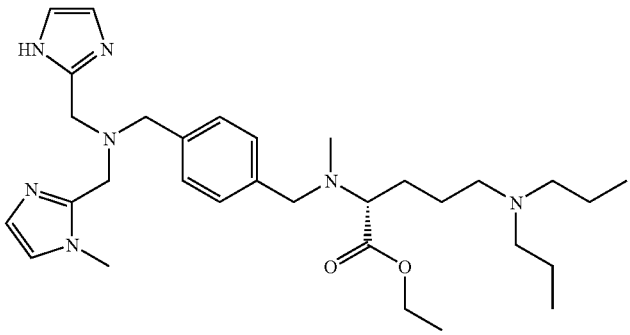 |
| 116 | 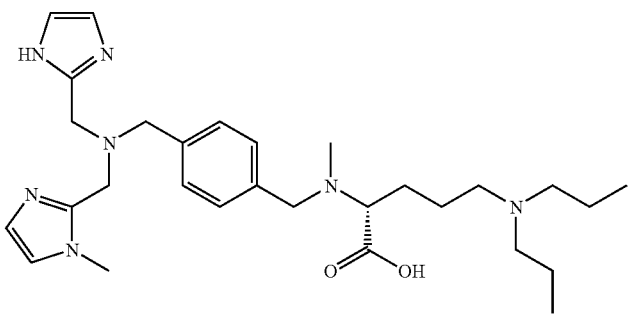 |
| 117 | 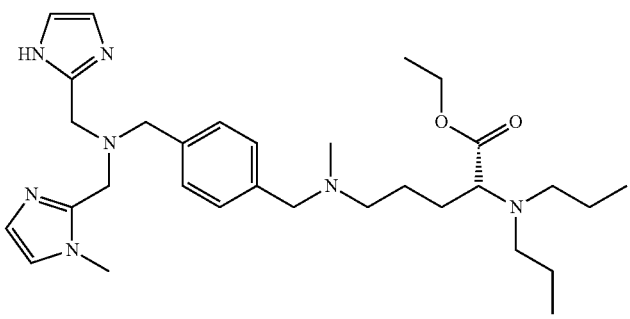 |
| 118 | 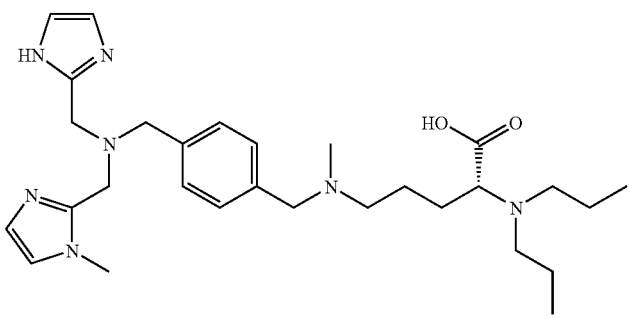 |

TABLE 1-continued

| No. | Structural Formula |
|-----|-------------------|
| 119 | |
| 120 | |
| 121 | |
| 122 | |

Next, results of activity tests and the like for the compound of the present invention are described.

TEST EXAMPLE 1

Immediately after infection, HIV-1$_{IIIB}$ infected MT-4 cells (3.0×10$^4$/well, MOI (Multiplicity of infection): 0.01) were added to a 96-well microtiter plate together with the test compounds having different concentrations. The cells were cultured in a carbon dioxide incubator at 37° C. for 5 days, and the number of living cells was measured in accordance with the MTT (tetrazolium) method (Pawels, et al., J. of Virol. Method, 20, 309-321 (1998)). The antiviral activity is represented by the concentration required for inhibition of cell disorder due to HIV infection by 50% (EC$_{50}$: 50% Effective Concentration) (μM), and the results are shown in Table 2.

TABLE 2

| Compound No. | EC50[μM] |
|---|---|
| 1 | 0.003 |
| 3 | 0.003 |
| 4 | 0.003 |
| 5 | 0.009 |
| 10 | 0.009 |
| 13 | 0.003 |
| 14 | 0.006 |
| 15 | 0.006 |
| 16 | 0.003 |
| 17 | 0.003 |
| 20 | 0.004 |
| 21 | 0.046 |
| 22 | 0.106 |
| 23 | 0.003 |
| 24 | 0.095 |
| 26 | 0.073 |
| 27 | 0.230 |
| 29 | 0.061 |
| 30 | 0.092 |
| 31 | 0.074 |
| 33 | 0.003 |
| 34 | 0.003 |
| 35 | 0.007 |
| 36 | 0.656 |
| 37 | 0.003 |
| 44 | 0.002 |
| 46 | 0.017 |
| 47 | 0.002 |
| 50 | 0.401 |
| 51 | 0.002 |
| 82 | 0.003 |
| 83 | 0.003 |
| 84 | 0.003 |
| 87 | 0.003 |
| 88 | 0.002 |
| 91 | 0.003 |
| 97 | 0.001 |
| 100 | 0.002 |
| 109 | 0.004 |
| 110 | 0.004 |
| 119 | 0.004 |
| 120 | 0.004 |
| 122 | 0.004 |

TEST EXAMPLE 2

MT-4 cells ($5 \times 10^6$/0.2 ml/well) were cultured on a 24-well microtiter plate. After the cells were incubated for 24 hours at 37° C. in a carbon dioxide gas incubator, a culture medium was replaced with a buffer solution (0.1% BSA-containing RPMI-1640). Together with a ligand $^{125}$I-SDF-1α (specific activity: 2,200 Ci/mmol; available from Daiichi Pure Chemicals Co., Ltd. (Tokyo)), test materials with various concentrations were subjected to a binding reaction for 2 hours under ice-cooling. Ligands that did not bind in cold PBS were washed out, and then the radioactivities of bound ligands were measured with a scintillation counter (available from Japan Packard (Tokyo)). Then, a rate of inhibition of the binding between radioactive ligands and receptors CXCR4 by a test material was calculated (a binding-inhibition % at 0.01 μM).

The results are shown in Table 3.

TABLE 3

| Compound No. | Inhibition rate (%) |
|---|---|
| 1 | 87.9 |
| 3 | 71.4 |
| 4 | 94.9 |
| 5 | 67.0 |
| 10 | 20.4 |
| 13 | 75.5 |
| 14 | 32.9 |
| 15 | 74.0 |
| 16 | 46.9 |
| 17 | 93.5 |
| 20 | 73.2 |
| 21 | 59.2 |
| 22 | 84.3 |
| 23 | 78.2 |
| 24 | 50.1 |
| 26 | 57.3 |
| 27 | 43.4 |
| 29 | 71.2 |
| 30 | 46.0 |
| 31 | 47.3 |
| 33 | 85.2 |
| 34 | 85.5 |
| 35 | 86.3 |
| 36 | 58.0 |
| 37 | 92.3 |
| 44 | 81.6 |
| 46 | 74.6 |
| 47 | 86.2 |
| 50 | 53.4 |
| 51 | 85.8 |
| 82 | 82.3 |
| 83 | 79.7 |
| 84 | 88.3 |
| 87 | 82.1 |
| 88 | 85.0 |
| 91 | 87.7 |
| 97 | 85.6 |
| 100 | 79.2 |
| 109 | 94.3 |
| 110 | 71.4 |
| 119 | 72.7 |
| 120 | 79.7 |
| 122 | 71.3 |

TEST EXAMPLE 3

The aforementioned compound was examined for acute toxicity. Specifically, 6-week-old SD mice (male) were divided into several groups (2 to 3 mice in each group). Subsequently, each of the compounds of Examples was dissolved in a physiological saline solution, and the solution was transvenously administered to the mice (dose: 2.5 mg/kg) once. Then, the number of dead mice was counted. The results are shown in Table 4.

As shown in Table 4, Test Example 3 confirmed that the administration of each compound did not cause any death and the compounds did not have acute toxicity.

TABLE 4

| Compound No. | Dead mice/ test mice |
|---|---|
| 1 | 0/3 |
| 3 | 0/3 |
| 4 | 0/3 |
| 5 | 0/3 |
| 10 | 0/3 |
| 13 | 0/3 |
| 14 | 0/3 |
| 15 | 0/3 |
| 16 | 0/3 |
| 17 | 0/3 |

TABLE 4-continued

| Compound No. | Dead mice/test mice |
|---|---|
| 20 | 0/3 |
| 21 | 0/3 |
| 22 | 0/3 |
| 23 | 0/3 |
| 24 | 0/3 |
| 26 | 0/3 |
| 27 | 0/3 |
| 29 | 0/3 |
| 30 | 0/3 |
| 31 | 0/3 |
| 33 | 0/3 |
| 34 | 0/3 |
| 35 | 0/3 |
| 36 | 0/3 |
| 37 | 0/3 |
| 44 | 0/3 |
| 46 | 0/3 |
| 47 | 0/3 |
| 50 | 0/3 |
| 51 | 0/3 |
| 82 | 0/3 |
| 83 | 0/3 |
| 84 | 0/3 |
| 87 | 0/3 |
| 88 | 0/3 |
| 91 | 0/3 |
| 97 | 0/3 |
| 100 | 0/3 |

TEST EXAMPLE 4

34.6% of the Compound No. 4, 34.6% of lactose (Japanese Pharmacopoeia; hereinafter, referred to as "(JP)"), 17.3% of corn starch (JP), 7.3% of hydroxypropylcellulose (JP), and 6.2% of low-substitution hydroxypropylcellulose (JP) were sieved and mixed well in a plastic bag. Purified water (JP) in an amount equal to those compounds was added to the mixture, and then a wet cake was obtained by kneading the mixture for 20 minutes with a biaxial kneader. The wet cake was granulated by using an extrusion granulating machine (diameter of cylindrical aperture: 1 mm), and then the granulated product was dried by using a fluidized-bed dryer (40° C., 30 minutes). The dried granules were sieved. Subsequently, magnesium stearate was added to the sieved product in the proportion of 1% of magnesium stearate to 99% of sieved product and then the whole was mixed well, followed by making tablets having an average weight of 292 mg by means of a tableting machine.

In addition, an undercoat solution was prepared by dissolving 8% of hydroxypropylmethylcellulose (JP) and 1.6% of macrogol 6000 (JP) in purified water (JP) so as to be 100% in total. An under coat tablet was prepared by: spraying the undercoat solution using a hicoater in a ratio of 5% with respect to the weight of the tablet which was previously made; and subjecting the sprayed tablet to drying for 20 minutes.

Subsequently, an enteric coating solution was prepared by dissolving 10% of hydroxypropylcellulose acetate succinate (Pharmaceutical excipient standards), 3% of triethyl citrate (JP), 2% of titanium oxide (JP), and 0.05% of hydroxypropylcellulose (JP) in purified water (JP) so as to be 100% in total. The enteric coating solution was sprayed by using a hicoater in a ratio of 10% with respect to the tablet weight. After the spraying, the tablet was dried for 30 minutes, thereby an enteric tablet was prepared. This enteric tablet had properties of not allowing a main component to be eluted within 2 hours in first liquid (JP), and allowing 80% or more of the main component to be eluted within 30 minutes in second liquids (JP).

TEST EXAMPLE 5

147 µl of human serum pool (manufactured by Cosmo Bio Co. Ltd.) or pool serum obtained by centrifugation (3,500 rpm for 10 minutes) of whole blood collected from a Crj:CD (SD) IGS male rat (manufactured by Charles River Laboratories Japan, INC.) was dispensed in a tube. 147 µl of a physiological saline solution (manufactured by Hikari Pharmaceutical Co., Ltd.) was dispensed thereto. Subsequently, the whole was preincubated for 3 minutes. The solution was added and mixed with a solution (3 µl) obtained by: diluting a 25 mmol/l DMSO solution containing the Compound No. 91 with a physiological saline solution to adjust to 500 µmol/l. The reaction was allowed to start in a thermomixer. After 30 minutes later, the solution was added with 0.1% formic acid/methanol solution (600 µl) and the whole was mixed. The solution was subjected to centrifugation (15,000 rpm for 5 minutes) and the supernatant was subjected to LCMS (liquid chromatograph mass spectrometry) measurement. As a result, it was confirmed that the Compound No. 91 was converted to the Compound No. 84. Table 5 shows the results.

TABLE 5

|  | Human | | Rat | |
|---|---|---|---|---|
|  | 0 minutes | 30 minutes | 0 minutes | 30 minutes |
| Compound 91 | 99% | 20% | 76% | 0% |
| Compound 84 | 1% | 80% | 24% | 100% |

INDUSTRIAL APPLICABILITY

The novel amine compound according to the present invention, a pharmacologically acceptable salt thereof, or a prodrug thereof can provide a new CXCR4 antagonist. The new CXCR4 antagonist of the present invention has a CXCR4 antagonism, and shows, based on the CXCR4 antagonism, excellent effects as a therapeutic or preventive drug for a disease such as: a viral infectious disease such as HIV; rheumatism; or cancer metastasis.

The invention claimed is:

1. A compound represented by the following general formula (1) or a pharmaceutically acceptable salt thereof:

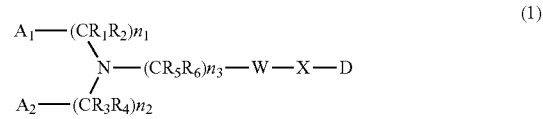

(1)

wherein
$n_1$, $n_2$, and $n_3$ represent an integer of 1;
$R_1$, $R_2$, $R_3$, $R_4$, $R_5$, and $R_6$ each independently represent a hydrogen atom;
$A_1$ and $A_2$, each independently represent a hydrogen atom, a substitutable monocyclic or polycyclic heteroaromatic ring, a partly saturated substitutable polycyclic heteroaromatic ring, a substitutable monocyclic or polycyclic aromatic ring, a partially saturated substitutable polycyclic aromatic ring, a substitutable heterocing, or a group represented by the following formula (2):

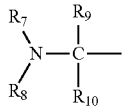
(2)

wherein $R_7$, $R_8$, $R_9$, and $R_{10}$ each independently represent a hydrogen atom, a substitutable alkyl group having 1 to 15 carbon atoms, a substitutable alkenyl group having 2 to 15 carbon atoms, a substitutable alkynyl group having 2 to 15 carbon atoms, or a substitutable cyclic alkyl group having 3 to 15 carbon atoms;

W represents a phenyl group;

X represents $CH_2$;

D represents a group represented by the following formula (6):

—Q—Y—B    (6)

wherein

Q represents $NR_{12}$, wherein $R_{12}$ represents $-CH_2)_m COOR_{36}$, wherein m represents an integer of 1 or 2 and $R_{36}$ represents a hydrogen atom or an alkyl group having 1 to 5 carbon atoms;

Y represents $-(CH_2)_{m3}-$ wherein m3 represents an integer of 0 to 6; and

B represents $NR_{25}R_{26}$ wherein $R_{25}$ and $R_{26}$ each independently represent a hydrogen atom, an alkyl group having 1 to 6 carbon atoms, or a cyclic alkyl group having 3 to 6 carbon atoms.

2. A compound and a pharmacologically acceptable salt thereof according to claim 1, wherein $A_1$ is an imidazole group and $A_2$ is an imidazole group or an imidazole group substituted with an alkyl group.

3. A compound and a pharmacologically acceptable salt thereof according to claim 1, wherein $R_{36}$ represents a hydrogen atom or an ethyl group.

4. A compound or a pharmacologically acceptable salt thereof according to claim 1, wherein $R_{25}$ and $R_{26}$ represent an alkyl group having 1 to 6 carbon atoms.

5. A compound or a pharmacologically acceptable salt thereof according to claim 1, wherein the compound is selected from the group consisting of:

3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid, [(4-dipropylamino-butyl)-(4-[[(1H-imidazol-2-ylmethyl)-(1-methyl-1H-imidazol-2-ylmethyl)-amino]-methyl]-benzyl)-amino]-acetic acid, and [[4-(dipropyl-amino)-butyl]-(4-[[1H-imidazol-2-ylmethyl)-(1-methyl-1H-imidazol-2-ylmethyl)-amino]-methyl]-benzyl)-amino]-acetic acid ethyl ester.

6. A medical composition, comprising as an active ingredient the compound, or the pharmacologically acceptable salt thereof, according to claim 1.

7. A CXCR4 antagonist, comprising as an active ingredient the compound, or the pharmacologically acceptable salt thereof according to claim 1.

8. An anti-HIV drug, comprising as an active ingredient the compound, or the pharmacologically acceptable salt thereof according to claim 1.

9. A compound or a pharmacologically acceptable salt thereof according to claim 5, wherein the compound is 3-[(4-dipropylamino-butyl)-(4-{[(1H-imidazol-2-ylmethyl)-(1-methyl-1H-imidazol-2-ylmethyl)-amino]-methyl}-benzyl)-amino]-propionic acid.

10. A compound or a pharmacologically acceptable salt thereof according to claim 5, wherein the compound is [(4-dipropylamino-butyl)-(4-[[(1H-imidazol-2-ylmethyl)-(1-methyl-1H-imidazol-2-ylmethyl)-amino]-methyl]-benzyl)-amino]-acetic acid.

11. A compound or a pharmacologically acceptable salt thereof according to claim 5, wherein the compound is [[4-(dipropyl-amino)-butyl]-(4-[[1H-imidazl-2-ylmethyl)-(1-methyl-1H-imidazol-2-ylmethyl)-amino]-methyl]-benzyl)-amino]-acetic acid ethyl ester.

* * * * *